United States Patent
Sobol et al.

(10) Patent No.: US 11,147,459 B2
(45) Date of Patent: Oct. 19, 2021

(54) WEARABLE ELECTRONIC DEVICE AND SYSTEM FOR TRACKING LOCATION AND IDENTIFYING CHANGES IN SALIENT INDICATORS OF PATIENT HEALTH

(71) Applicant: CareBand Inc., Chicago, IL (US)

(72) Inventors: Adam G. Sobol, Dayton, OH (US); Joseph T. Kreidler, Arlington Heights, IL (US); Brian A. Donlin, Chicago, IL (US); Jon G. Ledwith, Palatine, IL (US); Patrick J. McVey, Wheeling, IL (US); Ross D. Moore, Winnetka, IL (US); Peter Nanni, Algonquin, IL (US); Dwayne D. Forsyth, Deer Park, IL (US); Paul Sheldon, Arlington Heights, IL (US); Todd Sobol, Dayton, OH (US); John D. Reed, Dayton, OH (US)

(73) Assignee: CAREBAND INC., Chicago, IL (US)

(*) Notice: Subject to any disclaimer, the term of this patent is extended or adjusted under 35 U.S.C. 154(b) by 104 days.

(21) Appl. No.: 16/233,462

(22) Filed: Dec. 27, 2018

(65) Prior Publication Data
US 2019/0209022 A1 Jul. 11, 2019

Related U.S. Application Data

(60) Provisional application No. 62/709,126, filed on Jan. 5, 2018.

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0002* (2013.01); *A61B 5/0015* (2013.01);
(Continued)

(58) Field of Classification Search
None
See application file for complete search history.

(56) References Cited

U.S. PATENT DOCUMENTS 9,503,969 B1 * 11/2016 Zakaria ............. H04W 52/0229
9,652,955 B1    5/2017 Ray et al.
(Continued)

OTHER PUBLICATIONS

International Search Report and Written Opinion dated May 6, 2019 pertaining to International Application No. PCT/US2019/012116.

*Primary Examiner* — Carl H Layno
*Assistant Examiner* — Manolis Pahakis

(57) ABSTRACT

A wearable electronic device, a system and methods of monitoring with a wearable electronic device. The device includes a hybrid wireless communication module with wireless communication sub-modules to selectively acquire location data from both indoor and outdoor sources, as well as a wireless communication sub-module to selectively transmit an LPWAN signal to provide location information based on the acquired data. The device may also include one or more sensors to collect one or more of environmental data, activity data and physiological data. The device may transmit some or all of its acquired data to a larger system, including a cloud-based server to, in addition to providing location-based data, be used as a part of a predictive health care protocol to correlate changes in acquired data to salient indicators of the health of a wearer of the device. In one form, the predictive health care protocol uses a machine learning model.

20 Claims, 32 Drawing Sheets

(51) Int. Cl.
| | |
|---|---|
| *H04B 1/3827* | (2015.01) |
| *A61B 5/11* | (2006.01) |
| *G16H 40/67* | (2018.01) |
| *H04W 4/80* | (2018.01) |
| *H04W 4/029* | (2018.01) |
| *H04W 84/12* | (2009.01) |
| *H04W 4/02* | (2018.01) |
| *H04W 4/38* | (2018.01) |
| *G08B 25/01* | (2006.01) |
| *G06N 3/00* | (2006.01) |
| *A61B 5/318* | (2021.01) |
| *G16H 50/20* | (2018.01) |
| *G06N 20/00* | (2019.01) |
| *A61B 5/01* | (2006.01) |
| *A61B 5/029* | (2006.01) |
| *A61B 5/1455* | (2006.01) |
| *G08B 21/02* | (2006.01) |
| *G08C 17/02* | (2006.01) |
| *A61B 5/145* | (2006.01) |
| *A61B 5/021* | (2006.01) |
| *A61B 5/024* | (2006.01) |
| *A61B 5/08* | (2006.01) |

(52) U.S. Cl.
CPC .............. *A61B 5/0022* (2013.01); *A61B 5/01* (2013.01); *A61B 5/029* (2013.01); *A61B 5/1112* (2013.01); *A61B 5/1113* (2013.01); *A61B 5/1118* (2013.01); *A61B 5/14551* (2013.01); *A61B 5/318* (2021.01); *A61B 5/4088* (2013.01); *A61B 5/681* (2013.01); *A61B 5/6803* (2013.01); *A61B 5/6804* (2013.01); *A61B 5/7267* (2013.01); *A61B 5/7275* (2013.01); *A61B 5/7435* (2013.01); *G06N 3/00* (2013.01); *G06N 20/00* (2019.01); *G08B 21/0211* (2013.01); *G08B 21/0269* (2013.01); *G08B 21/0272* (2013.01); *G08B 21/0288* (2013.01); *G08B 25/016* (2013.01); *G16H 40/67* (2018.01); *G16H 50/20* (2018.01); *H04B 1/385* (2013.01); *H04W 4/025* (2013.01); *H04W 4/029* (2018.02); *H04W 4/38* (2018.02); *H04W 4/80* (2018.02); *H04W 84/12* (2013.01); *A61B 5/021* (2013.01); *A61B 5/02438* (2013.01); *A61B 5/0816* (2013.01); *A61B 5/14532* (2013.01); *A61B 5/14542* (2013.01); *A61B 5/686* (2013.01); *A61B 5/6822* (2013.01); *A61B 5/6829* (2013.01); *A61B 2560/0214* (2013.01); *A61B 2560/0242* (2013.01); *A61B 2560/0252* (2013.01); *A61B 2560/0257* (2013.01); *A61B 2562/029* (2013.01); *A61B 2562/0219* (2013.01); *A61B 2562/06* (2013.01); *G08C 17/02* (2013.01)

(56) References Cited

U.S. PATENT DOCUMENTS

| | | | |
|---|---|---|---|
| 9,722,803 B1* | 8/2017 | Ellingson | H04L 63/1458 |
| 9,928,359 B1* | 3/2018 | Vargas | G06F 21/42 |
| 10,216,924 B1* | 2/2019 | Vargas | G06F 21/78 |
| 10,335,060 B1* | 7/2019 | Kahn | A61B 5/1118 |
| 10,532,266 B2* | 1/2020 | Genova | H04W 4/80 |
| 2007/0287923 A1* | 12/2007 | Adkins | A61B 5/02405 |
| | | | 600/485 |
| 2011/0234397 A1 | 9/2011 | Fetzer et al. | |
| 2011/0245633 A1* | 10/2011 | Goldberg | A61B 5/486 |
| | | | 600/301 |
| 2012/0233679 A1* | 9/2012 | Shedrinsky | H04W 12/068 |
| | | | 726/7 |
| 2012/0242501 A1* | 9/2012 | Tran | A61B 5/0006 |
| | | | 340/870.02 |
| 2015/0143125 A1* | 5/2015 | Nix | H04L 9/0861 |
| | | | 713/171 |
| 2015/0244699 A1* | 8/2015 | Hessler | H04L 63/12 |
| | | | 726/7 |
| 2015/0334554 A1* | 11/2015 | Song | H04W 8/205 |
| | | | 455/558 |
| 2016/0018278 A1* | 1/2016 | Jeter, II | G16H 40/67 |
| | | | 340/665 |
| 2016/0139273 A1* | 5/2016 | Sobol | H04W 4/80 |
| | | | 342/357.52 |
| 2016/0173359 A1* | 6/2016 | Brenner | H04L 67/12 |
| | | | 600/301 |
| 2016/0270126 A1* | 9/2016 | Adams | H04W 4/021 |
| 2016/0294828 A1* | 10/2016 | Zakaria | H04L 41/0886 |
| 2016/0314255 A1 | 10/2016 | Cook et al. | |
| 2016/0366123 A1* | 12/2016 | Smith | H04W 12/122 |
| 2017/0006003 A1* | 1/2017 | Zakaria | H04L 9/0841 |
| 2017/0006595 A1* | 1/2017 | Zakaria | H04W 4/80 |
| 2017/0006643 A1* | 1/2017 | Zakaria | H04L 67/12 |
| 2017/0013569 A1 | 1/2017 | Braxton | |
| 2017/0017822 A1* | 1/2017 | Zimmerman | G06K 7/1452 |
| 2017/0053267 A1* | 2/2017 | Abel | G06Q 20/341 |
| 2017/0109656 A1 | 4/2017 | Cook et al. | |
| 2017/0134171 A1* | 5/2017 | Woxland | H04W 12/086 |
| 2017/0163685 A1* | 6/2017 | Schwartz | H04L 63/20 |
| 2017/0173262 A1* | 6/2017 | Veltz | A61B 5/0022 |
| 2017/0193787 A1 | 7/2017 | Devdas et al. | |
| 2017/0202484 A1 | 7/2017 | Al Shaery et al. | |
| 2017/0208426 A1 | 7/2017 | Komoni et al. | |
| 2017/0237719 A1* | 8/2017 | Schwartz | H04L 63/0485 |
| | | | 713/153 |
| 2017/0272842 A1 | 9/2017 | Touma et al. | |
| 2018/0001184 A1* | 1/2018 | Tran | G06F 1/163 |
| 2018/0042513 A1* | 2/2018 | Connor | G06K 9/22 |
| 2018/0085058 A1* | 3/2018 | Chakravarthi | A61B 5/14532 |
| 2018/0160907 A1* | 6/2018 | Verma | A61B 7/00 |
| 2018/0168464 A1* | 6/2018 | Barnett, Jr. | A61B 5/6826 |
| 2018/0247713 A1* | 8/2018 | Rothman | G16H 50/30 |
| 2018/0304742 A1* | 10/2018 | Maruthapillai | B60K 15/0409 |
| 2018/0316658 A1* | 11/2018 | Bartlett | H04W 12/069 |
| 2018/0375849 A1* | 12/2018 | Koskimies | H04L 9/3228 |
| 2019/0057189 A1* | 2/2019 | Frederickson | G08B 21/0446 |
| 2019/0147721 A1* | 5/2019 | Avitan | G08B 21/0446 |
| | | | 340/573.1 |
| 2020/0178906 A1* | 6/2020 | Bevan | A61B 5/1032 |
| 2020/0268261 A1* | 8/2020 | Ikegami | A61B 5/0022 |

* cited by examiner

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x01 | delay uint8 | uuid1 uint16 | | strength1 uint8 | uuid2 uint16 | | strength2 uint8 | uuid3 uint16 | | strength3 uint8 | padding 0x00 |

LoRaWAN - Beacon Data format

FIG. 3C

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x02 | delay uint8 | latitude uint32 | | | | longitude uint32 | | | | accuracy uint8 | fix uint8 |

LoRaWAN - GNSS Data format

FIG. 3D

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x04 | delay uint8 | battery uint8 | padding 0x00 | padding 0x00 | padding 0x00 | padding 0x00 | padding 0x00 | padding 0x00 | padding 0x00 | padding 0x00 | padding 0x00 |

LoRaWAN - Battery Data format

FIG. 3E

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x05 | delay uint8 | padding 0x00 | padding 0x00 | padding 0x00 | padding 0x00 | padding 0x00 | padding 0x00 | padding 0x00 | padding 0x00 | padding 0x00 | padding 0x00 |

LoRaWAN - Nurse Call format

FIG. 3F

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x06 | delay uint8 | uuid1 uint16 | | strength3 uint8 | padding 0x00 | padding 0x00 | padding 0x00 | padding 0x00 | padding 0x00 | padding 0x00 | padding 0x00 |

LoRaWAN - Nurse Response format

FIG. 3G

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x07 | delay uint8 | padding 0x00 | padding 0x00 | padding 0x00 | padding 0x00 | padding 0x00 | padding 0x00 | padding 0x00 | padding 0x00 | padding 0x00 | padding 0x00 |

LoRaWAN - Band Worn format

FIG. 3H

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x08 | delay uint8 | padding 0x00 | padding 0x00 | padding 0x00 | padding 0x00 | padding 0x00 | padding 0x00 | padding 0x00 | padding 0x00 | padding 0x00 | padding 0x00 |

LoRaWAN - Band Removed format

FIG. 3I

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x09 | delay uint8 | stationary time uint16 | | padding 0x00 | padding 0x00 | padding 0x00 | padding 0x00 | padding 0x00 | padding 0x00 | padding 0x00 | padding 0x00 |

LoRaWAN - No Movement format

FIG. 3J

Unit to Server

| Msg port (1-223) | Byte offsets | | | | | | | | | | |
|---|---|---|---|---|---|---|---|---|---|---|---|
| | 0 | 1 | 2 | 3 | 4 | 5 | 6 | 7 | 8 | 9 | a |
| 0x0A | delay uint8 | padding 0x00 | padding 0x00 | padding 0x00 | padding 0x00 | padding 0x00 | padding 0x00 | padding 0x00 | padding 0x00 | padding 0x00 | padding 0x00 |

LoRaWAN - Movement format

FIG. 3K

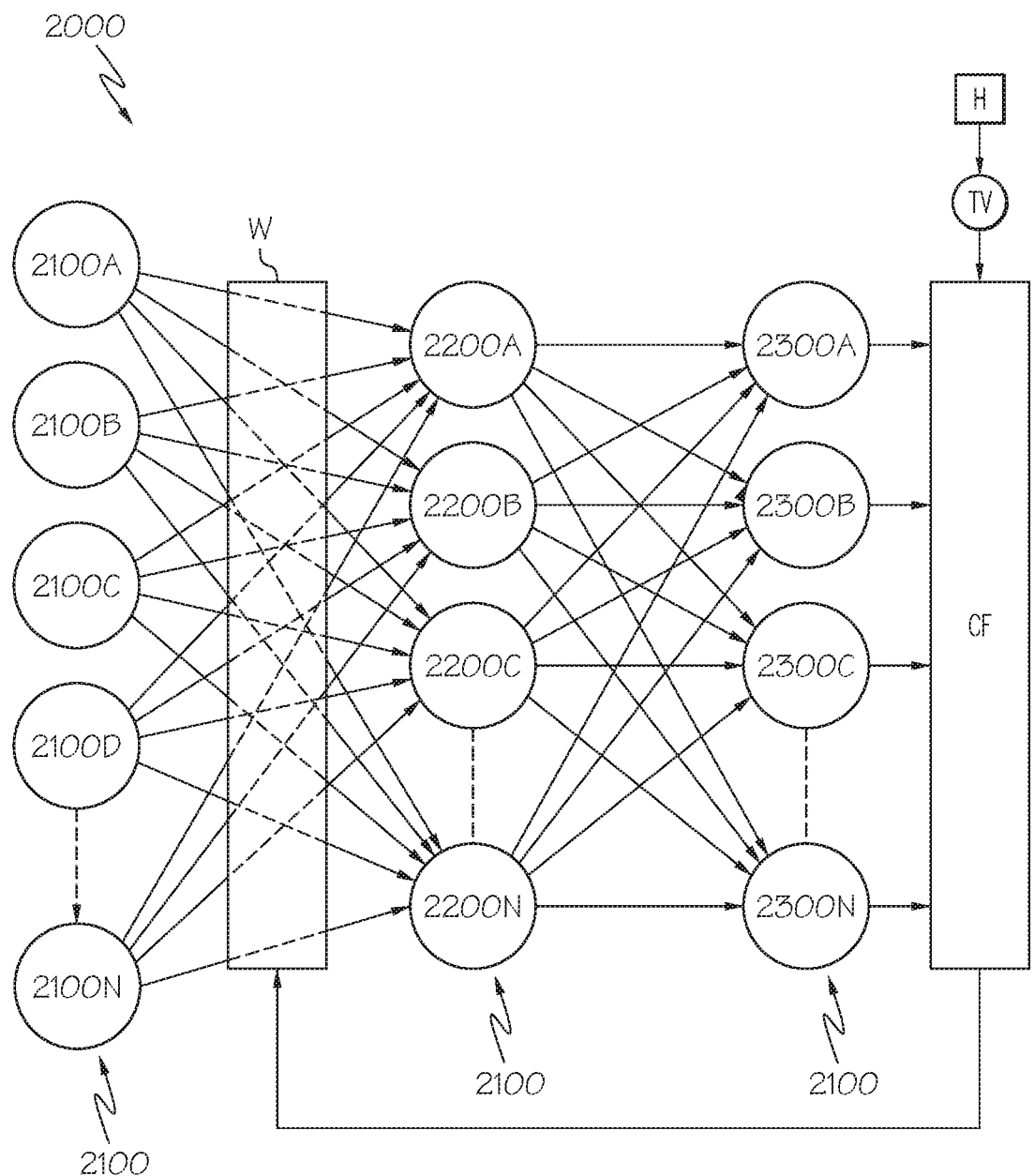
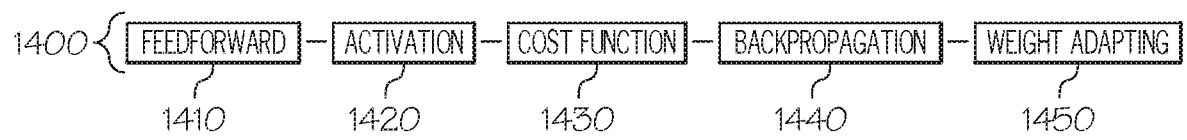
FIG. 7

START DATE: _____  ACTIVIES OF DAILY LIVING DOCUMENTATION

| | MO | TU | WE | TH | FR | SA | SU | MO | TU | WE | TH | FR | SA | SU | MO | TU |
|---|---|---|---|---|---|---|---|---|---|---|---|---|---|---|---|---|
| BATHING | S/S | PB | PB | S/S | PB | PB | PB | S/S | PB | PB | S/S | PB | PB | PB | S/S | PB |
| BATHING | PB | PB | PB | PB | PB | PB | PB | PB | PB | PB | PB | PB | PB | PB | PB | PB |
| MAJ JOINT MVMT | | | | | | | | | | | | | | | | |
| DAY | ✓ | ✓ | ✓ | ✓ | ✓ | ✓ | ✓ | | | | | | | | | |
| EVE | ✓ | ✓ | ✓ | ✓ | ✓ | ✓ | ✓ | | | | | | | | | |
| NIGHT | ✓ | ✓ | ✓ | ✓ | ✓ | ✓ | ✓ | | | | | | | | | |
| REPOSITION | | | | | | | | | | | | | | | | |
| DAY | ✓ | ✓ | ✓ | ✓ | ✓ | ✓ | ✓ | | | | | | | | | |
| EVE | ✓ | ✓ | ✓ | ✓ | ✓ | ✓ | ✓ | | | | | | | | | |
| NIGHT | ✓ | ✓ | ✓ | ✓ | ✓ | ✓ | ✓ | | | | | | | | | |
| PREV SKIN CARE | | | | | | | | | | | | | | | | |
| DAY | ✓ | ✓ | ✓ | ✓ | ✓ | ✓ | ✓ | | | | | | | | | |
| EVE | ✓ | ✓ | ✓ | ✓ | ✓ | ✓ | ✓ | | | | | | | | | |
| NIGHT | ✓ | ✓ | ✓ | ✓ | ✓ | ✓ | ✓ | | | | | | | | | |
| BOWEL MVMT | | | | | | | | | | | | | | | | |
| DAY | ✓ | ✓ | ✓ | ✓ | ✗ | ✓ | ✗ | | | | | | | | | |
| EVE | ✗ | ✓ | ✗ | ✓ | ✓ | ✓ | ✓ | | | | | | | | | |
| NIGHT | ✗ | ✗ | ✗ | ✗ | ✗ | ✗ | ✗ | | | | | | | | | |
| VOIDING # OF X | | | | | | | | | | | | | | | | |
| DAY | 2 | 2 | 2 | 2 | 2 | 1 | 1 | | | | | | | | | |
| EVE | 2 | 4 | 3 | 4 | 1 | 2 | 4 | | | | | | | | | |
| NIGHT | 3 | 2 | 2 | 3 | 4 | 3 | 1 | | | | | | | | | |
| TOILETING PER POC | | | | | | | | | | | | | | | | |
| DAY | | | | | | | | | | | | | | | | |
| EVE | | | | | | | | | | | | | | | | |
| NIGHT | | | | | | | | | | | | | | | | |
| INITIALS = COMPLETE | | | | | | | | | | | | | | | | |
| DAY | NB | NB | NB | NB | NB | NR | NR | | | | | | | | | |
| EVE | NC | NC | NC | NC | NC | NS | NS | | | | | | | | | |
| NIGHT | NI | NI | NI | NI | NI | NA | NA | | | | | | | | | |

S/S   SHOWER/SHAMPOO     L   LARGE

PB   PARTIAL BATH     I   INCONTINENT OF BLADDER

✓   COMPLETED     PREVENTATIVE SKIN CARE INCLUDES ANY OF THE FOLLOWING:

✗   NONE     APPLICATION OF PROTECTIVE PADS (DOWN, SHEEPKIN, PADDED, QUILTED) OR ANY CARE GIVEN FOR THE PURPOSE OF PREVENTING SKIN PROBLEMS, INCLUDING SOAK PROTECTIVE BOOTIES, ORTHOTICS, APPLICATION OF TOE PADS, TOE SEPARATORS, ETC.

SM   SMALL BOWEL MOVEMENT

M   MEDIUM

CIRCLED TASK INDICATED NOT COMPLETED. SEE EXPLANATION ON REVERSE

| INIT | SIGNATURE | INIT | SIGNATURE | INIT | SIGNATURE |
|---|---|---|---|---|---|
| | | | | | |
| | | | | | |

RESIDENT NAME: _____

FIG. 8

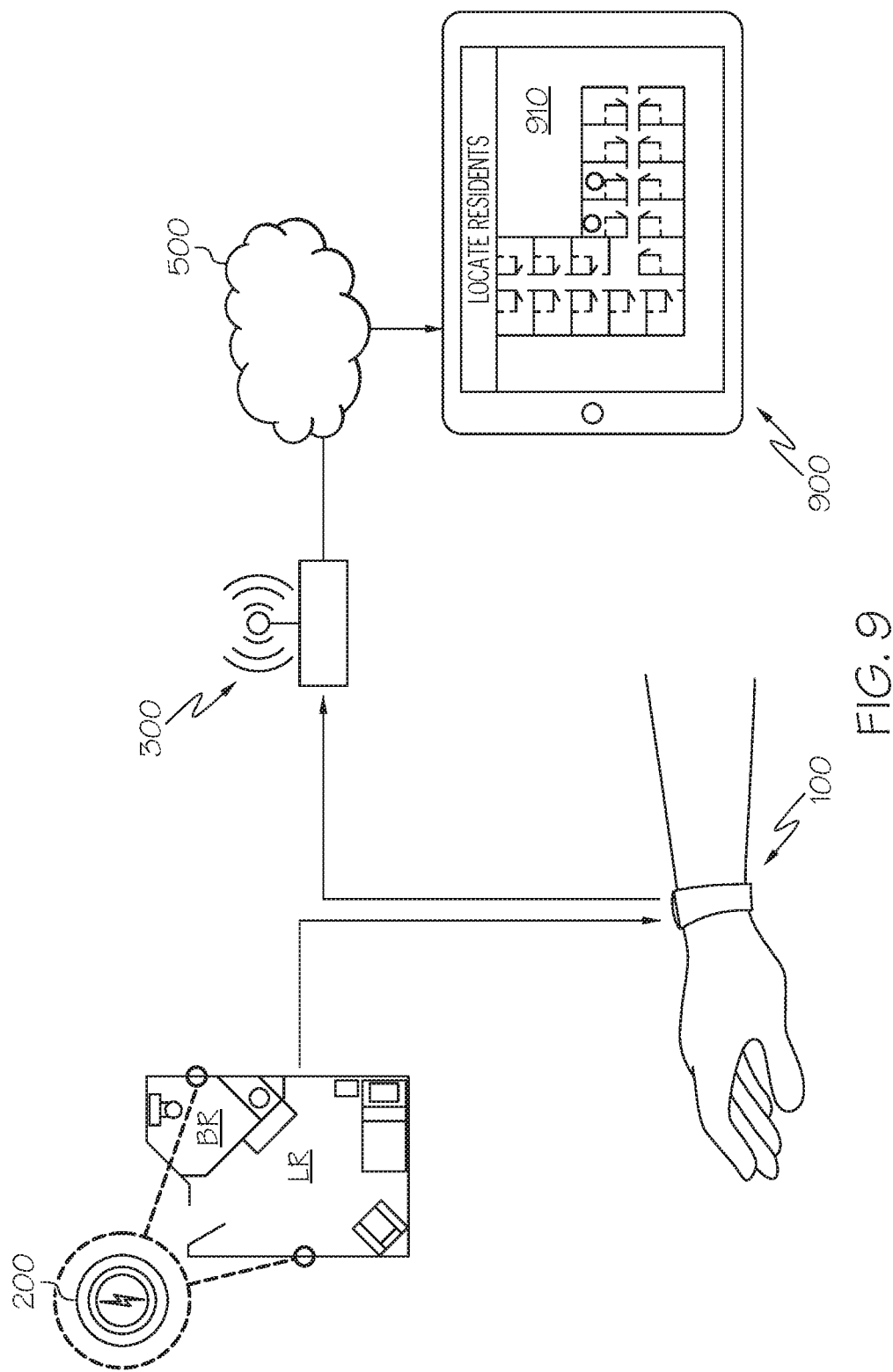

|              | Time |    |    |    |    |    |    |
|--------------|------|----|----|----|----|----|----|
| Room 1       | 15   | 16 | 17 | 18 | 19 | 20 | 21 |
| Bathroom     |      | 1  | 27 | 1  |    |    | 10 |
| Bedroom      |      | 2  | 66 | 32 |    |    | 25 |
| Dining Room  | 23   | 72 | 3  | 12 |    | 18 | 1  |
| Library      |      | 2  | 14 | 6  | 2  | 2  | 11 |

Name: _____  Dates: From _____ to _____

Cohen-Mansfield Agitation Inventory (CMAI) –Short Form

Instructions: For each of the behaviors below, check the rating that indicates the average frequency of occurrence over the last 2 weeks.

Physical/ Aggressive

| | | | | | | | |
|---|---|---|---|---|---|---|---|
| 1. Hitting (including self) | 1 | 2 | 3 | 4 | 5 | 6 | 7 |
| 2. Kicking | 1 | 2 | 3 | 4 | 5 | 6 | 7 |
| 3. Grabbing onto people | 1 | 2 | 3 | 4 | 5 | 6 | 7 |
| 4. Pushing | 1 | 2 | 3 | 4 | 5 | 6 | 7 |
| 5. Throwing things | 1 | 2 | 3 | 4 | 5 | 6 | 7 |
| 6. Biting | 1 | 2 | 3 | 4 | 5 | 6 | 7 |
| 7. Scratching | 1 | 2 | 3 | 4 | 5 | 6 | 7 |
| 8. Spitting | 1 | 2 | 3 | 4 | 5 | 6 | 7 |
| 9. Hurting self or others | 1 | 2 | 3 | 4 | 5 | 6 | 7 |
| 10. Tearing things or destroying property | 1 | 2 | 3 | 4 | 5 | 6 | 7 |
| 11. Making physical sexual advances | 1 | 2 | 3 | 4 | 5 | 6 | 7 |

Physical/ Non-Aggressive

| | | | | | | | |
|---|---|---|---|---|---|---|---|
| 12. Pace, aimless wandering | 1 | 2 | 3 | 4 | 5 | 6 | 7 |
| 13. Inappropriate dress or disrobing | 1 | 2 | 3 | 4 | 5 | 6 | 7 |
| 14. Trying to get to a different place | 1 | 2 | 3 | 4 | 5 | 6 | 7 |
| 15. Intentional falling | 1 | 2 | 3 | 4 | 5 | 6 | 7 |
| 16. Eating/drinking inappropriate substance | 1 | 2 | 3 | 4 | 5 | 6 | 7 |
| 17. Handling things inappropriately | 1 | 2 | 3 | 4 | 5 | 6 | 7 |
| 18. Hiding things | 1 | 2 | 3 | 4 | 5 | 6 | 7 |
| 19. Hoarding things | 1 | 2 | 3 | 4 | 5 | 6 | 7 |
| 20. Performing repetitive mannerisms | 1 | 2 | 3 | 4 | 5 | 6 | 7 |
| 21. General restlessness | 1 | 2 | 3 | 4 | 5 | 6 | 7 |

Verbal/ Aggressive

| | | | | | | | |
|---|---|---|---|---|---|---|---|
| 22. Screaming | 1 | 2 | 3 | 4 | 5 | 6 | 7 |
| 23. Making verbal sexual advances | 1 | 2 | 3 | 4 | 5 | 6 | 7 |
| 24. Cursing or verbal aggression | 1 | 2 | 3 | 4 | 5 | 6 | 7 |

Verbal/ Non-aggressive

| | | | | | | | |
|---|---|---|---|---|---|---|---|
| 25. Repetitive sentences or questions | 1 | 2 | 3 | 4 | 5 | 6 | 7 |
| 26. Strange noises (weird laughter or crying) | 1 | 2 | 3 | 4 | 5 | 6 | 7 |
| 27. Complaining | 1 | 2 | 3 | 4 | 5 | 6 | 7 |
| 28. Negativism | 1 | 2 | 3 | 4 | 5 | 6 | 7 |

Signature: _____  Date: _____

FIG. 13

WEARABLE ELECTRONIC DEVICE AND SYSTEM FOR TRACKING LOCATION AND IDENTIFYING CHANGES IN SALIENT INDICATORS OF PATIENT HEALTH

This application claims the benefit of U.S. Provisional Application Ser. No. 62/709,126 that was filed on Jan. 5, 2018.

The present disclosure relates generally to a wearable electronic device and corresponding system for monitoring one or more of location, environmental, activity and physiological (LEAP) data of a wearer of the device, and more particularly to a wearable electronic device that wirelessly communicates such data in a hybrid mode in order to allow such data to be used to proactively identify salient indicators of changing health of the wearer of the device.

BACKGROUND

Dementia-such as Alzheimer's Disease, Parkinson's Disease and related neurodegenerative conditions-corresponds to a decline in mental ability severe enough to interfere with one's daily life, including the activities of daily living (ADL). Over five million people suffer from dementia in the United States alone, and this number is predicted to increase.

One problem in caring for those suffering from dementia is that they may become confused of their surroundings and tend to wander and get lost. If these individuals are not located in a timely manner, they are at risk of injury. To compound the problem, many of the individuals suffering from dementia will not have the mental acuity to remember their name, place of residence or other identifying indicia even in the event that they do wander and encounter someone trying to assist them.

Another problem in caring for those suffering from dementia is that their decline is often accompanied by corresponding declines in mental or physical health, including the elderly and those experiencing early onset. For example, individuals suffering from dementia may be prone to infections, pneumonia, neuropsychiatric symptoms or other comorbidities.

Furthermore, these declines may not manifest themselves until the accompanying comorbidity is relatively advanced, as the person suffering from the condition may not be able to articulate symptoms that if otherwise identified early enough could be used to provide suitable medical intervention. One form of infection that afflicts the elderly in general and those suffering from dementia in particular is a urinary tract infection (UTI). Unfortunately, information that could indicate the presence of a UTI in such patients is difficult, time-consuming and expensive to acquire, requiring frequent or continuous monitoring by a caregiver of the patient's activities in order to determine if a UTI is imminent or present.

The problems associated with caring for an individual with such mental and physical conditions is exacerbated in situations where the caregiver—whether a doctor, nurse, therapist, home care aide, family member, friend or the like—is not able to be with the individual at all times of the day and night in order to determine whether the individual is symptomatic. For example, if the individual is still living at home by himself or herself, it is possible that extended periods of time may pass before health-related symptoms may be made known to the caregiver. Moreover, caring for persons that are suffering from—or are manifesting early signs of—either or both of mental and physical frailties is particularly difficult in group settings such as nursing homes, assisted living communities or related long-term health care centers, owing at least in part to the small number of staffed caregivers relative to the number of patients residing within.

SUMMARY

The devices, systems and methods of the present disclosure utilize a wearable, wireless application that improves the ability to track the location and associated environment, activity and physiological information of a person that is suffering from—or is manifesting symptoms associated with—dementia, infections, neuropsychiatric problems or other adverse health conditions in order to provide data-informed care insights for family members, nurses, doctors or other caregivers. Such devices, systems and methods may be used to supplant conventional data acquisition components and associated computer systems by promoting the collection of large amounts of data needed for such insights, along with the ability to then disseminate such data to remote locations over large geographic areas for extended periods of time without the need for complicated communications infrastructure. This solves the problem that is particularly acute in conventional data-acquiring device architectures that require significant amounts of electrical energy consumption in order to receive, process and transmit such data that is due at least in part to the seemingly incompatible goals of attaining long battery life and extended transmission range. For example, devices capable of sending data over wide areas (such as that associated with a cellular-based architecture) tend to consume large amounts of power, while devices capable of long battery life (such as those that receive and send using conventional Bluetooth and WiFi-based approaches) tend to have detection and transmission ranges that make them unsuitable for tracking the location of a wearer of the device either indoors within multi-room dwellings or outdoors over large geographic areas. The shortcomings associated with conventional computerized data acquisition approaches are remedied by the specific implementation of the data acquisition, computer structure and communication configuration according to the present disclosure.

According to a first aspect of the present disclosure, a wearable electronic device includes a platform configured to be secured to a person, a source of electric current and a hybrid wireless communication module supported by the platform and receiving electric power from the source of electric current. The hybrid wireless communication module includes various sub-modules made up of a first sub-module to selectively receive location data in the form of a beacon signal, a second sub-module to selectively receive location data in the form of a global navigation satellite system (GNSS) signal and a third sub-module to transmit a low-power wide area network (LPWAN) signal that provides at least location indicia of the wearable electronic device based on acquired location data from at least one of the first and second wireless communication sub-modules. Within the present context, the receipt and transmission of location data is understood to be selective insofar as an incoming signal (in the case of received location data) from a remote source is detectable by the wearable electronic device, or when an outgoing LPWAN signal (in the case of transmitted location data) from the wearable electronic device is detectable by a remote gateway or related receiver. As such, even though the hybrid wireless communication system may in one form involve the periodic or continuous sending or receipt of data, because the corresponding sources or recipients of such data may in certain circumstances be out of range, such receipt and transmission must—out of necessity—be deemed selective. In one form, the beacon signals used to provide the location data associated with the wearable electronic device include those from near-range, private-network infrastructure (i.e., those that do not require cellular or related public-network features in order to send and receive wireless signals) such as a Bluetooth Low Energy (BLE, also referred to as Bluetooth low energy technology) network for indoor operation. In addition, signals used to provide location data to the first wireless communication sub-module may include those from GNSS in order to satisfy outdoor, long-range location needs.

In one form, an embodiment of the first aspect may include numerous sensors, a non-transitory computer readable medium, a processor that is configured to perform a predefined set of operations in response to receiving a corresponding instruction selected from a predefined native instruction set, and a set of machine codes selected from the native instruction set and operated upon by the processor to receive or transmit LEAP data.

In one form, an embodiment of the first aspect may include one or more of the previous forms, in which another machine code determines a distance between the wearable electronic device and a source of the beacon signal.

In one form, an embodiment of the first aspect may include one or more of the previous forms, in which the machine code that transmits at least a portion of the LEAP data through the third wireless communication sub-module is used to convey such data through the third wireless communication sub-module while the data is in substantially unprocessed form.

In one form, an embodiment of the first aspect may include one or more of the previous forms, in which the machine code that transmits at least a portion of the received LEAP data through the third wireless communication sub-module is used to convey such data through the third wireless communication sub-module while the data is in substantially processed form.

In one form, an embodiment of the first aspect may include one or more of the previous forms, in which the machine code that transmits at least a portion of the received LEAP data through the third wireless communication sub-module is used to convey such data through the third wireless communication sub-module while the data is in partially processed form.

In one form, an embodiment of the first aspect may include one or more of the previous forms, in which at least one of the sensors that are configured to detect physiological data includes at least one sensor selected from the group consisting of a heart rate sensor, a breathing rate sensor, a temperature sensor, a respiration sensor, a pulse oximetry sensor, a respiratory rate sensor, an oxygen saturation sensor, an electrocardiogram sensor, a cardiac output index sensor, a systematic pressure sensor, a systematic systolic arterial pressure sensor; a systematic diastolic arterial pressure sensor; a systematic mean arterial pressure sensor, a central venous pressure sensor, a pulmonary pressure sensor, a pulmonary systolic arterial pressure sensor, a pulmonary diastolic arterial pressure sensor, a pulmonary mean arterial pressure sensor and a smell sensor.

In one form, an embodiment of the first aspect may include one or more of the previous forms, in which at least one of the sensors that are configured to detect activity data comprises at least one sensor selected from the group consisting of an accelerometer, a gyroscope, a magnetometer, an altimeter, a motion detector and an inertial measurement unit.

In one form, an embodiment of the first aspect may include one or more of the previous forms, wherein at least one of the sensors that are configured to detect environmental data includes at least one sensor selected from the group consisting of an ambient temperature sensor, an ambient pressure sensor, an ambient humidity sensor, an ambient light sensor, a motion sensor, a carbon monoxide sensor, a carbon dioxide sensor, a smoke detector and a microphone.

In one form, an embodiment of the first aspect may include one or more of the previous forms, further including a nurse call button that is supported by the platform and signally cooperative with the third wireless communication sub-module such that upon activation of the nurse call button, at least one signal is transmitted from the wearable electronic device over the third wireless communication sub-module.

In one form, an embodiment of the first aspect may include one or more of the previous forms, in which another machine code maintains the second wireless communication sub-module in a sleep mode until detection of either a waking event or a set period of time.

In one form, an embodiment of the first aspect may include one or more of the previous forms, wherein the waking event includes detecting that the wearable electronic device is outside of a range of detection of the first wireless communication sub-module.

In one form, an embodiment of the first aspect may include one or more of the previous forms, in which another machine code controls the transmission of data from at least two forms of the received wearable electronic device LEAP data through the third wireless communication sub-module.

In one form, an embodiment of the first aspect may include one or more of the previous forms, in which wherein the hybrid wireless communication module does not include a cellular wireless communication sub-module.

In one form, an embodiment of the first aspect may include one or more of the previous forms, wherein the platform is selected from the group consisting of a wrist-worn band, an ankle-worn band, an article of clothing (such as outerwear, underwear, a belt, a shoe or the like), a bandage, a pair of eyeglasses, a necklace or pendant, a clothing-affixable pin, a clothing-affixable patch or a subcutaneous implant.

In one form, an embodiment of the first aspect may include one or more of the previous forms, wherein the first wireless communication sub-module selectively receives location data in the form of a BLE signal.

According to a second aspect of the present disclosure, a system for tracking the location of an individual is disclosed. The system includes a wearable electronic device that includes a platform, and one or more of a battery, solar cell, capacitive device or other source of electric current, as well as a hybrid wireless communication module made up of at least first, second and third wireless communication sub-modules. The system additionally includes a gateway in wireless signal communication with the third wireless communication sub-module. The platform is configured to be worn or otherwise secured to the individual, while the hybrid wireless communication module is structurally supported by the platform and can receive electric power from the source of electric current. The first wireless communication sub-module selectively receives location data in the form of a beacon signal, the second wireless communication sub-module selectively receives location data in the form of a GNSS signal, while the third wireless communication sub-module transmits an LPWAN signal that provides location indicia of the wearable electronic device based on acquired location data from at least one of the first and second wireless communication sub-modules.

In one form, an embodiment of the second aspect may include having the wearable electronic device and the gateway cooperate with one another as part of a star (rather than mesh) topology network.

In one form, an embodiment of the second aspect may include one or more of the previous forms, and may further include a backhaul server in signal communication with the gateway.

In one form, an embodiment of the second aspect may include one or more of the previous forms, and may be configured such that one or both of the wearable electronic device and the backhaul server include a non-transitory computer readable medium, a processor and a set of machine codes selected from a native instruction set and operated upon by the processor. In addition, at least a portion of the set of machine codes are stored in the respective non-transitory computer readable medium or mediums. Data structures are made to correspond to various nodes of a machine learning model, such as the input, intermediate and output nodes of a neural network or the input and output nodes of a K-means clustering approach, and in one form may be implemented in the memory of the respective computer readable medium or mediums. Such data structures may be operated upon by a search algorithm implemented in machine codes for the respective one of the wearable electronic device processor or backhaul server processor.

In one form, an embodiment of the second aspect may include one or more of the previous forms, and may further include at least one beacon to communicate with the first wireless communication sub-module.

According to a third aspect of the present disclosure, a system for analyzing the health condition of an individual is disclosed. The system includes a wearable electronic device made up of a platform configured to be worn or otherwise secured to a person, a source of electric current and a hybrid wireless communication module structurally supported by the platform and receiving electric power from the battery. The hybrid wireless communication system includes a first wireless communication sub-module that during its operation selectively receives location data in the form of a beacon signal, a second wireless communication sub-module that during its operation selectively receives location data in the form of a GNSS signal, and a third wireless communication sub-module that during its operation transmits an LPWAN-based signal that provides location indicia of the wearable electronic device based on acquired location data from at least one of the first and second wireless communication sub-modules. Numerous sensors are supported by the platform such that during operation, at least one sensor detects a respective one of environmental data, activity data and physiological data from an individual to whom the wearable electronic device is secured. Additional components of the system include a gateway and a backhaul server. The gateway is in wireless signal communication with the third wireless communication sub-module, while the backhaul server is in signal communication with the gateway. Furthermore, the wearable electronic device and the backhaul server have at least a non-transitory computer readable medium, processor and set of machine codes selected from the native instruction set and capable of being operated upon by a respective one the processors in response to at least a portion of the set of machine codes that are stored in one, the other or both of the non-transitory computer readable mediums. As such, at least one of the backhaul server and the wearable electronic device has a machine code to execute a machine learning model to classify the health condition of the individual based at least in part on at least a portion of the LEAP data.

In one form, an embodiment of the third aspect may include having the machine learning model be a neural network that includes numerous input nodes each of which includes a memory location for storing an input value that corresponds to a portion of a respective one of the acquired LEAP data, numerous hidden nodes each of which is connected to at least one of the plurality of input nodes and includes computational instructions, implemented in machine codes of the respective processor, for computing a plurality of output values, respectively, and numerous output nodes each of which includes a memory location for storing the output value produced by the machine learning classification model.

In one form, an embodiment of the third aspect may include one or more of the previous forms, wherein at least a portion of the set of machine codes that are on at least one of the non-transitory computer readable medium of the wearable electronic device and the non-transitory computer readable medium of the backhaul server and that are operated upon by the respective processor further includes a machine code that compares at least a portion of the LEAP data to baseline data that forms a data structure that is stored on one or both of the non-transitory computer readable medium of the wearable electronic device and the non-transitory computer readable medium of the backhaul server.

In one form, an embodiment of the third aspect may include one or more of the previous forms, wherein the baseline data is selected from the group consisting of baseline data of the individual and baseline data of a demographic group representative of the individual.

In one form, an embodiment of the third aspect may include one or more of the previous forms, wherein at least a portion of the set of machine codes that are on one or both of the non-transitory computer readable medium of the wearable electronic device and the non-transitory computer readable medium of the backhaul server and that are operated upon by the respective processor further comprises a machine code to provide clinical decision support through the machine learning classification model.

In one form, an embodiment of the third aspect may include one or more of the previous forms, further including a machine code to provide a diagnosis through the machine learning classification model.

In one form, an embodiment of the third aspect may include one or more of the previous forms, further including a machine code to execute an ADL analysis of the individual using at least a portion part of the LEAP data.

In one form, an embodiment of the third aspect may include one or more of the previous forms, further including a machine code to send an alert through the third wireless communication sub-module when the transmitted location data indicates that an individual is situated outside a predetermined area.

In one form, an embodiment of the third aspect may include one or more of the previous forms, further including machine code to train the machine learning classification model, the machine code to train the machine learning classification model comprising (a) a machine code to cleanse at least a portion of the LEAP data, (b) a machine code to extract at least one feature vector from the cleansed data, and (c) a machine code to execute at least one algorithm based on the one or more feature vectors a machine code to execute at least one algorithm based on the at least one feature vector such that upon execution of the at least one algorithm, the machine learning classification model is configured provide a predictive analytical output of the health condition to a caregiver.

In one form, an embodiment of the third aspect may include one or more of the previous forms, wherein at least a portion of the machine code to train the machine learning model includes a machine code to segment at least a portion of at least one of the LEAP data into a training data set, a validation data set and a testing data set, as well as a machine code that refines the machine learning model based on the execution of the at least one algorithm on the training, validation and testing data sets.

In one form, an embodiment of the third aspect may include one or more of the previous forms, wherein the machine code to train the machine learning classification model is cooperative with the machine learning classification model through (a) a machine code that analyzes at least a portion of at least one of the location data, environmental data, activity data and physiological data once the machine learning classification model has been trained by the at least one algorithm, and (b) a machine code that causes at least one of the wearable electronic device and the backhaul server to output the analyzed data (such as to at least one of memory, a display, an audio alert or other use by a caregiver).

According to a fourth aspect of the present disclosure, a method of monitoring an individual with a wearable electronic device is disclosed. The method includes acquiring, using the wearable electronic device, location data from at least one of BLE location data and GNSS location data, and wirelessly transmitting the location data from the wearable electronic device to a wireless LPWAN receiver using a star topology network.

In one form, an embodiment of the fourth aspect may include acquiring, with numerous sensors that are formed as part of the wearable electronic device, at least one of environmental data, activity data and physiological data, and wirelessly transmitting such data from the wearable electronic device to the wireless LPWAN receiver.

In one form, an embodiment of the fourth aspect may include one or more of the previous forms, wherein the wirelessly transmitting of the LEAP data is performed using a hybrid wireless communication module that forms a part of the wireless electronic device.

In one form, an embodiment of the fourth aspect may include one or more of the previous forms, further including determining, using a machine learning model, a health condition of the individual, as well as providing an output of the health condition. The machine learning model is based at least in part on at least a portion of the LEAP data.

In one form, an embodiment of the fourth aspect may include one or more of the previous forms, wherein the determining includes operating at least a non-transitory computer readable medium, a processor and a set of machine codes selected from a native instruction set such that at least a portion of the set of machine codes are stored in the non-transitory computer readable medium. The set of machine codes includes a machine code that cleanses at least a portion of the acquired LEAP data, a machine code that extracts at least one feature vector from the cleansed data, a machine code that trains at least one machine learning algorithm using the one or more feature vectors, a machine code that analyzes at least a portion of at least one of the LEAP data once the machine learning model has been trained by the at least one algorithm, and a machine code that causes the analyzed data to be output a caregiver.

In one form, an embodiment of the fourth aspect may include one or more of the previous forms, wherein the machine code to train the machine learning classification model includes a machine code to segment at least a portion of at least one of the LEAP data into a training data set for use by the at least one machine learning algorithm, a machine code that segments at least a portion of at least one of the LEAP data into a validation data set for use by the at least one machine learning algorithm, a machine code that segments at least a portion of at least one of the LEAP data into a testing data set for use by the at least one machine learning algorithm, and a machine code that refines the machine learning classification model based on the execution of the at least one machine learning algorithm on the training, validation and testing data sets.

In one form, an embodiment of the fourth aspect may include one or more of the previous forms, wherein the machine learning model is executed on at least one of the wearable electronic device, a backhaul server and cloud.

In one form, an embodiment of the fourth aspect may include one or more of the previous forms, wherein the health condition is an adverse health condition selected from the group consisting of an infection and a neuropsychiatric condition.

In one form, an embodiment of the fourth aspect may include one or more of the previous forms, wherein the infection comprises a UTI such that at least a portion of the set of machine codes that are on at least one of the non-transitory computer readable medium of the wearable electronic device and the non-transitory computer readable medium of the backhaul server and that are operated upon by the respective processor further includes a machine code that executes at least a portion of a McGeer Criteria analysis based on at least a portion of the LEAP data.

In one form, an embodiment of the fourth aspect may include one or more of the previous forms, wherein the machine code that executes at least a portion of a McGeer Criteria analysis determines at least one of (a) new or marked increase in urination urgency, (b) new or marked increase in urination frequency, (c) new or marked increase in incontinence and (d) change in functional status, based at least in part on at least a portion of the LEAP data.

In one form, an embodiment of the fourth aspect may include one or more of the previous forms, wherein the infection comprises a pneumonia such that at least a portion of the set of machine codes that are on at least one of the non-transitory computer readable medium of the wearable electronic device and the non-transitory computer readable medium of the backhaul server and that are operated upon by the respective processor further includes a machine code that executes a pneumonia analysis based at least in part on at least a portion of the LEAP data.

In one form, an embodiment of the fourth aspect may include one or more of the previous forms, wherein the machine code to execute at least a portion of a pneumonia analysis comprises machine code to execute at least a portion of at least one of a PSI score, CURB-65 score, SMART-COP score and an A-DROP score based on at least one of the location data and activity data in conjunction with the physiological data that comprises at least one of respiratory data and heat rate data. These acronyms will be further defined in more detail later in this disclosure, where the pneumonia analysis may further include one or more factors from each of these scores.

In one form, an embodiment of the fourth aspect may include one or more of the previous forms, wherein the infection comprises influenza such that at least a portion of the set of machine codes that are on at least one of the non-transitory computer readable medium of the wearable electronic device and the non-transitory computer readable medium of the backhaul server and that are operated upon by the respective processor further comprises a machine code to execute an influenza analysis based on at least a portion of at least one of the location data, environmental data, activity data and physiological data.

In one form, an embodiment of the fourth aspect may include one or more of the previous forms, wherein the machine code to execute at least a portion of an influenza analysis comprises machine code to execute at least a portion of an influenza score based on at least one of the location data and activity data in conjunction with the physiological data that comprises at least one of temperature data, respiratory data and heat rate data.

In one form, an embodiment of the fourth aspect may include one or more of the previous forms, wherein the neuropsychiatric condition includes agitation such that at least a portion of the set of machine codes that are on at least one of the non-transitory computer readable medium of the wearable electronic device and the non-transitory computer readable medium of the backhaul server and that are operated upon by the respective processor further comprises a machine code to execute an agitation analysis based on at least a portion of at least one of the location data, environmental data, activity data and physiological data.

In one form, an embodiment of the fourth aspect may include one or more of the previous forms, wherein the machine code to execute an agitation analysis comprises machine code to determine whether the individual is pacing.

In one form, an embodiment of the fourth aspect may include one or more of the previous forms, wherein the neuropsychiatric condition includes cognitive impairment such that at least a portion of the set of machine codes that are on at least one of the non-transitory computer readable medium of the wearable electronic device and the non-transitory computer readable medium of the backhaul server and that are operated upon by the respective processor further comprises a machine code to execute a cognitive impairment analysis based on at least a portion of at least one of the location data, environmental data, activity data and physiological data.

In one form, an embodiment of the fourth aspect may include one or more of the previous forms, wherein the machine code to execute at least a portion of a cognitive impairment condition analysis comprises machine code to determine at least one of a stage of dementia selected from the group consisting of at least one of (a) early stage dementia, (b) moderate stage dementia, (c) late stage dementia and (d) terminal stage dementia.

In one form, an embodiment of the fourth aspect may include one or more of the previous forms, wherein indicia of the at least one stages of dementia is determined by at least one of wherein indicia of the early stage dementia is selected from the group consisting of lack of initiation of activities, confusion about places and times, inordinate amount of loss of personal items, withdrawn personality, negative change in at least one activities of daily living event or instrumental activities of daily living event, increase in irritability; indicia of the moderate stage dementia is selected from the group consisting of increase in suspicion of others, increase in an amount of full-time supervision, increased need of assistance with mobility, heightened problems with reading, writing and performing calculations, making up stories in order to fill in the increasingly frequent gaps in memory, loss of impulse control, emotional lability, restlessness, sloppiness, outbursts of anger, frequent sleeping, nighttime wandering, incontinence of urine, childlike behavior, paranoia, diminished social activity, increased frequency of falls, increased frequency of falls in attempting to transfer from one place or position to another; indicia of the late stage dementia is selected from the group consisting of complete lack of ambulatory activity, having poor safety awareness, increased rate of mental decline after an acute hospitalization event, forgetting when a last meal was eaten, little capacity for self-care, requirement for help with all bathing, dressing and eating activities, loss of bowel control, prone to making verbal utterances not related to pain, increased amount of sleeping, difficulty in communicating with words, difficulty with liquids, coughing after taking a drink, lack of appetite and weight loss even with a good diet; and indicia of the terminal stage dementia is selected from the group consisting of the patient experiencing recurrent aspirations even with thick liquids, pressure ulcers even with frequent turnings and related good quality of care, as well as unawareness of external stimuli.

In one form, an embodiment of the fourth aspect may include one or more of the previous forms, wherein the neuropsychiatric condition is analyzed through a regression-based machine learning model.

According to a fifth aspect of the present disclosure, a method of using a machine learning model to evaluate a health condition of an individual is disclosed. The method includes acquiring, using a wearable electronic device, location data from one or both of BLE location data and GNSS location data and acquiring, with a plurality of sensors that are formed as part of the wearable electronic device, at least one of environmental data, activity data and physiological data. The method also includes wirelessly transmitting at least a portion of the LEAP data from the wearable electronic device to a wireless low power wide area network receiver using a star topology network, as well as executing a machine learning model based at least in part on at least a portion of the LEAP data. The executing takes place using a non-transitory computer readable medium, a processor and a set of machine codes within a predefined native instruction set. In this way, a predefined set of operations is performed by the processor in response to receiving a corresponding instruction selected from the set of machine codes that includes a machine code that analyzes at least a portion of at least one of the LEAP data once the machine learning model has been trained by at least one algorithm, and a machine code that causes the analyzed data to be output to a caregiver.

In one form, an embodiment of the fifth aspect may include one or more of the previous forms, wherein the machine learning model is trained by the at least one machine learning algorithm that includes a machine code that cleanses at least a portion of at least one of the LEAP data, a machine code that extracts at least one feature vector from the cleansed data, and a machine code that executes the at least one machine learning algorithm using the at least one feature vector.

In one form, an embodiment of the fifth aspect may include one or more of the previous forms, wherein the machine learning model comprises an unsupervised approach that comprises K-means clustering.

In one form, an embodiment of the fifth aspect may include one or more of the previous forms, wherein the machine learning model comprises an unsupervised approach that comprises a neural network.

In one form, an embodiment of the fifth aspect may include one or more of the previous forms, wherein the machine learning model comprises a hybrid approach that comprises a supervised approach in cooperation with an unsupervised approach.

In one form, an embodiment of the fifth aspect may include one or more of the previous forms, wherein the supervised approach comprises a neural network and the unsupervised approach comprises K-means clustering.

According to a sixth aspect of the present disclosure, a method of performing cognitive assessment of an individual is disclosed. The method includes receiving data from a plurality of sensors of a wearable electronic device that is secured to the individual, the data corresponding to at least a portion of LEAP data, converting such data into a labeled feature vector that describes at least one attribute of the data, comparing the labeled feature vector to baseline data using a machine learning model, determining a cognitive status of the individual based on an output from the machine learning algorithm, and conveying the cognitive status to a caregiver.

In one form, an embodiment of the sixth aspect may include performing an ADL analysis that uses at least a portion of the LEAP data as input.

According to a seventh aspect of the present disclosure, a non-transitory computer readable medium is disclosed. The medium has executable instructions thereon that when executed on a machine cause the machine to receive location data from at least one of a beacon signal and a GNSS signal through a hybrid wireless communication module that forms at least a part of a wearable electronic device, and transmit the location data as an LPWAN signal through the wireless communication module.

In one form, an embodiment of the seventh aspect may further include causing the machine to acquire sensed activity, environmental and physiological data from at least one sensor that forms at least a part of the wearable electronic device.

In one form, an embodiment of the seventh aspect may include one or more of the previous forms, wherein the executable instructions further causes the machine to use at least a portion of the LEAP data in order to determine whether an individual associated with the wearable electronic device is at an increased risk of developing an adverse health condition.

In one form, an embodiment of the seventh aspect may include one or more of the previous forms, wherein the executable instructions further causes the execution of a machine learning model that (a) is trained using at least at least one training algorithm along with at least a portion of the LEAP data and (b) analyzes at least a portion of the LEAP data once such machine learning classification algorithm has been trained to output indicia of such increased risk of developing an adverse health condition based on results generated by the machine learning model.

In one form, an embodiment of the seventh aspect may include one or more of the previous forms, wherein the indicia of such increased risk of developing an adverse health condition is based at least in part on a comparison of at least a portion of the LEAP data to baseline data.

According to an eighth aspect of the present disclosure, a wearable electronic device for tracking a patient is disclosed. The device includes a processor, a power source electrically connected to the processor, a first wireless communication sub-module with a BLE chip communicatively connected to the processor and configured to receive BLE location information, a second wireless communication sub-module with a GNSS chip communicatively connected to the processor and configured to receive GNSS location information, and a third wireless communication sub-module with an LPWAN chip communicatively connected to the processor. The third wireless communication sub-module provides location indicia of the device based on location information from at least one of the first and second wireless communication sub-modules.

According to another aspect of the present disclosure, a computerized method of using a wearable electronic device that includes determining whether a patient is at risk of developing a UTI is disclosed. According to still another aspect of the present disclosure, a computerized method of determining whether a patient is at risk of developing an adverse health condition based on an ADL determination is disclosed. According to yet another aspect of the present disclosure, a computerized method of determining whether a patient is demonstrating increased agitation is disclosed. According to yet another aspect of the present disclosure, any of the previous aspects may include wirelessly transmitting the data acquired from the wearable electronic device to a wireless LPWAN receiver (such as the gateway) using the star (rather than mesh) topology network. According to still another aspect of the present disclosure, a radio signal strength indication (RSSI)-based transmission protocol from one or more beacons to the wearable electronic device may be replaced with another direction-finding protocol such as those based on angle of arrival (AOA), angle of departure (AOD) or related approach to deliver real-time location functionality. According to still another aspect of the present disclosure, one or more machine learning models such as neural networks, K-means clustering or related approaches may be used to analyze the LEAP data acquired by the wearable electronic device. It will be appreciated that the number of aspects and their respective use of the components and configurations is not limited to those enumerated above, and that others will be apparent from the totality of the present disclosure.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 2I depicts a perspective view of an alternate embodiment of the wearable electronic device where it is formed in a bandage-like flexible, hybrid manner for direct affixing to a wearer's skin or article of clothing according to one or more embodiments shown or described herein;

FIG. 3C depicts a BLE an eleven byte beacon data format for some of the messages of FIGS. 3A and 3B;

FIG. 3D depicts an eleven byte GNSS data format for some of the messages of FIGS. 3A and 3B;

FIG. 3E depicts an eleven byte battery data format for some of the messages of FIGS. 3A and 3B;

FIG. 3F depicts an eleven byte nurse call button data format for some of the messages of FIGS. 3A and 3B;

FIG. 3G depicts an eleven byte nurse response data format for some of the messages of FIGS. 3A and 3B;

FIG. 3H depicts an eleven byte band worn data format for some of the messages of FIGS. 3A and 3B;

FIG. 3I depicts an eleven byte band removed data format for some of the messages of FIGS. 3A and 3B;

FIG. 3J depicts an eleven byte no movement data format for some of the messages of FIGS. 3A and 3B;

FIG. 3K depicts an eleven byte movement data format for some of the messages of FIGS. 3A and 3B;

FIG. 7 depicts a program structure in the form of a neural network according to one or more embodiments shown or described herein;

FIG. 8 depicts a data structure in the form of a portion of a sample patient ADL documentation chart that may be automated through data gathered by the wearable electronic device and system of FIG. 1 according to one or more embodiments shown or described herein;

FIG. 9 depicts the wearable electronic device and apportion of the system of FIG. 1 and their wireless connectivity through the cloud to ascertain the location and activity of a patient within a multi-patient dwelling, as well as to provide patient information in display form to a remote computing device according to one or more embodiments shown or described herein;

FIG. 13 depicts a data structure in the form of an inventory chart to correlate the LEAP data gathered by the wearable electronic device and system of FIG. 1 to indicia of patient agitation according to one or more embodiments shown or described herein;

Figure 1:
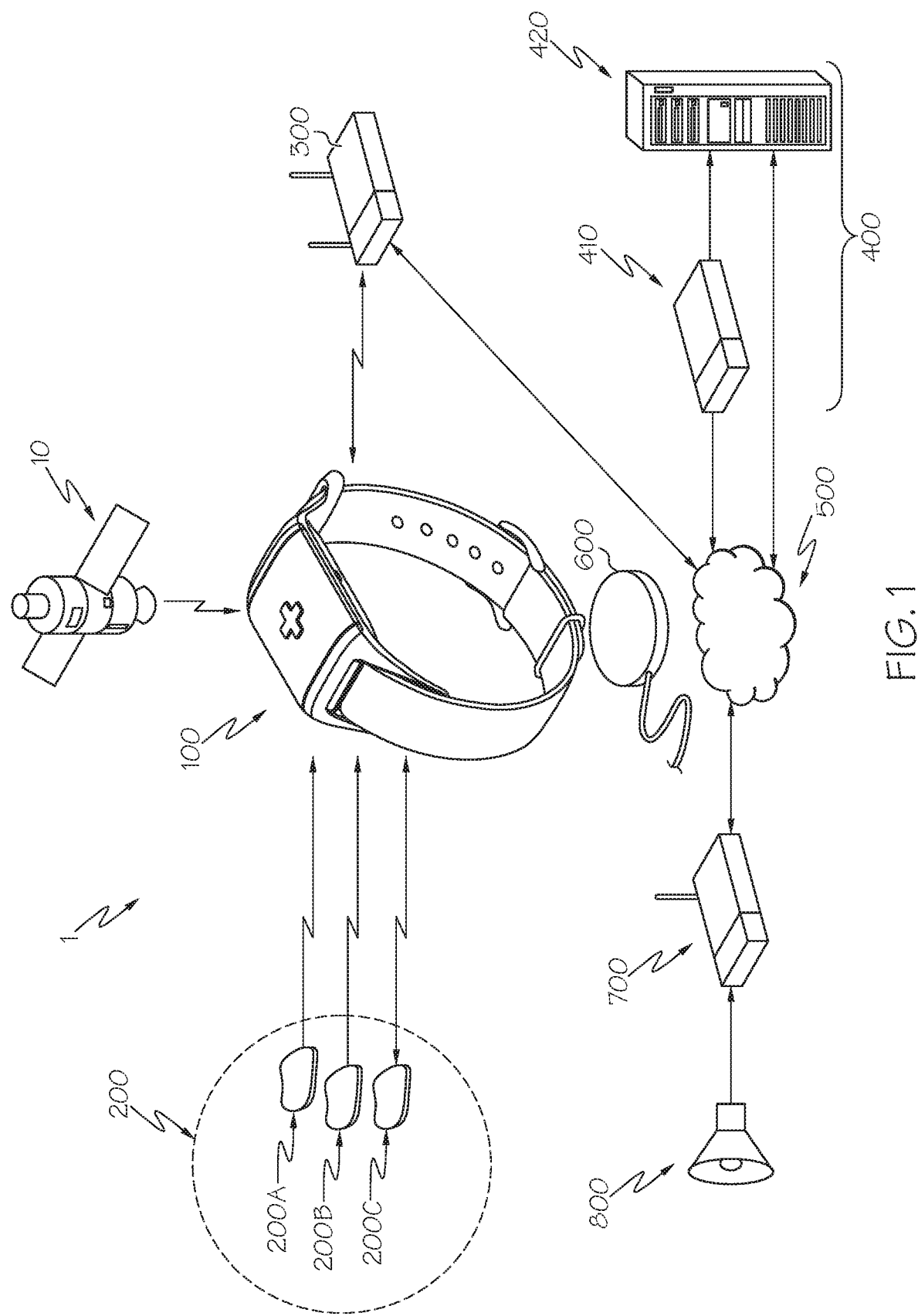
FIG. 1 depicts a simplified view of wireless signal connectivity between a wearable electronic device and other parts of a patient monitoring system according to one or more embodiments shown or described herein.

It will be appreciated that for the sake of clarity, elements depicted in the drawings are not necessarily to scale, and that certain elements may be omitted from some of the drawings. It will further be appreciated that certain reference numerals may be repeated in different figures to indicate corresponding or analogous elements.

DETAILED DESCRIPTION

The disclosed devices, systems and methods allow for real-time location tracking, in addition to the utilization of a smart internet of things (IoT) configuration to provide data-informed care insights for indicators of potential health complications. Such an approach as disclosed herein is particularly beneficial in medical or health conditions that have traditionally been difficult to diagnose, such as Alzheimer's Disease and other forms of dementia. By utilizing a hybrid wireless communication module, the wearable electronic device has the ability to receive both a GNSS signal and a BLE signal, as well as the ability to transmit an LPWAN signal (in general) and a Long Range Wide Area Network (LoRaWAN™) signal (in particular) to provide data that may be used by the system to not only provide indicia of a patient's current location, but also through the recognition and analysis of one or more of patient environmental, activity and physiological data (possibly in conjunction with the location data) to help a caregiver to identify changes in one or more salient indicators of the health of that patient, including whether such changes may necessitate caregiver intervention. Moreover, having the wearable electronic device be affixed or otherwise secured to a wearer allows for continuous monitoring, as well as the ability to be scaled-up to allow the monitoring and analysis of large groups of individual wearers. Furthermore, such an architecture permits such monitoring and analysis to take place in actual user environments, such as a home, assisted living community or the like. In addition, the temporal nature of the collected data-coupled with using various data-gathering modalities for such data collection and other determination- allows increased contextual insight into a wearer's moment-to-moment activities, which in turn promotes greater accuracy in the ability to analyze the health of the person wearing the device. Furthermore, the automated nature of the data being collected by the wearable electronic device alleviates human-error concerns associated with required user input of a particular event such as activity and event recording, pressing a daily in-room "check-in" style button or the like. As will be discussed in more detail later, this may be particularly beneficial in avoiding the inclusion of erroneous data into a machine learning or cloud analytics model where the presence of false positives or false negatives from such erroneous data may be both hard to identify and destructive of the accuracy of the data corresponding to the person being monitored.

In addition to the wearable electronic device, the present disclosure teaches a system that may track and monitor the device, log the collected data, perform analysis on the collected data and generate alerts. The data and alerts may be accessed through a user interface that can be displayed on a remote computing device or other suitable device with internet or cellular access. Another component of the system may be that a specified predetermined area in which the patient can move freely can be set by placing reference point or sentry beacons; in one form, such predetermined area may be set up as a geofence or the like so that if the patient wanders outside the predetermined area, a signal is sent to the central processing unit, which then generates a signal or alarm to notify one or more of the patient, family members, medical professions and other caregivers.

I. Configuration Overview

Referring first to FIG. 1, an overview of the patient monitoring system 1 architecture is shown. In one form, the system 1 includes a wearable electronic device 100, one or more BLE beacons 200, a gateway 300 and backhaul server 400 the last of which may function as a carrier-grade data network. In another form, the wearable electronic device 100 may be operated at least partially independent of the system 1 in order to acquire-among other types of data-location data from a GNSS 10 and the BLE beacons 200. Within the present disclosure, GNSS is the standard generic term for satellite navigation systems that provide autonomous geo-spatial positioning with global coverage and is meant to includes specific embodiments such as global positioning system (GPS), the Russian global navigation satellite system (GLONASS), Galileo, Beidou and other regional systems. In this latter form, at least some of the data acquired by the wearable electronic device 100 may be operated upon locally by the wearable electronic device 100 itself, while other operations (such as those requiring larger amount of processing capability) may be performed remotely within the backhaul server 400 or other component within system 1. Either of these forms—as well as a hybrid of both—are deemed to be within the scope of the present disclosure. As such, some or all of the data being acquired, as well as operations performed on such data for the purpose of tracking the location of or analyzing the health condition of an individual associated with the wearable electronic device 100 may be optimized depending on the need. Within the present disclosure, an individual, patient or other person is deemed to be "associated with" the wearable electronic device 100 when such device is worn, affixed or otherwise coupled to the individual such that data acquired from such individual or pertaining to such individual's immediate environment may be used to help ascertain or determine one or more of location and health condition information for such individual. Additionally within the present disclosure, the terms "location data", "location information" and their variants are meant to encompass information that establishes (either directly or through additional calculations) absolute or relative location or position of the wearable electronic device 100 based on signals it receives from RSSI or GNSS sources such as those discussed herein. Thus, for example, the data contained within an emitted RSSI signal may be translated into a relative location between the source of such signal and the wearable electronic device 100, in which case such emitted RSSI data is deemed to be location data.

The flexible deployment of the wearable electronic device 100 and its wireless connectivity to various other components within system 1 may in one form enable edge computing (also referred to as fog computing, in either event, where the wearable electronic device 100 functions as an edge device where some or all of the sensors 121 are deployed) that would allow the wearable electronic device 100 to function as an IoT device as part of a low-cost, highly-adaptable private network, especially allowing increased interaction with a cloud 500 or related data acquisition or analysis equipment through the gateway 300. In one form, single chip packages or chipsets may be used to provide edge computing capability; an example of such an approach may be found in Microsoft's Azure Sphere or Amazon's AWS. The modular nature of the wearable electronic device 100 allows it to function as an IoT device with hardware and software features to manage the flow of LEAP data, as well as provide—or at least help to provide—analytics of the acquired LEAP data. In one form of such edge computing, the wearable electronic device 100 may carry out a significant portion of the processing, storage and communication functions at a local level. In another form, the gateway 300 may possess at least some of the logic capability (such as through its own logic device 173 and associated circuitry and infrastructure) to be able to make decisions about the LEAP data, as well as send alerts or data to other equipment either within system 1 or beyond. In one form, the gateway 300 could also act as a mini server and make all data decisions on its own to then send the data to external devices such as a phone or web browser, thereby forming another type of edge computing configuration. Additional improvements in data and connection security may also be realized with such edge-style interoperability, including the added security of having system redundancy in situations where the internet or cloud 500 is inoperable. Such edge computing is beneficial in that can leverage the increased computational and storage capabilities that are associated with cloud computing to the physical location of the wearable electronic device 100, irrespective of its location within the network. Such a configuration in turn helps promote reduced network latency through a combination of real-time computing and localized resource pooling, as well as providing increases in user data security with on-device storage of at least certain portions of the acquired data. Significantly, because the size of the data packages being sent from the wearable electronic device 100 to the gateway 300, backhaul server 400 and cloud 500 is relatively small, communication-based bandwidth problems may be avoided.

In situations where more than one of the BLE beacons 200 are used in a given patient environment, such BLE beacons 200 may exhibit one or both of structural and functional differences in the form of room beacons 200A, elopement beacons 200B and nurse ID beacons 200C. For example, the room beacon (also referred to as a reference point beacon or navigation beacon) 200A is the first type of BLE beacon 200 and may be used in a transmit-only mode of operation to broadcast a unique identification that can be correlated to a particular fixed location (such as a particular room within a multi-room dwelling) to the wearable electronic device 100. The second type of BLE beacon 200 is the elopement beacon (also referred to as a sentry beacon) 200B that may also be used in a transmit-only mode of operation to broadcast that a person equipped with the wearable electronic device 100 is attempting to leave a permissible zone (such as by exiting an external door) in a manner relatively similar to an RFID device. The third type of BLE beacon 200 is the nurse ID beacon (also referred to as a personnel beacon, such as in the form of a card beacon or the like) 200C that is used to transmit to the server 400 through the gateway 300 that a particular caregiver who is uniquely identified with each nurse ID beacon 200C is in a position to either respond to a particular patient request, measure touchpoints between patient visits (as an indicator of nurse/patient interactions) or has complied with routine patient visits commensurate with of his or her job description or related employee obligations.

In one form, the nurse ID beacon 200C may be integrated into a mobile telephone to take advantage of the telephone's Bluetooth or other communication capability so that in such form the nurse ID beacon 200C might also possess (in a manner unlike the both the room beacons 200A and elopement beacons 200B) both transmit and receive capabilities.

In one form, some of these types of beacons 200 that differ based on their function may still exhibit some similarity in their structure. For example, the room beacon 200A and the elopement beacon 200B may be made from the same hardware or structure (including battery, radio and processor), while differences in their function may be based on adjustments made to certain operational attributes such as the scan rate or power output (which in turn helps the wearable electronic device 100 determine which beacon is closer). Likewise, the nurse ID beacon 200C—in addition to possibly having a different form factor—may have its scan rate or power preset to different (for example, lower) levels. In one form, the nurse ID beacon 200C may have a 100 millisecond scan rate and a power level of −20 dBm, thereby ensuring that the nurse or other caregiver associated with a particular nurse ID beacon 200C is physically close to the patient that sent the nurse call request. This in turn increases the likelihood that the nurse or caregiver actually responded to the request for assistance.

In one form for a location where multiple patients may be equipped with the wearable electronic device 100, the transmission between the various BLE beacons 200 to the various wearable electronic devices 100 may be arranged in a mesh topology network that differs from the star topology of the transmission that takes place from the various wearable electronic devices 100 to the one or more gateways 300. In addition, various form factors for BLE beacon 200 may be used. In one form, the BLE beacon 200 may be lithium-chip battery powered, such as that associated with the disk-shaped variant, the coin variant and the credit card-shaped variant. In another form, the BLE beacon 200 may take its power from an alternating-current source such as that of the wall outlet-mounted or computer expansion slot-mounted variants either of which may include a high definition multimedia interface (HDMI) or universal serial bus (USB) slot or mount. Irrespective of the shape or power source, BLE beacon 200 is configured to transmit an RF signal at various frequencies such as 915 MHz (US), 868 MHz (Europe) and 430 MHz (Asia). In one form, the BLE beacon 200 could be configured as the coin beacon such as that embodied by the BlueCats BC413, while the gateway 300 can be a BlueCats edge relay, both manufactured by BlueCats.com of Austin, Tex. In one form, the BLE beacon 200 may be run entirely within a private network, while in another, it may be made to communicate securely with the cloud 500 or a related high-performance computing (HPC) equipment.

The previously-discussed transmit-only functionality of the room beacons 200A and the elopement beacons 200B in their communication with the one or more of the various wearable electronic devices 100 promotes lower-cost and less complicated installation and maintenance than in situations where two-way communication between the wearable electronic devices 100 and the BLE beacons 200 may be present. Such an arrangement also helps to avoid communication ambiguity between the wearable electronic devices 100 and these two forms of the BLE beacons 200.

In one form, the nurse ID beacon 200C may be used to track the activities of the remote computing device 900 that is associated with a particular nurse or related caregiver in response to a data transmission from one or more of the wearable electronic device 100 and system 1. One example of the nurse ID beacon 200C is in a card-shaped format such as that manufactured by Kontakt.io, Inc. of New York, N.Y. In this form, the nurse ID beacon 200C may be wearable or otherwise affixable to the caregiver (such as employees of an assisted living community) through his or her corresponding remote computing device 900. As such, one functional difference between the room and elopement beacons 200A and 200B and the nurse ID beacon 200C resides with the nurse ID beacon 200C additionally having a limited receive capability in order to receive an alert, warning or other important message from a separate source such as a remote computing device 900 (that will be discussed in more detail in conjunction with FIGS. 4 and 5) or related call center, monitoring station or the like. For example, should an individual press a nurse call button 131 (also referred to as a help button, and that will be discussed in more detail in conjunction with FIGS. 2A and 2H) that is located on the wearable electronic device 100, the corresponding distress or related request for assistance is sent from the wearable electronic device 100, through the gateway 300 and one or more of the backhaul server 400 and cloud 500 and to patient-monitoring equipment such as the remote computing device 900 in order to then have a message sent (for example, over a wireless internet, WiFi, cellular or other suitable connection) to the various nurse ID beacons 200C so that one that is in closest proximity or readily-available to lend assistance may do so. Another functional difference among the various types of beacons 200A, 200B and 200C may be in their transmit power, identifier or the like. It will be appreciated that these and other similarities and differences may be adjusted in order to configure the BLE beacon 200 for a particular application, and that all such variants are deemed to be within the scope of the present disclosure. For example, the room beacon 200A may be arranged to cover a relatively large area such as a room, and as such may transmit at a power sufficient to cover the entirety of such room as part of an RSSI or other distance-based finding approach. In this type of operation, the room beacon 200A sends an identifier such as a universally unique identifier (UUID) or similar data package, so that the wearable electronic device 100 may measure RSSI and use this measurement to assist with location determination of the relative position between them. Likewise, the elopement beacon 200B and the wearable electronic device 100 cooperate in a nearer-field manner to emulate a radio frequency identification (RFID) arrangement such that should a person wearing the electronic device 100 pass from a permitted space and through door or other point of egress where the elopement beacon 200B is situated, the identifier being sent from the elopement beacon 200B is received by the wearable device 100 that in turn can transmit a signal that indicates such patient proximity to the gateway 300 and server 400 the latter of which is equipped with internet, cellular or other backhaul-connected modes of communication to notify suitably-configured electronic devices (such as remote computing devices 900). Similarly, the nurse ID beacon 200C may have an even lower power setting than the elopement beacon 200B such that upon touch activation of the nurse call button 131 (that will be discussed in more detail in conjunction with FIG. 2H) on the wearable electronic device 100, a portion of a hybrid wireless communication module 175 (that will be discussed in more detail in conjunction with FIG. 2F) on the wearable electronic device 100 is activated in order to act like a tracker that receives the identifier being sent from the one or more nurse ID beacons 200C that may be in the vicinity. In this way, a particular one of the nurse ID beacons 200C that is identified as having the strongest transmission signal (and therefore deemed to be in close proximity to the patient) can in turn receive a corresponding signal from the server 400 to instruct the caregiver to attend to the individual who activated the nurse call button 131. Because the identifier being transmitted from the nurse ID beacons 200C can be coded to also include identification of a particular caregiver, better control over caregiver actions, whereabouts, patient response times or the like can be established. For example, activation of the nurse call button 131 may also trigger another portion of the hybrid wireless communication module 175 to send an LPWAN-based signal to a data repository that may be maintained on the backhaul server 400, cloud 500 or elsewhere to particularly identify the responsible caregiver and his or her subsequent activity.

BLE beacon 200 broadcasts a radio signal through its RF connection such that the contents of its data package is made up of a combination of letters and numbers transmitted on a regular interval. As will be appreciated, the UUID or related identifier information is context-specific in that its meaning is dependent upon another application (such as that running on the server 400 or another external device or other program in order to recognize the meaning of the data that corresponds to the identifier information). In such circumstance, the wearable electronic device 100 merely has to read the UUID broadcast from the BLE beacon 200 and send the information to the external device application such that the program performs the remaining location-determining calculations. When a dedicated external device application recognizes the wearable electronic device 100 as a nearby BLE-enabled device, the application links the device to an action or piece of content (such as that which may be stored in the cloud 500) and displays it to a local or suitably-connected remote user. In one form, an online-based approach lets a user manage, configure and update BLE beacons 200 and their profiles. For example, a display-based dashboard may be visible on a web page that is signally coupled to a patient database that permits as-needed updating. Because the BLE beacon 200 is configured to transmit its signals over relatively short distances (for example, tens of meters or less), its hardware may be of simple, low-cost construction, often including only a CPU, RF radio and a battery; such a lower per-unit cost may become an important factor in total infrastructure costs, particularly where large numbers of BLE beacons 200 may be installed in a single facility or group of facilities. Significantly, the low current draw associated with the BLE format allows the batteries that are used to power the BLE beacons 200 to consume far less energy than conventional Bluetooth-based devices while maintaining a comparable (or even greater) communication range.

Various communications standards (also referred to as pseudo-standard software protocols, such as iBeacon, Eddystone or AltBeacon) may be used to determine the BLE beacon 200 transmission characteristics and interaction with other wireless devices for proximity awareness. Among other things, the communication standard controls the data format and content of the advertising packet payload that is structured to have one or more of the UUID or related identifier, a media access control (MAC) address, major and minor fields, manufacturer identification or the like. While each standard has some individually-defining characteristics, including the nature and size of the advertising packet that makes up the location-based signals being sent to the wearable electronic device 100, they all follow a relatively uniform data format to allow the operating system of the wearable electronic device 100 to adapt, regardless of how such location information is being sent from the beacon 200. For example, if the BLE beacon 200 is transmitting using the iBeacon standard, the advertising data packet format includes 30 bytes of total payload of which the UUID proximity is 16 bytes, a 1 byte preamble, a 2 byte major, a 2 byte minor and a 1 byte transmit power. Regardless of which standard is used, when the wearable electronic device 100 is within the radio range of at least one room beacon 200A, the wearable electronic device 100 receives the UUID or related identifier to allow both identification and RSSI-based information. In one form, when the UUID and its associated signal strength are passed to the cloud 500 through the wearable electronic device 100, gateway 300 and the backhaul server 400, the cloud 500 is able to determine a ground truth through mapping the UUID of a corresponding one of the BLE beacons 200 to a physical location. The one or more room beacons 200A each send out their respective UUIDs at regular intervals (such as about ten times every second, although depending on the settings, such frequency can be increased or decreased). In addition to using the UUID or related identifier as a way to acquire relative location between the BLE beacon 200 and the wearable electronic device 100, when a dedicated application that has been set up on the wearable electronic device 100 as well as other remote computing devices 900 of FIGS. 4 and 5 recognizes the UUID, it links the location-based information from the RSSI signal to the backhaul server 400, cloud 500 or the like that in turn can be sent (such as over the internet) for display to a caregiver, family member or other interested party that has a suitably-equipped application on their own remote computing device 900. One exemplary form of the room beacon 200A type of BLE beacon 200 is the coin beacon Model BC413 mentioned previously; this beacon employs a stand-alone profile with extended (for example, 1 year) battery life, Bluetooth 4.0+ specification operating in the 2.402 GHz to 2.480 GHz range with normal operation range of about 100 meters.

One notable feature is that in the namespace ID (which may be part of a payload data unit (PDU)), the wearable electronic device 100 not only acquires beacon advertisements or related signal broadcasts, but is also able to ascertain what type of BLE beacon 200 is transmitting the signal. Based on that information, the wearable electronic device 100 can respond differently. For example, if it sees a nurse ID beacon 200C, it will know to turn off the nurse call button 131. Likewise, if it sees an elopement beacon 200B it will send the message through a third wireless communication sub-module 175C (that is part of the hybrid wireless communication module 175 of FIG. 2F) faster than a normal room beacon 200A could. With this, in the nurse ID beacon 200C for example, (1) the fact that it is in response to the nurse call button 131 on the wearable electronic device 100 having been pushed can be known, and (2) which nurse the nurse ID beacon 200C belongs to, for example, that 01 equates to a nurse call, and that 12 equates to a particular nurse (such as "nurse Betty"). Significantly, this enables the wearable electronic device 100 to act as a dynamic instrument rather than merely as static read and relay device where the nurse call beacon could be represented in the 16-bit UUID format with a certain number, for example: 01 12 00 00 00 00 00 00.

While conventional WiFi or Bluetooth (such as Bluetooth Classic and other non-BLE versions) may be used to transmit or receive location-based signals with the wearable electronic device 100, the authors of the present disclosure have discovered that reliability and cost concerns favor the use of BLE beacons 200 for sending indoor location-detecting signal transmissions to the wearable electronic device 100, particularly when the assisted living community, hospital, home or other dwelling or place of recovery is of older construction where one or more of building layout, choice of construction materials or other factors can degrade a WiFi signal or Bluetooth signal relative to a BLE signal. In one form, the transmitted signals from the BLE beacons 200 can be received by a nearby BLE radio (for example, in the form of a chip that cooperates with or makes up a part of a first wireless communication sub-module 175A that will be discussed in more detail in conjunction with FIG. 2F). Furthermore, the authors of the present disclosure have discovered that providing both indoor and outdoor location-detection capability is particularly beneficial in situations where the person that is secured to the wearable electronic device 100 is in danger of wandering (such as due to the various forms of cognitive deficit, impairment or related frailties discussed herein). In this regard, the short range of conventional WiFi, RFID or other "indoor-only" approaches is prone to losing contact with a wander-prone individual during periods where the individual gets beyond such range and is most vulnerable to harm, such as during adverse weather conditions, or while in a dangerous topographic, high-vehicular traffic or high-crime area. Relatedly, GNSS or a related "outdoor-only" approach is incapable of tracking such individuals indoors where the overwhelming majority of their daily activities are spent, as many of these individuals are already residing either at home or in an assisted-living or other specialty-care facility where access to outdoor endeavors is significantly limited.

Within the present context, the term "LPWAN" will be understood to include low power, low data bit-rate wireless communications that are capable of sending a transmission over long ranges in general, where various proprietary and open-system protocols (for example, Sigfox, Ingenu and LoRa the last of which forms a part of the previously-discussed LoRaWAN™ under the guidance of the LoRa® Alliance) may be used as specific implementations, for example, as a MAC layer protocol for controlling the communication of LPWAN gateway 300 and the wearable electronic device 100. As such, both the general (for example LPWAN) and the specific (for example, LoRaWAN™ or the like, with its use of the LoRa as the physical layer with its chirp spread spectrum (CSS) modulation) are understood within the present context to be the vehicle through which one or more components of the collected LEAP data are communicated from the wearable electronic device 100 to the system 1 through gateway 300, and that the understanding of the specific or the general will be apparent from the context. Moreover, the authors of the present disclosure have discovered that using LPWAN (including its LoRaWAN™-specific variant) is preferable for the transmission of collected data from the wearable electronic device 100 to the gateway 300. In one form, the LPWAN signal used to convey data collected by the wearable electronic device 100 is predominantly used in a one-way flow of such information in an uplink manner to the gateway 300. Consistent with any of Classes A, B or C communication and an attendant bidirectional communication capability, some form of downlink may also be employed in order to establish security updates, data transmission (i.e., received packet) acknowledgement, other over-the-air updates or the like. In such downlink communication, an application server 420 that is part of the backhaul server 400 may communicate with a network server 410 that is also part of the backhaul server 400 and that in turn sends each downlink message to a single gateway 300 that then transmits the message to the wearable electronic device 100, such as through an LPWAN signal to the third wireless communication sub-module 175C.

As mentioned previously, distances may be measured with RSSI-based methods such as to acquire indoor localization. Such a simplified approach permits a relatively accurate range and distance calculation without having to rely on the infrastructural complexities such as scannable or multiple antennas associated with time of arrival (TOA), time difference of arrival (TDOA, such as multilateration, AOA or triangulation) and related angle measurement approaches, among others. Rather than rely upon relative time measurements, synchronized clocks or the like, RSSI employs a simple measured signal strength approach that can achieve a desired level of location accuracy without the complexity or power-consuming attributes associated with other systems. In addition, RSSI used in localization activities may be coupled to either deterministic or probabilistic algorithms that allow the signal being broadcast to be translated into distances from BLE beacon 200 points by means of theoretical or empirical radio propagation models. For example, a deterministic model stores scalar values of averaged RSSI measurements, while a probabilistic model selects a location from a known RF map with the highest likelihood of being correct. In one form, the RSSI can use the following expression to account for a general radio propagation model.

$$P_r = P_t \left(\frac{\lambda}{4\pi d}\right)^* G_t G_r$$

In it, the received power is Pr, while the transmitted power is Pt, λ the wavelength of the radio signal, Gt and Gr the gains of the respective transmitter and receiver antennas 140, d the distance separating the two antennas 140, and n is the path loss coefficient, typically ranging from 2 to 6 depending on the environment. By using RSSI, the BLE beacons 200 and associated wearable electronic device 100 avoid the need for—as well as cost associated with—multiple antennas or a scannable antenna. Likewise, by removing the need for engaging in costly training and complex matching algorithms, the architecture of the present system 1 is simplified. One approach that may be used to estimate the location of the wearable electronic device 100 through RSSI involves so-called fingerprinting, where a pre-recorded ground truth map of the area of interest is created to infer locations through a best-matching method. Such an approach is relatively immune to the types of diffraction, reflection, multipath and other non line-of-sight conditions, interferences and other shadowing effects that are prevalent in multi-unit dwellings such as assisted living communities, as well as homes where there may be clear lines of demarcations between various rooms therein. In one form, RSSI may be combined with other BLE-based attributes such as adaptive frequency hopping to allow the transmission of data over a large number (for example, 40) channels with physical layer options that support data rates from 125 kbps to 2 Mbps, as well as multiple power levels from 1 mW to 100 mW to promote clear, interference-resistant signals. The previously-mentioned AOD approach may be used, depending on the antenna configuration of the signal transmitting and receiving devices. In one form, these AOA and AOD approaches may use the emerging Bluetooth 5 and its IoT-specific mode of BLE operation.

Also as mentioned previously, in situations where even greater location accuracy may be required (such as an absolute value of the location of the wearable electronic device 100), hyperlocation-based approaches may be used, including those that augment or replace RSSI with some form of AOA or AOD that are equipped with adaptive digital beamforming algorithms in conjunction with multiple-antenna arrays. The beamforming algorithms may be based on a subspace-based estimator such as multiple signal classification (MUSIC), Bartlett's method, correlative interferometry, the Welch method, the Capon algorithm or the like that can measure the location of the wearable electronic device 100 for situations where the AOA or AOD is detected by an array of at least two antennas positioned with a known geometry. In another form different than that of AOA or AOD, TOA, TDOA and related time-of-flight (TOF) approaches may be used. Such forms may employ a two-step TDOA approach to measure travel time and trilateration using (i) time delay estimation and (ii) sound source localization to measure the time delays between the signals coming from each of various sensors 121. It will be appreciated that such an approach will introduce a more comprehensive level of setup, equipment and related infrastructure than the purely RSSI-based approach and as such may be contingent upon infrastructure and related budgetary constraints. In one form, augmented antenna arrays corresponding to AOA communications may be included in or on a housing 110 and support tray 120 in a manner generally similar to antenna 140. In another form, location tracking for use with the BLE beacons 200 may also include triangulation positioning, fingerprint and Kalman filtering algorithm-based approaches.

By using an LPWAN-based communication protocol to transmit data from the wearable electronic device 100 to the gateway 300, overall system 1 architecture and operability is significantly improved. In particular, such a protocol and its low bit-rate data transmission avoids the necessity to connect the wearable electronic device 100 over a cellular, GMS, LTE or related high-bandwidth network. In addition to reducing user cost by not requiring a cellular contract or data plan, the LPWAN-based communication protocol also simplifies system installation in that its standalone structure does not require complex information technology (IT) infrastructure installation, integration or upgrading. Furthermore, adopting an LPWAN-based approach avoids causing the end-use devices (that is to say, the wearable electronic device 100) to become obsolete or otherwise incompatible with the remainder of the system 1 in the manner of cellular-based protocols (such as the progression from 2G to 3G to 4G, as well as the imminent 5G). The LPWAN network architecture improves operability relative to cellular-based networks and their reliance upon smartphones or related high-power, high-bandwidth user devices for the transmission of relatively smaller size data packets. As such, a significant portion of the LPWAN's computing capability may be moved to other places within the system 1, as well as to external equipment, such as the cloud 500. As such, the LPWAN-based mode of communication, coupled with the compact multimodal sensing provided by the wearable electronic device 100, is capable of virtualizing numerous network node functions into a modular, reconfigurable approach to establishing device communication with downstream caregiver and analytic resources without the need for custom hardware and associated configuration requirements for each network function. LPWAN operation may fall under one or more standards, including IEEE 802.15.4k, 802.15.4g, 802.11 long range low power, IETF 6LPWA/

LPWAN, LoRaWAN™, Weightless SIG, Dash7 Alliance or the like, depending on whether certain proprietary or open-source chipsets are employed. In one form, the LoRaWAN™-based approach is used for the LPWAN signal transmission where data rates of between 20 kbps and 50 kbps (with a particular data rate of about 35 kbps, in one form) are possible over transmission ranges of between roughly 1 mile and 10 miles (depending on the line-of-sight attributes of the ambient environment), with multiple uplink and downlink channels over a star-based gateway topology and 128 bit data encryption.

The gateway 300 is a data-bearing router-based intermediary between the low power network packet-based transmissions of the wearable electronic device 100 and the high bandwidth networks (such as internet protocol, cellular or WiFi) associated with the cloud 500. It acts as a duplicating, packet-forwarding device by first receiving LPWAN radio signals from events recorded and stored in memory 173B (that will be discussed in more detail in conjunction with FIGS. 2F and 2G) of the wearable electronic device 100. The gateway 300 takes these events and forwards them to the backhaul server 400. In one form, the gateway 300 may be operated with a full operating system such that the software used for packet-forwarding is operating in the background while other software may be adjusted as needed, while in another form operated almost exclusively with dedicated packet-forwarding software. In addition, in one form, communication between the wearable electronic device 100 and the gateway 300 may be configured such that up to six different LoRaWAN™ network credentials may be stored to allow hopping between credentials seamlessly if one isn't available or otherwise loses connectivity. Such functionality may also work in situations when a private network between these components is being employed (such as for a nursing home, assisted living facility or the like) to then allow as-needed switching to a public network (such as that provided by internet service providers (ISPs) for example). In one form, each gateway 300 can serve numerous (for example, in excess of a thousand or more) wearable electronic devices 100. Having multiple gateways 300 may be helpful in establishing a star topology for a network formed between such gateways 300 and the one or more of the wearable electronic devices 100. In addition to that manufactured by the previously-mentioned BlueCats, other examples of gateway 300 include those manufactured by Link Labs, Multitech and Laird, among others. In one form, gateway 300 may be battery powered, while in another, it may be powered by a conventional alternating current (AC) outlet. When configured as part of the previously-discussed edge computing capability, the gateway 300 may further be configured to have redundancy in the event of a power outage. For example, should the gateway 300 lose its electrical power supply, it can convert from using an ethernet-based backhaul to a cellular-powered one.

The backhaul server 400 is coupled to cloud 500 and is shown presently in the form of the network server 410 and the application server 420, although it will be appreciated that in an alternative form, the two servers may be subsumed under a single server, and that functions associated with the backhaul server 400 may be combined with other computers or servers (not shown) on an as-needed basis. Likewise, within the present context, in some embodiments, the system 1 may exclude one or more of the components disclosed herein, while in some embodiments it may add another component to those presently disclosed, and that it will be appreciated that these and other variants are all deemed to be within the scope of the system 1 of the present disclosure. In the present context, the term "backhaul", "backhaul server" and its variants represents the portion of system 1 that provides the intermediate links between the internet or associated network and wearable electronic devices 100 that define the data-gathering (including sensor-based data gathering) that takes place at the so-called network edge. Unlike the private-network infrastructure associated with the connection between the wearable electronic device 100, the BLE beacons 200 and gateway 300, backhaul communication between the servers 400 of the system 1 and the internet may take place by public-network infrastructure, including telephone companies or ISPs, as well as through a public broadband backhaul. In one form, a portion of server 400 may function as a cloud server (also referred to as a virtual server or virtual private server) over the internet as part of an infrastructure as a service (IaaS) based cloud service model. In one form, the system 1 and its servers 400 along with suitably-connected databases contained therein or on the cloud 500 may engage in data exchange through standardized protocols such as those associated with public-private key exchanges, hypertext transfer protocol (HTTP), secure HTTP (HTTPS), advanced encryption standard (AES), web service or native application programming interfaces (APIs, that is to say, "apps") or other electronic information exchange approaches. Similarly, in one form, the exchange of data between the system 1, servers 400 and cloud 500 may take place over the internet, VPN, a packet-switched network, local area network (LAN), wide area network (WAN) or related packet-switched network.

The network server 410 functions to provide hardware and peripheral equipment support access, disk space for file storage or the like to other computers in the system 1, as well as handle software, configuration or security updates. In one form, the network server 410 acts as the interface between the wearable electronic device 100 and the application server 420 in a manner defined by the LoRa Alliance to eliminate duplicate packets, schedule acknowledgements, adapt data rates, and provide encrypted communication. In one form, the network server 410 acts as a database server, and may also include checking and verifying device identification functions for the wearable electronic device 100, performing message integrity code (MIC) or MAC checks as well as serving as a duplicate filter (all for data uplinks). The network server 410 then proceeds to send the messages to the application server 420. The network server 410 is used in order for an LPWAN radio such as that embodied in the third wireless communication sub-module 175C of the wearable electronic device 100 to communicate with the application server 420. For example, when the LPWAN signal is transmitted, the network server 410 eliminates duplicate packets, schedules acknowledgements, adapts data rates and provides encrypted communication with the wearable electronic device 100, as well as other devices. Such strong encryption, device and user authentication methods, as well as filtering of incoming signals, can help to secure the wearable electronic device 100 from unauthorized access, as well as provide enhanced intrusion detection. In one form (not shown) a firewall, bastion host or other security component may be used to establish a security perimeter to help isolate, segment and control data traffic flows between the wearable electronic device 100 and the remainder of the system 1.

The application server 420 is part of the cloud 500 and serves as a computing nerve center for system 1 to run protocols and interfaces, such as web-based protocols and the previously-mentioned APIs. Functions provided by the application server 420 include (i) reception of LoRa-based messages from the network server 410, including the decoding of messages or packets, (ii) archival of events such as location, nurse calls, battery level or the like that are sent from the wearable electronic device 100, (iii) configuration data such as identification of users, devices, beacon location, audio files or the like, (iv) rules for sending notifications to caregivers and family applications, (v) security and (vi) storage of new firmware versions for the wearable electronic device 100. In one form, the application server 420 is coupled with a web server (that in one form is subsumed under network server 410) that may be coupled to the cloud 500, while in another form it is an integral part of such a web server to be referred to as a web application server that can during data uplink act as a medium for (among other things) data storage, visualization and message uplink triggers. For example, the application server 420 may be configured in a manner similar to Amazon Web Services (AWS), and as an IoT device or the like to provide cloud-based infrastructure, where in one form various code, logic or the like may be developed and implemented. For particular downlink operations, the application server 420 may also perform packet encryption and packet queueing functions. In one form, data streaming may be set up by creating notification targets for the wearable electronic devices 100 so that the notification target configures the network server 410 to stream wearable electronic device 100 uplinks to a user-specified destination such as the remote computing devices 900. Such data streaming may be used in situations where the need for real-time analytics based on the acquired LEAP data through the wearable electronic devices 100 is of time-sensitive.

Within the present context, the cloud 500 (and cloud computing) is understood to be the delivery of services over the internet, as well as the hosting of such services. In this way, the server 400 is separated from the service being provided. This allows for simplification of the end user equipment (in this case, the wearable electronic device 100 and gateways 300) such that in one form, much or all of the data and models (such as machine learning or cloud analytics models as discussed elsewhere in this disclosure) may be hosted on a server in the cloud 500, allowing the end user to access it through the internet. In one form, the application server 420 is a cloud-based computing device that serves as a so-called "nerve center" for the system 1, and may be loaded with software that provides instructions for operation of the system 1, including (i) the reception of messages from the network server 410, (ii) the archival of events (for example, acquired LEAP data, system or component status or operability such as remaining life of a battery 180 (that will be discussed in more detail in conjunction with FIG. 2F) that is used to provide electric power to the wearable electronic device 100, time-stamping, alerts or notifications, or the like) sent from the wearable electronic device 100, (iii) configuration data (such as users, devices, beacon location, audio files or the like), (iv) rules for sending notifications to caregivers and family applications, (v) security and (vi) storage of new firmware versions for the wearable electronic device 100. As with the application server 420, the cloud-based approach may leverage known scalable virtual machines, such as AWS EC2, AWS Elastic Beanstalk, AWS Lambda or the like.

In one form, ancillary equipment may include an inductive-charging device 600 for periodic reenergizing of the wearable electronic device 100 and its battery 180. The inductive-charging device 600 may be based on the Qi open interface standard for low power inductive transfer. In one form, the inductive-charging device 600 may receive its power through a conventional AC electrical outlet where, for example, thirty minutes can provide enough charge to the battery 180 to have it last about three days. In addition, a WiFi router 700 may be included to transport audio to a standalone WiFi speaker 800 that may be used in addition to or in place of a speaker included in the wearable electronic device 100. The WiFi router 700 is either provided by the care facility or can be part of the system 1 installation, whether at home, a care facility or elsewhere where patient monitoring may be needed.

In one form, the conceptual model on how at least a portion of the system 1 and the wearable electronic device 100 are arranged to standardize their various communication functions, especially when coupled to an external network such as the cloud 500, as well as between the servers 400 and the WiFi router 700 and WiFi speaker 800, follows the Open Systems Interconnection (OSI) hierarchical communication model. This model employs a communication protocol stack that partitions a communications into seven abstraction layers that specify how data should be packetized, addressed, transmitted, routed and received; these are the application, presentation, session, transport, network, data link and physical layers. As with the previously-discussed LPWAN-based mode of communication and its associated virtualization of numerous network node functions into a modular, reconfigurable way to establish communication between devices, organization into the various layers under this model is beneficial in that it allows system 1 functionality to be described without regard to the underlying physical structure of the various components, which in turn promotes an increased amount of component or computing device independence. It will be appreciated that multiple possible abstraction layer configurations are possible in the deployment of a network used to support the operation of the system 1 disclosed herein, and that the use of the unique architecture of the wearable electronic device 100 in general and the particular arrangement of the hybrid wireless communication module 175 disclosed herein will assist in improvements in overall operability of the system 1.

Within the seven layers of the OSI model, the lowest three are often grouped together as media layers, while the upper four are often grouped together as host layers. The physical layer is the fundamental layer within the media layer group, and supports the logical data structures of the higher level functions of other layers, and includes the networking hardware transmission technologies responsible for transmitting raw bits of information rather than logical data packets, and provides an electrical, mechanical and procedural interface to the radio frequency (RF) transmission medium. With particular regard to the system 1 when configured as an RTLS, the physical layer is embodied as the wireless RF communications discussed herein. In such case, the BLE beacons 200 may act as tags and (at least in the room beacon 200A types) fixed reference points. The data link layer is the protocol layer that transfers data between adjacent network nodes in a WAN or between nodes on the same LAN. The data link layer may also include error-correction features. In one form, the combination of the data link layer and the physical layer of the OSI protocol stack may be thought of as the functional equivalent of the so-called link layer of the transmission control protocol/internet protocol (TCP/IP) model. The data link layer includes a MAC sublayer that makes it possible for several network nodes (such as the LPWAN gateways 300 and wearable electronic devices 100 of the disclosed system 1) to communicate over a shared medium. In one form, LPWAN may use an ALOHA-style scheme in the MAC layer that in combination with the physical layer enables multiple wearable electronic devices 100 to communicate at the same time but using one or both of different channels and orthogonal codes (i.e., spreading factors). In the LoRaWAN™-specific version discussed elsewhere within the present disclosure, the MAC layer protocol for managing communication between the gateway 300 and the end-node wearable electronic device 100 is maintained by the LoRa Alliance. The network layer responds to service requests from the transport layer (discussed below) and issues service requests to the data link layer in order to provide routing and data packet-forwarding from a source to a destination through one or more routers. As will be discussed in more detail below in conjunction with FIGS. 3A through 3I, a data packet includes control information as well as user-specific payload. The transport layer is responsible for flow control setup, and reliability for host-to-host communications. The session layer provides the mechanism for opening, closing and managing a session between various end-user applications through various requests and responses that take place among such applications. This layer is used to maintain and—if necessary-recover a connection through either full duplex or half-duplex operation, as well as through the use of synchronization in the stream of exchanged messages. The presentation layer acts as the data translator for the network through the formatting of information to the application layer for downstream activities such as information displaying or additional processing. In so doing, it avoids having to have the application layer (discussed below) resolve syntactical differences in data representations within various end-user systems. The application layer acts as the user interface responsible for displaying received information to the user by standardizing communication based on activities within the underlying transport layer protocols. In this way, it can establish and manage respective data transfer channels and data exchange between network components. In one form, such interface may include those for visualization, such as through a display. More particularly, while wearable electronic device 100 and gateway 300 may be arranged at least in part on the OSI layer communication model, it will be appreciated that different combinations of layers could be used within a given protocol stack.

In another form, the conceptual model on how at least a portion of the system 1 and the wearable electronic device 100 are arranged to standardize their various inter-node communication functions follows the TCP/IP protocol. The TCP/IP model has four abstraction layers that are used to generally describe design guidelines and implementations of specific protocols for network-based communications, these are the application, transport, internet and network access layers. The application layer provides applications with the ability to access the services of the other layers and defines the protocols that applications use to exchange data; examples of the application layer include file transfer protocol (FTP), the previously-mentioned HTTP and simple mail transfer protocol (SMTP), among others. The transport layer (an example of which is transmission control protocol (TCP)) accepts data from application layer, and then divides it up for subsequent conveyance to the network layer through host-to-host logical connection. The internet layer provides logical addressing, path determination for the segments to be sent and forwarding to ensure that the segment is moved across the networks to a destination network. One common protocol of this layer is the internet protocol (IP). The network access layer provides the protocols and hardware required for connection of a host to a physical network (such as a LAN or WAN), as well as to deliver data across such network. As with the previously-discussed OSI model, the use of the TCP/IP model to describe the communications functionality of at least portions of one or both of the wearable electronic device 100 and system 1 is beneficial in that it allows device independence through describing such functionality without regard to the underlying physical structure of the various components. It will be appreciated that both of the OSI and TCP/IP models are within the scope of the present disclosure.

Generally, the three top layers in the OSI model—the application, presentation and session layers—correspond to the single application layer in the TCP/IP model such that they are grouped together in the latter, while the two lowest layers—the data link and physical layers—correspond to the single network access layer in the TCP/IP model. Regardless of which model is employed, it will be appreciated that the uppermost layers (i.e., those that correspond to the application, presentation and session layers of the OSI model, as well as those that correspond to the application layer of the TCP/IP model) are those that are logically closer to the end user, while the lower layers (such as the data link and physical layers of the OSI model and the network access layer of the TCP/IP model) are logically closer to the physical transmission of the data. Thus, when the wearable electronic device 100 utilizes LoRa-based communication between it and the gateway 300, the LoRaWAN defines the communication protocol and system 1 architecture for the network while the LoRa physical layer defines the long-range communication link.

In another conceptual way of visualizing the structure of the system 1 when used in conjunction with the wearable electronic device 100 is as an IoT device (as disclosed later in conjunction with FIGS. 3A and 3B) as part of a cloud 500 infrastructure. In such understanding, the structure may be defined with five major layers, including a device layer for the various components and firmware, a communication layer for radio-based connectivity with one or more networks through the gateway 300, server 400 or the like, a cloud services layer (also referred to as a software layer) to receive and analyze the data at scale, an application layer and a security layer.

With particular regard to the system 1 of the present disclosure, some of the sensing and hybrid wireless communication module 175 activities may not require the services and functionality of some of these higher layers (also referred to as middleware layers made up of the transport, session and presentation layers), and as such may build applications directly on top of the network layer of the seven layer stack of the OSI model, or the internet layer of the four-layer stack of the TCP/IP model.

By way of example, under either an OSI or TCP/IP model or protocol stack, one or more data processing layers may define signal processing, data analytics or the like where the acquired raw LEAP data from an individual is cleansed and placed in a more structured form—often with reduced dimensionality—such that it can be manipulated by the logic device 173 (or its equivalent in system 1) for subsequent feature extraction, testing and use in predictive analytics such as those associated with one or more of the machine learning models discussed herein. In one form, the various data processing layers associated with models that provide analytics to system 1 may be included with—or formed to cooperate with—a lower (such as physical) layer that may include various hardware components such as sensors 121 that collect and convey signals that correlate to event data. In this way, the organization of events into data structures storable in memory 173B of the wearable electronic device 100 (or its equivalent memory 173B in system 1) may include various forms of data tables with labeling or identification, such as the type of event being sensed or detected, a particular activity category (such as ADL) of the person being monitored, spatio-temporal contextual information for an event, a scalar value of the sensed event, as well as others.

In addition to events, other tangible things may likewise be organized as a data structure. For example, various systems of the human body (such as the urinary tract) may be modeled as one or more data structures with input features (suitably configured, for example, in vector form) that may include various physiological data such as that discussed elsewhere in this disclosure. As is discussed elsewhere in the present disclosure, other forms of the LEAP data may be used in conjunction with the physiological data in order to help infer whether an individual that is associated with the wearable electronic device 100 is at risk of developing an adverse health condition based on a quantifiable mathematical interaction of the defining attributes of such things with one or both of the event data that is collected by the wearable electronic device 100 and baseline data that may be either taken from the wearable electronic device 100 or a lookup table or other local or remote source of such data.

In one form, the system 1 is part of a network equipped with one or more applications including a caregiver application, configuration application and family application, all of which may be operated over the internet, a conventional cellular (i.e., 3G, 4G, GSM) network or the like through the remote computing device 900 that will be discussed in more detail in conjunction with FIGS. 4, 9 and 10A through 10F. In one form, the configuration application may be used for initialization, setup, debugging or the like, the caregiver application may be used for responding to alerts or messages pertaining to the individual being monitored (and as such may include caregiver location or proximity functionality in a manner as described elsewhere in this disclosure), while the family application may be used in a manner roughly similar to the caregiver application in that it may receive a message or alert but without a caregiver location or response feedback.

Portions of the system 1, as well as portions of the network, may include devices, components or the like that are configured to operate in various network layers. By way of non-limiting example, one or both of the servers 410, 420 may include modules configured to work within an application layer, a presentation layer, a data access layer (DAL) and a metadata layer. Similarly, one or both of the servers 410, 420 may include access to one or more data sets that make up a data layer. Thus, various data sets may be stored on one or more data storage devices. One or more web-based APIs—such as those associated with I/O interfaces—may operate in the application layer. Likewise, one or both of the servers 410, 420 may include components and various hardware or software modules that work in the presentation layer, where they can support various web services and functions. In one form, a web application, web service or the like may access some or all of the data sets through the data access layer that may in one form be divided into one or more independent DALs for accessing individual ones of the data sets. In one form, these individual DALs are known as data sockets or adapters. The DALs may utilize metadata from the metadata layer to provide the web application or the web service with specific access to the data sets. For example, the one or more DALs may include operations for performing a query of the data sets in order to retrieve specific information for the web application or web service. In a more particular form, the DAL or DALs may include a query for patient records associated with a wearer of the wearable electronic device 100, especially in situations where changes in the salient indicators of the patient's health are identified or suspected. Within the present disclosure, the phrases "salient indicators of the patient's health", "indicia of a health condition" and their variants describes one or more components of the LEAP data that when analyzed by a processor 173A in response to executable instructions stored in a non-transitory computer readable medium (such as memory 173B) provides information that may be output to a caregiver in such a way that enables the caregiver to predict in advance of—rather than react after the onset of—deleterious changes in the health of the patient. Likewise within the present disclosure, it will be understood that the discussion of the four components of the LEAP data refers to any or all such components, whether individually, in part or in toto, and that their identification as such will be apparent from the context. Moreover, the analysis of the LEAP data, such as by one or more of the machine learning models discussed herein, can produce biomarkers that correlate to one or more quantitative estimates of such a health condition, and as such include clinically-relevant information. As will be discussed in more detail later, these biomarkers may be based on comparisons with baseline data, statistical norms, commonly-accepted clinical scores or the like.

Figure 2A:
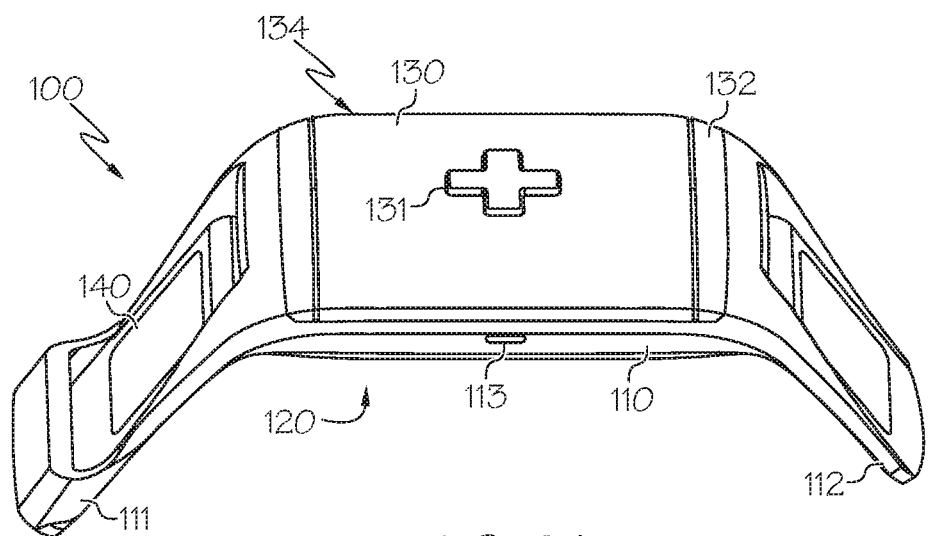
FIG. 2A depicts an upper perspective view of the wearable electronic device of FIG. 1 according to one or more embodiments shown or described herein.
Figure 2B:
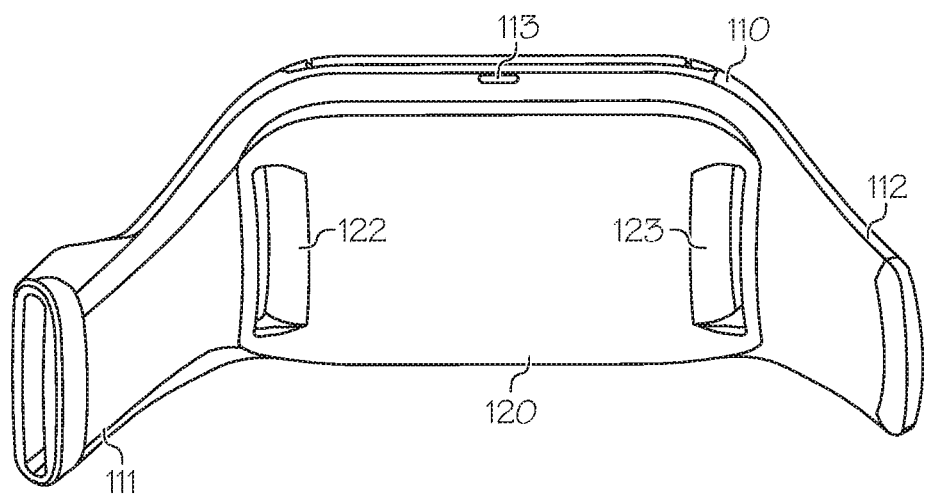
FIG. 2B depicts a lower perspective view of a main housing assembly of the wearable electronic device of FIG. 2A with a support tray in an as-assembled condition according to one or more embodiments shown or described herein.
Figure 2C:
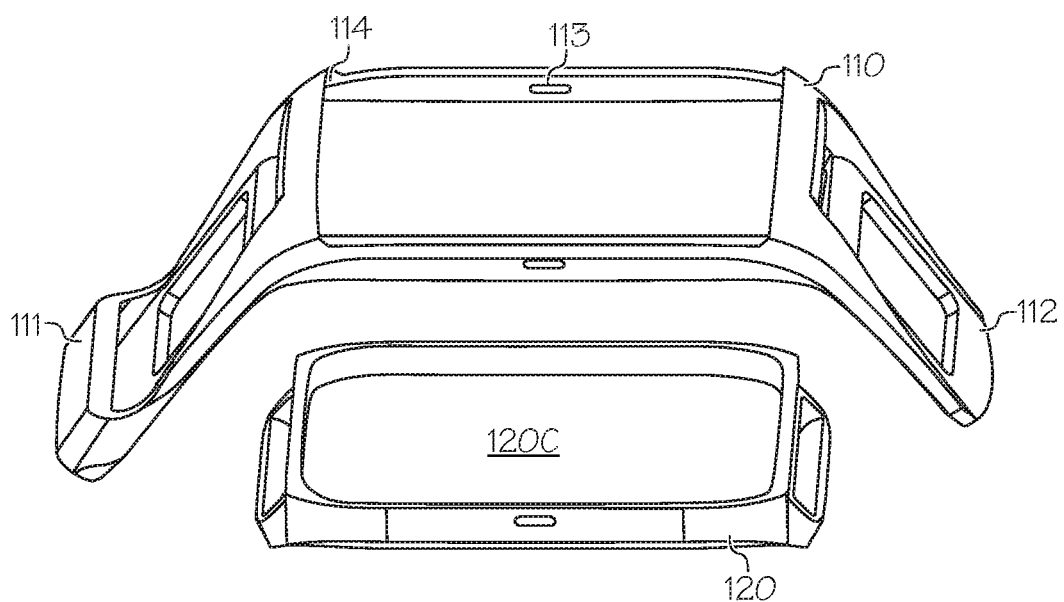
FIG. 2C depicts views an upper perspective view of the main housing prior to attachment to the support tray of FIG. 2B according to one or more embodiments shown or described herein.
Figure 2D:
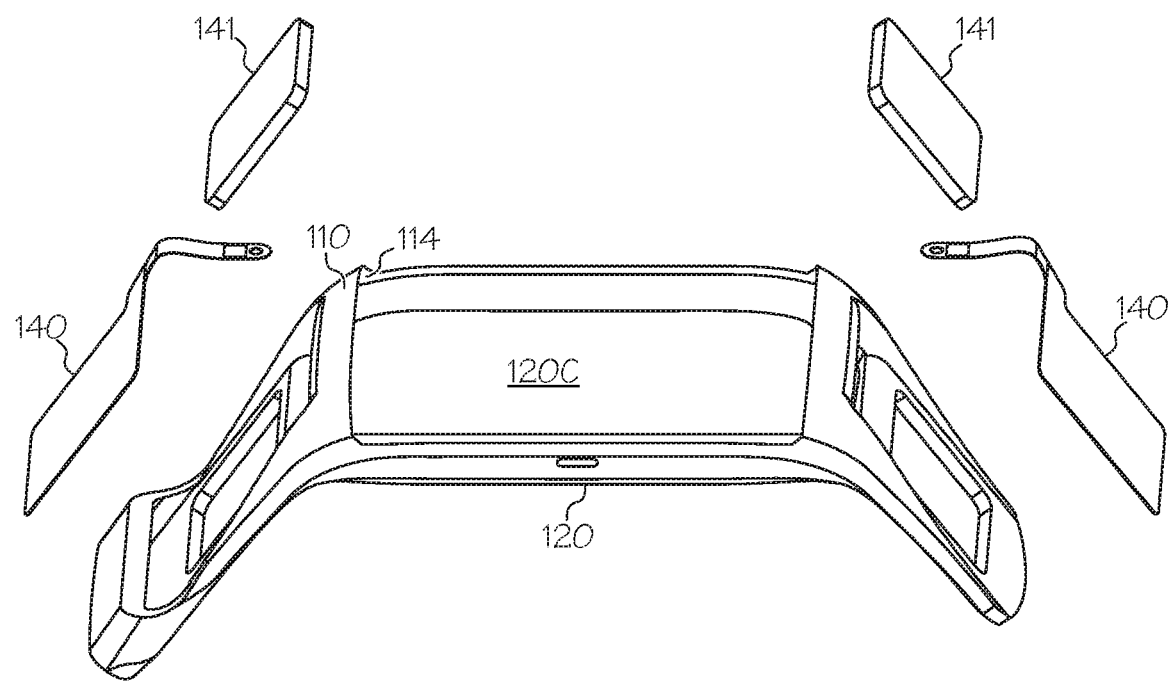
FIGS. 2D and 2E depict upper perspective views of the main housing assembly of FIG. 2C in a partially-assembled state with antennas prior to (FIG. 2D) and after (FIG. 2E) connection therebetween according to one or more embodiments shown or described herein.

Referring next to FIGS. 2A through 2I, details associated with two different embodiments of the wearable electronic device 100 are shown where FIGS. 2A through 2H depict a first of these embodiments and FIG. 2I depicts a second of these embodiments. In one form of the first embodiment, the wearable electronic device 100 is configured to be worn on the wrist of the patient such that it defines a band or related wristwatch-like form factor.

Referring with particularity to FIG. 2A, the wearable electronic device 100 includes a main housing assembly made up of the housing 110 and the support tray 120. As such, one or both of the housing 110 and support tray 120 act as a worn platform upon which some or all of the remaining components that make up the wearable electronic device 100 may be supported, secured or otherwise affixed. The housing 110 includes a central body, as well as two opposing lateral extensions 111, 112. As will be discussed in more detail below, these lateral extensions 111, 112—in addition to providing a mounting location for a strap (such as the one shown in FIG. 2H as a conventional NATO-style band 190) such as that used with a wristwatch—may provide a trough or cavity-like recess into which the sensors 121, antennas 140 or other electrical or signal-based components may be placed. Formed in a side edge of the body of the housing 110 is a slot 113 that can be used to allow a fingernail or small sharp object to be inserted as a way to unlock the housing 110 from a top cover 130.

Figure 2E:
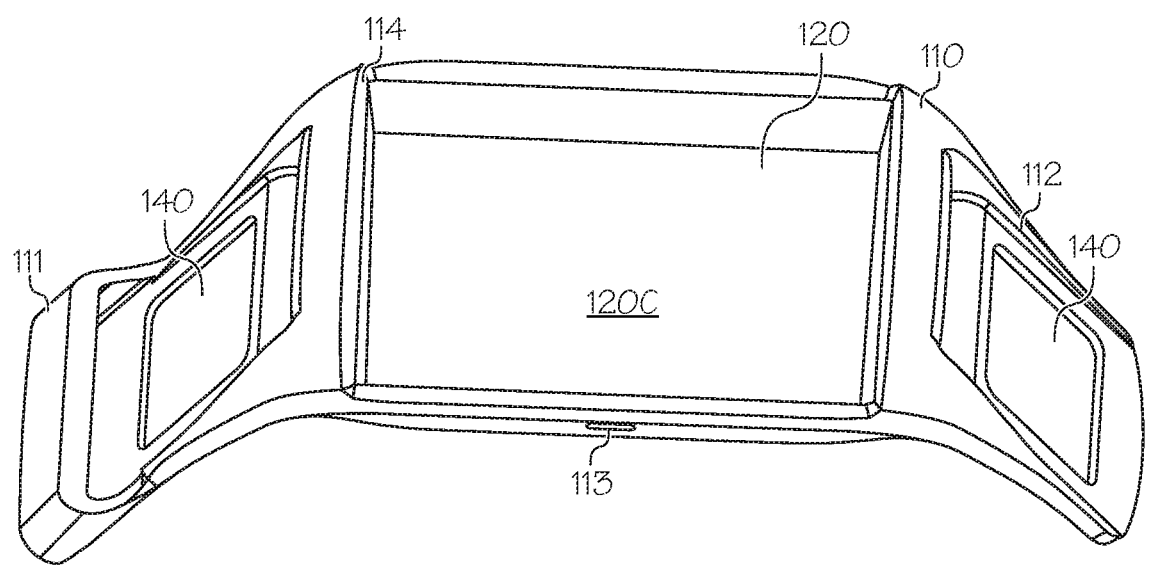

Referring with particularity to FIGS. 2B through 2E, various partially-assembled views are used to show the construction of the housing 110, support tray 120 and certain electronic and structural components. For example, the shape of the support tray 120 defines a cavity 120C where the electronic components reside upon assembly of the wearable electronic device 100. In one form factor, the underside of the wearable electronic device 100 as defined by the support tray 120 may include different contours or different sizes in order to accommodate different wrist sizes of an individual wearer, as well as slots 122, 123 through which the band 190 (as shown in FIG. 2H) may pass. For example, different contours may include those defining relatively small, medium and large radii of curvature. In another form factor, an adapter may be either permanently or removably affixed to the housing 110 or support tray 120 in order to provide a more secure fit to corresponding small, medium or large wrist sizes. When the housing 110 and support tray 120 are joined together, such as by a snap-fit connection, gluing, friction fit or the like, the cavity 120C that is formed provides a volumetric space for the mounting of the various electrical and structural components such as some of the sensors 121, logic device 173, hybrid wireless communication module 175, battery 180 or the like. This modular construction of the housing 110, support tray 120 and the various structural components, as well as the electrical components that will be discussed in more detail in conjunction with FIGS. 2F and 2G, allows the wearable electronic device 100 to have varying degrees of sensing functionality, depending on the end-use needs. For example, if a larger number (or a large number of different types) of physiological sensors 121C (shown in FIG. 2F) are needed for particular forms of bodily function monitoring, different modular packages or options made of differing combinations of such sensors may be placed within the housing 110 and support tray 120. In one form, this modularity may be enhanced through structure that can accept various smaller components or component sets. For example, and as shown in FIG. 2E, a ledge 114 may act as a mounting surface to a complementary-sized and shaped underside of the top plate 130, thereby promoting a volumetric space for the secure placement of one or more smaller components.

Figure 2F:
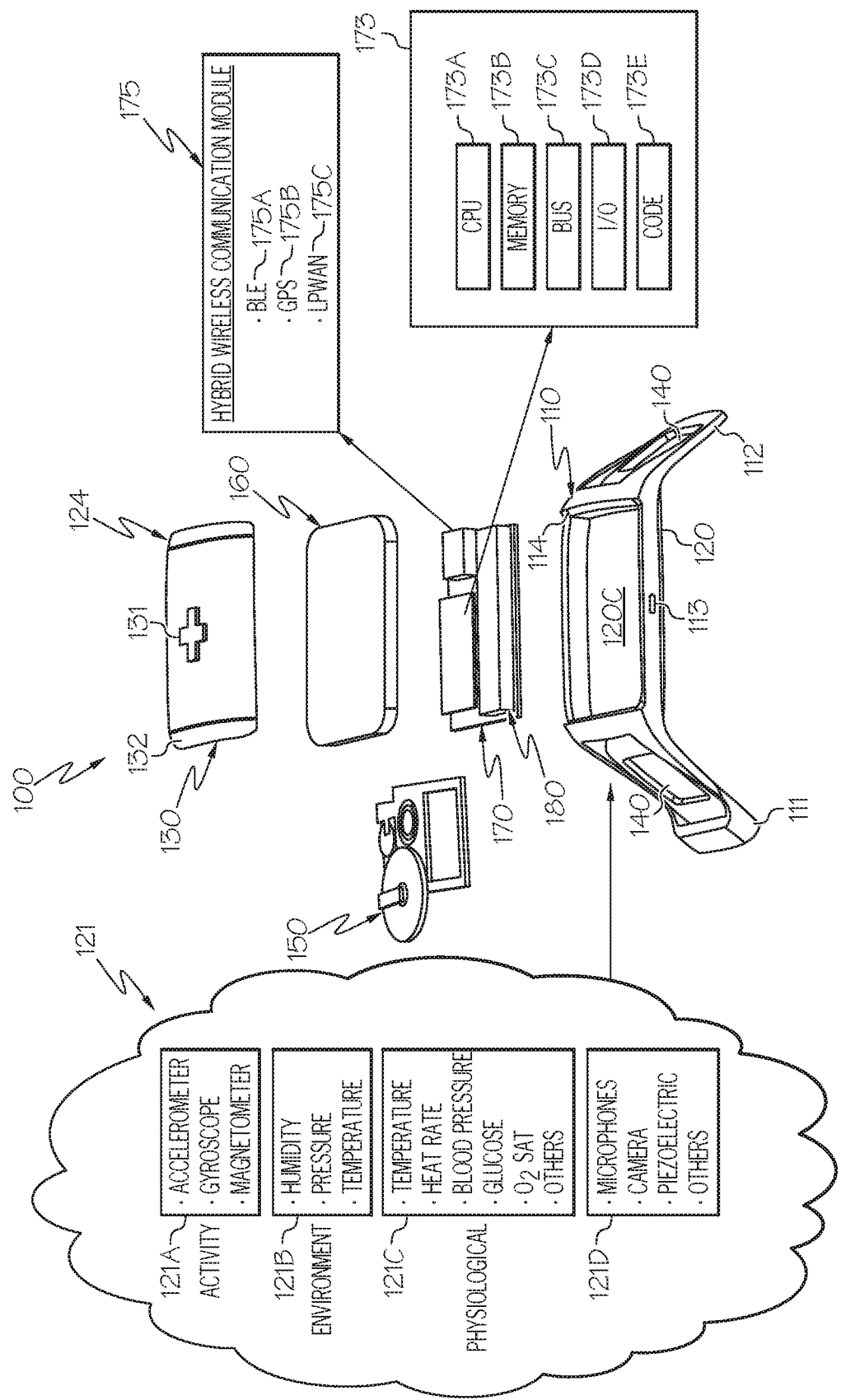
FIG. 2F depicts an exploded upper perspective view of the wearable electronic device of FIG. 2A, as well as a block diagrammatic representation of the logic device, various sensors and hybrid wireless communication module according to one or more embodiments shown or described herein.
Figure 2G:
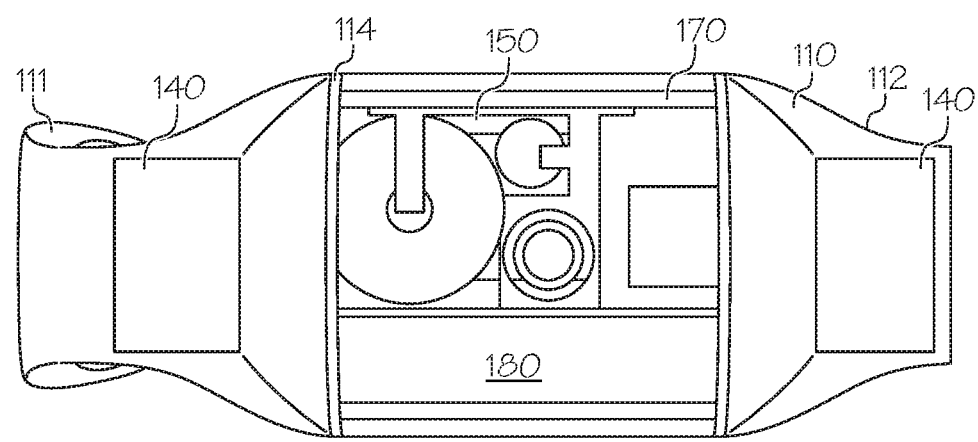
FIG. 2G depicts a top view of the main housing assembly of the wearable electronic device of FIG. 2A with the top cover removed according to one or more embodiments shown or described herein.
Figure 2H:
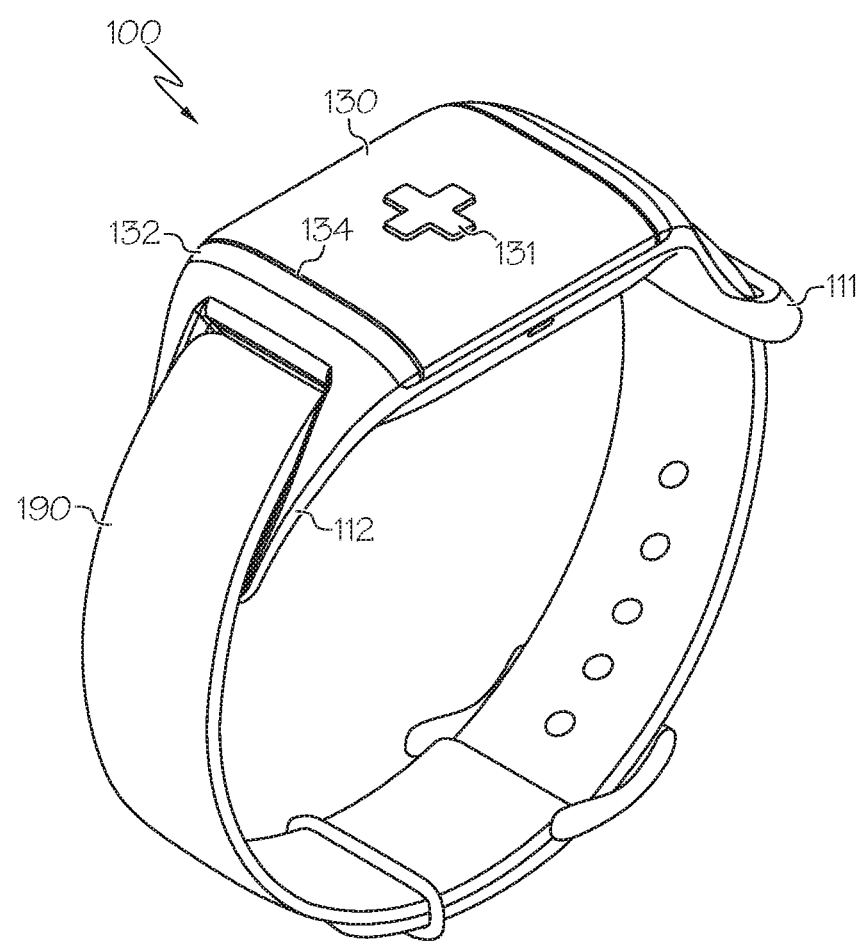
FIG. 2H depicts an upper perspective view of the wearable electronic device of FIG. 2A with an attachable strap according to one or more embodiments shown or described herein.
Figure 21:
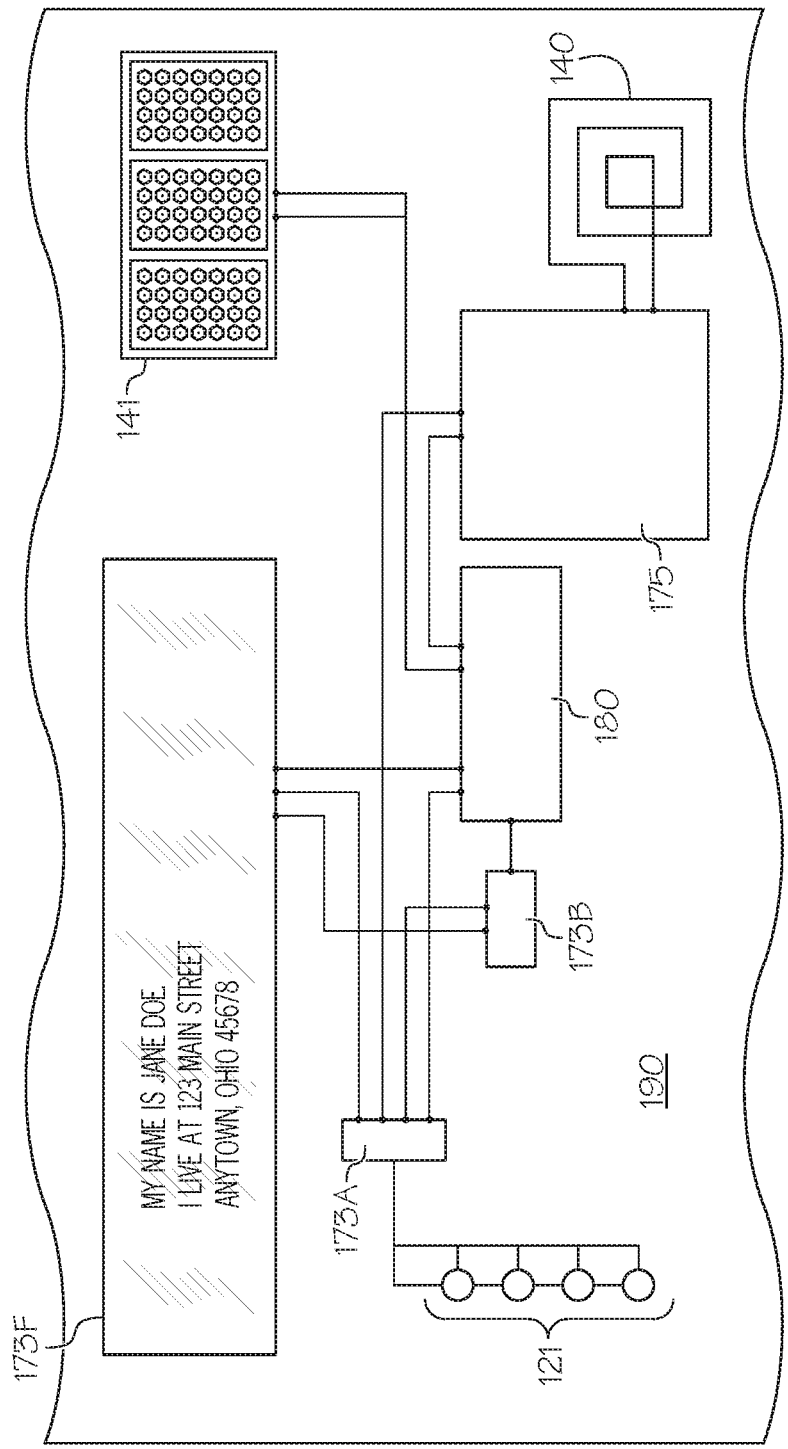
Figure 3A:
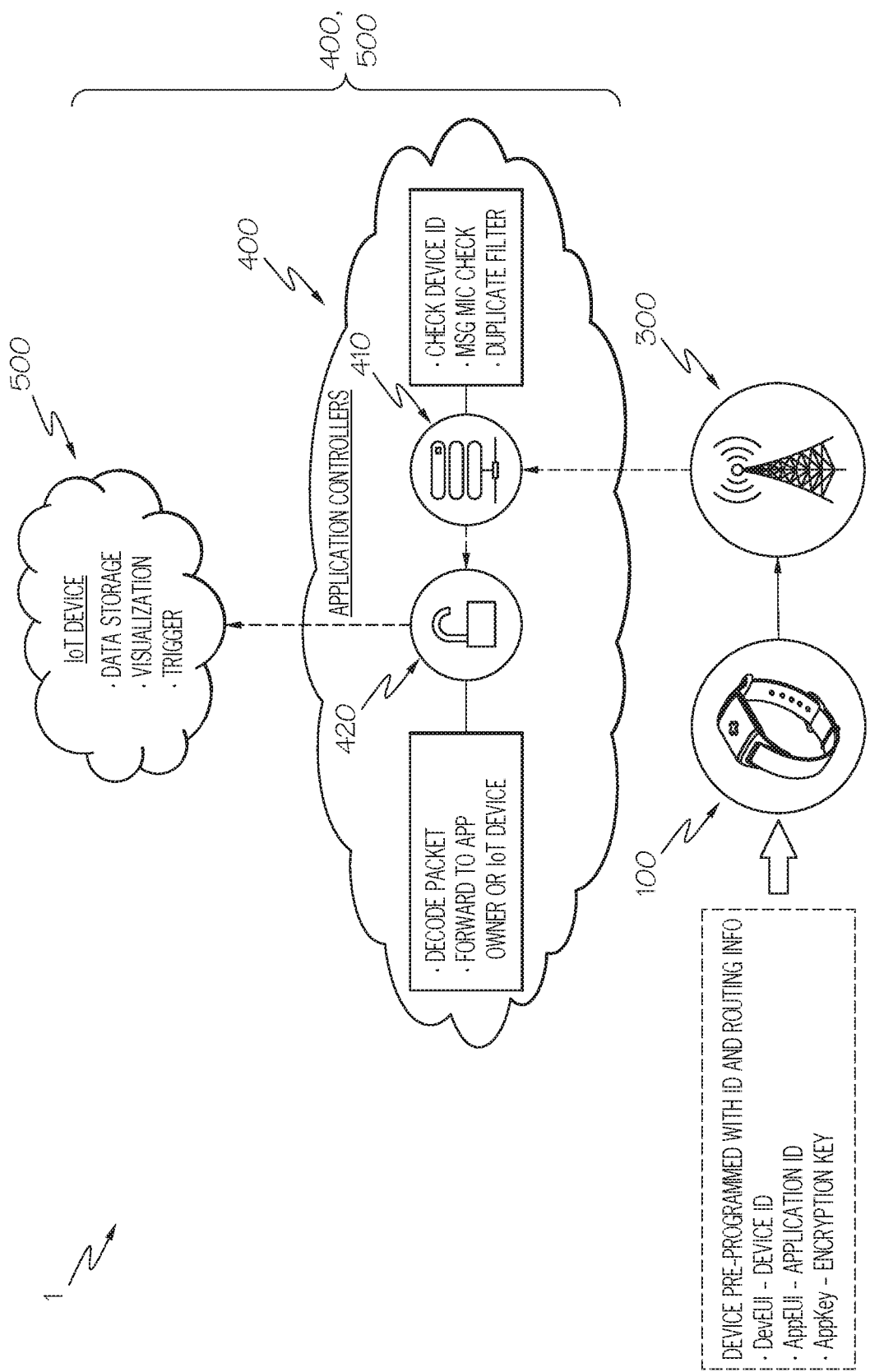
FIGS. 3A and 3B depict notional cloud-based uplink and downlink messages between the wearable electronic device and system of FIG. 1.
Figure 3B:
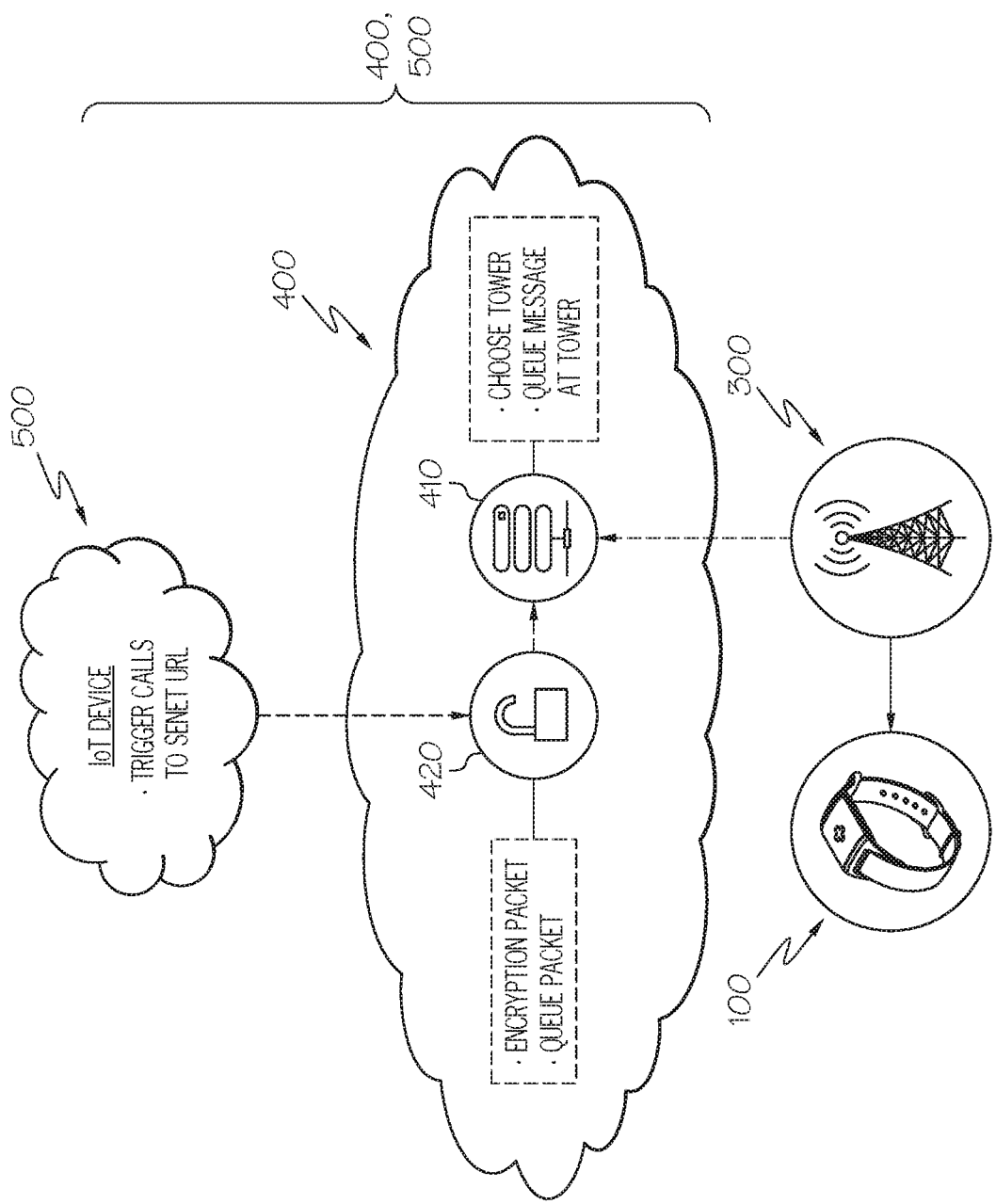

Referring with particularity to FIGS. 2F and 2G in conjunction with FIG. 1, the electronic components that make up the power, processing, communication and sensing functions of the wearable electronic device 100 are shown in a disassembled (exploded) view in FIG. 2F and an as-assembled view in FIG. 2G. The components include a flex circuit 150 with ERM charging coil, hall effect proximity and capacitance sensor, a structural mid-frame 160 and printed circuit board (PCB) assembly 170 that acts as a mount for the battery 180 and one or more of the logic device 173 (that may include one or more of a processor 173A, memory 173B, bus 173C, input/output 173D) and the hybrid wireless communication module 175 that attains its hybrid status by virtue of being made up of various wireless communication sub-modules 175A, 175B and 175C. One or more of the hybrid communication sub-modules 175A, 175B and 175C, as well as portions of the logic device 173 may be formed (such as by printing) on a single substrate of the PCB assembly 170. In one form, the logic device 173 may include various ancillary components such as filters, amplifiers, limiters, modulators, demodulators, data transmission signal conditioners, analog-to-digital and digital-to-analog converters or the like in order to perform the various processing, control, communication, and related operations as described herein.

The GNSS 10 of FIG. 1 includes a set of satellites (only one of which is shown) that determine the latitude and longitude position of the wearable electronic device 100 through well-known methods. A second wireless communication sub-module 175B contained within the wearable electronic device 100 is configured to act as a receiver of signals from GNSS 10; such signals are used to determine location when the patient or other person wearing the wearable electronic device 100 is not in range of any of the BLE beacons 200. Machine code 173E (such as that resident on memory 173B) may cause the third wireless communication sub-module 175C to preferentially transmit the data received by the first wireless communication sub-module 175A when the wearable electronic device 100 is within a predetermined distance from a source of a signal emanating from the corresponding BLE beacon 200, as well as cause the third wireless communication sub-module 175C to preferentially transmit the data received by the second wireless communication sub-module 175B when the wearable electronic device 100 is beyond the predetermined distance from a source of the BLE beacon 200 signal.

In one form, processing and related computation can take place on an architecture that is based on the processor 173A that is in the form of one or more central processing units (CPUs). In another form, processing and related computation can take place on an architecture that is based on an application-specific integrated circuit (ASIC). In another form, processing and related computation can take place on an architecture that is based on a field-programmable gate array (FPGA). In still another form, processing and related computation can take place on an architecture that is based on a graphical processor unit (GPU) such as the Tesla V100 or GTX 1080 series, both manufactured by NVIDIA Corporation of Santa Clara, Calif.; processors such as GPUs and ASICs are particularly beneficial when the calculations being performed involve large-scale matrix multiplication, such as those associated with deep learning neural networks or other machine learning approaches where large amounts of parallel data may need to be processed. In still another form, a tensor processing unit (TPU) such as those being developed by Google to be used in conjunction with its open-source library TensorFlow may be used specifically for neural network applications, particularly for its ability to conduct analytics not just in the cloud 500, but also as part of autonomous or semi-autonomous hardware that is specific to system 1 or wearable electronic device 100. As will be discussed in more detail later, GPU-based processing may be used as a training tool as part of a deep learning neural network as a way to extract meaningful health-related analytics from the large amount of acquired data from the wearable electronic device 100. All of these and their variants are deemed to be within the scope of the present disclosure. Although not shown as part of system 1, it will be appreciated that the logic device 173 and its various components (such as processor 173A, memory 173B, bus 173C, input/output 173D and related modules or components) and the concomitant functionality may be similarly replicated in other parts of the system 1, such as the servers 400, as well as in the cloud 500. Such replication may include scaling up the number of such logic devices 173 on an as-needed basis for situations, such as those associated with running one or more analyses of the health condition of the person being monitored as will be discussed in more detail later. In one form, an analysis may include a clinical decision support (CDS) model that helps a caregiver use the data being acquired by the wearable electronic device 100 in order to determine, among other things, adverse changes in the health of a person being monitored. Depending on the complexity of the inquiry, CDS—whether or not as part of a machine learning model—may involve the use of massive parallelism or related increases in computational power, making the use of the processing and related computational power discussed herein particularly beneficial. It will likewise be appreciated that conceptually these various components of the logic device 173 may be grouped or otherwise arranged in various ways to define circuit-based modules to perform specific tasks or subtasks associated with identification of changes in the one or more salient indicators of changes in the health of an individual that is associated with the wearable electronic device 100. In one form, such modules may be arranged to perform specific tasks (for example, instruct the sensors 121 and other equipment to acquire data, perform calculations to filter, extract and process the data, as well as control the communication of the data, in addition to performing fail-safe checks, system or device monitoring, or the like) in a manner analogous to the hybrid wireless communication module 175. For example, the logic device 173 may include one or more of a sensing module, a prediction module (including having or otherwise being cooperative with machine learning-based algorithms and ensuing models) or an alert module, among others.

By configuring one or both of the wearable electronic device 100 and the system 1 with components such as these, a measure of customization of the particular architecture—as well as improvements in system 1 functionality—may be achieved in a manner not possible with a general, all-purpose computer. In one form, GPUs or FPGAs may be used in conjunction with a model (such as a machine learning model as discussed in more detail later) to compute predicted outcomes derived from the data being acquired by the wearable electronic device 100. In one form, a GPU-based approach may be used in conjunction with deep learning library-based frameworks (such as TensorFlow, Microsoft Cognitive Toolkit, PyTorch or the like) to train, validate and test certain machine learning models (such as deep learning models) that are computationally-intensive. In such case, these libraries may use additional libraries (for example, the deep learning library Keras) to organize layers of a deep learning neural network model as a way to expedite the analysis of the LEAP data. As such, high-level neural network APIs like Keras or related libraries help to simplify the amount of code that is required to train a neural network, and may be used in cooperation with Theano, TensorFlow or other back-end frameworks. In another form, FPGAs are useful in training scenarios where the acquired data may or may not be ordered in the structured, array-based form that GPUs are accustomed to receiving. Regardless, GPUs and FPGAs are both constructed with numerous simpler cores compared to CPUs, and as such may be particularly well-suited for performing large-scale distributed processing tasks each involving relatively simple computations in a manner that CPUs (with their central-processing and management functionality) might not; such large degree of distributed processing is particularly beneficial in situations such as those associated with machine learning workloads. On the other hand, CPUs may be beneficial in situations where the libraries (such as Scikit-Learn) might not provide any GPU support and where the inclusion of such support might compromise the ability to function with differing hardware and operating system combinations.

The logic device 173 is configured to receive data from one or more sensors 121 and provide logic-based instructions to one or both of the wearable electronic device 100 and the system 1. As will be appreciated by those skilled in the art, the processor 173A forms the primary calculation functions of the logic device 173, and as such may be a singular unit such as the CPU, ASIC, GPU or FPGA discussed previously, or one of a distributed set of units. In addition to being resident on the wearable electronic device 100, one or more equivalent processors 173A may be present in other parts of system 1, including the server 400, as well as in signally-coupled computers or related components in the cloud 500. In one form, such processor or processors 173A may be programmed to perform machine learning functions, such as through a trained artificial neural network to determine, among other things, whether a patient associated with a particular wearable electronic device 100 is at risk of developing an infection or other adverse health condition, as will be described in more detail elsewhere within this disclosure. As such, the processor 173A may comprise or be coupled to memory 173B for storing not only programmed instruction sets, but also machine code that makes up such a neural network, K-means clustering or other machine learning model. In one form, bus 173C provides the electrical or signal connectivity for the various components within the logic device 173, and in one form may also provide the connections to and from the logic device 173 for the sensors 121, hybrid wireless communication module 175, battery 180 or other components within the wearable electronic device 100.

A structural description of the elements that make up the various computer software features is described next. Within the present disclosure, the organized collection of instructions and computer data that make up such software includes both API software and system software (such as operating system software and basic input/output that relates to the operation of the computer itself). In one form, the application software acts as an interface between a user and the system software, while the system software acts as an interface between the application software and the computer hardware. In one form, both the system software and the application software may be stored on memory 173B. Taken in their totality, such software provides programmed instructions that may be implemented on the logic device 173 to allow it to interact with the wearable electronic device 100, system 1 or other computer-based equipment in order to perform one or more of the LEAP data acquisition, processing, communicating, analysis and related functions disclosed herein. For example, source code created by a programmer may be converted into executable form as machine code 173E for use by the processor 173A; such machine code 173E is predefined to perform a specific task in that they are taken from a machine language instruction set known as the native instruction set that may be part of a shared library or related non-volatile memory that is specific to the implementation of the processor 173A and its particular Instruction Set Architecture (ISA). As with the previous discussion of the OSI and TCP/IP conceptual models on system 1 and wearable electronic device 100 to describe communication functional operations between adjacent layers, the ISA provides a conceptual model of the layer that describes the specific implementation of logic device 173 in such a way to correlate various programming functional operations. Thus, whereas the OSI model assumes seven conceptual layers, in one form the ISA is one of four, as above it are the application software layer and the system software layer, and below it the hardware layer. Among other things, the ISA is responsible for organization of memory and registers, data structures and types, what operations are to be specified, modes of addressing instructions and data items, as well as instruction encoding and formatting. Thus, the ISA acts as an interface between the hardware of the processor 173A and the system or application software through the implementation of the machine code 173E all of which are predefined within the ISA. As such, the machine code 173E imparts structure to the successive architectures of processor 173A, logic device 173, PCB assembly 170 and wearable electronic device 100, specifically in the form of a program structure that may be made up of a set of individual codes that together may be depicted herein as a flow diagram or related sequence that operates on the data structure that itself may be in one form an organized list, array, tree or graph of collected LEAP data. In one form, such a structural relationship exists between the processor 173A, the memory 173B and the machine code 173E regardless of whether additional computational activities (such as those associated with the machine learning algorithms and models that are discussed elsewhere in this disclosure) are or are not being used. As such, software instructions as embodied in the corresponding portion of the machine code configure the logic device 173 to provide the functionality as discussed herein.

With this understanding, the machine code 173E taken from the native instruction set in turn is arranged as a specific structural conduit to allow the processor 173A and memory 173B to communicate with particular system or application software. Accordingly, the predefined structure embodied in the machine code 173E allows them to become a part of the processor 173A in a necessary way such that together they can implement unique operations in response to the particular commands from the program structure; such operations may include data handling operations, arithmetic operations, control flow operations, addressing operations, logic operations and memory location operations, as well as others. In one form, the machine code 173E may be made to reside on memory 173B to facilitate cooperation with the processor 173A. In this way, the machine code 173E forms a machine-specific symbiosis with the processor 173A and memory 173B to delimit the operation of the logic device 173 through the creation of numeric values that can only have meaning imparted to them through this necessary relationship. More particularly, this allows the logic device 173 to—among other things—cause the sensors 121 and hybrid wireless communication module 175 of the wearable electronic device 100 to detect one or more forms of wearer-specific LEAP data and wirelessly transmit such data to a remote receiver using an LPWAN signal. Furthermore, this allows the logic device 173 to implement—or cooperate with—a machine learning classification model (such as a neural network, decision tree, Bayesian network or other approach as discussed elsewhere in this disclosure) to automatically perform predictions of potentially adverse health conditions for a person from whom one or more forms of the LEAP data is being acquired via the wearable electronic device 100. Likewise, the data that is being input to, manipulated by or output from the wearable electronic device 100 (including the data acquired by the various sensors 121), as well as any data that is operated upon by such a machine learning classification model, may be stored in memory 173B as data structures or related contents in the form of arrays (including vectors as their one-dimensional tensor variant, matrices as their two-dimensional tensor variant and tabbed matrices as three-dimensional and subsequent n-dimensional variants such as so-called notebook tabs), link lists, stacks, queues, tree structures, graphs, or the like. In this way, these multidimensional arrays differ from tensors in that while they are both types of objects, the tensor is a type of function with an array of numbers arranged on a regular grid with a variable number of axes while the multidimensional array forms a data structure that may be used to represent the tensor in a coordinate system, thereby giving it unique higher dimensional attributes.

Examples of data such as the LEAP data acquired by sensors 121 and stored within a portion of memory 173B may include raw data, processed data, time-stamped data, baseline data or the like. As such, the processor 173A and memory 173B cooperate to execute or otherwise use the data structures that correspond to the object being described or the event being performed. In particular, the CPU, ASIC, GPU, FPGA or related processors may execute program instructions by utilizing state information of such program instructions as a way to make the electronic circuitry associated with the logic device 173 into a special-purpose machine. Within the present context, such data structures form a concrete embodiment of a space that is formed within memory 173B by one or more particular abstract data types (ADT) that are used to specify the operations (that in one example are configured as the previously-mentioned program structures) that can be performed on the data structure. Diagrammatic representations of some of these data structures will be discussed elsewhere in this disclosure in conjunction with FIGS. 3A through 3K, as well as FIGS. 8, 12 and 13.

In one form, the CPU, ASIC, GPU or FPGA may include varying degrees of component integration, including that of the processor 173A and memory 173B in order to mimic system-on-a-chip configuration where scenarios such as those encountered in Bayesian-like decision making (that is, finding the likelihood of an event given historical or experiential information about similar events) for determining the health of a person based on a statistical analysis of the data gathered by the wearable electronic device 100 may be encountered. As such, various machine learning models (including the ones discussed in more detail later) may be executed by such a system-on-a-chip configuration, including for situations where cloud-based training (such as that implemented on system 1) is implemented. For example, the memory 173B may include random access memory (RAM), read-only memory (ROM) and flash variants as part of a computer readable medium that can store data structures, program modules, machine codes, native instruction sets, computer readable instructions or other data. Furthermore, the memory 173B may store a trainable machine learning algorithm that can be accessed and executed by the processor 173A in order perform a classification, regression or clustering-based model or analysis, as well as to update the state of the machine learning algorithm through corresponding updates to the memory 173B. In a particular form, the memory 173B can be configured to store in-memory analytics such that the machine learning algorithms and related models can be made to run in or be shared by memory 173B such that direct memory access of the analytics is enabled, thereby providing the ability to perform more real-time calculations on the acquired LEAP data. Likewise, the data being evaluated by the in-memory analytics can be spread across numerous parallel or distributed computing processors 173A as a way to divide larger amounts of data processing to further promote real-time activities.

The various sensors 121 may be advantageously located on or inside the wearable electronic device 100 such as in or on the housing 110, lateral extensions 111, 112, support tray 120 or the like. As such, the sensors 121 are non-invasive in that they need not be ingested or in percutaneous, subcutaneous or intravenous form. In one exemplary form, some sensors 121 that are shown generally as being embedded in support tray 120 may otherwise be placed anywhere in or on the wearable electronic device 100 in such a manner as to facilitate acquiring data that in turn may be used by a behaviorist model (including machine learning and CDS variants) that can run as a set of instructions on the system 1 in order to correlate, manipulate and transform the data into a form such that it can provide indicia of one or more LEAP traits associated the wearer of the wearable electronic device 100. In one form, the sensors 121 may act in conjunction with one another—as well as with instructions that are stored on a machine-readable medium such as memory 173B—to aggregate (or fuse) the acquired data in order to infer certain activities, conditions or circumstances. Such sensor fusion can significantly improve the operability of the wearable electronic device 100 by leveraging the strengths of each of the sensors 121 to provide more accurate values of the acquired data rather than if only coming from one such sensor 121 in isolation. For example, rotation-based gyroscopic measurement alone can lead to accumulating errors, while the absolute reference of orientation associated with accelerometers and magnetometers may be prone to high noise levels. By fusing the acquired raw data, the sensors 121 and accompanying data-processing instructions can filter the information in order to compute a single estimate of (six degree-of-freedom, 6 DOF) movement, orientation or position, which in turn simplifies downstream computational requirements. For example, such fusing may occur through integrating the orthogonal angular-rate data from the gyroscopes in order to provide orientation information, and then measuring the linear acceleration vectors within a particular wearer frame of reference and then rotating into wearer navigation coordinates using a rotation matrix as determined by the gyroscopes in order to remove gravitational effects.

In one form, feature extraction of acceleration-related data may take the form of normalizing individual Cartesian axis input vectors for gravity compensation. After being gravity-compensated, the acceleration data may be double-integrated in a manner similar to the gyroscopic data in order to provide suitable location or position information, while combining such measurements with other location-detecting means (such as GNSS or BLE, both as discussed herein) may be used to help avoid drift that may result from accelerometer bias error or gyroscope rotation error. Likewise, applying temporal filters may help to extract suitable movement feature information. By way of example, the movement data (which in one form may include falls, high or low gait speed or other forms of movement) acquired from the accelerometer and gyroscope may be used in order to determine whether sudden changes in motion are present; such an approach may include the calculation of derivatives, moving averages or the like in order to make it useful for one or more classification or regression machine learning models such as a decision tree-based or random forest-based classifier. Likewise, a portion of the machine code may be dedicated to controlling sampling intervals for various forms of the LEAP data, particularly those data signals that have significant temporal components such as activity data. In one non-limiting example, such sampling intervals can be made to take place in various fractions of a second (such as 0.01 second, 0.1 second or the like), various multiples of a second (such as 1 second, 2 seconds, 5 seconds, 10 seconds or the like) or as fractions or multiples of larger time intervals, depending on the accuracy needs associated with the data being acquired. In one form, both the presently-acquired data and any historical or baseline data (including those with significant temporal components as discussed herein) may be placed in memory 173B in order to provide appropriate signatures that correspond to the LEAP data for subsequent comparison or analysis purposes.

In one form, accelerometers, gyroscopes and related MEMs-based embodiments of sensors 121 are used to acquire baseline data for either an individual patient or from a group of patients the latter of which may be representative of a particular patient's demographics (such as by age, weight, gender, activity level, known health conditions or the like). For example, activity-based baseline data may include known inter-patient or intra-patient activity that is taken from previous activity signatures that are stored in memory 173B; such data may be either acquired through prior operation of the sensors 121 or taken from a historical record such as contained within a lookup table or the like. In one form, baseline activity data such as that acquired from sensors 121 that are in the form of accelerometers, gyroscopes and the like may be created through examples that can be correlated to known movements of the individual being monitored. For example, the individual may go through various sitting, standing, walking, running (if possible) and related movements that can be labeled for each activity where classification is desired. As will be discussed in more detail later, such labeling may be useful in performing supervised machine learning, particularly as it applies to training a machine learning model.

Understanding that location data is acquired significantly or exclusively through the hybrid wireless communication module 175, in one form, the sensors 121 may be placed into three major groups for the acquisition of the other components of the LEAP data. In one form, sensors representative of these other three major groups include environmental sensors 121A, activity sensors 121B and physiological sensors 121C. For example, activity sensors 121B that are used to collect activity data may include accelerometers, gyroscopes, magnetometers or the like, while the environmental sensors 121A used to collect environmental data may include those configured to acquire temperature, ambient pressure, humidity, carbon monoxide, carbon dioxide, smoke or the like, and the physiological sensors 121C used to collect physiological data may include those configured to acquire heart rate, breathing rate, glucose, blood pressure, cardiac activity, temperature, oxygen saturation, smells (such as total volatile organic compounds (TVOC)) or the like. Additional ones of sensors 121D used for other functions, such as cameras, microphones, wear-detection sensors or the like may also be included, and all such sensors and their related modalities are deemed to be within the scope of the present disclosure. As such, numerous combinations of sensors 121A, 121B, 121C and 121D may contribute to a fusion of the acquired data in order to improve the accuracy of the inferred event.

Moreover, the acquired data-which is received in raw form—may subsequently be labeled in order to correlate it to one of the LEAP data categories. Such labeled data may then correspond to an event that may be further grouped according to time, date, type of sensor or the like that may be stored in memory 173B. In one form, the events being stored in memory 173B may be in feature vector form, and may include activations and learned weights for each one of the sensors 121. The memory 173B may further store a training data set and a validation data set that in one form may be taken from the same acquired LEAP data set, as will be discussed in more detail later. In one form, the wireless communication sub-modules 175A, 175B and 175C may be formed independently of the sensors 121, while in another, each wireless communication sub-module 175A, 175B and 175C may include its own integrated, dedicated sensor or sensors (not shown). Furthermore, the placement of the sensors 121 relative to the various wireless communication sub-modules 175A, 175B and 175C as shown in FIG. 2F is for visual convenience, and that it will be appreciated that such placement—as well as that of other components of the wearable electronic device 100—may be dictated by utilitarian concerns, and that all variants of such placement is deemed to be within the scope of the present disclosure.

Relatedly, the LPWAN-based RF signal transmission features (as well as the GNSS and BLE receiving features) may be embodied in various forms, including as a device, module or chip, and that all such variants are deemed to be within the scope of the present disclosure. Regardless of the manner in which the various sensors 121 and wireless communication sub-modules 175A, 175B and 175C are packaged within the housing 110 or support tray 120 of the wearable electronic device 100, the transmission of data signals, control signals or the like from the third sub-module 175C to the gateway 300, backhaul server 400 or related receiver in the system 1 may be made in a direct wireless manner without the need for intervening near-field wireless communication components and attendant complexity. For example, the use of LPWAN allows the wearable electronic device 100 to avoid the extra architectural complexity associated with master/servant relationships such as those where the collected data must first be transmitted a short range through wearable signal relay units, repeaters or the like, even if such units or devices are situated near the data collecting sensor (such as those situated on another part of the body of the individual being monitored). Thus, by forming the various sensors as part of the wearable electronic device 100 (such as by direct mounting to the device's chassis, substrate, housing 110 or the like, or indirectly through a PCB or other component that is itself directly mounted to the chassis, substrate or housing 110), size, weight, packaging and related architectural efficiencies can be realized. Moreover, portions of the wearable electronic device 100 that correspond to the first wireless communication sub-module 175A—while used primarily for receiving BLE beacon 200 signals to determine location—may also be used to receive configuration parameters and firmware updates from a suitably-equipped mobile device such as that which will be discussed in conjunction with FIGS. 4 and 5.

In one form, some of the electronic components of the wearable electronic device 100 include:

- additional memory (such as that associated with EEPROM Serial-I2C 10K-bit 10K×1 2.5V/3.3V/5V 8-Pin UDFNT/R, as manufactured by Microchip/Amtel as part number ATECC508A-MAHDA-T);
- the wireless charger 600 (such as that associated with Qi (WPC) Compliant Highly Integrated Secondary-Side Direct Lithium Ion Charger, 4 V Min Input, 28-pin DSBGA (YFP), Green (RoHS & no Sb/Br, as manufactured by Texas Instruments as part number BQ51050BYFPR);
- a haptic motor (such as that associated with VIBRATION MOTOR COIN 3V FLEX, as manufactured by Jinlong Machinery & Electronics as part number C0720B001F);
- a capacitive sensing controller chip (such as that associated with CAPSENSE EXPRESS CONTROLLERS WITH SMARTSENSE AUTO-TUNING 16 BUTTONS, 2 SLIDERS, PROXIMITY SENSORS, as manufactured by Cypress as part number CY8CMBR3108-LQXIT);
- one or more accelerometers (such as that associated with microelectromechanical (MEMS) Digital Output Motion Sensors: Ultra-Low-Power High-Performance 3-Axis "Femto" Accelerometer, 1.71 to 3.6 V, −40 to 85 degrees C., 12-Pin LGA, RoHS, Tape and Reel, as manufactured by STMicroelectronics as part number LIS2DH12TR);
- a battery level detection chip (such as that associated with ether IC FUEL GAUGE LI-ION ICELL 8TDFN or IC COMPARATOR SGL LP 4UCSP, both as manufactured by Maxim as part numbers MAX 17048G+ and MAX9063EBS+TG45 respectively);
- a BLE radio and microcontroller module to correspond to the first wireless communication sub-module 175A (such as that associated with MOD BLE 4.2 NORDIC NRF52832 SOC, as manufactured by u-blox as part number nINA-B111);
- a GNSS receiver module to correspond to the second wireless communication sub-module 175B (such as that associated with Module: GPS GLONASS; ±1.5m; I2C, SPI, UART; −165 dBm; −40° C. to −85° C.; SMD, as manufactured by Origin GPS as part number ORG1510-MK04);
- a LoRaWAN™ tx/rx module to correspond to the third wireless communication sub-module 175C (such as that associated with RF TXRX MODULE ISM<1 GHZ SMA ANT, as manufactured by Microchip as part number RN2903-I/RM095);
- a signal expander (such as that associated with IC PORT EXPANDER 18BIT 25FIPCHIP, as manufactured by STMicroelectronics as part number STMPE1801BJR); and
- a fast charging battery 180 (such as that associated with a lithium polymer version as manufactured by Alium as a custom-designed part).

It will be appreciated that these components are merely exemplary, and that a greater number or a lesser number of components—as well as different components—may be used, depending on the sensory, processing, data storage, wireless communication or other needs of the wearable electronic device 100. For example, solar cells 141 may be present in certain embodiments of the wearable electronic device 100 to provide electric power or other source of electric current in a manner generally similar to battery 180. In such embodiments, the solar cells 141 may be used as a renewable source of power that would allow the wearable electronic device 100 to operate for longer continuous time periods. In one form, such solar cells 141 could be formed as part of the top plate 130 or over the strap portion that covers the antennas 140. In another form, electric power sufficient to power the wearable electronic device 100 may be harvested from the motion of the person wearing the wearable electronic device 100 during person movement, for example, by swinging his or her arm while walking, or from the thermal energy generated the person wearing the wearable electronic device 100, such as through conductive heat exchange from the skin or other part of the body of the person to the wearable electronic device 100, including when the configuration is similar to the one depicted in FIG. 2I that will be discussed in more detail later.

In one form, the hybrid wireless communication module 175 is a wireless communications protocol stack that establishes standardized rules for (among other things) wearable electronic device 100 authentication, data representation, signaling, co-existence and error detection. Within the present context, the hybrid wireless communication module 175 that includes numerous wireless communication sub-modules 175A, 175B and 175C may be embodied in different forms as a way to receive and send RF signals. In one form, each of the various wireless communication sub-modules 175A, 175B and 175C may be formed as disparate, relatively discrete systems that are distinguished from the others by the particular components or construction, such as those mentioned in the previous paragraph that may be dictated by the form of communication (such as by frequency, range, mode of propagation or the like) that they employ. In another form, each of the various wireless communication sub-modules 175A, 175B and 175C may share some or all common circuitry, antennas 140, and other features as part of a highly-integrated module for configurations or packaging where it is desirable to avoid component redundancy. It will be appreciated that the choice of how the wireless communication sub-modules 175A, 175B and 175C are configured within the larger hybrid wireless communication module 175 may be dictated by—in addition to the aforementioned packing requirements—the particular signals or data being processed, received or transmitted, and that all such variations are deemed to be within the scope of the present disclosure. The hybrid wireless communication module 175 includes—or works in conjunction with—one or more antennas 140 to perform the wireless transmitting and receiving functions between the RF signals and the various wireless communication sub-modules 175A, 175B and 175C. In addition to a flex-based architecture, the antenna 140 may in one form be configured as a microstrip, patch, shorted patch, planar inverted-F (PIFA), printed, diversity/dipole or any other form-factor suitable for use with the wearable electronic device 100. For example, in an embodiment where the wearable electronic device 100 is configured as a wrist-wearable device (such as depicted in FIGS. 2A through 2H), the antenna 140 may be encased within the laterally-extending ends 111, 112 of the housing 110 as a flex antenna 140.

In one form, the various communication wireless communication sub-modules 175A, 175B and 175C may include corresponding chips or chipsets such as a BLE chipset, a GNSS chipset, WiFi chipset, LPWAN chipset or the like. In one form, chipsets used to effect a LoRa-based configuration of the third communication sub-module are manufactured by Semtech Corporation of Camarillo, Calif., and may include (among others) the SX1261, SX1262 or SX1268 chipsets. LoRaWAN™ wireless connectivity between the wearable electronic device 100 and the gateway 300, network server 410 and application server 420 and related equipment that make up the remainder of system 1 may be achieved through a suitable lightweight publish/subscribe messaging transport IoT connectivity protocol, such as a Constrained Application Protocol (CoAP) or a MQTT (Message Queue Telemetry Transport) protocol. CoAP mimics the HTTP that is used for transmitting web pages, while an MQTT broker-based approach has been widely adopted for mobile IoT applications where limited data packet bandwidth or small code footprint remote location connection is required. In addition, security can be enhanced through the use of secure socket layers (SSL), transport layer security (TLS) or the like. By using an orthogonal sequence spread spectrum mode of transmission such as that associated with the CSS with a spark-gap transmitter as embodied in the chipsets mentioned previously and the previously-discussed star topology, significant geospatial coverage may be achieved with a relatively modest investment in wearable electronic device 100 and gateway 300 or related base station infrastructure. For example, one or more of the previously-discussed gateways 300 may be placed through a wide area (such as various places within a city) in order to take advantage of the range of the wearable electronic device 100.

In addition to allowing the wearable electronic device 100 to avoid the extra architectural complexity associated with master/servant relationships as previously discussed, the use of LPWAN with CSS transmission, multiple sequences and associated star topology promotes a more centralized, simple way to receive and transmit the various data forms, thereby further improving the way that both the wearable device 100 and the associated system 1 may function, especially when the system 1 may be operating with a limited link budget. Moreover, the very lower power settings of the LoRaWAN™ protocol as discussed herein are particularly beneficial for the sensors 121 and the wearable device 100 that send small packets of data intermittently. In particular, because of LPWAN's high link budget, the wearable electronic device 100 can send the acquired data at extremely low data-rates over extremely long ranges. For example, receiver sensitivity may be as low as −136 dBm, which when combined to an output power of +14 dBm provides for a link budget of up to 150 dB. This in turn can lead to the approximately 10 miles (or theoretically, up to between 13 and 14 miles) of transmission range in direct line-of-sight links and up to roughly 1 to 3 miles in urban environments (where the transmitted signal going may be made to pass buildings and related structures). In one form, to promote longer battery 180 life, each packet (as will be shown and described in conjunction with FIGS. 3A through 3K) being sent through the third wireless communication sub-module 175C is relatively small, corresponding to eighty eight bits (i.e., eleven bytes). Likewise, the total amount of data being sent over a 24 hour period may be as little as about 1000 bytes in situations where the individual being monitored is relatively sedentary, and more if the individual is relatively ambulatory. Moreover, in situations where so-called "true" RTLS is desired, the message-sending may need to take place with enough frequency to ensure adequate coverage. By way of example in such a circumstance, messages may be sent about once per second; in such a situation, this would amount to 86,400 seconds (in a day) times eleven bytes, leading to up to roughly 1,000,000 bytes in a 24 hour period. Furthermore, in order to protect against side channel attacks, all messages have a LoRa payload length of this eleven byte transmit packet size. Messages that don't require all eleven bytes may further pad unused bytes with the hexadecimal 0x00. In one form, the third wireless communication sub-module 175C may also include various additional components with which to achieve its LPWAN-based communications; such additional components may include a clock or timer, antenna, analog-to-digital converter, digital-to-analog converter, message generator, logical channel selector, packetizer, governor, physical channel random selector or the like. Moreover, the third wireless communication sub-module 175C may be configured as a simplex or half-duplex device. As such, the wearable electronic device 100 is able to operate in long-range, low-power situations while remaining connected to the internet or a related large-scale network.

Referring with particularity to FIG. 2H, in one form, the nurse call button 131 is formed on an upper surface of the top plate 130. Within the present disclosure, although the nurse call button 131 includes the term "nurse" in its name, it is understood that such terminology is for semantic purposes, and that the button is not limited to sending a wireless communication to a nurse, but to any other caregiver that through contractual or duty-bound relationship is tasked with providing care or similar assistance to the individual associated with the wearable electronic device 100. In addition to the nurse call button 131, at least a pair of opposing lateral edges 132 of the top plate 130 may be made from a transparent or translucent material such that a light-emitting diode (LED) source that may be formed on the PCB 170 assembly can be made to pass through the opposing lateral edges 132 in order to have an outward-illuminating effect. In one form, light pipes may convey the light from the LED source to the opposing lateral edges 132. Although the top plate 130 is shown with an activatable nurse call button 131, it will be appreciated that the wearable electronic device 100 may be configured with different top plates 130. Such variants may include a frame-like top cover that can contain a family picture, a fidget plate or other features. For configurations where the nurse call button 131 is an active device, in one form, a small magnet may be included as part of the circuitry to have a capacitance sensor. Likewise, in a configuration where the nurse call button 131 feature is not installed, there is no capacitance sensor or magnet that is sensed such that the nurse call feature of the wearable electronic device 100 is disabled. In operation, when the nurse call button 131 is activated, a portion of the circuit associated with the nurse call button 131 may—through the cooperation of the third wireless communication sub-module 175C—transmit an alert or related request for assistance over the low-power wide area network signal such that the request may be received by a suitably-equipped remote computing device 900 that will be discussed in more detail in conjunction with FIGS. 4, 5 and 9. Furthermore an API may be included on the one or more remote computing devices 900 in order to display additional information, such as inter-room and intra-room data, where such data may correspond to the architectural plans or engineering drawings of a particular dwelling such as a home, assisted living facility or the like.

If an individual who is associated with the wearable electronic device 100 is in distress, he or she presses the nurse call button 131 (shown with particularity in FIG. 2H) such that an alert may be generated and sent to the remote computing device 900 to indicate one or more of the individual's identification, location and time of request. In another form, a passive variant of the signal being sent from the nurse ID beacon 200C in response to activation of the nurse call button 131 may be provided. This passive variant may emit a signal either continuously or at intermittent times as a way to show when a nurse or other caregiver associated with a particular one of the nurse ID beacons 200C is in close proximity to a patient that is associated with a particular wearable electronic device 100. As will be discussed in more detail in conjunction with providing one or more of a clinical diagnosis and CDS for situations where the acquired data indicates a worsening of a health condition of the individual associated with the wearable electronic device 100, the nurse call button 131 may be used to send an alert in a roughly comparable manner over a third wireless communication sub-module 175C that makes up the hybrid wireless communication module 175 that will be discussed in more detail in conjunction with FIG. 2F. In such an approach, a generated alert may be sent over the third wireless communication sub-module 175C to at least one caregiver that has the suitably-equipped remote computing device 900, thereby having the alert function in a manner similar to when the person associated with the wearable electronic device 100 has wandered or otherwise moved to a location that is not permissible or otherwise not advisable. In one form, the nurse ID beacon 200C may be situated on the remote computing device 900.

In one form, when the patient presses the nurse call button 131, the first wireless communication sub-module 175A can be awoken or otherwise activated in order to detect the presence of an identifier transmission from one or more nearby nurse ID beacons 200C that are installed in or otherwise associated with a corresponding one of the remote computing devices 900. In addition, an LPWAN-based signal is transmitted through the third wireless communication sub-module 175C to the gateway 300 and then on to one or both of the network server 410 and application server 420 for subsequent relay to indicate that the individual needs help, as well as provide a location of the individual to a caregiver. The communication from the application server 420 to facility staff (nurses, aides, management or other personnel that is uniquely identified with a particular one of the nurse ID beacons 200C) informs the facility staff that a patient to whom the wearable electronic device 100 is attached is in need of assistance, while a location of the patient based on determinations made by one or the other of the first and second wireless communication sub-modules 175A, 175B is also provided. When a staff member or other caregiver reaches the patient, they can clear the call by depressing the nurse call button 131, as this instructs the tracker feature of the first wireless communication sub-module 175A to start searching for the transmitted identifier from the nurse ID beacon 200C that is being worn by the staff member. Because the transmit power of the nurse ID beacons 200C is relatively low, the close proximity of the particular nurse ID beacon 200C of the caregiver that responded to the signal corresponding to the activated nurse call button 131 will be understood by the wearable electronic device 100 to be the only one permitted to cancel or otherwise close out the request for assistance that was made by the patient through the nurse call button 131. In another form, additional simplicity for the patient may be provided by not having to have the nurse or related caregiver depress the nurse call button 131, but instead clear the alert merely by being in such close proximity to the patient, or by waving near or touching to the wearable electronic device 100 by the nurse ID beacon 200C.

In one form, the wearable electronic device 100 may include a lock (not shown) that can prevent the patient from removing the wearable electronic device 100. The lock, which is disclosed in co-pending U.S. patent application 62/761,961 (the '961 application) and entitled WRISTBAND LOCKING MECHANISM, WRISTBAND, WEARABLE ELECTRONIC DEVICE AND METHOD OF SECURING AN ARTICLE TO A PERSON that was originally filed provisionally on Apr. 12, 2018 the contents of which are hereby incorporated by reference, may be secured using a latch mechanism, magnets, RFID technology, a wireless signal, or any other mechanism that allows only a caregiver or authorized personnel to remove the wearable electronic device 100.

In certain embodiments, the wearable electronic device 100 may include a screen formed in the top plate 130 such that the screen is capable of displaying information collected by wearable electronic device 100, including any alerts generated. Such information may include, for example, patient's location, information collected by any sensors 121, or information pre-programmed into the memory of the wearable electronic device 100 such as the patient's name, address or health information (e.g., illnesses, allergies, medication). In a similar manner, at least some forms of data and instruction processing, memory and related data storage functions that make up a portion of the wearable electronic device 100 may be dedicated to—or in some circumstances form a part of—the sensors 121 such that at least some data processing or manipulation takes place in an edge-like, autonomous manner (that is to say, without regard to the nature of the system 1 or other information transmission and processing backhaul).

Moreover, the acquired LEAP data may be sent from the wearable electronic device 100 in general (and the third wireless communication sub-module 175C in particular) to the gateway 300 or other parts of the system 1 in substantially unprocessed form, in substantially processed form or in partially processed form. For example, data in substantially unprocessed form may include that which is raw in that little or no CPU or other processor-based computation or related manipulation of such data takes place prior to being passed from the wearable electronic device 100 to the gateway 300 or other parts of the system 1, whereas data in substantially processed form may include that which experiences one or more transformative changes (including one or more of cleansing and related preprocessing, extraction and other manipulation as discussed elsewhere within the present disclosure) that through the CPU. GRU, ASIC or FPGA and associated algorithmic intelligence places the data in different or better form for subsequent predictive analytics or related use. Thus, in one form, a machine code that is part of the set of machine codes that are stored in the non-transitory computer readable medium (that is to say, memory 173B or the like) may instruct the third wireless communication sub-module 175C to transmit some or all of the acquired wearable electronic device LEAP data without any significant on-device cleansing or related preprocessing, extracting, training, testing or analysis, while in another form, such instructing may be performed after another portion of the set of machine codes first conduct some or all of such cleansing, preprocessing, extracting, training, testing or analysis locally (that is to say, on the wearable electronic device 100) prior to transmitting the data to the gateway 300, backhaul server 400 or cloud 500. It will be appreciated that both variants are within the scope of the present disclosure.

The wearable electronic device 100 may also be equipped with notifiers configured to provide the patient with any alert generated by the processor 173A. These notifiers can be in the form of any technology that would catch the attention of the patient or caregiver to bring attention to the fact that he or she is aware that the processor 173A has received information that may correspond to a change in status of the patient, as well as other alerts, such as whether the patient could be in danger. Some exemplary notifiers include vibration (i.e., haptic) motors, LED lights and an audio speaker. Thus, in one form, the wearable electronic device 100 is to be able to play spoken voice, music, or sound that may be used to help comfort an elderly wearer of the device, particularly a wearer who may be suffering from dementia. This feature can also be used to produce an audible alarm when a wearer of the device is passing a specific choke point, such as walking out a door in a manner similar to RFID functionality. Thus, when a patient with the wearable electronic device 100 is close to a specific beacon such as one or more of the previously-discussed elopement beacons 200B, the wearable electronic device 100 sends an event signal over the internet to the cloud 500 to play an audio file on the speaker. Likewise with displayed images, such files may be customized with the image or sounds of a person or persons familiar to the patient, which in turn may have a soothing, calming effect, as well as heighten the cognitive state of the patient. Relatedly, the wearable electronic device 100 may be configured to allow for caretakers, family members and other responders to communicate directly—and in real-time—with the patient through the display, audio speaker, audio microphone or the like. In one form, such a message may also be played through one or more of the WiFi speakers 800 that may be placed in a convenient location in the patient's home, apartment or related dwelling. Within the present context, terms such as "real-time", "near real-time" or the like are meant to include those where any delays in the processing and RF transmission of data are substantially imperceptible to a user. As such, delays that are measured in no more than a few seconds are deemed to be real-time, whereas delays that are measured in minutes, hours or more would not be deemed to be real-time. Likewise, the terms "real-time", "near real-time" or the like when used in conjunction with the acquisition of one or more forms of LEAP data are meant to distinguish such data from that acquired earlier for baseline or historical purposes. As with the use of these terms in conjunction with the alerting and response times between a monitored individual and his or her caregiver as mentioned above, the meaning will be apparent from the context.

Referring with particularity to FIG. 2I, compared to the stand-alone, wristband-based platform with the rigid structural housing 110 of FIGS. 2A through 2H, FIG. 2I depicts a flexible platform 190 that can be worn, imbedded in or affixed to the patient's skin, clothing or accessories such as belts, shoes, hats, eyeglasses or the like. For example, the wearable electronic device 100 can be configured as an adhesive bandage-like device to define a conformal skin patch or related surface-level device. Within the present disclosure, a bandage or bandage-like flexible platform 190 or related configuration is meant to include all substantially conformal adhesive-based skin patches, regardless of how temporary the adhesion. For example, in one form, the adhesive properties may be such that when the wearable electronic device 100 is embodied as a bandage, it is configured for short-term use, such as over the course of a few hours or a day or two, while in another form, it may be configured for longer use, such as the duration of the life of the battery 180, or even longer, if needed. Likewise, when the wearable electronic device 100 is embodied as a bandage, the various electronic modules, chips, systems and related components (such as those shown in FIG. 2F and that may include one or more of the previously-mentioned processor 173A, memory 173B, bus 173C, input/output 173D and machine code 173E that in one form is stored on memory 173B), as well as a presently-shown display 173F, may be substantially encased in order to give the wearable electronic device 100 water-proof (or at least water-resistant) properties. Besides the wristband-based and bandage-based embodiments shown and described herein, it will be appreciated that other platform configurations (not shown) are within the scope of the present disclosure, including those that may be fastened, clipped, pinned or otherwise secured indirectly to the patient (such as through an article of clothing) or otherwise secured directly to the patient, the last of which may include a subcutaneous implant. In the latter form depicted in FIG. 2I, a resiliently-deformable skin-adaptive layer may be used for skin contact and adhesion, while one or more layers may be formed on the skin-adaptive layer to form a data-collection circuit layer and one or more containment or packaging layers. The circuit layer may be formed by known methods such as textiles, thin-film printing (including ink jet, flexography, screen, gravure or the like), and may include circuitry configured to include one or more of an accelerometer, gyroscope, temperature sensor, strain moisture sensor, acoustic sensor, inertial sensor, optical sensor, pressure sensor, chemical sensor or the like.

Electronically, the logic device 173 and the corresponding portion of the machine code may be configured to take context-based scenarios into consideration. In particular, a database of the acquired or baseline signatures associated with a particular form of the LEAP data that is stored in memory 173B may be adjusted to take into consideration the location of the wearable electronic device 100 on an individual being monitored. As such, in situations where the wearable electronic device 100 is affixed to an individual's wrist (such as when configured as a wristband, watchband or the like), it may produce different activity, environmental or physiological data signatures than when embodied in a belt, hat, shoe or other article of clothing. Such context-specific information may be adjusted through manipulation of the data by a portion of the machine code in order to enhance data accuracy. It will be appreciated that where the wearable electronic device 100 includes subcutaneous, on-skin or skin-attachable features (such as, but not limited to, one or more of the sensors 121), the platform (and computational architecture) may be simplified to minimize complexity, reduce volume or weight or to offload some computational activities.

As can be seen from the configurations of both FIGS. 2H and 2I, improvements in the architecture of the wearable electronic device 100 include a lightweight, small wrist-wearable or thin profile form factor that permits unobtrusive addition to a person being monitored. Moreover, the use of a power supply in the form of a coin lithium battery 180 combines long life with a thin profile that is easier to integrate into the main housing assembly 110. In addition, low power supply consumption is achieved by removal of a cellular, GSM, 3G, 4G (including LTE, LTE-A and LTE-A Pro variants) or upcoming 5G connection and its emphasis on high-throughput machine-to-machine ($M_2M$) rather than person-to-person ($P_2P$) communication, as well as through controlling the wearable electronic device 100 to be in a sleep mode during periods of inactivity, as well as through the use of the aforementioned Class A ALOHA-style communication for its LPWAN wireless communication sub-module 175C. As previously mentioned, the wearable electronic device 100 includes the third wireless communication sub-module 175C; in one form, the wearable electronic device 100 may be configured to provide Class A, ALOHA-style asynchronous transmission that can support bidirectional communication (although the latency and power requirements may differ depending on whether the wearable electronic device 100 is in an uplink mode or a downlink mode). In Class A operation, the wearable electronic device 100 does not wait for a particular time with which to communicate with the gateway 300, but instead transmits when data is ready to be sent. Such mode of communication is beneficial in that the wearable electronic device 100 in general and one or more of its wireless communication sub-modules 175A, 175B and 175C in particular may remain in a so-called "sleep" (i.e., dormant) mode until needed, at which time it can be awoken; as such, an uplink message may be sent at any time, after which a pair of receive windows may be opened at specified times such that the backhaul server 400 can respond to either window. This in turn helps to contribute to a low duty cycle for reduced battery 180 power consumption. As discussed elsewhere in the present disclosure, so-called sensor events that may trigger an awakening from the sleep mode include a waking event or a set period of time, where the former includes things such as movement that exceeds a threshold, receipt of an external control signal or the like.

Furthermore, long range transmitting in the wireless communication sub-module 175C of the hybrid wireless communication module 175 allows for better system 1 data collection and associated backhaul functionality, where the range may be more than ten miles with direct line-of-sight and over one mile in urban and related multi-bounce environments. In one form, the data that is received by the gateway 300 uses frequency shift keying (FSK) via the CSS so that the data packets received from the wearable electronic device 100 arrives in chirp-like digital representation symbols that are subsequently parsed down to the frequency domain and then modulated. In one form, the modulation rate may be reduced while simultaneously keeping the same transmit power; this in turn promotes stronger transmitted signals from the third wireless communication sub-module 175C. The continuous interaction between the wearable electronic device 100 and the gateway 300 allows the data transmission to effectively hop to other frequency channels to more efficiently take advantage of limitations imposed by power, speed, duty cycle and range of the wearable electronic device 100. In addition to efficiency improvements made possible by the FSK shifting of the input signal frequency, adaptive data rate (ADR) may be used to have the wearable electronic device 100 communicate with the network server 410 to boost the data rate through analysis of recently-sent messages to determine if range and data transfer rates may be traded off against one another.

Furthermore, the hybrid architecture takes advantage of the low current requirements of the LPWAN mode of signal transmission, which in turn allows a more compact prismatic-shaped battery 180 (as shown) or a "coin cell" battery (not shown) to be used rather than one or more volumetrically inefficient batteries such as "AA" sized batteries. In one form, the wearable electronic device 100 can selectively enable or disable certain ones of the hybrid wireless communication sub-modules 175A, 175B or 175C upon detection of certain forms of connectivity between the wearable electronic device 100 and the BLE beacons 200. For example, the sleep mode (or at least a reduced capacity mode) can be adopted to avoid using GNSS location sensing as long as lower-power modes of communication (such as the BLE-based approach of the hybrid wireless communication second sub-module 175B) are being used. In one form, the wearable electronic device 100 has a battery 180 life of at least about three days. In sleep mode, the hybrid wireless communication module 175 may consume only several microamps of current, while when transmitting or receiving only consuming no more than about 150 milliamps, after which it returns to its sleep mode. Significantly, this leads to an average current consumption of no more than about 1 milliamp, depending on the broadcast interval and transmit power setting.

Referring next to FIGS. 3A through 3K, a notional depiction of the use of a LoRa-based LPWAN to communicate between the wearable electronic device 100 and the gateway 300 and downstream system 1 components (including backhaul server 400 and cloud 500) to form an IoT device is shown for uplink (FIG. 3A) and downlink (FIG. 3B), as well as the data format packets (FIGS. 3C through 3K) for the various LPWAN-related communication functions of the wearable electronic device 100. As can be seen, in one form, much of the control activity may be conducted in other parts of the system 1, including the backhaul server or servers 400, as well as with the cloud 500. Within the LoRaWAN™ address space, a number of preprogrammed identifiers, keys or addresses with routing information may be used in order to establish communication between the wearable electronic device 100 and the gateway 300 and backhaul server 400. As such, participation in a LoRaWAN™ network may achieve additional security by having each wearable electronic device 100 be personalized and individually activated. In one form, this may be achieved in a multi-step process known as over-the-air activation (OTAA), where the wearable electronic device 100 must follow a key-based join procedure prior to participating in data exchange activity. For example, the wearable electronic device 100 may first be personalized with a device identifier key DevEUI, an application identifier key AppEUI and a 128-bit AES encryption key AppKey. Second, a pair of MAC messages are exchanged with the network server 410 in order to initiate a join request and corresponding join accept. Third, the wearable electronic device 100 sends the join request message that includes the application and device identifier keys AppEUI and DevEUI of the wearable electronic device 100 followed by a random value DevNonce that is assigned to the wearable electronic device 100 in order to avoid replay attacks. Fourth, the join request message can be transmitted using a suitable data rate and frequency hopping sequence across the specified join channels. Fifth, the network server 410 will respond to the join request message with a join accept message. Sixth, after activation, the wearable electronic device 100 is configured with three additional keys known as a device address key DevAddr, a network session key NwkSKey and an application session key AppSKey along with the application identifier key AppEUI. The network session key NwkSKey for control and the application session key AppSKey for data act as security enhancements that are made known solely to both the wearable electronic device 100 and the application server 420; these two keys allow the signature and secure encrypted transmission of the data and information packets. Besides OTAA, activation may take place through a process known as activation by personalization (ABP), although OTAA is often used because of its higher degree of security. In one form, the network session key NwkSKey is used by both the network server 410 and the wearable electronic device 100 to calculate and verify a message integrity code (MIC) of all data messages as a way to ensure data integrity. In one form, the application session key AppSKey is used by both the network server 410 and the wearable electronic device 100 to encrypt and decrypt the payload field of the various application-specific data messages.

In one form, the device identifier key DevEUI is a 64 bit global identifier that is assigned to each wearable electronic device 100 by the chip manufacturer. The device address key DevAddr is a 32 bit non-unique device address assignment that is responsible for all communication between the wearable electronic device 100 and the application server 420 where some of the 32 bits are fixed for a particular network (for example, an open IoT LoRaWAN™ device such as the Things Network or the like) and the remainder of the bits can be assigned to individual ones of the wearable electronic devices 100 through either the OTAA or ABP activation approaches mentioned previously. The application identifier key AppEUI is a 64 bit global identifier that addresses space and uniquely identifies the application provider (for example, the owner of an assisted living facility or—in the case of an installation in a private residence—the wearable electronic device 100 manufacturer or retailer) of the wearable electronic device 100 such that when an application is created, the network server 410 allocates the application identifier key AppEUI from a predefined address block. In one form, the application identifier key AppEUI is used along with the device identifier key DevEUI to derive the network session key NwkSKey, application session key AppSKey and the device address key DevAddr. As with the device identifier key DevEUI, a comparable key known as the gateway identifier key GatewayEUI may be implemented in a similar way (along with the equivalent keys AppKey and AppEUI) in order to register the gateway 300 on the particular network. As with the application identifier key AppEUI, the gateway identifier key GatewayEUI is a 64 bit unique and embedded identifier, now specifically for the gateway 300. Some of these keys may be depicted as message headers that may be used by various APIs of certain devices that are either used in conjunction with the wearable electronic device 100. For example, the LoRaWAN™ message header "uint64_t" that corresponds to the device identifier key DevEUI or the "uint32_t" that corresponds to the device address key DevAddr may be used to identify which wearable electronic device 100 selected from numerous wearable electronic devices 100 the message was received from. Keys and message headers such as these are helpful in situations, such as an assisted living community or other multi-person dwelling, as a way to more particularly identify acquired data with a corresponding individual.

Various data formats (also referred to as packet structure byte maps in a manner similar to a memory map or related data structure) are shown for communication of information between the wearable electronic device 100 and the system 1. These data formats include BLE beacon 200 data format (FIG. 3C), GNSS 10 data format (FIG. 3D), battery 180 data format (FIG. 3E), nurse call button 131 data format (FIG. 3F), nurse response data format (FIG. 3G), band worn data format (FIG. 3H), band removed data format (FIG. 3I), no movement data format (FIG. 3J) and movement data format (FIG. 3K) all of which are shown within each eleven byte data packet framework. These packets of data may include the control portion and a payload (or user) portion such that when sent over a packet switching or a related network, the data placed in the header (i.e., the control portion) may be used to direct the packet to its internet or cloud 500 (or other system 1) destination and perform error detection to allow substantive operations on the payload portion of the data. In one form, Internet Protocol version 6 (IPv6) and its 128-bit address may be used to locate and identify various computers on one or more networks, as well as to direct data traffic over internet or cloud 500.

In one form, the system 1 achieves wireless communications between the wearable electronic device 100 and the application server 420 using the LoRaWAN™ version of the LPWAN specification. The wearable electronic device 100 operates as a Class "A" device using a Data Rate 0 (zero), although it will be appreciated that the other data rates (such as those disclosed herein) may also be used. The LoRaWAN™ specification has a number of defined fields in the message headers that are used by the application. For example, the LoRaWAN™ port field may be used to identify the type of message that is being received by the application server 420, while the LoRaWAN™ payload field contains the message data. In one form, various messages are supported, including the previously-discussed data of FIGS. 3C through 3K each of which will be discussed in more detail as follows.

Referring with particularity to FIG. 3C, the LoRaWAN™ beacon 200 data format is shown, and will have a port number of 0x01, as well as corresponding from one to three BLE beacons 200 that are currently visible to the wearable electronic device 100; the message corresponding to this portion of the data format will be issued by the wearable electronic device 100 as needed. The BLE beacon 200 entries will be filled in the order of 1, 2 then 3. Unused entries will have a strength of 0xff, while the message port is 0x01. The number of seconds the message may be held before being sent to the LoRa portion of the hybrid wireless communication module 175 (specifically, the third wireless communication sub-module 175C) module is referred to as the delay, where 255 is the maximum value as measured in seconds. The UUID identifiers may be used for each BLE beacon 200, presently represented by uuid1, uuid2 and uuid3. Depending on the choice of firmware module, either the actual RSSI is reported, or the estimated distance is reported from each BLE beacon 200 to the wearable electronic device 100. In situations involving the former, received signal strength (such as RSSI-measured signals) are represented by strength1, strength2 and strength3, where the higher the number is correlated to the wearable electronic device 100 being farther away from the BLE beacon 200. An entry of 0xFF specifies a blank beacon entry in the message, while an entry of 0xFE represents the maximum value of 254 or more. In one form, the defined flags values for a particular message may be set as shown in TABLE 1 to determine which of the BLE beacons 200 are configured as elopement beacons 200B.

TABLE 1

| Flag Value | Associated BLE Elopement Beacon |
|---|---|
| 0 | None |
| 4 | Beacon 1 |
| 2 | Beacon 2 |
| 1 | Beacon 3 |
| 6 | Beacons 1 and 2 |
| 5 | Beacons 1 and 3 |
| 3 | Beacons 2 and 3 |
| 7 | All |

Referring with particularity to FIG. 3D, the LoRaWAN™ GNSS 10 data format is shown. The message will have a port number of 0x02, and will contain the location of the wearable electronic device 100 relative to a GNSS 10 fix. This message will be issued by the wearable electronic device 100 as needed. The message port will have the 0x02 entry. The delay is the part of the message similar to that as previously described in the LoRaWAN™ beacon 200 data format of FIG. 3C. The latitude/longitude entry corresponds to the coordinates of the GNSS 10 fix. The data is encoded as a 32 bit signed integer; for example: 0xFAC159DA=− 87.991846. The accuracy corresponds to the number (in meters) for which the wearable electronic device 100 enjoys at least a 90% confidence level of its location. For the fix, the NMEA GGA "fix quality" field is passed from the GNSS 10 unit. The NMEA defined values are: 0x00=invalid, 0x01=GNSS 10 fix (SPS), 0x02=DGNSS fix, 0x03=PPS fix, 0x04=real-time kinematic, 0x05=float RTK, 0x06=estimated (dead reckoning) (2.3 feature), 0x07=manual input mode, 0x08=simulation mode. For the wearable electronic device 100, the following codes have been added by the management software used for GNSS 10. 0xFE means that the GNSS 10 did not respond to message after communications was established, and 0xFF means that the GNSS 10 did not respond to the first message.

Referring with particularity to FIG. 3E, the LoRaWAN™ battery 180 data format port is shown, where 0x04 is the port number, while the delay is the part of the message similar to that as previously described in the LoRaWAN™ beacon 200 data message format of FIG. 3C. The battery charge status is shown, where values 0x00 to 0x64 correspond to the percentage of battery life remaining.

Referring with particularity to FIG. 3F, the LoRaWAN™ nurse call button 131 data format message will have a port number of 0x05 that is issued when the user presses the nurse call symbol 131 that is formed on the cover 130 of the wearable electronic device 100. As before, the delay is the part of the message similar to that as previously described.

Referring with particularity to FIG. 3G, the LoRaWAN™ nurse response data format message will have a port number of 0x06 that is issued when the nurse call status of the wearable electronic device 100 is cleared. The delay is the part of the message similar to that as previously described in conjunction with FIGS. 3E and 3F. The UUID is the unique identifier of the closest nurse beacon or tag at the time the nurse call status was cleared. Likewise, the strength of the closest nurse beacon or tag is included in the message. This field is in the same units as the beacon data message.

Referring with particularity to FIG. 3H, the LoRaWAN™ band 190 worn data format message will have a port number of 0x07 that is issued when the wearable electronic device 100 detects that it is being worn. The delay is the part of the message similar to that as previously described in conjunction with FIGS. 3E, 3F and 3G.

Referring with particularity to FIG. 3I, the LoRaWAN™ band 190 removed (i.e., not worn) data format message will have a port number of 0x08 that is issued when the wearable electronic device 100 detects that is has been removed. The delay is the part of the message similar to that as previously described in conjunction with FIGS. 3E through 3H.

Referring with particularity to FIG. 3J, the LoRaWAN™ no movement data format message will have a port number of 0x09 that is issued when the user has been stationary for a threshold amount of time. The delay (measure as the number of seconds the message was held before it was sent to the LoRa module) may be set with a maximum value of 255, which means more than 4 minutes and 24 seconds. Stationary time is the number of seconds the user has been stationary. This field will report 65535 for times longer than 65535 seconds.

Referring with particularity to FIG. 3K, the LoRaWAN™ movement data format message will have a port number of 0x0A that is issued when the user begins moving after having been stationary. As before, the delay is the number of seconds that the message was held before it was sent to the LoRa module.

Referring again to FIGS. 1, 2F, 3A and 3B, unlike relying upon traditional WiFi or BLE to transmit the collected LEAP data, where numerous routers or hubs would have to be deployed in an ad hoc mesh topology through repeaters or related devices to pass information from one device to another in order to ensure signal reception over the entirety of an assisted living community facility or multi-room private dwelling, the LPWAN-based approach disclosed herein allows coverage of the entire facility with a smaller number of gateways 300 in a star topology with long-range connectivity such that a wireless network formed between the wearable electronic device 100 and the gateway 300 has sufficient redundancy to ensure that data signals being transmitted from the wearable electronic device 100 arrive at the backhaul server 400, regardless of the failure of a single gateway 300 or other wearable electronic devices 100 that may also be signally cooperating with one or more gateways 300. As such, overall installation architecture is improved by avoiding complexity, as well as eliminating the need for having only AC-powered devices or nodes be capable of receiving and transmitting data and other information between nodes. Significantly, using a single gateway 300 (or no more than a small number for very large facilities and system 1 deployments) can reach the backhaul server 400 with minimum amount of installation time and expense, as well as no (or limited) need to integrate into existing WiFi infrastructure that may already be present within the facility. Gateways 300 transfer a received packet from the wearable electronic device 100 to the cloud-based network server 410 via some additional backhaul (such as cellular, ethernet, satellite or WiFi), and can do so through any other gateway 300 (if needed) that is within signal range, making the wearable electronic device 100 and its LPWAN-based transmission approach disclosed herein easier to pair the to the cloud 500. Gateway 300 (like all radio systems) cannot hear anything while it is transmitting; as such, the bidirectional communication capability of LPWAN is primarily used as an uplink-based network such that the wearable electronic device 100 is acting as an end-node other than times where it initiates the communication. In addition, the scalability of the LPWAN-based approach allows a system operator, developer or installer to deploy as many gateways 300 as needed without concern for overloading the network.

Similarly, using an LPWAN-based approach to transmit from the wearable electronic device 100 to one or more gateways 300 avoids the cost and complexity of cellular-based approaches such as those associated with existing machine type communications (eMTC, such as LTE-Cat M1) or narrowband IoT (NB-IoT, such as LTE Cat-NBI) technologies that rely upon licensed portions of the spectrum and non-mobility of the end node device, as well as the imminent 5G massive machine type communications (mMTC). Likewise, unlike relying upon cellular towers and related infrastructure to transmit the collected LEAP data, gateway 300 employs an agnostic (that is to say, stateless) protocol where neither receipt acknowledgement nor information is retained by the transmitting or receiving devices. In addition to providing enhanced data security, such a protocol simplifies system 1 architecture in that memory allocation of the transmitted and received data need not be done dynamically during the duration of the communication. Moreover, neither the wearable electronic device 100 nor the gateway 300 have to establish a session to communicate, instead having some of the more complex operations moved downstream, such as to the backhaul server 400 and its cloud-based network server 410. This allows simplification of the gateways 300 that in turn reduces the costs associated with the deployment of system 1.

Furthermore, the star topology between the wearable electronic devices 100 and the various gateways 300 avoids the need to use a wireless neighborhood area network (WNAN) or crowdsearching GNSS-based protocol both of which rely on an associated mesh-like network of adjacent mobile telephones or wireless broadcasters that in turn depend upon interphone node-to-node communication with which to achieve their range-extending along with attendant increases in network complexity and decreases in battery life and network capacity. The spoke-hub distribution of the star network topology ensures wide area coverage for patient location without the mesh network multi-hop routing drawbacks. In particular, the approach employed by the wearable electronic devices 100 and the various gateways 300 of the present disclosure differs significantly from crowdsearching GNSS-based methods or WNAN methods in that there is no requirement to have strangers share their mobile telephone or broadcaster resources in order to have the patient location data sent from such stranger devices to the caregiver, family member or other responsible party, nor is there a need to repeatedly send a UUID or related identifier to nearby ones of these stranger devices in order to have them communicate with a main server to update location information of the patient. Not only does the central management of the communication between the wearable electronic devices 100 and the various gateways 300 of the architecture disclosed herein promote long-range, simple connection infrastructure, but it also provides enhanced data security, which may be valuable in situations where sensitive information pertaining to the patient is being transmitted. Furthermore, using the third wireless communication sub-module 175C along with the gateway 300 in a star topology network rather than a mesh topology network avoids the need for maintaining the hybrid wireless communication module 175 of each wearable electronic device 100 as a relay or source for signals from other similarly-equipped wearable electronic devices 100 which in turn means that the hybrid wireless communication module 175 need not remain in an active communication mode with consequent increases in battery 180 power consumption.

Figure 4:
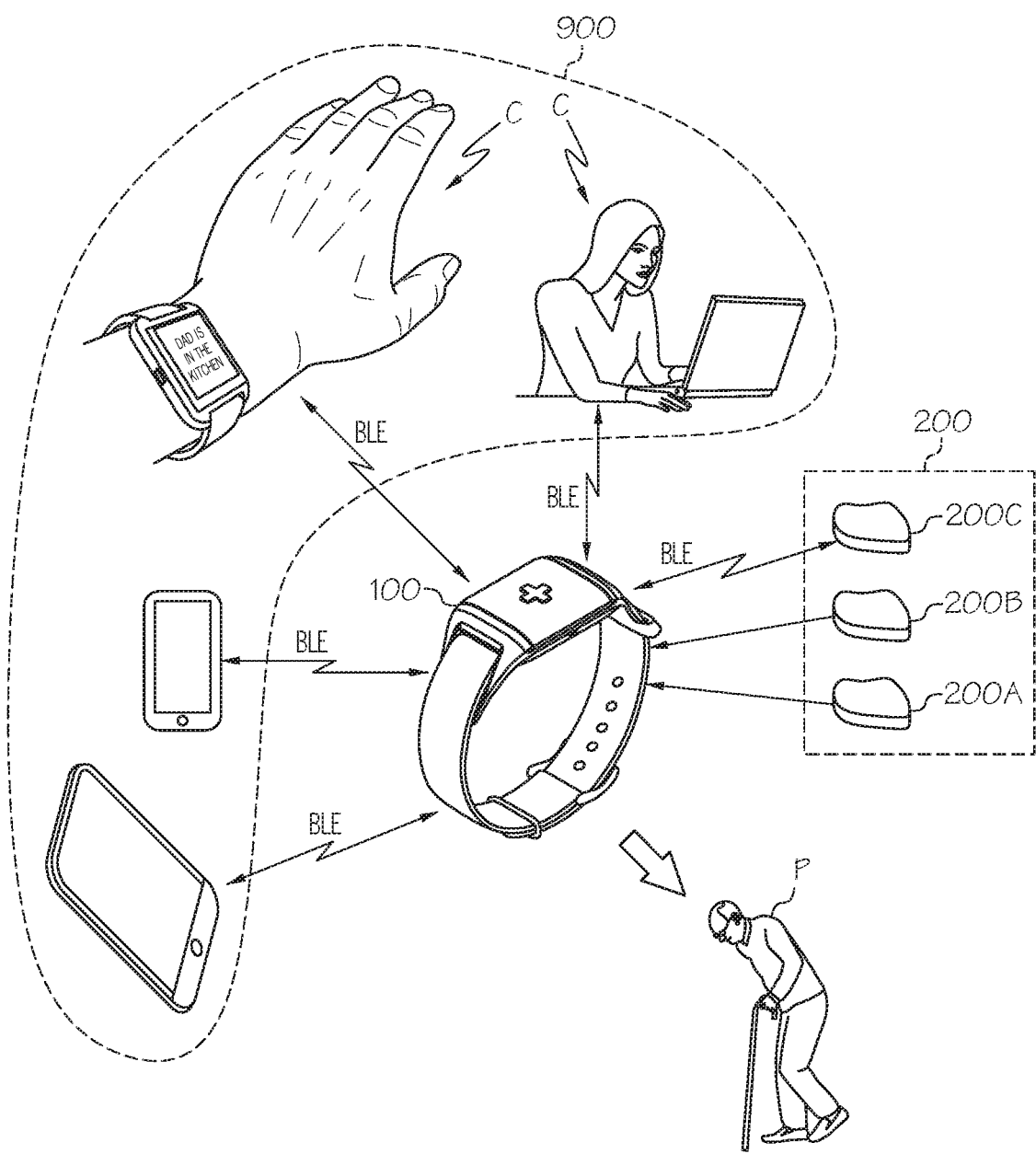
FIG. 4 depicts a simplified view of initialization, maintenance and charging of the wearable electronic device of FIG. 1 according to one or more embodiments shown or described herein.

Referring next to FIG. 4, the configuration application is used to activate the wearable electronic device 100, associate the wearable electronic device 100 with a patient P (or person P) to whom the device is attached, manage BLE beacons 200 and perform software updates of wearable electronic device 100 firmware. In particular, the configuration application can be made to run on a client device in the form of the previously-mentioned remote computing device 900 that can be used by family, friends, nurses, doctors or other interested caregivers C. In one form, the remote computing device 900 may be a caregiver C workstation, mobile telephone, smartwatch, tablet computer or other device capable of receiving location, status updates, alerts or related information about an individual associated with the wearable electronic device 100, as well as conveying such information to the corresponding caregiver C. In use that takes place during initial pairing or setup, the communication for the configuration application may be established through BLE-equipped connectivity features as long as the wearable electronic device 100 and remote computing device 900 are within suitable range of one another. In one form, the registration of the wearable electronic device 100 with one or more BLE beacons 200 is performed automatically through the first wireless communication sub-module 175A of FIG. 2F upon determination by the wearable electronic device 100 that it is within range of a UUID-bearing signal being transmitted by at least one the BLE beacons 200. Likewise, such registration may be performed semi-automatically through an application initiated by a caregiver C or other user from the remote computing device 900. In either event, the configuration application allows a patient P or caregiver C to create an account for the patient P, as well as to associate the wearable electronic device 100 with that account using the UUID. In one form, the configuration application may be used to establish a system maintenance view that provides a display or related indicia to show how other devices (including those within system 1) may interface with the wearable electronic device 100 in order to facilitate such configuration, as well as to provide operability status of the various components and sub-components, as well as of the wearable electronic device 100 for—among others—a charging status of the battery 180. In one form (such as that associated with a mobile telephone, smartwatch or the like), the communication used in conjunction with the configuration application may be established through Bluetooth-equipped connectivity features, while in another (such as that associated with laptop computers or other hardwired machinery) the communication may be established through landline-equipped internet connectivity features such as a web browser or the like. Various setups and configurations are possible, including (1) over-the-air firmware updates, (2) initial network settings (such as initial GNSS seed location of the facility where the wearable electronic device 100 will be deployed), (3) off-network (i.e., a setting to allow a wearer to leave the facility under supervised conditions such as with family or friends), (4) BLE beacon 200 scanning and event transmission rules, (5) as well as other configuration data to be determined.

Figure 5:
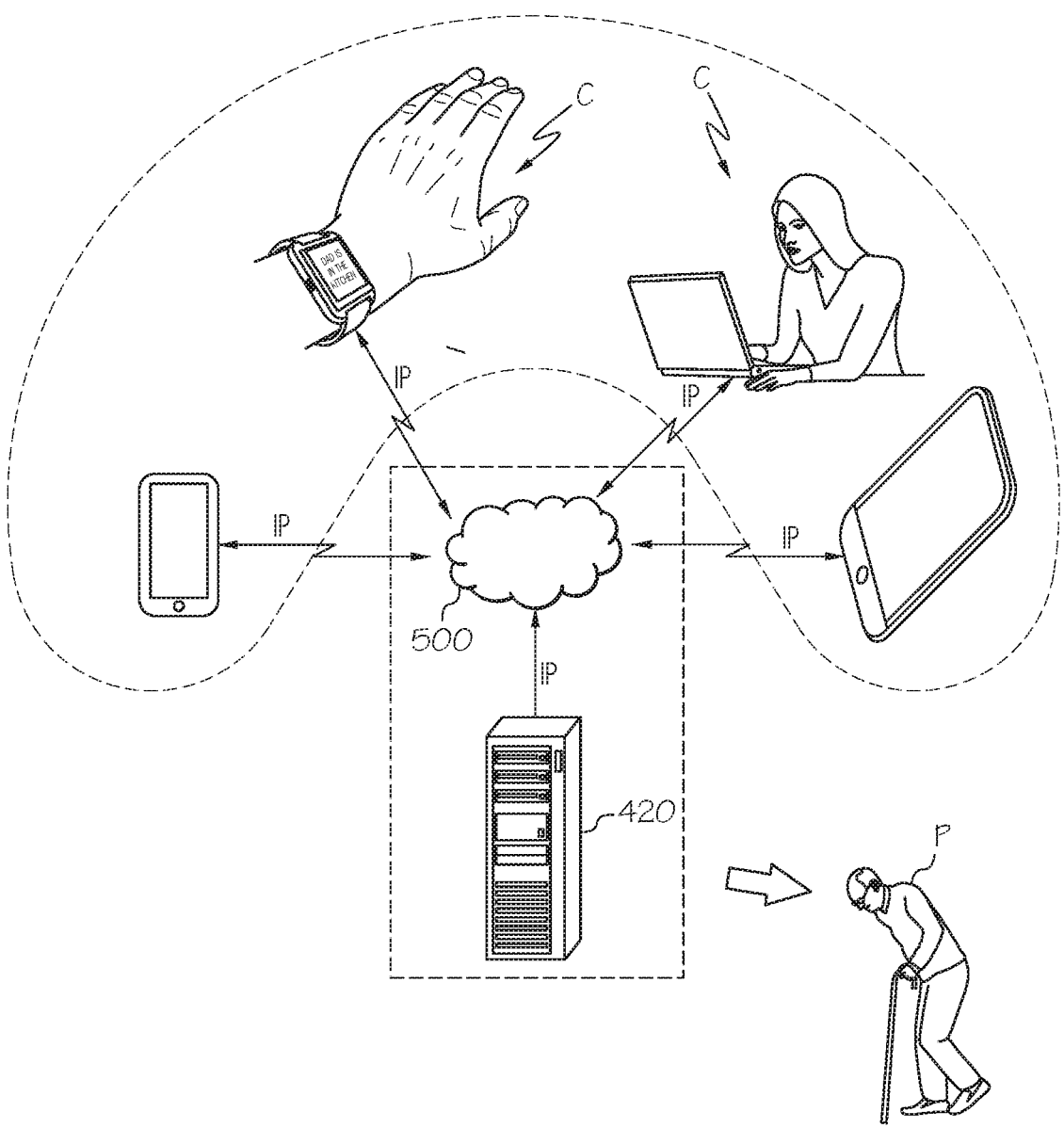
FIG. 5 depicts a simplified view of a cloud-based connectivity between various interested parties receiving information from the patient location and activity monitoring system of FIG. 1 according to one or more embodiments shown or described herein.

Referring next to FIG. 5, when the caregiver application or family application is loaded on a suitably-configured remote computing device 900, various events may be tracked, including (1) location change relative to a BLE beacon 200 position that is closest to the wearable electronic device 100, (2) change in position relative to GNSS 10 position, (3) battery 180 remaining life, (4) nurse call and subsequent response, (6) placement on or removal from a patient P of the wearable electronic device 100 and (7) patient P movement or lack thereof. In one form, and upon receipt of a suitable signal from the wearable electronic device 100 through gateway 300 (neither of which is presently shown in FIG. 5), the various different remote computing devices 900 may be made to interact with one or both of the application server 420 and cloud 500 in order to be notified of events or to check on a person associated with the wearable electronic device 100, such as over an internet protocol (IP), cellular network or the like. Thus, in one form, the wearable electronic device 100 may form a front-end portion of a cloud-based full-stack IoT configuration while the remote computing devices 900 may form the corresponding back-end which may also collect and store large amounts of so-called "big data" from the wearable electronic device 100 to provide the detection and associated analytical activities discussed herein. It will be appreciated that cloud 500 may be used in conjunction with closed-source or open-source database software and commercially-available large-scale processing services to achieve some or all of its functionality.

As previously mentioned, in one form, the identifier being sent from the nurse ID beacon 200C may include code that particularly identifies the staff member such that this code and the particular staff member's response to a patient P request from the nurse call button 131 is sent to the application server 420 or cloud 500. This identifier may be logged to allow the system 1 to keep track of information including when a person P (that is to say, patient P) calls for help, how long it took for help to arrive, and particular identification of which staff member or other caregiver C provided the help to the patient P. In addition, caregivers C and other personnel within a multi-resident dwelling (such as the previously-mentioned assisted living facility) will have the ability to monitor residents from a centralized location, which in turn increases the regularity and efficiency of checking in on the residents. In addition, this will help simplify and make more efficient the passing of medication in that rather than searching endlessly for peripatetic residents, the location-tracking feature provides real-time information on resident whereabouts. Moreover, with the gyroscopes, accelerometers, impact sensors and other forms of sensors 121, fall detection alerts are also conveyed automatically and in real-time, which is particularly beneficial in situations where the fallen resident is out of reach an emergency cord. This automation ensures that a suitable alert is sent, regardless of whether the nurse call button 131 is engaged by the fallen resident. Furthermore, because the nurse ID beacon 200C uses BLE to broadcast and track the whereabouts of caregiver C, detection ranges suitable for a home or an assisted living community-sized facility are easily achieved without having to install large numbers of repeaters, routers or hubs. In one form, the transmission of alerts from the wearable electronic device 100 may be sequenced or prioritized based on the relative importance of the type of caregiver C to the individual that is sending the alert, by proximity of the various caregivers C to the wearable electronic device 100, or by some other approach.

It will be appreciated that when BLE beacons 200 are placed in one or more rooms such as one of living room LR and BR (both as shown in FIG. 9) as well other rooms (such as a kitchen, bedroom or the like, none of which are shown), the UUID of the BLE beacon 200 must be associated with a unique one of these locations, and that this association must be stored in a database, such as within the backhaul server 400. Likewise, the one or more sensors 121 of a specific wearable electronic device 100 may need to be registered. As such, in one form, a unique identifier for a particular one of the sensors 121 must be associated with a location and a specific function (such as activity, physiological aspect or the like); this associated data must also be stored in a database (again, in one form in the backhaul server 400). In doing so, such sensor 121 will provide data for only a specific patient that is associated with that particular wearable electronic device 100. In one form, such registration may be performed manually, while in another, in an automated fashion. Furthermore, the registration process may be performed with a mobile device (such as the remote computing device 900) that has been equipped with a registration application in a manner similar to the applications depicted in FIGS. 4 and 5.

II. Machine Learning for Analysis of Wearable Electronic Device Data

Regardless of where the computational activities used to operate upon the LEAP data take place (that is to say, either locally in an edge computing manner on the wearable electronic device 100, on the gateway 300 or remotely within the backhaul server 400, cloud 500 or other component cooperative with or within system 1), such activities may employ machine learning approaches that synthesize rules solely from the acquired data rather than through the explicit programming instructions of an a priori rules-based protocol. Within the present context, machine learning is understood to include the use of one or more algorithms to extract information from raw data and represent it in some type of model. In one form, the acquisition and extraction of the data goes through a training process with the algorithms as part of a n ordered workflow that will be discussed in more detail as follows. As part of this workflow, the resulting model may then be used to infer things about other data that has yet to be modeled. More particularly, such a machine learning-based analysis of the LEAP data may convert such data into clinically-relevant predictions with which to help caregivers C determine whether a person P to whom the wearable electronic device 100 is attached is at risk of an adverse health condition. In this way, rather than start with an expert-based predetermined logic pertaining to a particular health issue (such as UTIs, pneumonia, various neuropsychiatric conditions or the like) and then applying the acquired data to such logic, the approach of the present disclosure may employ an observation-based or example-based way to create new forms of probabilistic health diagnosis logic. This in turn provides a method of performing analysis of the data collected by the wearable electronic device 100 in order to automate the building of data-driven clinical decision-making models with limited human intervention.

Examples of machine learning include those grouped as supervised learning, unsupervised learning and reinforcement learning, and one or more approaches under these groups may be useful for such analysis of the acquired data. Particular examples of supervised learning may include Bayesian approaches (such as naïve Bayes, Bayesian belief, Bayesian linear regression and dynamic Bayesian networks that includes Markov-based models), decision tree approaches (such as classification and regression trees (CART) or C4.5), ensemble approaches (such as random forests, boosting and bootstrap aggregating (bagging)), instance-based approaches (such as k-nearest neighbor (kNN)), regression approaches (such as linear regression, least-squares regression or the like), support vector machine (SVM) approaches and some forms of deep learning (particularly when used as a classifier, such as with a convolutional neural network (CNN)). Particular examples of unsupervised learning may include clustering approaches (including K-means, k-medians, expectation maximization, hierarchical, density-based or the like), dimensionality reduction approaches (including principal component analysis (PCA), linear discriminant analysis (LDA) or the like), and at least some form of neural networks with their acyclic connected graph (ACG) feedforward, and recurrent variants which may be further grouped into, among others, perceptrons, sequential/recurrent, long short-term memory (LSTM), Hopfield, Boltzmann machines, deep belief networks, auto-encoders or the like. Particular examples of reinforcement learning (which in some forms is a variant of supervised learning) may include Q-Learning, Deep Q-Learning, Actor Critic, PPO, Policy Gradients or the like, where maximum expected outcomes are grouped as either value-based, policy-based or model-based approaches. It will be appreciated that the use of a particular machine learning approach such as the ones discussed herein is dictated by numerous factors including the type of data (for example, the size and structure of such data) being acquired, what subsequent analysis of the data is being required, the availability of computational time and how soon results are needed. Moreover, it will be appreciated that hybrid approaches of more than one of the machine learning models discussed herein may be employed in order to infer changes in one or both of physical and mental status of an individual from whom data is being gathered by the wearable electronic device 100, and that all such variants of such models are deemed to be within the scope of the present disclosure. As such, descriptions of analyses as being performed on the acquired LEAP data by, substantially by or based on a particular machine learning model within the present disclosure will be understood to include such models or hybrids regardless of minor variations in their functionality so long as their underlying functionality is preserved. For example, a K-means clustering-based model will be understood to possibly include variations on its functionality of using a series of iterations to create clusters of the acquired LEAP data into data points that have similar variance and minimized cost function without a loss in generality or applicability of the model to the underlying analysis of the LEAP data.

In addition to grouping machine learning models based on whether they are supervised or unsupervised, they may be grouped according to their output, where in one form, a binary classification model provides a yes/no answer, whereas a regression model provides an answer that exists along a continuum of answers. Examples of classification models include SVM, kNN, decision trees, Naïve Bayes, logistic regression and random forests, among others, while examples of regression models include linear regression and nonlinear regression.

Some of the machine learning approaches that may be relevant to the problem of predicting potential health risks of a person P using the wearable electronic device 100 will now be discussed in more detail, particularly as they relate to the ability of one or both of the wearable electronic device 100 and system 100 (possibly working in conjunction with the gateway 300, the cloud 500 or other equipment) to statistically model the health of a person P who is wearing the wearable electronic device 100 with as much predictive accuracy as possible with the minimum amount of machine learning model resources as possible. In one form, the machine learning model used to predict whether a particular person P is manifesting signs of infections such as a UTI, respiratory tract infection (RTI), skin and soft tissue infection (SSTI) or gastrointestinal tract infection (GII), mental or cognitive changes, respiratory problems or the like can take into consideration numerous factors in order to enhance its utility. For example, the relative importance between model accuracy, stability, predictive interpretability and simplicity may be adjusted in order to meet a particular end-use objective. In some cases (for example, low-bias cases where the likelihood of a health condition or other outcome being predicted is relatively balanced such that the data set includes indicia where a "yes" answer is about the same as a "no" answer in a classification-based model), accuracy as a performance metric may be important, whereas in circumstances where the likelihood is imbalanced, accuracy may not be as important of a metric as the previously-mentioned sensitivity, specificity, receiver operating characteristic (ROC) and area under the ROC curve (AUC) or the like. Within the present context, a balanced likelihood is one where when both possible outcomes are relatively equal.

Bayesian-based statistical inference includes supervised learning approaches that are useful to analyze distributions in acquired data not just to represent the distribution values, but also to determine the belief (that is to say, the probability, or likelihood) that each one is a true value, as well as a probability that to-be acquired data will indicate changes in the object from which the data was acquired. In one form, Bayesian-based approaches form probabilistic graphical models that in turn can provide classification guidance data based on such beliefs or likelihoods. For example, a Bayesian-based approach applied to the collection of data from the wearable electronic device 100 may look for correlations between location, activity or other data and a particular medical condition. Because Bayesian-based approaches consume relatively small amounts of processing capability, the resulting inference can be performed locally (such as on the wearable electronic device 100) without the need to first convey large quantities of the LEAP data to the backhaul server 400 or other parts of system 1. Bayesian networks generally perform well on data with large amounts of samples, as well as for temporal (i.e., time series) data such as electronic medical records (EMRs). Bayesian-based approaches are probabilistic by nature, such that once symptom-based data is presented to the model, it can be used to compute the probabilities of imminent adverse health conditions of the person P from whom the wearable electronic device 100 is acquiring data. Moreover, Bayesian-based approaches are well-suited to showing event causation through their modeling of conditional dependence. Depending on the nature of the data being acquired, Bayesian-based approaches may exhibit similar predictive its performance to neural network-based and decision tree-based approaches. Tracking patient activity using the sensors 121 that are present within the wearable electronic device 100 include those approaches for gaining insights into static activity (using, for example, Naïve Bayes for text analysis, kNN, SVM, decision trees or the like), and temporal activity (using, for example, Dynamic Bayesian, Hidden Markov Model (HMM) and Conditional Random Field (CRF) probabilistic modeling approaches). In one form, the Bayesian approach allows a user to encode one or more prior beliefs about how the model should look irrespective of what the data indicates, especially in situations where the amount of acquired data from the wearable electronic device 100 may be limited. Thus, Bayesian-based techniques may be used to conduct HAR and ADL studies on an individual person P basis, as well as to infer changes in the health of such person P, using the wearable electronic device 100, either in conjunction with the results of the HAR and ADL studies, or directly from the data itself without regard to such HAR and ADL information; as will be discussed in more detail later. In such case, the Bayesian model may be used to form a target (i.e., response) variable of the desired corresponding HAR, ADL or change in health status. Such a model may be supervised in that training data with known targets that are correlated to one or more health conditions may be used during training to model to learn to predict such change in health from HAR or ADL that in turn is based on the other variables that are in the form of the data being acquired by the wearable electronic device 100. Likewise, such a model may be unsupervised in that K-means clustering or other approaches are used, where only limited size data sets are available. In this way, unsupervised learning can be viewed colloquially as finding patterns or structure in the acquired data without understanding it. Moreover, depending on the desired output, the HAR, ADL or change in health may determine if the model is a classification one or a regression one. For example, certain changes in health status—such as periodic outbursts by a person P exhibiting one or more neuropsychiatric conditions—may be seen as existing over a continuum (making it a regression problem), while distinguishing between other types of changes could be construed as a classification problem.

A Markov model is one form of a memoryless Bayesian network model used for event recognition by ensuring that events that occurred before a current state do not influence the current state; in this way, future states only depend only on the current state. In other words, the Markovian process assumes that if the present state of a measured condition is known, the future state is independent of the past state. As such, Markov-based approaches form a comparatively simple way to model random temporal-based sequences such as those associated with motion-based activity data that can be acquired by activity sensors 121B, possibly in conjunction with location data as acquired by the hybrid wireless communication module 175. Markov model analysis of temporal sequences is particularly useful in situations where a large amount of data is available in order to recognize complex temporal events, and further where an ample amount of training to ensure a suitable tradeoff between bias and variance (in a manner similar to the use of error and regularization terms to minimize cost function) is present. One specific variant, HMM, is an adaptive (that is to say, feedback-based), generative, probabilistic approach in which the system being modeled is assumed to be a Markov process with unobserved (i.e. hidden) states. With an HMM, knowledge of the correlation between a physical event and a particular state is not as important as matching each state to a given output as a way to observe the output over time to determine the sequence of such states. Thus, an HMM facilitates the modeling of a given event or process with a hidden state that is based on observable parameters, particularly in determining the likelihood of a given sequence. Such a framework is particularly useful for modeling events that have temporal-based data structures (such as that associated with movement or positional data that is acquired from accelerometers or gyroscopes, as well as speech recognition, speech generation and human gesture recognition) in that an HMM can be visualized as essentially a quantization of a system's spatial components into a small number of discrete states, together with probabilities for the time-based transitions between such states. By way of example, a multi-room dwelling such as a house, assisted living facility or the like may be modeled with a Markov-based approach such that one or more of various rooms or spaces (for example, a kitchen, a dining room, a bedroom, a bathroom, a hallway or the like) may be outfitted with one or more BLE beacons 200. By collecting and conveying location data about a wearer within such a dwelling, the movement, activity and location-sensing components within the wearable electronic device 100 may be used in conjunction with HMM to make a series of predictions about which room the wearer may enter next, based at least in part on sets of probabilities for each room. By performing such an analysis over large number of iterations (including temporal-based iterations), the HMM model may be able to improve the accuracy of predicting which room the wearer is likely to occupy next in order to form one or both of baseline wearer state of health and changes to such health.

Decision tree-based learning is supervised learning that uses a hierarchical disjunctive normal form of logic for either recursive classification or regression problems to maximize information gain (that is to say, reduction in calculated variable entropy). In situations where the target variable can take a discrete or categorical set of values, the learning is called a classification tree, where each point in the data is represented as an internal node, each so-called branch represents the outcome of a test, and the so-called leaves represent the resulting classification. In one form, each decision tree within the model is created using a different, random subset of so-called weak-learner attributes and observations from the original training data set such that they can work in conjunction with one another to become a stronger algorithm. In one form, decision tree classification may be used in medical diagnosis and disease identification, where the output of a classification tree is a class ("yes" or "no"), such as answering the question "will a patient have a heightened risk of contracting a UTI?" Likewise, in situations where the target variable can take continuous values, it is called a regression tree an example of which could involve predicting how long will a patient's length of stay be in a hospital. Decision trees may be formed over numerous parametric iterations, using factor-based analyses and related approaches to remove extraneous or duplicative data. In one form, such as CART, decision trees can be used to form output variables that are extremely homogeneous, thereby allowing subsets of data (for example, whether a demographic group used as part of a baseline set of data for inter-patient baselines has a particular condition that may be used to identify potential co-morbidities in a patient being monitored with the wearable electronic device). This in turn may form the basis for an analysis to determine what combination of sensed parameters may best be indicative of an emerging adverse health condition such that one or both of additional analysis and intervention by a physician is warranted. Decision tree models may be interpreted by humans, as opposed to neural networks and other black box-based models that provide no insight into how the model was derived. As such, decision trees may be configured such that a particular set of training data can be described in a way to better understand the relationship between the input variables that are used to form a predictive analysis. Decision trees may tend to produce high-variance, low-bias results. Decision trees may be used for complex forms of data, such as those acquired from accelerometer-based sensors 121, as the model does not assume a simple parametric relationship between the accelerometer counts and the measurable indicia of a patient's activity, which in turn allows the model the flexibility to determine which parts of the acquired acceleration signal may be more probative of the patient's actual activity. Decision tree-based approaches tend to work well with relatively small data samples.

Logistic regression-based learning is a popular supervised learning model that (despite its name) is used for binary classification to predict a specific discrete outcome where a qualitative rather than quantitative response variable is produced, an example of which may be that a given person P has a set of symptoms, is it possible to attribute such symptoms to one of numerous possible medical conditions. Its use of the sigmoid-based activation function allows any real-valued input number to be mapped into an output value between 0 and 1 such that it can be transformed into one or the other based on a threshold classifier. Logistic regression does not require a lot of computational resources, which makes it easier to implement on the wearable electronic device 100 where processor power may be less than that of the server 400 or cloud 500. In addition, training a logistic regression algorithm in order to arrive at a predictive health condition model is relatively easy. As with decision trees, logistic regression-based approaches tend to work well with relatively small data samples. In addition, they tend to be most useful when used in binary (that is to say, "yes/no") classification problems. On the other hand, if continuous rather than categorical outcomes are desired, logistic regression may be limited in its predictive ability. It may also be necessary to identify all of the important independent variable features that mathematically describe the instances with a suitable label, as well as perform some form of feature engineering such as feature extraction in order to reduce highly-correlated duplicate data, as well as to gain some insights from the raw LEAP data form which a meaningful feature may be formed.

Ensemble-based approaches may aggregate other learning models as a way to improve predictive performance. In one form, the ensemble may perform bootstrap approaches, including bootstrap aggregating (that is to say, bagging) as a way to estimate a quantity from a data sample by using independently-trained subsets of the data to separate more important predictors from less important predictors. Random forest is one type of supervised ensemble model that can be used for both classification and regression problems, and in one classification form may be constructed as an ensemble of numerous decision trees where each of the decision trees is based on a subset of attributes and observations from an original data set. After each decision tree is "grown" using a training data set and applied to a test data set, a resulting classification is returned that best matches the classifications provided by the largest number of individual decision trees. Ensemble-based approaches may also employ boosting-based approaches for classification problems through the weight-adjusted iterative addition of single-level decision trees (and related weak-learning models) so that the resulting classifier is strengthened. In this way, boosting, bagging and related ensemble-based approaches may be useful to determine a particular adverse health condition, such as when a person P associated with the wearable electronic device 100 is at greater risk of contracting a UTI. In one form, an ensemble of other models (such as those based on neural networks) may be used in order to increase the accuracy of data analytic-based predictions of UTIs or other adverse health conditions. Some ensemble-based approaches such as the random forest functions well with small data sets and—like a Naïve Bayes approach—can perform multiclass classification functions.

Instance-based learning approaches construct hypotheses directly from the input/output training data pairs themselves without the need for separate training. This can be advantageous in that it permits the model to adapt to new data, as well as to ignore data that may no longer be relevant, which in turn permits the hypothesis to grow in complexity as the amount or nature of the acquired data grows. Instance-based approaches may also keep the amount of data (and the concomitant amount of memory requirements and overfitting risks) tractable using one or more instance reduction models. Thus, in situations where the acquired data possesses many features, memory and related storage may become an issue such that the instance-reduction algorithms may help reduce the need to keep an entire training data set in memory. Contrarily, when using one popular form of instance-based learning (in particular, kNN), it may be advantageous to either operate on smaller data-sets or employ an instance-reduction algorithm as part of a multi-layered analysis where a disease or other medical condition is first classified based on the acquired LEAP data and then detected for its actual presence using some or all of the same LEAP data. For example, a process may use kNN for the initial classification to identify a disease subset (also known as a diagnosis class) to which a particular disease or medical condition belongs based on commonality of symptoms, after which other classifier algorithms as discussed herein that are trained, validated and tested on the LEAP data perform detection-specific analyses of the likelihood of a particular disease using the symptom information inferred by the acquired data from the wearable electronic device 100. In other words, kNN takes into consideration one or more nearest neighbor data points with which to make a classifying prediction of a particular data point where the prediction is the known output for the one or more nearest neighbor training points through calculating a distance between the particular data point and the training point, sort the distances in increasing order, taking the various items with shortest distances to the particular data point, finding a majority class among the various items and then returning the majority class as the prediction for the class of the particular data point. Such an approach may be particularly useful in correlating the LEAP data to symptoms that in turn may be related to a particular disease or medical condition, particularly when combined with access to symptom data that may be used to correlate the acquired data to a particular disease. In one form, the symptom data-much like other forms of baseline data as discussed herein—may be made to reside within memory (which in one form may be similar in structure or function to memory 173B as discussed herein) the backhaul server 400, the cloud 500 or elsewhere that is accessible to system 1. As will be discussed in more detail below in conjunction with FIG. 6, a machine learning workflow may be used to take the acquired data to be cleansed (or preprocessed), extracted and put into a feature vector in order to have the data be in better form for subsequent analysis. By way of example, such cleansing may include putting it into more unified, structured or standardized form, reducing its dimensionality, checking for missing values, arranging data by category, labeling data points, placing proper temporal sequencing, removing data outliers or the like.

Regression-based approaches tend to be used in situations where the classes of acquired data are made up of a continuous (that is to say, measurable) set of numerical values for linear cases or countable values for discrete cases. Regression-based models correlate a predicted (i.e., output, or dependent) variable to a combination of coefficients (i.e.

weights) multiplied by a set of input variables, and also use an error term to take random sampling noise into consideration as a way to come up with a single estimate of the predicted variable based only on training data. Such models may be used to predict changes in the patient's condition, compared to a classification model that may be used to predict in a binary yes/no way what the impact will be of a particular change in LEAP data. As will be discussed in more detail later, ADL data (with its continuum of activity data) may be coupled with a regression-based model in order to determine the likelihood that a particular patient is manifesting signs of cognitive decline or is at risk of developing an infection or related adverse health care condition. In one form, regression-based approaches may be used to correlate such changes through comparison of acquired data with known (or previous-acquired) baseline data. As previously mentioned, periodic outburst that are associated with neuropsychiatric conditions may be relatively easily modeled using a regression-based machine learning approach. Significantly, because the data being acquired by the wearable electronic device 100 is complex, including coming from different sensors 121 that are measuring different parameters, the inherent ability of regression-based approaches to handle multiple variables may form a useful way to correlate the various forms of acquired LEAP data into a single predictive output. Regression-based approaches tend to be among the fastest machine learning models.

SVM-based approaches are a supervised form of learning used to build a model that represents data examples as points in space that are mapped in a manner to place the examples into clearly separated categories. New examples may then be mapped to opposing sides of a gap that is used between the separated categories. In one form, SVM may be used in conjunction with the kinematic ones of the sensors 121 of the wearable electronic device 100 to detect and classify various activities. For example, accelerometers, gyroscopes and other kinematic or spatial-sensing approaches, taken in conjunction with one another can measure ambulation, body movements and body orientations for a better understanding of HAR; the use of SVM may be used for acquiring such activity or movement-related data, especially when the activity being sensed is scarce or abnormal. These in turn may be correlated to standardized activity codes such as those found in the Compendium of Physical Activities, a globally-used reference that provides a unified five-digit coding scheme for the classification of specific physical activities by rate of energy expenditure with a corresponding metabolic equivalent (MET). As such, changes in postural orientation (such as those associated with changes from sitting, laying down, standing, patient movement, walking, running, falling or the like) may be used to infer levels of activity that may in turn be correlated to changes in an individual's present condition relative to a previously-defined baseline condition. Likewise, various movement anomalies, such as those associate with gait or the like, may be sensed for correlation to a particular condition such as how changes in gait could be tied to spatial navigation difficulties that in turn may be tied to the breakdown of cognitive mapping and the onset of dementia as all are identified as taking place within similar regions of the brain. This temporal frame data collected from the various sensors 121 may be processed and used to classify activity into an ADL category, such as through comparison to known ADLs that were previously acquired or stored in memory 173B (such as in the form of a lookup table or the like). In a manner similar to random forests and unlike the Bayesian classification or neural networks methods, the SVM method may be used for training with small sets of data.

Clustering-based approaches involve grouping a set of objects that exhibit high degrees of similarity through an iterative process that involves trial and error. As such, clustering-based approaches are well-suited for the detection of anomalies that may show up in imbalanced data sets where the various classes of data will have a different number of examples and where accuracy of the information contained in one or more so-called minority classes is important to the decision-making process. Depending on the data being acquired, balancing (such as weight balancing discussed elsewhere herein or sampling-based balancing) of the data sets may be beneficial. In one form, a clustering approach is an unsupervised approximation to supervised classification approaches examples of which include expectation-maximization and kNN, particularly for their ability to ascertain a particular form of cognitive impairment where the data is in the form of movement and related activity data where similarity or differences of such activity over time may be ascertained and then correlated to changes in patient behavior and patterns. Thus, where the model is based on K-means or related clustering approaches, each data point in the data set may be considered a vector of valued attributes, which is the unsupervised analogue to supervised machine learning feature vectors except that the features are not specifically labeled. In another form, clustering may be understood to create parameter values and classification of the acquired data in order to provide identifying labels for observations as an initial step to converting unsupervised learning into supervised learning. For example, clustering-based models may be used in trying to determine human activity recognition (HAR), ADL or instrumental ADL (IADL) by separating similar activities from dissimilar ones using pattern vector partitioning.

In one form, K-means clustering can generate a minimum variance grouping of the LEAP data through minimization of the sum of squared Euclidean distances from centroids within the cluster that in one form may initially be chosen arbitrarily such that received data becomes distributed among the chosen cluster domains based on minimum distances. Once the data has been distributed, the cluster centers may be iteratively updated to reflect the means of all the records in the corresponding cluster domains until some measure of convergence is attained. In fact, K-means clustering could be used as the front-end part of a hybrid unsupervised/supervised approach, particularly in situations where the amount of LEAP data collected is relatively small (such as from a single patient), making the model a K-means clustering-based one. From the K-means front-end, the data can be re-run on a classification back-end. In this way, the differences between the real-time data and the baseline data that otherwise may go undetected in another approach that is not adept at analyzing such small, sparse amounts of data as correlate such differences to incipient changes in the health condition of a patient become much more easily identified. K-means clustering identifies which data points belong to a corresponding one of the K clusters that, through a series of iterations, creates groups (i.e., clusters) of these data points that have similar variance and that minimize a given cost function, and does so with relative ease of implementation especially in view of the relatively small amount of data being collected for a given patient. While K-means clustering is particularly useful when the substantial entirety of the acquired data set is used, some of the other clustering approaches, such as hierarchical clustering (for discovering embedded structures in the data) or density-based clustering (for discovering hitherto unknown numbers of clusters, particularly when small groups of nearby clusters may be segmented). As with other unsupervised approaches, K-means clustering may be good for exploratory analysis and data sets where dimensionality reduction is important.

Thus, in one form, a hybrid supervised/unsupervised approach may start off by having the model be trained on at least a portion of the LEAP data as the person P associated with the wearable electronic device 100 performs a one or more movements, such as hand gestures, transitional movements (such as those discussed in more detail in conjunction with FIGS. 11A and 11B) or the like that can be labeled. The acquired data (some of which may be taken from one or more of sensors 121) may then be processed to calculate signal spatio-temporal or other characteristics that may then be subjected to unlabeled clustering in order to assign them to an appropriate cluster depending on the movement being categorized. HAR and related ADL or IADL categorization may then be performed based at least in part on the clusters that were formed during training. As such, this hybrid approach may be understood to make up a K-means clustering-based approach.

Dimensionality reduction-based approaches can produce a set of principal (that is to say, more relevant) variables that are more homogeneous and less voluminous than the raw data, especially by removing highly correlated features from the number of total amount of data acquired from the wearable electronic device 100. This is helpful because this data involves both high frequency in the form of large numbers of observations per second and high-dimensionality in the form of myriad sensor 121 types that are collecting multiple forms of data simultaneously such that each different sensor 121 forms an input variable that may correspond to one dimension of a multidimensional space. As such, dimensionality reduction may be used as factor analysis in order to group features together. As will be discussed in more detail below, such reduction may be a predecessor to, or be a part of, both feature selection (i.e., the approaches try to find a subset of the original variables that contain accurate, relevant input data, examples of which include neighborhood component analysis, regularization, sequential feature selection, stepwise regression or the like) and feature extraction (also called feature transformation, where the data is placed into a feature space of fewer dimensions while maintaining accuracy) as a way to spot rules, trends or related likelihoods. This reduction in the number of variables involved may help keep classification-based models from overfitting. Together, such feature selection and feature extraction take the raw data that has been acquired from the sensors 121 and form derived features for use in subsequent learning and generalization activities within the algorithms used to create the corresponding model through stronger positive and negative correlations. For example, one positive correlation may be relating the number of trips to the bathroom (which can be measured directly based on location data) to the increased likelihood of a UTI, while a negative correlation may be that sedentary activity (which also can be measured directly based on location data) is an indication that the patient being monitored is not exhibiting symptoms associated with agitation. One common form of dimensionality reduction algorithm is the PCA that through search optimization transforms feature variables into a smaller number of principal component variables, in this way, the modified vector representation of these features allows additional insight into how important they are to the output. Oher forms of dimensionality reduction may include kernel density estimators, Gaussian mixture modules, singular value decomposition, expectation maximization or the like. In one form, these estimators may be used in conjunction with (or are supported by) various data sets, feature selection, model selection and other machine learning modules to significantly improve the ability of a machine learning algorithm to only have to use parameters that have probative value. Tuning of hyperparameters, which involves identifying the most relevant parameters for a given machine learning model, can be used in an iterative manner along with one or more training algorithms as a way to help achieve dimensionality reduction of the data. Other forms of transforming the features associated with the acquired LEAP data to extract more relevant feature vectors may eigendecomposition, whitening transformations or the previously-mentioned LDA.

Figure 6:
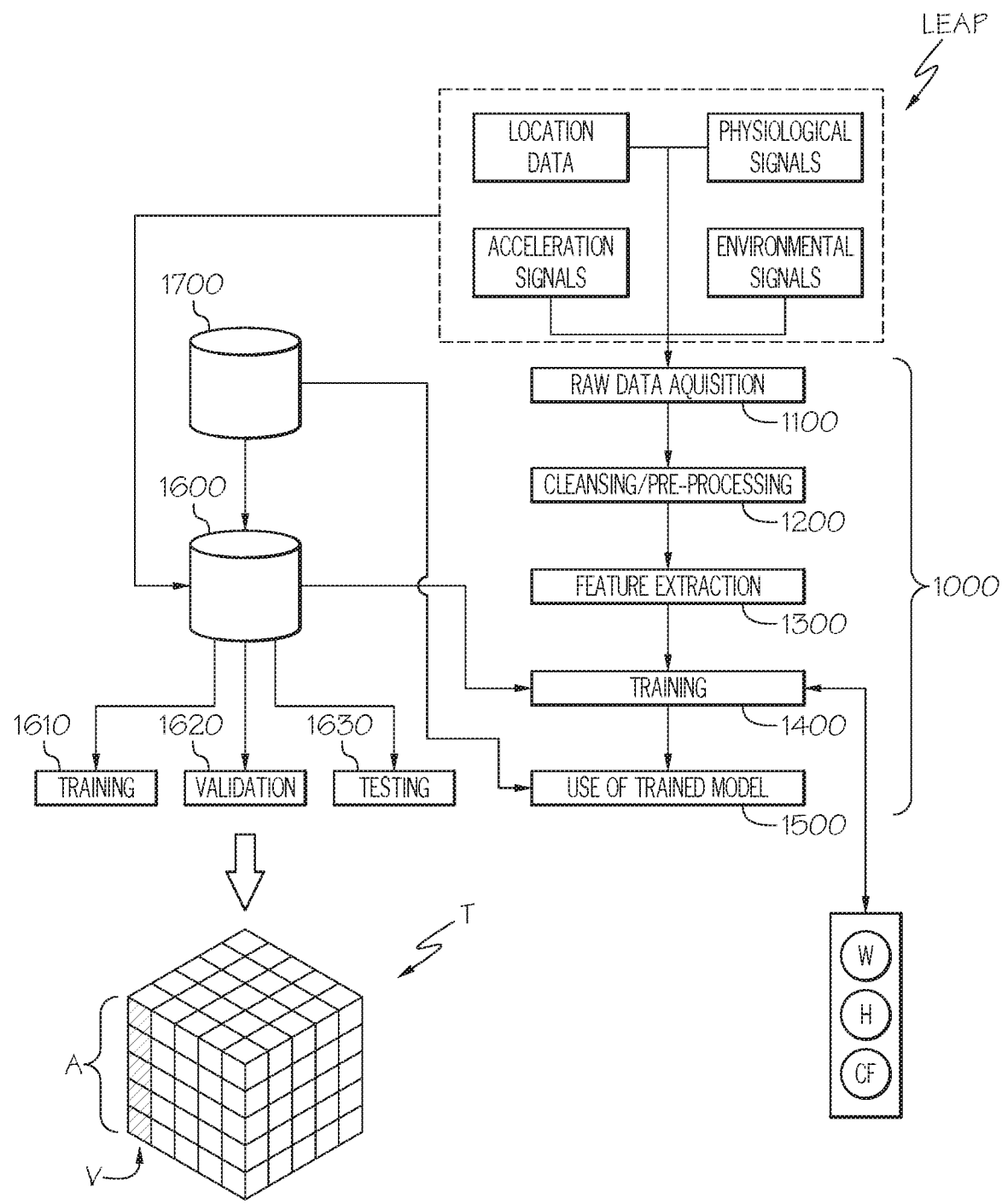
FIG. 6 depicts a program structure in the form of a flow diagram of how the wearable electronic device and system of FIG. 1 may be used to develop a machine learning model according to one or more embodiments shown or described herein.

Referring next to FIG. 6, the various machine learning approaches may in one form follow an ordered sequence of operations performed on the LEAP data acquired by the wearable electronic device 100. Moreover, this ordered sequence (which is referred to herein as a machine learning workflow 1000) may include the following steps: (1) a raw data acquisition (first) step 1100; (2) a raw data cleansing or otherwise preprocessing (second) step 1200, such as through the use of signal processing via noise filters, normalization or the like as a way to separate out various redundancies and related noise in order to process only the data that will bring about a statistically significant increase in predictive or explanatory power; (3) a feature extraction (third) step 1300 of derived values which may include placing the data into the previous-mentioned feature vector or related form, and which may involve some form of data mining or related exploratory data analysis; (4) a training (fourth) step 1400 for application of an iterative machine learning algorithm to fit or create a machine learning model; and (5) a model use (fifth) step 1500 with which to operate the trained machine learning model on some or all of the acquired LEAP data (in particular, the real-time or other presently-acquired variants) in order to draw inferences from such acquired data. In one form, this ordered sequence may be used to provide predictive analytics to assist in the diagnosis (such as through online analytical processing (OLAP)) or the like by doctors, nurses and other caregivers C of the health condition of a person P. In another form, the ordered sequence may be used to perform its own autonomous diagnosis without human intervention. In yet another form, this ordered sequence may be used to perform an action plan so that it can provide guidance on changes in medication dosages, changes in dietary or activity protocols, changes in occupational or physical therapy plans or the like. Moreover, because such diagnosis is based on the acquired LEAP data that is specific to a particular individual, such diagnosis and the ensuing action plan could qualify as personalized medicine and related individualized-profile clinical decision-making. The first three steps 1100, 1200, 1300 form the core of data management, while the last two steps 1400, 1500 make up learning, inference or related analytics to acquire intelligence from the initial voluminous data set. As such, it will be appreciated that the first three steps 1100, 1200, 1300 may be performed independently—as well as part of—a machine learning-based analysis, and that both variants are within the scope of the present disclosure.

In one form, one or both of baseline data 1700 and presently-acquired data 1600 (such as the activity portion of the LEAP data, for example) may be stored in memory 173B in an unstructured, flat file format such that during the cleansing or related preprocessing associated with the second step 1200 of the machine learning workflow 1000, improvements in data uniformity may be realized. In one form, grouping the acquired data (from either the wearable electronic device 100 or elsewhere, such as lookup table based on known prior data of a particular patient or group of patients with similar health demographics) can be through an unsupervised clustering model; such an approach may be particularly good at segmenting the data into several different groups. In one form, this baseline data 1700 may be annotated for use in training-based activity, behavior or related parametric information that can be compared to real-time (i.e., presently-acquired) data in turn can be operated upon by one or more of the machine learning models discussed herein. The baseline training examples may include representative temporal sequences, including being further annotated or labeled in order to be scene-specific or situation-specific as a way to provide context for the model, as well as for model training. In one form of baseline data 1700, a combination of one or more sensed or known parameters may be used to HELP define a behavioral profile so that the individual's daily activities are known. As shown by the three-dimensional representation of data in the figure, any or all forms of data may be expressed as a vector V, array A or multidimensional array (that is to say, tensor T) in order to be in appropriate feature vector form for subsequent use of the independent LEAP data.

As part of the cleansing or preprocessing second step 1200, the acquired data may be tagged or identified, including through the use of spatio-temporal identifiers including location, time stamp, sensor class (for example, accelerometer, gyroscope, temperature, electrical, piezoelectric, piezoresistive or the like) or unique sensor identification codes. Data acquisition libraries, such as those available from MATLAB (Mathworks, Inc., Natick Mass.), may be used to provide sensor-based data acquisition support for such tagging and identification; such support may include other forms of data preprocessing, including class-labeling, noise filtering and related cleansing or scrubbing, as well as data balancing, all as a way to transform the data into a form that may be used by the subsequent feature extraction, algorithm selection, training and eventual predictive analytics model usage. In one example, the acquired data that has been operated upon by some or all of these libraries may be subjected to receiver operating characteristic (ROC) analysis as a way to quantify the performance of an activity classification algorithm. In one form, such an analysis may be in the form of a curve to provide visual comparison between various classification models where the area under the ROC curve (AUC) provides a measure of a particular model's accuracy. This model evaluation, which takes place once a model is tested and evaluated, may also be based on other criteria such as mean squared error, accuracy, sensitivity, specificity or the like. In this way, the activity classification algorithm can use known diagnostic performance metrics such as ROC and area under the ROC curve (AUC) values, positive and negative predictive value, sensitivity, specificity or the like to allow a comparison against physician-based expert diagnoses. Such an approach may be particularly beneficial when there are imbalances in the classes of data being used as part of a particular data set. In one form, a biquad or other high-pass filter may be used so that the gravitational effects of the accelerometer may be removed to allow subsequent analysis (such as through one or more of the machine learning models discussed herein) to focus on the inertial, movement of the patient rather than on the wearable electronic device 100. In this way, bodily acceleration components are removed from the data, which in turn may be used to classify different movements (such as between running and walking) using nothing other than mean, root-mean-square and related statistical features of the signal. In one form, such classification may form the basis of a neural network. Likewise, filters may be applied to control data sampling rates or the like. In one form, features that capture the frequency content of the accelerometer data may be extracted to distinguish between various ambulatory events (such as walking versus running, climbing versus travel or level ground, or the like) where ROC may be applied to each of the training, validation and testing data sets that will be discussed in more detail later. In one form, statistical-based feature extraction may be used on the raw data acquired by the accelerometer or accelerometers such that the resulting set of such features may be presented for use as input in a subsequently-created machine learning model. In one form, the feature extraction of sensed activity or movement data such as that acquired by gyroscopes, accelerometers or the like may be accomplished through adders, multipliers, impulse filters, band-pass filters or related mathematical operation circuitry contained within the logic device 173 or elsewhere. For example, peak analysis may be used to find important frequency content (such as through Fast Fourier Transform or the like), pulse and transition metrics to derive rise time, fall time and other signal characteristics, as well as spectral measurements to determine bandwidth, frequency and power information.

While it is understood that different kinds of data may involve different methods for the cleansing or preprocessing second step 1200, there are some methods that tend to be employed for almost all forms of data, including the LEAP data discussed herein. As part of this second step 1200 of the machine learning workflow 1000, the LEAP data that is being acquired by the sensors 121 may be filtered, amplified and converted, either onboard the wearable electronic device 100 the wearable electronic device 100 or remotely (such as on the gateway 300 or servers 400), in either event via local processor, memory and executable instructions. For example, the acquired LEAP data may go through a normalization process in situations where features (that is, the columns within a matrix or array of data) have different ranges. With normalization, the numeric values of the data are adjusted to a common scale while substantially preserving differences in the ranges of values in order to avoid gradient upsets (and a consequent failure to converge) during subsequent optimization steps. In addition, the acquired raw data is typically transformed into vectors or related meaningful numeric representation, as discussed elsewhere within the present disclosure. Thus, for every row of a particular type of data is converted into suitable integer values as a way to populate an input matrix. Furthermore, the data may have missing values, in which either zero-value or interpolated mean value placeholders may be inserted into the respective column of the matrix.

As previously mentioned, such cleansing or preprocessing second step 1200 need not be a part of a machine learning-based approach, and instead may be used for other forms of analysis where improvements in data uniformity and manageability are needed. Regardless of whether the various forms of data cleansing and other manipulation are used in a machine learning-based approach or not, the architecture of the wearable electronic device 100 is such that it not only improves the operation and efficiency of the reception and transmission of various forms of data, but also of the data gathering itself in that by acting as a single point for data gathering, the aggregation of the data gathering and dissemination need not be dispersed over larger portions of a network. This in turn helps promote consistency of the data. Moreover, by providing a singular, unitary platform (such as through the housing 110-based containment structure discussed previously in conjunction with FIGS. 2A through 2H, as well as the conformal configuration of FIG. 2I), the wearable electronic device 100 is able to provide for a relatively unobtrusive wearer experience that is particularly beneficial for patients with dementia or other cognitive frailties and who might otherwise object to having to wear a device that has a more distributed architecture that employs multiple component securing locations.

This second step 1200 of the machine learning workflow 1000 is also useful in making subsequent analytic inferences from the LEAP data more tractable. For example, redundancy and size of an initial set of raw features taken from the sensed data can make such data difficult to manage, especially as it relates to providing a meaningful way to classify a particular HAR, ADL, IADL or health condition. In particular, the acquired data is often diverse and complex, even for the same person P doing different activities at different times. The amount of information associated with such baseline data 1700, as well as subsequently-acquired ADL or IADL data that is taken from sensors 121, is potentially voluminous, and often of a heterogeneous nature. In addition to ensuring that the data is uniform as a prerequisite for rendering it useful for its intended purpose of extracting machine learning insights, another prerequisite may be to reduce its dimensionality. Such dimensionality reduction may be seen as a portion of the second step 1200 of the machine learning workflow 1000 five-step ordered sequence. In one form, the data interpretation may be performed by one or more portions of machine code that are operated upon by one or more processors 173A that are associated the wearable electronic device 100, gateway 300, backhaul server 400 or cloud 500 such that output of the analysis is provided for use by a caregiver C. In one form, the results of the analysis that are associated with such output may be stored in memory 173B, as well as provided in transient, real-time to a display, audio device, graphical user interface (GUI) or the like all of which may form a part of the remote computing device 900.

In one form, the process of converting the raw LEAP data that is taken from sensors 121 into a form suitable for use in a machine learning algorithm and subsequent model 1500 may form part of an activity known as extraction, transformation and loading (ETL) that may make up part of the previously-discussed second and third steps 1200, 1300 of the machine learning workflow 1000. Within the present context, ETL may be used to decompose multi-sensor data into a suitable feature vector within a given feature space that can then be correlated through subsequent fitting and evaluation of the fourth and fifth steps 1400, 1500 of the machine learning workflow 1000 in order to produce one or more model-based performance metric results for certain types of predictive analytic activities, such as those associated with a monitored individual's ADL, IADL or corresponding health condition where determination or prediction of the health condition is in one form derivative of the ADL or IADL output and in another form is determined directly (that is to say, without the need to first determine ADL or IADL). By way of example, a feature space in two dimensions may be represented through the two axes of a common x-y graph, while additional representations along a third axis (for example, the z-axis) may be made to correspond to outputs, such as those of one of more hidden layers in a neural network in order to define a feature space in three (or more) dimensions in a manner analogous to a tensor. Within the present disclosure, the term "converting" and its variants are understood to include all steps necessary to achieve ETL functionality, including cleansing of the data or reducing its dimensionality the latter of which in the form of feature selection will be discussed in more detail later.

The models employed by system 1—which may include machine code 173E that can be written in or converted from one of several programming languages such as Python, Java, R or the like—as well as employing their corresponding machine learning libraries or toolkits, such as MATLAB, NumPy, Weka, kernlab, SciPy, LIBSVM, SAS, SVMlight, Scikit-Learn, JKernalMachines, Shogun or others-engage in iterative approaches to update the decision-making process as a way to learn from the various forms of data being acquired by the wearable electronic device 100 and its various sensors 121. For example, a machine learning library such as Scikit-learn is used with the Python programming language to provide various classification, regression and clustering algorithms including SVM, random forests, gradient boosting and K-means. In addition, it operates in conjunction with Python numerical and scientific libraries NumPy and SciPy. Moreover, APIs (such as TensorFlow, $H_2O$, Spark MLlib or the like) may be used to help determine the best machine learning model to use, while some of the libraries mentioned above may include unified APIs to facilitate ease of use of a particular machine learning model. In one form, an open-source machine learning core library such as NumPy is used for performing fast linear algebra and related scientific computing within the Python programming language. NumPy provides support operations for multidimensional array and matrix (but not on scalar quantities) data structures, along with a large collection of high-level mathematical functions to operate on these arrays. For example, the linear equations that represent linear algebra are presented in the form of matrices and vectors that may be memory-mapped as data structures for computing complex matrix multiplication relatively easily. Because the LEAP data that is being acquired by the wearable electronic device 100 and its various sensors 121 is multidimensional and takes place over time for the same patient or individual, multidimensional data structures known as Pandas (that is to say, PANel DAta Sets) may be used for the initial preprocessing of the LEAP data. As will be discussed in more detail later, such LEAP data may be input into vectors such as Pandas data structures (also referred to as dataframes) or NumPy arrays such that they can later be broken up into training data sets, validation data sets and test data sets for machine learning use.

Moreover, it is possible through feature extraction-based parameter-reduction techniques such as gradient descent, backward propagation (also referred to herein as backpropagation) or the like to prune a network (such as a deep learning neural network) and improve the mapping between LEAP data input and output to achieve minimized cost functions associated with classifying the corresponding health condition being predicted. Thus, at least in supervised machine learning models, feature extraction takes advantage of knowledge already known to help provide those predictive features most likely of use for a physician or other caregiver C in order to make a clinical diagnosis. Such reduction techniques, as well as those associated with convolutional weighted kernels, filters, channels or the like, are additionally helpful in their ability to reduce the processor 173A and memory 173B requirements associated with deep learning algorithms and models, thereby allowing them to operate on mobile and embedded equipment in the form of wearable electronic device 100. In one form, at least some of the acquired data may be processed locally on the wearable electronic device 100, such as through an on-device embedded library, software module or the like This in turn may lead to inferring the successively more detailed ADL and IADL data. Depending on the available processing power and battery life that is on-board the wearable electronic device 100, increasingly comprehensive portions of the assessment of the wearer's health status may be conducted locally, rather than at the system 1 level, and that all degrees of computational operations conducted locally at the wearable electronic device 100 or remotely at the system 1 are deemed to be within the scope of the present disclosure. For example, a comparison of real-time LEAP data to a baseline data 1700 (such as that stored in a lookup table or related data structure) in order to determine if there is an excessive deviation may be performed locally on the wearable electronic device 100. In another form, some or all of the acquired data may be processed on the gateway 300 such that it promotes edge computing, fog computing or related functionality as previously mentioned. In yet another form, some or all of the acquired data may be processed on the backhaul server 400 or cloud 500. In yet another form, some or all of the predictive analytics (such as that associated with the one or more machine learning models discussed herein) may be performed on any or all of the gateway 300, backhaul server 400 or cloud 500. For example, in one form, the gateway 300 may perform some or all of the machine learning. Thus, in such form it may include functionality beyond that associated with sending data from the wearable electronic device 100 to the other parts of the system 1, the cloud 500 or the like.

Within the machine learning context, various analogies and terms may be useful in understanding how the LEAP data that is being acquired by the wearable electronic device 100 about the individual being monitored may be correlated to information pertaining to the individual's location, mobility, heath condition or the like. For example, terms related to the data being acquired, analyzed and reported include "instance", "label", "feature" and "feature vector". An instance is an example or observation of the data being collected, and may be further defined with an attribute (or input attribute) that is a specific numerical value of that particular instance, while a label is the output, target or answer that the machine learning algorithm is attempting to solve, the feature is a numerical value that corresponds to an input or input variable in the form of the sensed parameters, whereas a feature vector is a multidimensional representation (that is to say, vector, array or tensor) of the various features that are used to represent the object, phenomenon or thing that is being measured by the sensors 121 or other data-gathering components of the wearable electronic device 100. Visually, the instance, label and feature can populate a data table (or spreadsheet) such as the previously-mentioned x-y graph or x-y-z graph where the instances may be listed as numerous rows within a single label column, whereas the features populate various labeled columns for each row. To think of it colloquially, the use of machine learning to solve a classification, regression or other problem can be analogized to preparing a meal, where (a) the data being acquired by the wearable electronic device 100 corresponds to the ingredients to be used, (b) the mathematical code that is the algorithm is a sequence of actions that may be analogized to the tools, equipment, appliances or the like that operates on the ingredients, (c) the model is the recipe that is used in conjunction with the algorithmic tools to provide a framework for repeatability and (d) the label is the desired output in the form of the finished dish. Thus, the model may be understood as the recipe that is formed by using the correct number and quantity of ingredients from the data that have been subjected to trial-and-error training through the use of the tools that make up the algorithm. As such, the model is a mathematical description of how to convert input data into a labeled output; a new model may be generated with the same algorithm with different data, or a different model may be generated from the same data with a different algorithm. Thus, within the context of machine learning, the algorithms discussed herein are constructed to learn from and make predictions in a data-driven manner based on the data being acquired by the wearable electronic device 100, and from these algorithms, a model may be built for subsequent use in identifying salient indicators of the health of an individual that is being monitored by the wearable electronic device 100. In this way, the model is the resulting output once a machine learning algorithm has been trained by data.

In one form, the feature vectors (which may occupy a corresponding feature space) are subjected to a scalar multiplication process in order to construct a weighted predictor function. Moreover, feature construction may be achieved by adding features to those feature vectors that have been previously generated, where operators used to perform such construction may include arithmetic operators (specifically, addition, subtraction, multiplication and division), equality conditions (specifically, equal or not equal) and array operators (specifically, maximums, minimums and averages) among others. In one form, the analytics associated with these feature vectors may be performed in order to ascertain classification-based results (for example, whether the sensed parameter or attribute is less than, equal to or greater than a threshold that may itself be based on a known relative baseline, absolute baseline or other measure of interest), or to perform a regression in order to determine whether the sensed parameter or its attribute can be correlated to the likelihood of an event outcome. Within the present context, a feature vector could be a summary of one or more of a patient's kinematic data (which may form indicia of activity) and related location data, physiological data, or environmental data such that the ensuing clinical observation of symptoms may lead to an enhanced diagnosis of a particular condition (such as UTI, Parkinson's disease symptoms or other neuropsychiatric conditions, for example).

In one form, some or all of the program structure that defines the last three steps 1300, 1400, 1500 (that is, feature extraction, algorithmic training and use of the subsequent model to generate useful analytical output or prediction) of the multistep machine learning workflow 1000 may be embodied in machine code 173E. In this way, particular forms of data extraction may be performed through the manipulation of this data through the cooperation of the processor 173A and the machine code 173E, as can one or more of the machine learning algorithms discussed herein for use with the training and subsequent machine learning model-based analysis. As such, the use of mthe wearable electronic device 100, or whether given that such condition is already present, whether it is becoming worse.

Referring next to FIG. 7, an example of a machine learning model could be a neural network 2000 used to determine whether a person P from which the data is being collected is at risk of developing an adverse medical condition that could be meliorated through an early intervention action plan. By way of example, the analysis using the neural network 2000 may be in the form of a classifier or regression-based approach either of which that trains on one or more components of the LEAP data in order to determine if a person P to whom the wearable electronic device 100 is attached is in danger of developing a UTI; such predictive input data may in one form be used in lieu of—or in conjunction with—traditional descriptive indicia of UTIs, including baseline data 1700 such as that gathered from the medical records of person P or from a representative population database (either of which may also be cleansed, formatted or otherwise extracted in order to make up one of the previously-discussed feature vectors) as a way to produce a classified output. In one particular form, the health change being analyzed by the neural network 200 pertains to UTIs where historical indicia, such as uropathogen counts, CFU/ml, leukocyte esterase, epithelial cells, dipstick analysis or the like, while useful in traditional clinical diagnoses where a physician already has some advance warning of a UTI, are generally not available until such time as after the physician has either (a) seen a patient who has already become symptomatic or (b) conducted various diagnostic tests after having seen a patient and determined that a UTI may be present. Instead of such retroactive mitigation of an already-present likelihood of a UTI, the data collected by the wearable electronic device 100 and processed either on the wearable electronic device 100 or other parts of the system 1 or cloud 500 may be used in a proactive way in order to prevent the UTI from happening in the first place.

Additional details associated with the neural network 2000 are presented in more detail as follows, particularly for diagnosing UTIs and other impending health condition changes. As shown, the neural network 2000 includes an input layer 2100, at least one hidden layer 2200 and an output layer 2300. In a deep learning form, multiple hidden layers 2200 may be used in order to perform increasingly complex analyses; such deep learning is a subset of neural networks where the number of hidden layers 2200 is greater than one. With deep learning (often with the help of advanced processors such as the previously-mentioned GPUs), these stacked hidden layers 2200 can help the system 1 to learn by creating hierarchical representations of certain activities, where subsequently-created layers form an abstraction of previously-created layers as a way to formulate an understanding of complex correlations between the acquired data and a desired output such as a particular health condition. In one form, the hierarchical representation may be used to depict relationships between different primitive actions and more complex actions, where a binary decision process is repeated until the system 1 correlates the data being sampled to movements that may be correlated to HAR or ADL. Moreover, the architecture associated with the neural network is such that it may be developed using a hierarchical approach as a way to readily accommodate new forms of, or relative weighting to, the input data, including those forms of data that represent varying degrees of activity granularity or detail, where in one form such granularity may be associated with how frequently temporal-based data (such as activity data) is being acquired. By way of example, in situations where an analysis of movement is being performed (such as to develop insight into a patient's movement signature), accelerometer data may be fed into a decision tree to allow binary classifications over multiple decision layers. As such, a first level decision may be whether there is movement or not, whereas a second level decision may be to determine the type of movement (in the event that the first level detected movement such as distance traveled, number of steps taken, number of stairs climbed or descended, or the like) or the orientation or position of the wearer (in the event that the first level detected no movement). Likewise, subsequent levels may be used to determine transitions from one movement or position to the next, as well as what such movements mean within a larger context such as social setting, scene-specific position, and so on. From there, the various complex movement or lack thereof may be correlated to various classified signals. In one form, implementation of a supervised form of a deep learning model may generally follow the last four steps 1200, 1300, 1400 and 1500 of the five-step machine learning workflow 1000 that was previously discussed in conjunction with FIG. 6, with slight variations to the machine learning workflow 1000 in order to account for deep learning's specific functionality. For example, a deep learning neural network may (a) initialize parameters and define hyperparameters, (b) iterate over the network using forward propagation and backward propagation for parameter updates, (c) use trained parameters to predict labels and (d) test the predictions on examples.

In one form, the data of the input layer 2100—once suitably preprocessed, extracted and algorithmically trained—can be used to determine through the model and its back-and-forth among the one or more multiple hidden layers 2200 in order to arrive at the output layer 2300 that represents a desired target or output. For example, the output layer 2300 may correspond to ADL or IADL the latter of which may be through a composite of more primitive ADL data that itself is either the target of a prior operation or its own form of input features such as that used as the input layer 2100. Within the present context, the composite nature of the IADL versus the ADL may be aggregative in that it involves inferring the former from various disparate types of the latter, while in another it may be temporal in that it involves inferring the former from the sequential correlation of a series of the latter. Likewise, it could be a combination of both aggregative and temporal components, and that all such composite variants are deemed to be within the scope of the present disclosure. Moreover, the ADL data may in turn be based on location data as well as on more coarse position or activity (including HAR) data, environmental data and physiological data all as discussed elsewhere within this disclosure. In this way, it will be appreciated that the ADL may be a composite of various forms of HAR data in a manner similar to how the IADL is a composite of the ADL, and that the IADL could be a composite of one or both of the HAR and ADL. In one form, the ADLs include postural or ambulatory activities in a manner similar to—or based upon-HAR information, while IADLs include those activities that reflect both physical and cognitive components. As such, a deep learning form of the neural network 2000 can combine one or more LEAP events in order to convert them into complex (i.e. multimodal) events that correspond to ADL or IADL. If it is assumed that a certain percentage of the data being sensed is of questionable validity, a bagging or related probabilistic selection approach may be employed to ensure more relevant data, while dimensionality reduction may be used to remove redundant (that is to say, non-orthogonal) data that otherwise could degrade the performance of the model, particularly when used to perform activity classification. As will be discussed later, reduction of such redundancy is particularly beneficial when analyzing the acquired data in order to form HAR, ADL or IADL analyses while reducing the risk of the model over-generalizing. From such dimensionality reduction or related removal of data redundancy, an ensemble or other aggregating classification algorithm or model may be enabled. In other words, the inclusion of a new feature from the list of various ADL or IADL activities provides additional input data with which to conduct even more detailed machine learning analysis.

Such a model, as well as its corresponding algorithmic tools, may include configuring processor 173A to execute programmed software instructions by using a predefined set of machine code 173E such that the neural network which may receive data from the various sensors 121 in the form of various nodes 2100A, 2100B, 2100C . . . 2100N of the input layer 2100, where each of these input nodes 2100A, 2100B, 2100C . . . 2100N can store its corresponding input data value within a particular location of memory 173B. In one form, the data corresponding to the various nodes 2100A, 2100B, 2100C . . . 2100N of the input layer 2100 could be that of the LEAP data taken from the various sensors 121, the hybrid wireless communication module 175, inter-patient or intra-patient baseline data or other sources that would contribute to the analysis performed by the neural network 2000 for the determination of HAR, ADL, IADL and related changes in a patient's health condition. In addition, the one or more hidden nodes 2200A, 2200B, 2200C . . . 2200N of the hidden layer 2200 may be connected to each input node 2100A, 2100B, 2100C . . . 2100N such that the computational instructions (which are based on, or in the form of, activation functions such as step/threshold, binary sigmoid, piecewise linear, Gaussian that correspond to hyperbolic tangents, rectified linear units (ReLUs) or the like that are used to introduce nonlinearity into the feature space of a neural network) that are implemented in machine code 173E that form a part of the processor 173A, may be used to calculate output nodes 2300A, 2300B, 23300C . . . 2300N of the respective output layer 2300. Furthermore, each of the one or more output nodes 2300A, 2300B, 2300C . . . 2300N can store its corresponding output data value within a particular location of memory 173B in such a way that an output signal provides indicia of one or more classifications performed by the model. By way of example, each block or portion within these figures may represent a module, segment or portion of machine code such as that which forms one or more executable instructions for implementing a particular specified logical function or functions. As such, each block, module, segment or portion may be implemented by the particular arrangement of the components and systems discussed herein, especially to perform the specified functions or acts needed for operation of the wearable electronic device 100 and system 1 and ancillary structure.

The neural network 2000 is meant to mimic the neurons in the human brain through the various interconnecting nodes 2100A through 2100N, 2200A through 2200N and 2300A through 2300N of the three primary layers 2100, 2200 and 2300 such that a model trained with these nodes may determine a response in the output layer for data received into the input layer through adjustable weights W made within the hidden layer or layers 2200. The interconnectivity between the nodes of the various layers ensures that the nodes from one layer influence nodes from the other layers to allow the neural network 2000 to observe all components of the acquired LEAP data, as well as how the disparate pieces of such data may or may not relate to one another in a manner that roughly analogizes the human brain. As with the Bayesian-based approaches (and unlike the decision trees and logistic regression mentioned previously), neural network methods typically work with large data samples. In some instances (i.e., deep learning) multiple hidden layers 2200 may be used in order to perform increasingly complex analyses through regular updates of the neural network model by using some labeled data and even more unlabeled data. The parallel or connectionist-based computation of the neural network 2000 differs from the sequential processing of most computer architectures in that it forms a specific cycle in order to make logical inferences, which in turn facilitates heuristic discovery of both non-linear and multiplicative relationships between myriad input and output variables. As such, a neural network may process multiple variables (often in the form of hundreds or thousands of input nodes) to model complex relationships such as identifying the onset and progression of infections, cognitive impairment or other diseases or related health conditions. As with neurons in the human brain, each of the nodes of the neural network 2000 either acts as an input (nodes 2100A through 2100N), output (nodes 2300A through 2300N) or performs a single activation function (nodes 2200A through 2200N) such as those discussed previously, rather than attempting to model an entire relationship in the a priori logic of most computer models. For example, the input nodes 2100A through 2100N of input layer 2100 take in values of attributes relevant to the receipt of various forms of the LEAP data to be subsequently manipulated by weights W for use in the hidden nodes 2200A through 2200N of the hidden layer 2200.

One way to achieve the training step 1400 of FIG. 6 for the neural network 2000 of FIG. 7 is to use a multi-pronged algorithmic approach. In such an approach, for each particular node n, a weighted hypothesis H (also referred to as a hypothesis function) that represents a certain output (i.e., target or response) created through the operation of a feedforward algorithm 1410 in conjunction with an activation algorithm 1420 is imposed upon the input data such that when different from a desired target value TV based on a cost function algorithm 1430 is then subjected to a backpropagation algorithm 1440 in order to correct (that is to say, educate) the initial hypothesis H through reduction in a cost function CF (also referred to as a loss function or an objective function the latter of which occurs when the data is not linearly separable as a way to reduce the influence of data points on the wrong side of a hyperplane or related linear decision boundary) through an adapting algorithm 1450 that updates the weights W. Examples of algorithms used as part of the training step 1400 may include conjugate gradient, gradient descent, Levenberg-Marquardt, Newton's Method and Quasi-Newton. In one form, these algorithms may be used to fit to certain weights W such that the training parameters are used to develop the hypothesis H.

In particular, the input of the LEAP data from one or more of the sensors 121 and the first and second wireless communication sub-modules 175A, 175B and that are associated with the nodes 2100A through 2100N are fed through the feedforward algorithm 1410 to the hidden layer 2200 while being manipulated by the weights W and the activation algorithm 1420. The new values generated with the hidden layer 2200 are then forwarded (also through the feedforward algorithm 1410) to the output layer 2300, while being manipulated again by the weights W and activation algorithm 1420. The feedforward algorithm 1410 is of the general form $$Hn_l = \sigma \Sigma_{l-1}(W_l i_{l-1})$$

where σ is an activation function represented by the activation algorithm 1420, $Hn_l$ is the hypothesis H value at a given node n on a given layer l, while W is the weight value being applied to layer l, and i is the value on the immediately preceding layer. In this way, n and l act as respective shorthand for the previously-discussed nodes 2100A . . .

2100N, 2200A ... 2200N or 2300A ... 2300N and layers 2100, 2200 and 2300. All of the input values associated with the LEAP data being analyzed are fed to each of the respective nodes 2100A ... 2100N of the first layer 2100. In this way, each node 2200A ... 2200N of the first of the hidden layers 2200 receives the sum of all the nodes 2100A ... 2100N from the input layer 2100 multiplied by the weights W, after which the summed value is then subjected to the activation algorithm 1420 to generate a randomized output (at least in situations where the initial choice of weights W is random).

In one form, the activation algorithm 1420 may be described by the activation function σ (also referred to as the logistic function or standard sigmoid function) that is of the general form $$\sigma(x) = \frac{1}{1+e^{-x}}$$

such that the value of the output σ(x) is always bounded between zero and one so that regardless of how high or low the value of the input x as a way to provide a nonlinear representation of a weight or confidence associated with node n. It will be appreciated that other activation functions besides the sigmoid variant of the activation function a may be used.

After the application of the feedforward and activation algorithms 1410, 1420, the target of the hypothesis H is compared to the desired target value TV in order to calculate the cost function CF through the use of the cost function algorithm 1430 that is of the general form $$C = \tfrac{1}{2}(Hn_l - TV)^2$$

After this, the backpropagation algorithm 1440 is run in order to expose the error from the cost function CF to the derivative of the activation function σ to educate the hypothesis H based on the margin of the error. In this way, the error generated within each layer may be thought of as a recursive accumulation of change up to that time that has contributed to the error as seen by each node n. The back propagation algorithm 1440 is of the general form $$\delta_l = (\Delta E_{n_l} * \sigma'(Hn_l))$$

where past values of the weights W are subjected to chain rule partial differentiation in order to fit the following layer of nodes n, as shown by the sequence below $$\frac{\partial E}{\partial n} = \delta_L = [TV(W_{l+1} * \delta_{l+1} * Hn_l(1 - Hn_l)]$$

The gradient of these randomly initialized weights W and biases B of the neural network 2000 may be obtained by the previously-discussed backward propagation in conjunction with a library such as Numpy. Regardless of how it is conducted, this allows correlation to an individual one of the weights W by multiplying it by the weight's activated input node value that is of the general form $$\frac{\partial E}{\partial W} = \frac{\partial E}{\partial n} * Hn_{l-1}$$

The changes are then used in the adapting algorithm 1450 to adapt the values of the weights W where η represents the learning rate. The adapting algorithm 1450 is of the general form $$W = W - \left(\eta * \frac{\partial E}{\partial w}\right)$$

By repeating these algorithms over and over again, the future inputs are manipulated in a manner such that the accuracy of the hypothesis H will improve. Thus, the training step 1400 determines errors in hypothesis H through the computed cost function CF, after which the weights W may be adjusted; such an approach is particularly useful in situations involving imbalances in the training data set 1610. In one form, iterations may be used to test the various algorithms through the use of a confusion matrix that compares classifications made by the trained model with known quantities from labeled examples. More particularly for the present disclosure, the training step 1400 allows the final neural network 2000 to be optimized for a particular sensed parameter, such as (i) location information (such as amount or time of day spent in a particular room), (ii) local environmental conditions such as temperature, smells, time of day or the like, (iii) amount or frequency of patient ambulatory activity or (iv) various physiological conditions such as body temperature, heartrate or the like. In this way, each parameter being measured by the wearable electronic device 100 may have its corresponding neural network 2000 of FIG. 7 that has been trained using the five-step machine learning workflow 1000 of FIG. 6 with the algorithms 1410 through 1450 of FIG. 7.

Moreover, as mentioned elsewhere in the present disclosure, the training step 1400 (along with its associated algorithms 1410, 1420, 1430, 1440 and 1450) and use step 1500 of the five-step machine learning workflow 1000 (as well as the ensuing model) may be performed on any suitably-configured processor 173A and memory 173B combination that is situated on the wearable electronic device 100, server 400, cloud 500 or other equipment that is associated with system 1, subject to processing and storage capabilities. As such, any of the previously-discussed ASIC, CPU, FPGA, GRU or other comparable integrated circuit (IC) that is used with or forms part of processor 173A can be used to execute a machine learning algorithm that has been trained on LEAP data acquired by the wearable electronic device 100 and stored in memory 173B, possibly in conjunction with baseline data 1700 from sensory or other sources for use in a resulting model. It is also possible to perform different portions of the five-step machine learning workflow 1000 with different pieces of equipment associated with system 1. For example, in one form, at least the training may be performed as part of a cloud-based application, while at least the data acquisition and some preprocessing may be performed by the wearable electronic device 100. Other portions of the workflow 1000, such as extraction and analysis may be performed on some of all of the components discussed herein. In other forms, some or all of the training and analysis may be performed on the wearable electronic device 100, server 400, cloud 500 or other equipment that is associated with system 1.

The neural network 2000 depicted in FIG. 7 is but one type of machine learning model. In one form, the neural network 2000 may be a recurrent neural network (RNN) such as the previously-discussed LS™ in order to mimic the highly recursive networks in the human brain through loops that allow information to persist, as well as to take advantage of the time series nature of the acquired LEAP data and the associated need to predict arbitrary future location, activities or behaviors. Such an approach may in turn perform forecasting or prediction of time series events, particularly those that take place over relatively long sequences. The RNN version of the neural network 2000 is particularly adept at modeling sequential data such as that taken from sensors 121, particularly those which are capable of spatio-temporal data acquisition. In one form, an RNN may be represented as an expanded feedforward network through the inclusion of a recurrent loop, one or more state variables or the like. In such case, a RNN in a given state may be deemed the equivalent of the output of one or more of a neural network's hidden layers 2200. RNNs are helpful in overcoming situations where a conventional feedforward neural network would otherwise not operate because of the latter's inability to accept sequential data, work with inputs of different sizes or utilize memory to store information about previous states.

Other forms of the neural network 2000, such as a CNN and related deep learning approaches, are well-suited for computer vision and related approaches where kernel-based feature extraction operations for spatial-based information are required. Thus, whereas the previously-discussed RNN extends a neural network across time, CNN extends a neural network across space. More particularly, while two dimensional CNNs may be employed for image recognition problems, one-dimensional variants work well for identifying simple patterns from shorter segments of acquired data, such as time sequence data acquired from accelerometers or gyroscopes that make up a portion of the activity sensors 121B. In one form, such a machine learning model used to predict an individual's health condition based on the acquired LEAP data can take in the raw input from sensors 121 and pass the data to one or more of these intermediate hidden layer 22 filters to process through weighted kernels that are trained to detect specific features with a high degree of correlation to a known quantity. For an example as applied to the present disclosure, these weighted kernels may be in the form of the symptoms or symptom intensity of a particular health condition (such as a UTL cancer, cognitive impairment or the like), or to the types of movement, activity or behavior of a patient that has a high degree of correlation to the particular health condition. Thus, even though CNNs—with their convolutional layers and pooling layers—are commonly used to analyze handwriting, facial recognition and other image-related data, they may also be used in HAR or ADL for the relatively coarse accelerometer and gyroscope data that is being provided by the wearable electronic device 100. Unlike other machine learning models, CNNs are capable of automatically learning features from time-based sequence data, in order to provide direct output for use in multi-step forecasting, such as what will happen to a patient over a future period of time, such as the next twenty four hours in a given day, the next seven days in a given week, the next month, or the like. In addition, a CNN may be trained through the use of relatively simple modular approaches such as the previously-mentioned Keras API, especially in situations where the size of the training data sets is relatively small, as well as situations where the analysis is being conducted on the cloud 500, such as through AWS, Microsoft Azure, IBM Cloud or the like.

As mentioned in conjunction with FIG. 6, baseline data 1700 may be predetermined, user definable or acquired from known inter-patient or intra-patient standards or norms all of which may be stored in one or more databases within memory 173B. As such, baseline data 1700 that corresponds to a health condition may be in the form of (a) personalized data that is specific to the individual associated with the wearable electronic device 100, (b) specific to a particular group that may exhibit one or more demographic similarities, or (c) universal such that it covers relatively broad swaths of the population at large. One example of a such baseline data 1700 may be acquired from the National Institute of Health (NIH) *Unified Medical Language System*. Such additional information may include conventional UTI indicia such as the previously-mentioned uropathogen counts, CFU/ml, dysuria, leukocyte esterase, epithelial cells and other parameters such as those detectable using a dipstick analysis (such as specific gravity, pH, leukocytes, nitrites, proteins, glucose, ketones, urobilinogen, bilirubin and erythrocytes). Moreover, the use of the data acquired by the wearable electronic device 100 may be performed as part of a larger causal-based medical inquiry such as those using network science that may further include the use of a phenotypic disease network. In one form, either or both of the intra-patient and inter-patient baseline data 1700 may be embodied in data structures stored in various data management configurations, such as in memory 173B that is either local to the wearable electronic device 100, the system 1, the cloud 500 or elsewhere. For example, sensor-acquired data may be stored in a data management center such as that contained within Microsoft Azure or a related cloud-based computing service. In one form, the interpatient baseline data 1700 may include any physical, cognitive, neuropsychiatric or related clinical condition.

In one exemplary form, the various flow diagrams of FIGS. 6, 11A, 11B and 14A through 14C, in addition to the neural network of FIG. 7, form program structures while the arrays (including the previously-discussed multidimensional arrays), linked lists, trees or the like of FIGS. 3A through 3K, 8, 12 and 13 form data structures both of which constitute specific structural features or elements that are recited in one or more of the claims and that help to illustrate the architecture and operation of the various forms of the wearable electronic device 100 and system 1. Thus, by describing the various computer software elements in conjunction with the various functional activities that are depicted in these flow diagrams, neural networks or the like, the machine code 173E cooperates with one or both of the processor 173A and memory 173B to perform a set of particular manipulations of the acquired LEAP data to constrain the operation of one or both of the wearable electronic device 100 and system 1 in a particular way for the purposes of identifying patient, activity, location or health condition. In one form, these may be used for situations where one or more machine learning algorithms and models are being used to convert the data that has been acquired through the operation of the wearable electronic device 100 into clinically-relevant predictions. In a similar manner, the cooperation between these structural features is such that they perform a set of operations in response to receiving a corresponding instruction selected from a predefined set or portion of such machine code 173E for non-machine learning operations as well. For example, in one form where the acquired data is being used to determine if a person P associated with the wearable electronic device 100 is at risk of developing a UTI or other identifiable medical condition, a classification-based neural network machine learning model may be carried out on one or both of the system 1 and cloud 500, as well as (depending on its computational capability) the wearable electronic device 100.

Regardless of the form of the machine learning model, some training under the fourth step 1400 of the machine learning workflow 1000 may be used in order to allow the model to adapt to new, changing data. Thus in one form, where the data is used to build a machine learning model for predicting health conditions about a patient or group of patients comes from the presently-acquired data 1600 from the LEAP data, it is broken up into three sets known as the training data set 1610, the validation data set 1620 and the testing data set 1630. With supervised learning, the training data set 1610 provides a set of examples used to fit the parameters through weighting. In one form, the acquired data that is initially segmented into the training data set 1610 may be between about 70% and about 75% of the total data, while the remaining 25% to 30% is reserved. In one form, the process of segmenting the data may be performed in a random manner, while in another by known algorithms, such as regularization algorithms and others found in a Scikit-Learn function library for the previously-mentioned Pandas dataframes or NumPy arrays. All such data set splitting helps ensure that the model is not overfitting, or that the predictor variables associated with the input data avoid a covariate shift associated with an improper choice of training and testing data sets 1610, 1630. In a supervised learning model, the already-known paired inputs and outputs form the training data set 1610, and in one particular form may be labeled in a vector, matrix, array or other data structure for ease of identification and previously-accepted veracity such as that associated with ground truth annotated human data. For example, annotated HAR data for training may include those associated with publicly available or proprietary data sets. More particularly, at least some of the inputs of the sensed data may be arranged into features within the data table such that multiple inputs form an input vector, one exemplary form of which accelerometer-based or gyroscope-based activity data. As will be apparent from the totality of the present disclosure, the attributes of the acquired data correspond to—upon suitable cleansing and extraction-features that may be stored (such as in memory 173B) in quantifiable feature vector form. In addition, the labeled answers are in the form of targets (for example, a scalar) that the machine learning model is trying to predict. Similarly, some of the input data may be included in a scalar quantity, such as that associated with temperatures, pressure or other forms of environmental data; this too may be included in the data table. In one form, the size or number of entries of such data within a table corresponds to the dimensionality of the previously-discussed data structures that are part of memory 173B.

In one form, counting how many instances in the training data set 1610 fall outside the training data set 1610 space helps to determine which values constitute an error of false positives and false negatives that can be minimized by balancing specificity and generality of the hypothesis H. The preliminary model that results from the use of one or more training algorithms on the training data set produces a result which is then compared with the target. Various modes of testing the training data set 1610 may be used, including leave-one-out or different types of cross-validation such as n-fold cross-validation. The results are in turn used to adjust the preliminary model's parameters to promote better fitting (that is, to avoid overfitting).

The validation data set 1620 is then introduced to provide an unbiased evaluation of how well the fitted preliminary model from the training data set predicts an outcome. In one form, the validation data set 1620 is taken from the data that was reserved from the initially acquired data. In this way, the algorithm is being trained without learning from the validation data set 1620. In one form, this outcome of observations made in the validation data set 1620 may be used to decide when the preliminary model can stop training, such as to avoid the overfitting mentioned previously. In one form, when the machine learning model is in the form of the neural network 2000 of FIG. 7, the validation data set 1620 may also be used to tune the model's hyperparameters (that is to say, the number of hidden units) in view of the fact that the correct answer is already known at this time. In addition to evaluating how well an algorithm fits on the training data set 1610, the validation data set 1620 may be used to tune the various hidden nodes of the hidden layer 2200 of the neural network 2000 in order to enhance the ensuing model's predictive ability. In one form, the tuning of the nodes 2200A through 2200N of the hidden layer 2200 is through the use of the preset hyperparameters that (along with input data) define the structure of the network being built to allow the network to be tailored to a specific imminent adverse health condition. Stated another way, hyperparameter optimization involves finding the hyperparameters of a particular machine learning algorithm that produce optimum performance when measured on a validation data set 1620. Examples of such hyperparameters include the previously-discussed hidden node activation functions and weights W, as well as others including the algorithmic weight optimizers (examples of which include stochastic gradient descent, batch gradient descent or mini batch gradient descent), number of layers 2100, 2200, 2300 (that is to say, depth), number of hidden nodes 2200A through 2200N (that is to say, width) within each layer, learning rates (that is to say, size of the parameter updating steps) and mini-batch size (that is to say, the number of training examples that are used to update the parameters). In another form, default values for one or more of the hyperparameters may be used. Moreover, certain approaches that perform evaluations based on previous trials, such as Bayesian-based ones, may be particularly good for determining hyperparameters in a timewise-efficient manner to help them reason about the best set of hyperparameters to evaluate.

Finally, the testing data set 1630 is used to provide an unbiased evaluation of the performance of the final version of the algorithm that was fitted to the original training data set 1610. The testing data set 1630 is independent of—but statistically similar to—the training data set 1610, thereby minimizing any adverse effects from discrepancies in the data, as well as providing a challenge opportunity to determine whether the preliminary model satisfactorily performs on previously unseen portions of the LEAP data. In particular, because the testing data set 1630 already contains known values for the target, it is easy to determine whether the predictions made by the preliminary model are correct or not. Once the algorithms have been fully trained and analyzed with all three data sets 1610, 1620 and 1630, they can be used as a classifier or other machine learning model.

Within the context of a classifier-based machine learning model, a training operation such as the previously-discussed training step 1400 of FIGS. 6 and 7 is used to learn classifier parameters from the acquired data through the conversion of activity or other forms of baseline data 1700 into feature vectors through the previously-discussed algorithmic cleansing and subsequent extraction activities. Testing of the extracted data may take place as part of an algorithmic fitting activity. Subsequent evaluation of the acquired LEAP data may take place, including comparing between the extracted feature vectors of the baseline data 1700 and presently-acquired LEAP data. Stated another way, in one form, at least a portion of the training function performed by the machine learning algorithms discussed herein is made up of one or more of representation, evaluation and optimization functions in order to (i) convert the raw data into more useful form, (ii) define through the previously-discussed cost function CF what learning the representation function will undertake and (iii) optimize the representation function as a way to improve the evaluation metric for subsequent model-based analysis of the acquired LEAP data.

Depending on their architecture, types of data accepted, number of layers used, network topology, types of activation functions used and the way they are trained, the neural network 2000 may be generally lumped into either (i) a feedforward neural network or (ii) a forward propagation or backward propagation recurrent network, although other categorization is also possible. Within these broad categories, numerous particular architectures may be used, including some of those as previously discussed such as perceptrons and CNNs in the first, and long/short term memory networks, Hopfield networks, Boltzmann Machine networks and deep belief networks in the second. Neural network 2000 is particularly adept at retaining historical input data, due at least in part to its interconnected nodal arrangement such that the temporal output of previous nodes (for forward propagation variants) or previous or subsequent nodes (for recurrent variants) are used at any particular node. The hierarchical cluster of simulated neurons in a CNN or other form of neural network 2000 may be used in such a way that each of the neurons may detect low level characteristics of an input stimulus, after which they can communicate with one another within the hierarchy in order to develop a high level detection of one or more objects that are associated with the acquired data through a "big-picture" type of aggregation. In this way within a CNN, there exists locally connected patches of nodes between layers rather than as being fully connected in a traditional multilayer neural network. Weights W are used to spatially extend the network. Thus, at least certain variants of the neural network 2000 may take advantage of this hierarchical structure in order to learn increasingly complex feature representations from the acquired raw data. In other words, the raw data taken from the input layer 2100 of a deep learning version of the neural network 2000 may be transformed into more complex feature representations by successively combining outputs from a preceding layer. By way of example, early detection of a patient at risk for developing a UTI may be made by analyzing one or more sensed features, such location or activity data that may indicate the number of times or how recently a patient had a drink, how often or how much time the patient spent in the bathroom (possibly in conjunction with the drink-specific data) or other time-related activities. In one form, such early detection may then be followed by subsequent physician-directed testing and diagnoses, such as taking a urine culture.

As previously mentioned, the physician may be one of the caregivers C who receives through his or her remote computing devices 900 the output through the third wireless sub-module 175C of a machine learning model where such output may be in the form of CDS information or the like. As such, a physician may use the results of a machine learning model such as that taught with data acquired by the wearable electronic device 100 to help predict the likelihood of an imminent onset of a disease such as a UTI, dementia or the like, as well as situations where comorbidities may exist where one condition may be linked to another. For example, a patient who may be manifesting early signs of Alzheimer's disease may be unable to recognize a change in his or her health status, as well unable to convey such changes to a physician, nurse, family member or other caregiver C; use of data acquired by the wearable electronic device 100 in conjunction with a machine learning model such as that discussed herein could be used to anticipate whether such patient is at risk of developing a UTI in such situations even absent direct communication from the patient. Relatedly, using such a machine learning model with the acquired data in order to divine changes in ADL or IADL patterns may in turn be used to provide early insight into whether the patient is symptomatic for Alzheimer's disease as well as other forms of dementia. As mentioned previously, training for these models may include comparing the extracted data (in the form of features, feature vectors or the like) to corresponding baseline data 1700 such as predicted data from an inter-patient or intra-patient set of control data model, after which an error value may be generated that in turn may be used (such as through subsequent weight W adjustments or the like) to update a training algorithm. In another form, the output may in turn form the basis for additional analysis such that a machine learning model-based diagnosis is produced directly from the data that has been acquired by the wearable electronic device 100 and processed by either on-device or remote logic device 173.

From the foregoing, it will be appreciated that a machine learning model or a hybrid of two or more such models may be used to provide additional proactive insights into the health of a patient or other individual from whom data is being gathered by the wearable electronic device 100. For example, a machine learning model may form a classifier-based approach that is capable of partitioning a particular condition into various training classes based on the taxonomy of the condition being assessed. In one form, the condition being assessed forms the target or output of the classifier model, where in a more particular form such classification may be into one or more health conditions, such as healthy or normal, as well as one or more anomalous conditions such as mild cognitive decline, significant cognitive decline, UTI, imminent UTI or other condition. Thus, if the concern is that a particular patient is at risk of a UTI, recursive approaches can use the taxonomy indicia in order to generate classes of training data sets that correspond to symptoms (as well as symptom intensity) of a UTI. From this, the output (in the form of larger inference class data sets) may be generated in order to determine the likelihood of a UTI. Significantly, such an approach may be done in conjunction with, or instead of, assessments using traditional markers for a UTI, such as those discussed previously in conjunction with the NIH UnifiedAMedical Language System. For example, the performance of a trained machine learning model in conducting UTI classification may include the previously-discussed ROC analysis where the AUC is a helpful figure of merit in graphically evaluating the predictive accuracy of a given machine learning model.

Figure 11A:
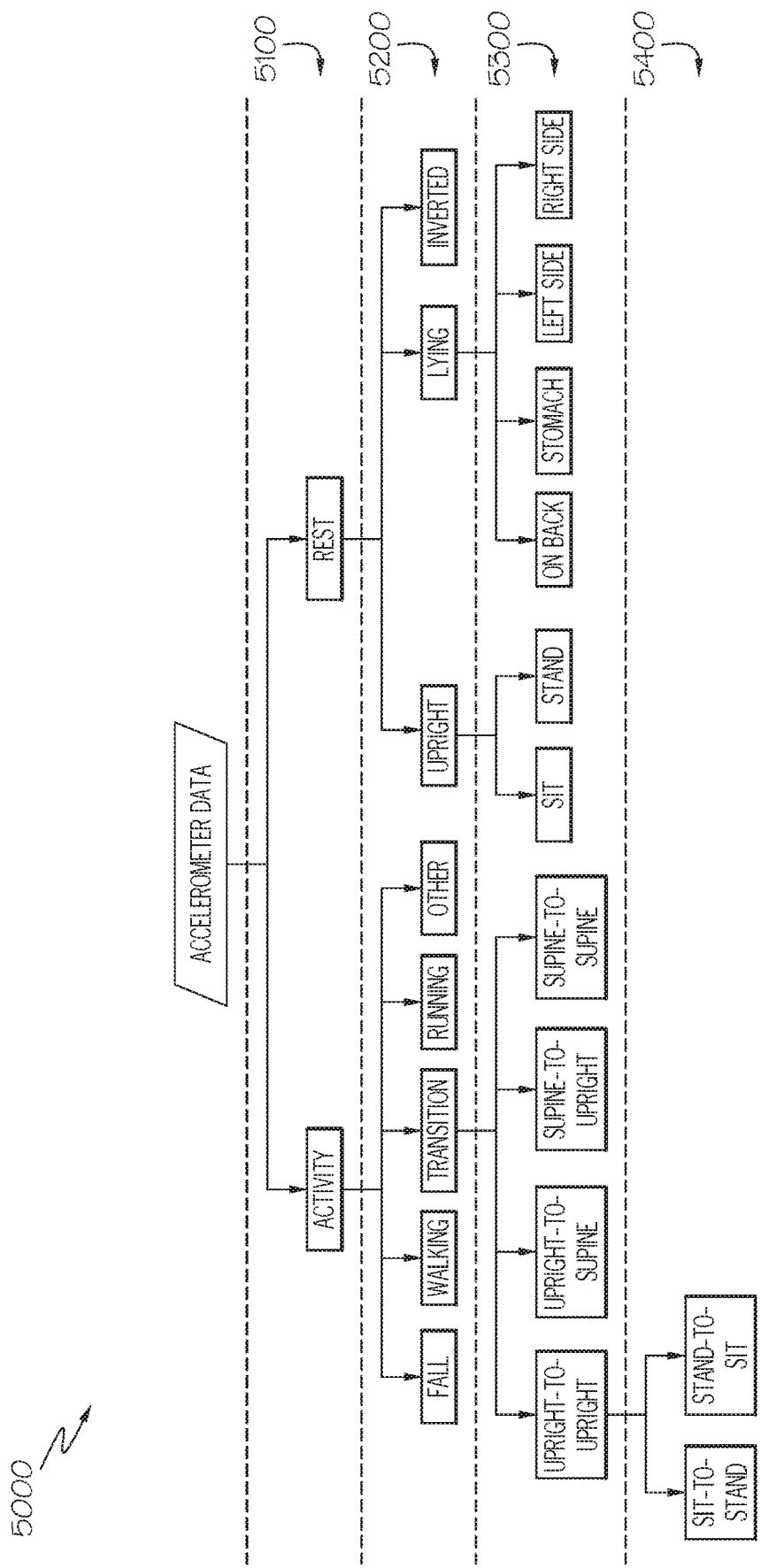
FIG. 11A depicts a program structure for hierarchical relationships of particular HAR-related movements that may be determined based on LEAP data generated by the wearable electronic device and system of FIG. 1 according to one or more embodiments shown or described herein.
Figure 11B:
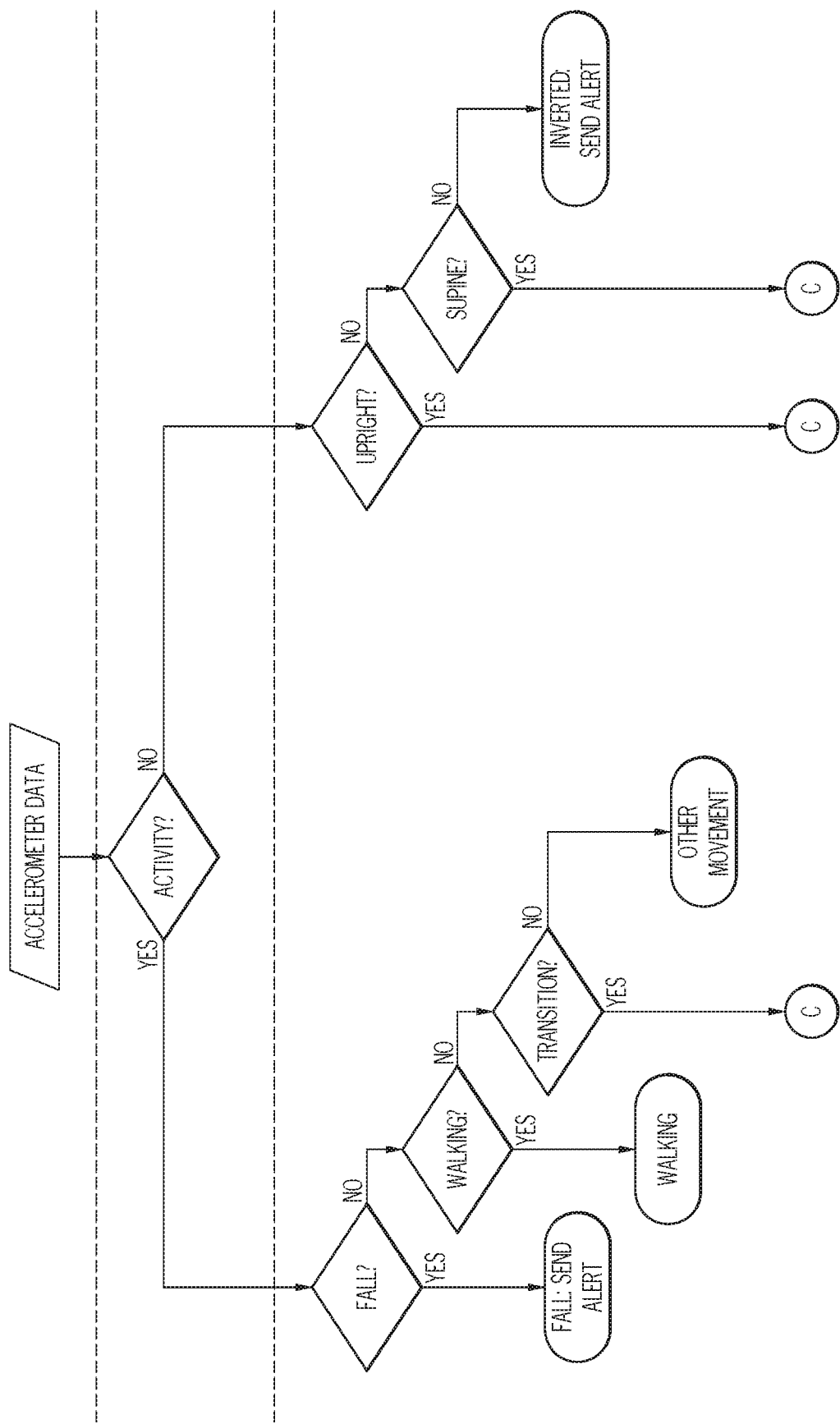
FIG. 11B depicts a program structure for a decision tree of certain HAR-related movements based on an accelerometer portion of the LEAP data generated by the wearable electronic device and system of FIG. 1 according to one or more embodiments shown or described herein.
Figure 11B:
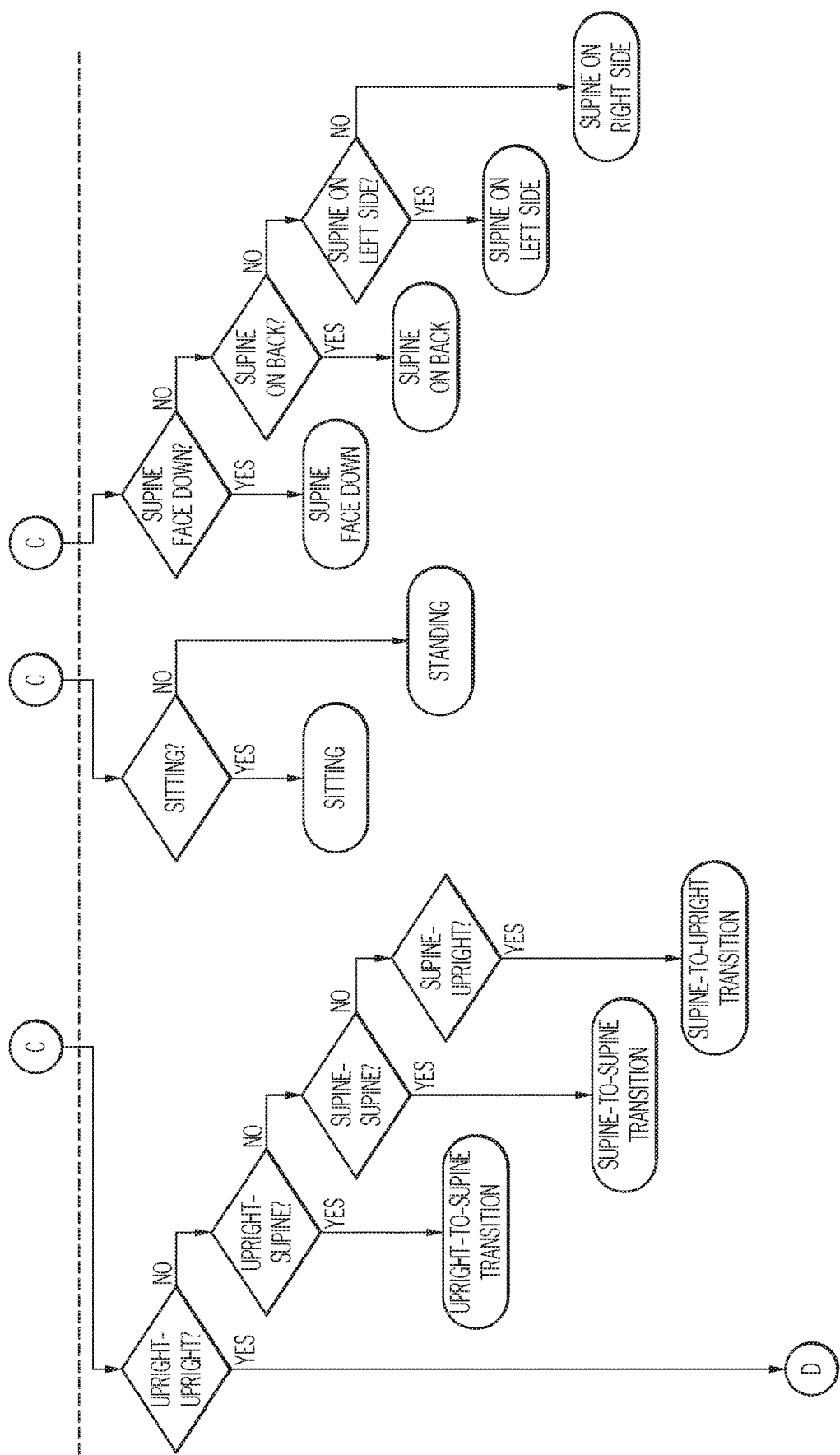
Figure 11B:
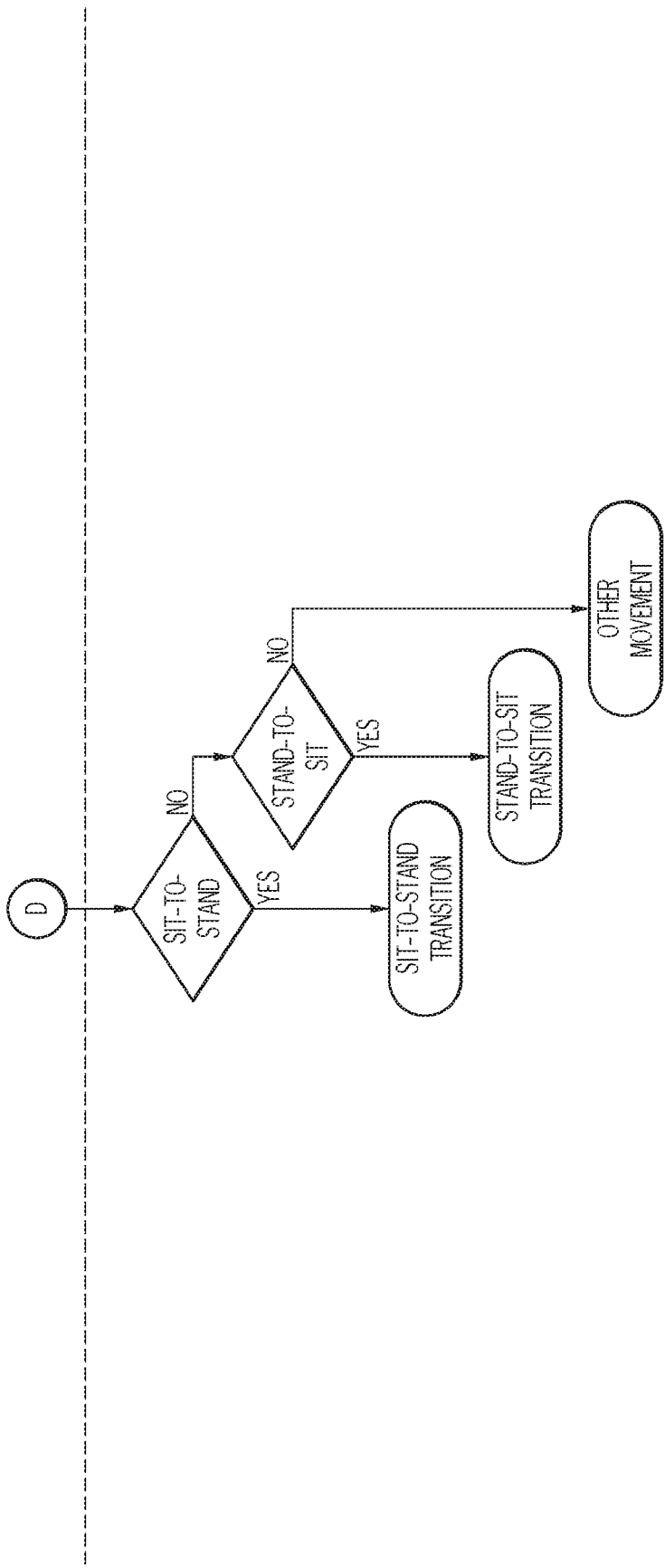

Referring next to FIGS. 11A and 11B, a representative program structure 5000 shows a hierarchical way to identify and classify various movements that may be used to correlate measurements taken from various forms of sensor 121 data (such as those associated with activity sensors 121B including accelerometers, gyroscopes, magnetometers or the like of FIG. 2F) with certain movements that may in turn be correlated to one or more of HAR events. Referring with particularity to FIG. 11A, various strata 5100, 5200, 5300 and 5400 are shown such that broader, more sweeping activity classifications are made within the upper strata 5100, while more detailed classification is shown in the successively lower intermediate strata 5200 and 5300 to the lowest strata 5400. For example, within the uppermost strata 5100, a distinction between movement (activity) and no movement (static) is shown, while (using the "activity" labeled classification as an example) analysis of the type of activity, such as whether the movement-based activity of the highest-level strata 5100 can be more particularly identified as a fall, walking, transitional movement or something else, and from there (using the "transitional" category as an example) whether it involves transition between upright positions, transition from upright to a supine position, transition from supine to upright, transition between supine positions or the like. From this, the attempt at a particular classification proceeds from an understanding of more certain (but less granular) activities at the higher strata 5100 to less certain (but more granular) activities at the intermediate and lowest strata 5200 through 5400. In a similar manner, different classifications within a given strata represent activities that are understood to be independent of—and independently measurable from—one another based on readings taken from activity sensors 121B.

Referring with particularity to FIG. 11B, once the activity is better understood down to a fairly detailed level through the strata 5100 through 5400 of FIG. 11A, there is enough semblance of order to use a binary decision approach to permit correlation of the activity sensor 121B data (shown presently as accelerometer data) and its related movement classification to HAR recognition. In one form, this correlation may be subsequently conveyed to and displayed on the remote computing device 900, as well as to a machine learning algorithm in order to correlate HAR and ADL information in order to (as shown and discussed in conjunction with FIGS. 14A through 14C) determine if the patient is at risk of developing one or more adverse health conditions, as will be discussed in more detail in Section IV. For example, by detecting static period body postures and then understanding what dynamic activities take place between such postures allows an inference to be drawn about the likelihood of certain transitional movements. Likewise by differentiating between types of dynamic movements (such as through a frequency-based spectral analysis of the accelerometer data and comparison to known movement thresholds, including those from the previously-discussed intra-patient or inter-patient baselines), additional inferences may be drawn that in turn helps in the overall classification. Furthermore, in certain movements such as a fall an alert, alarm or related message may be sent through the third wireless communication sub-module 175C, gateway 300 and system 1 to the remote computing device 900.

In one form, context weighting may be included to allow for considerations of more significant portions of the data set. Likewise, data mining procedures may be undertaken in order to help in classification activities, such as the identification of patterns within the acquired data; such mining may be particularly beneficial in situations where the amount of sensed or otherwise collected data is large. Furthermore, by using machine learning, such mined data and the resulting patterns can be implemented in an automated (rather than manual) way. It will be appreciated that such data mining and machine learning may be employed as a component of cognitive computing to help extend conventional predictive analytics in order to provide CDS (in one form) or more comprehensive diagnosis activities (in another form). Moreover, if the amount of data becomes voluminous (which may be the case with agitation-related movement or related activity data taken over frequent time windows each with high acquisition frequencies and lengthy patient monitoring timeframes in order to understand the data with a high degree of granularity and consequent finer level or more specific level of detail), storage of such data may be done in larger forms of memory 173B such as that which resides either within server 400 memory, or in the cloud 500 through the internet. In one form, daily routines that are common in geriatric patients would correspond to relatively granular levels of detail. Likewise, when large, granular data sets are present, the chips or chipsets used to achieve various data processing within the logic device 173, as well as chips or chipsets used in the hybrid wireless communication module 175, may be configured with power-efficient machine codes 173E or firmware to collect and process such granular data for use by a caregiver C. In one form, this logic may be implemented in web and mobile applications. Other logic (which may also be embodied as machine code 173E, firmware or the like) may be developed to ensure that the wearable electronic device 100 communicates properly with the cloud 500 to provide reliable data flow.

III. Analysis of Device-Acquired Data for ADL or IADL

Referring next to FIG. 8 in conjunction with the previously-discussed FIGS. 11A, 11B, examples are shown of how sensed data from the wearable electronic device 100 may be used by the system 1 to better understand HAR events (FIGS. 11A and 11B) that in turn may be used to infer ADL events, as well as how to use this improved understanding to identify changes in the salient indicators of the health of an at-risk patient. In one form, the wearable electronic device 100 and the system 1 of FIG. 1 may be used in conjunction with one another to monitor and analyze one or more of the sensed LEAP data as evidence of HAR or ADL, and from there, whether such monitoring and analysis indicates a change in the health of the patient. In one form, machine learning may be used to help distinguish various ADL events, including those of a more complex, fine-grained nature from more coarse-grained ones. By way of example, an HAR-based coarse-grained understanding of an event may be the detection that a person P is in a sitting position, while an ADL-based fine-grained understanding of the same event is where such sitting is taking place (for example, sitting in a chair versus sitting on a floor), as well as a more thorough understanding of the context within which event takes place.

Referring again and with particularity to FIGS. 11A and 11B, a representative program structure according to the present disclosure may include taking one or both of the HAR-related movements to correlate to ADL data. The signals (such as accelerometer signals) from at least some of the intermediate strata 5200, 5300 may be subjected to low-pass filtering (such as a Butterworth filter set to an appropriate cutoff frequency) in order to produce a signal was used in certain coarse HAR sensing, such as position or posture detection of the person P being monitored. Likewise, accelerometer signals that correlate to higher-frequency movement and activity may be subjected to high-pass filtering in order to distinguish between static and dynamic behavior, again using an appropriate frequency cutoff. Distinctions between static and dynamic activities may further be inferred by applying thresholds (such as g-force thresholds) to the high-pass filter results. For example, distinctions between posture detection and postural transition and related movement may be determined based on the size or frequency of accelerometer signal variations. In one form, the static posture detection may be based on angular components of the accelerometer signal in longitudinal and forward-facing directions, where baseline values may be taken from for the healthy elderly population reference databases, or empirically ascertained through a sample training data set from the presently-acquired LEAP data. The various types of dynamic motion associated with activity, movement, postural transition or the like may be compared to the static posture types (for example, sitting, lying supine or standing) as a way to detect such activity, and in one form may be subjected to an algorithm (including a rule-based algorithm, one capable of machine learning, as well as hybrid rule-based machine learning (RBML)) in order to select from likely transitions between the postures. By way of example, a transitional activity between a sitting posture and a standing posture may be equated to the movement associated with standing up, whereas the opposite transactional activity may be equated with sitting down. The addition of contextual information, such as the location of the person P during these transitional activities, may be subjected to yet another algorithm (again, either a rule-based one, a machine learning one or an RBML one) in order to infer an ADL or IADL event as will be discussed in more detail as follows.

Referring with particularity to FIG. 8, a sample patient ADL documentation chart is shown. This chart shows a representative four week period broken down by each of the days of the week along the X-axis, as well certain ADL functions along the Y-axis. In this way, a caregiver C may enter data corresponding to whether the person P being monitored has completed certain activities. Such a chart may be either in hardcopy (that is to say, paper) form, or electronic, either of which may be entered into a suitable electronic data file (EDF) as a data structure into memory 173B. In one form, at least some of the LEAP data gathered by the wearable electronic device 100 and system 1 and processed by a suitable algorithm (such as one or more of the machine learning algorithms discussed herein) may be entered into electronic versions of the chart of FIG. 8 to show completion of at least some of these indicators of ADL.

Based on the foregoing, HAR may be thought of as a more coarse or primitive form of ADL in that the accelerometer and gyroscope data may first be converted into position, movement or related activity information, while the addition of one or more forms of location, environment and physiological (that is to say, static) data may be added as a way to gain contextual insight into the successively more detailed information associated with ADL, as well as the even more detailed, composite information associated with IADL. As is discussed elsewhere in this disclosure, the various measurable forms of HAR may be used to infer ADL that in turn can provide a valuable way to determine if a person P is at risk of contracting a disease or related medical condition based on deviations of one or more of these factors from baseline or related normative values. A significant barrier in applying HAR or ADL patterns in a manner that can correlate empirical observations with a disease or condition prediction is the lack of large training sets that reflect accurate aspects of a given activity such as particular patient movements with known predefined spaces within his or her living quarters. In particular, while there are large numbers of sensor 121 readings to make up data input for various patient activities such as the various ADLs (that is to say, the previously-discussed eating, cooking, bathing and toileting, communication, dressing, grooming, hygiene and ambulatory functions), there may be relatively few instances associated with a particular activity that is being classified or otherwise observed. While such sparse instance data normally cannot be used to learn a complete model of an activity, it can contain enough important information to correspond sensor 121 patterns to certain highly correlative activities such as ambulatory capability or the like. In one form, filtering techniques may be used to separate important signals being acquired by the sensors 121 from noisy ones as a way to identify true causal relationships from spurious ones.

In situations where the amount of LEAP data may be sparse, the hypothesis H of FIGS. 6 and 7 may be tested by using the previously-discussed cross-validation or bootstrapping such that the LEAP data is reused as the FIG. 6 training and validation data sets 1610, 1620. By considering these factors in a machine learning context, the authors of the present disclosure have determined that in order to determine if there is an ample supply of data for a given analysis, it may be beneficial to determine the number of input variables or their corresponding numerical attributes (that is to say, the features that are the things that can characterize the object or activity in question) relative to the number of observations (that is to say, the object in question). Within the present disclosure, four general groups of attributes may be measured, corresponding to the various forms of LEAP data. For example, if there are a large number of attributes and relatively few observations, this may be indicative of an insufficient amount of acquired data. Contrarily, once the amount of data is determined to be sufficient, relative errors between the testing data set 1630 and the training data set 1610 may provide indicia of how a preliminary version of the model is performing. For example, if the testing data set 1630 error is much higher than the error of the training data set 1610, the learning (that is to say, preliminary) model may be experiencing memorization-like overfitting, as it is having a hard time distinguishing between data and noise. Generally, the overfitting problem is increasingly likely to occur as the complexity of the neural network increases. In other words, an overfitted model is more complex than can be justified by the data. The opposite situation-underfitting—is where the model is too simple, and as such will be insensitive to the actual attributes within in the data, producing predictions with poor accuracy. Moreover, the complexity of any given model may necessitate trading off bias in the data (which corresponds to the expected error between a predicted (i.e., target) value and the ground truth such as that taken from the previously-mentioned training data set 1610) versus variance V in the data (which measures the changes in model prediction for a given data point). As generalization is a measure of how well a machine learning model predicts outcomes for new data, a complex model that over-generalizes has high variance because its output changes too much based on insignificant details about the data. This situation may be remedied by getting more training data or reducing the number of redundant features during the algorithmic phase. On the other hand, if the model is suffering from high bias, acquiring more data won't be helpful as the model is already underfitting the hypothesis H. Errors during training decrease when the complexity of the model increases, while errors during testing decrease at first, then increase. As such, these errors can provide an indication of how any given model is performing. The success of the machine learning models discussed herein involve a finely balanced trade-off between the amount of LEAP data in the training data set 1610, the level of the generalization error (that is to say, overfitting or underfitting) on new instances of the LEAP data, and the complexity of the original hypothesis H that was fitted to the LEAP data.

Referring again with particularity to FIGS. 11A and 11B, basic (that is to say, primitive) ADLs such as those that can be correlated to various HAR may include eating, cooking, bathing, toileting, communicating, dressing, grooming, hygiene and ambulatory functions. Additional details for ADL assistance may be found in The Centers for Medicare & Medicaid Services Minimum Data Set (MDS) 3.0 entitled *Resident Assessment Instrument (RAI) Manual v*1.15 of Oct. 1, 2017, Section G entitled *Functional Status*. In particular, a quantifiable scoring system may be used, where Table 2 shows a functional decline may involve a 0 to 4 scale for an individual's self-performance of different ADLs for an activity occurring 3 or more times and that can be compared to baseline scores for the same individual where—as shown in FIG. 6—could be embodied as baseline data 1700. Guidelines are used to quantify the score as follows:

TABLE 2

| | |
|---|---|
| 0 | Independent: no help or staff oversight at any time |
| 1 | Supervision: oversight, encouragement or cueing |
| 2 | Limited assistance: resident highly involved in activity; staff provide guided maneuvering of limbs or other non-weight bearing assistance |
| 3 | Extensive assistance: resident involved in activity, staff provide weight-bearing support |
| 4 | Total dependence: full staff performance every time during a 7 day period |

In one non-limiting example, scores may be given in various areas such as the following from Table 3.

TABLE 3

| | | |
|---|---|---|
| 1 | Bed mobility | How the resident moves to and from lying position, turns side to side, and positions body while in bed or alternate sleep furniture |
| 2 | Transfer | How resident moves between surfaces including to and or from: bed, chair, wheelchair, standing position |
| 3 | Locomotion: | How the resident moves between locations |
| | a. | Walk in room: how resident walks between locations in his/her room |
| | b. | Walk in corridor: how resident walks in corridor or unit |
| | c. | Locomotion on unit: how resident moves between locations in his/her room and adjacent corridor on the same floor. If in wheelchair, self-sufficiency once in chair |
| | d. | Locomotion off unit: how resident moves to and from off-unit locations (e.g., areas set aside for dining, activities, or treatments). If facility has only one floor, how resident moves to and from distant areas on the floor. If in wheelchair, self-sufficiency once in chair |
| 4 | Dressing | How resident puts on, fastens, and takes off all items of clothing, including donning/removing prosthesis or TED hose. Dressing includes putting on and changing pajamas and housedress |
| 5 | Eating | How resident eats and drinks, regardless of skill. Do not include eating/drinking during medication pass. Includes intake of nourishment by other means (e.g., tube feeding, total parenteral nutrition. IV fluids administered for nutrition or hydration) |
| 6 | Toilet Use | How resident uses the toilet room, commode, bedpan, or urinal; transfers on/off toilet; cleanses self after elimination; changes pad; manages ostomy or catheter; and adjusts clothes. Do not include emptying bedpan, urinal, bedside commode, catheter bag, or ostomy bag |
| 7 | Personal Hygiene | How resident maintains personal hygiene, including combing hair, brushing teeth, shaving, applying makeup, washing/drying face and hands (excludes baths and showers) |

As with ADLs, IADLs are those which require interaction with objects and people. Examples of such interaction may include using telephonic (or related) communications, shopping, meal preparation, adherence to medication-taking protocols, money management, house-cleaning activities, pet care, child-rearing or the like. IADLs, while not imperative for basic functioning, are indicative of the ability of person P to perform more complex cognitive tasks. In situations where data collection may be limited, some ADLs and IADLs may be deemed to better predict overall patient health than others, while some may be deemed to be harder or easier to acquire. In one form, it may be helpful to balance ease of collection versus predictive potential for the various ADLs. For example, directly acquiring information pertaining to taking medication, eating, ambulating and socializing may be more difficult than others, regardless of their probative value.

One way to gain insight into HAR, ADL or IADL metrics is to first establish the patient baseline data 1700 (shown in FIG. 6) that can be used to establish certain activity, health or behavioral norms. An intra-patient version of such baseline data 1700 may be created through an experimental protocol where the patient is first equipped with one or more wearable sensors (which in one form may include the sensors 121 similar to or the same as the ones that make up the wearable electronic device 100) and asked to perform routine daily functions under so-called normal conditions such as those encountered in one's home or other familiar environment. In another form, an inter-patient version of such baseline data 1700 may be created through comparison of that patient's activities as acquired by the wearable electronic device 100 to those of a larger sample population of people who share one or more traits of the patient being baselined, such as by age, weight, gender, prior medical history or the like, such as those described in the previously-discussed NIH *Unified Medical Language System*. Moreover, such baseline data 1700 may be established for one or more events or activities, such as those of a single ADL, as well as from different ADLs. Such an approach may simplify that data, including taking into consideration historic ADL states and those that evolve over time for comparison to those of a current ADL state. In one form, the establishment of a baseline need not comprise a full set of baseline data 1700, but instead merely for the parameters which are determinative of the HAR, ADL or inferred health condition at issue for the individual being monitored.

In another form, intra-patient versions of the baseline data 1700 may be gleaned from other data forms. For example, answers to questionnaires may be used to establish such norms. This can be used to help establish HAR or ADL baselines as well, as a battery of questions administered to a person P (such as in a clinically-controlled environment in the form of a routine office visit to his or her primary doctor or the like) may help the caregiver C determine what types or quantities of LEAP data may need to subsequently be acquired. Using the previously-mentioned ADL metrics (eating, cooking, bathing, toileting, communication, dressing, grooming, hygiene and ambulatory functions) as an example, a series of questions might involve the following:
1. Do you feed yourself?
2. Do you cook for yourself?
3. Do you bathe or shower yourself?
4. Do you use the toilet yourself?
5. Are you able to place and answer telephone calls?
6. Do you dress yourself?

It will be appreciated that other ADL-related questions may be used, depending on the situation-specific needs of the individual being monitored. In one form, these questions can be made to mimic an ADL impairment screening questionnaire, the Katz Index of Independence in ADL, or the like. Likewise, these and other ADL-related questions may have a hierarchical component to them. For example, if the patient answers "yes" to Question 4 above, a subsequent question may involve whether the patient has any trouble controlling his or her bladder or bowels, while other questions may relate to how many trips per day are made to the bathroom, whether there is any pain associated with going to the bathroom, or the like.

Once answers to these questions are known, a general ADL composite form of the baseline data 1700 may be formed. This in turn permits an individualized tailoring of which of the subsequently-acquired LEAP data may be most beneficial. For example, particular inferences or weightings may be included in order to give certain sensor 121 readings preference in the types of acquired data that will be sent to the logic device 173. Thus, if the ADL variant of the baseline data 1700 (whether in the form of answers to questions, previously-acquired normative data or the like) raises ambulatory or mobility concerns, the data that is subsequently acquired through the wearable electronic device 100 for comparison may be biased toward accelerometers, gyroscopes, magnetometers or other motion-related ones of the activity sensors 121B. Likewise, if the ADL baseline data 1700 raises concerns over bodily responses to certain activity, the data that is subsequently acquired through the wearable electronic device 100 for comparison may be biased toward the physiological sensors 121C that may individually include the heart rate sensor, breathing rate sensor, temperature sensor, respiration sensor, pulse oximetry sensor, respiratory rate sensor, oxygen saturation sensor, electrocardiogram sensor, cardiac output index sensor, systematic pressure sensor, systematic systolic arterial pressure sensor, systematic diastolic arterial pressure sensor, systematic mean arterial pressure sensor, central venous pressure sensor, pulmonary pressure sensor, pulmonary systolic arterial pressure sensor, pulmonary diastolic arterial pressure sensor and pulmonary mean arterial pressure sensor as discussed elsewhere in the present disclosure. In addition, and regardless of which of the sensors 121 are deemed to provide the most relevant data for a particular HAR, ADL or IADL, the subsequently-acquired real-time data from the sensors 121 may be biased to take place in a sequenced or connective manner based on certain patterns of movement or behavior identified in the corresponding baseline data 1700. Furthermore, if a caregiver C has concern that the person P being monitored is at risk of developing a particular disease or health condition or the like, certain highly correlative parameters may be used in order to bias the type of information being subsequently acquired by the sensors 121. This can be used in conjunction with various decision states that correspond to contextual situations to help better inform such movement, behavior or other lifestyle activities. Thus, by combining sensory data with such contextual information, a more complete picture of the activity, behavior or health condition of person P may be gleaned. In one form, the contextual information may be infrastructure-related configurational data (such as the floorplan or layout information of the rooms in the house or other building where the individual resides). In this way, inferences regarding unusual spatial-temporal activity data may be identified more easily. In one form, this can be set up through various logical ("if", "then", "and", "or", "neither", "nor", "not" or the like) inquiries within the logic device 173.

As previously discussed, the system 1 may be configured to analyze the significance of the data either with intra-patient or inter-patient baseline data 1700, including for algorithmic training where a data set may be stored in local or remote memory 173B that contains classified or labeled examples with known instances of location, movement or other useful biometric measures of individual activity. This training data set 16010 may be input into one or more of the machine learning algorithms discussed herein such that once the algorithm is optimized through validation and testing of respective data sets 1620, 1630, a suitable classification rule for use in the ensuing model is established. This allows presently-acquired data unique to the individual being monitored to be input into the machine learning model in order to determine whether the current (that is to say, real-time) activity from the individual indicates whether the risk of a particular medical condition is heightened.

In one form, other assessment tools, such as the Functional Independence Measure (FIM), may be used to form a score of an individual to show a degree of independence based on motor and cognitive functions. The score may be used to assess how well an individual can be expected to meet ADL minimums. In addition, an FIM score—which may be based on a previous visit to a physician in a doctor's office under controlled conditions—may help establish useful intra-patient baseline data 1700. Depending on the nature of the health condition, other assessment tools or rating scales may be used to establish baseline data 1700. For example, if Parkinson's Disease is suspected, the Unified Parkinson's Disease Rating Scale (UPDRS) may be used to clinically assess whether an individual is at risk of developing the disease. It will be appreciated that other diseases and their scales for assessment may be correlated to some or all of the LEAP data being acquired by the wearable electronic device 100, and that the inference of all such diseases through the correlation of one or more of their criteria with such data is within the scope of the present disclosure.

In one form, ADL may be modeled using Bayesian-based approaches. Rather than relying primarily on piezoelectric, piezo-resistive, pressure or touch-based sensors mounted to everyday objects that could expect to be handled by the person P being monitored, or upon RFID tags, either of which may have to be distributed throughout a patient's living space as part of a complex information-gathering infrastructure, the approach disclosed herein may take advantage of high levels of location accuracy determination derived solely from information collected by the wearable electronic device 100 in order to infer one or more of these ADL and IADL events. In particular, a simple cooking step such as preparing a can of soup may be inferred from the spatial proximity of the patient to objects being used such as pots, pans, bowls, stoves or the like) or by brushing one's teeth, which can be inferred by proximity to a toothbrush, toothpaste, bathroom sink or the like. In one form, such an inference may be made with a Bayesian belief network, where the structure of the network is kept very simple while also relying on as large a number of observations related to the location, movement or other spatial or temporal indicia of a particular individual's whereabouts or activity that in turn is used to infer a particular ADL or IADL event.

HMM variants of the Bayesian approaches may also be used in situations where substantial amounts of training data are needed, particularly in view of the fact that changes in the temporal segmentation of an observation about a patient's activity may contain valuable information about such activity, especially because various metrics such as HAR, ADL and IADL are not directly measured but are instead inferred from patterns in the acquired raw data from sensor 121 readings. The previously-mentioned CRF is a graphical-based discriminative (rather than generative, such as HMM) probabilistic model that may be used as a classification model in a manner roughly similar to Bayesian and Markovian approaches. By being multiscale, CRF-based models are particularly well-suited for analyzing acquired temporal (that is to say, sequence-based) wearable electronic device 100 data, particularly as it relates to a fusion of disparate forms of information from the various gyroscopes, accelerometers and other activity-measuring sensors 121. The graphic-based structure of CRF models, with its feature extraction-based observational sequences (as input) and hidden states (as to-be-determined output) has the virtue of being relatively free of biases, particularly label bias, that may impact non-probabilistic sequence-oriented models, such as HMM and other forms of Markov models. CRF may be beneficial in situations such as compound or concurrent activities (where, for example, the individual being monitored with the wearable electronic device 100 is talking with another while also preparing dinner) that may be difficult for an HMM to represent due at least in part to a potential lack of independence in the overlapping activities. As with some ensemble-based models, CRF may be augmented by boosting for classification problems, particularly those involving data sets that involve small numbers of data classes.

Rather than rely upon disparate sources of sensor-based data acquisition, such as through the use of fixed, static infrastructure-mounted sensors such as television or closed-circuit cameras (with their attendant data accuracy, privacy and cost concerns), the sensors 121 used on the wearable electronic device 100 help improve its operability by—among other things as discussed herein—avoiding (a) the awareness by the individual of such monitoring and how that could cause the individual to adjust his or her behavior to a degree sufficient to skew the acquired raw data, (b) the use of notorious indicia (such as facial and voice recognition) of the individual being monitored that could lead to concerns that "Big Brother" is watching, and (c) the extensive amount of facility modification or retrofitting needed to accommodate such various sensing modalities being affixed to a pervasive number of objects with which the individual may interact in his or her daily activities. For example, privacy concerns are reduced when the sensors 121 only acquire discrete pieces of information (such as the fact that a patient is in the bathroom rather than the specific details associated with urinating or defecating), whereas more comprehensive levels of sensed visual information detail such as cameras actually show in detail when the patient is engaged in such activities while in the bathroom.

This organization of the acquired LEAP data is useful for subsequent analytic-based operations, such as comparison of a presently-acquired set of data to previously-acquired data from the same individual, as well as to reference or baseline data 1700 from other individuals (such as those in the same or similar demographic features). In one form, pre-defined threshold values may be used such that when the acquired data exceeds or falls below the threshold, alerts may be generated. By way of one non-limiting example, the wearable electronic device 100 or system 1 may send an alert for various situations that are deemed by one or more of the machine learning models discussed herein to present actionable changes in the health condition of the person P being monitored, such as unusual sleeping habits, low or high frequency of bathroom visits (as well as excessive time spent in the bathroom), when the person P has fallen, when the person P is in a room or location deemed risky or inappropriate, where an inordinately large or small amount of activity by the person P is detected, or ambulatory activity of the person P at unusual times (such as leaving the premises in the middle of the night), as well as others. In one form, the previously-discussed geofence may be set up such that when the individual associated with the wearable electronic device 100 wanders beyond a designated space, the wearable electronic device 100 sends out an appropriate alert through the third wireless communication sub-module 175C. Such an alert may be displayed, such as on a dashboard or related display on the one or more remote computing devices 900.

In one form, various machine learning visualization packages may be used to facilitate easy-to-read displays on the remote computing devices 900; examples may include plotting libraries such as Matplotlib, Seaborn and Plotly, as well as custom-generated ones. Thus, in addition to storing event data, configurable (that is to say, user-definable) parameters may be stored in memory 173B or its system-level or cloud-level equivalent for use with the logic device 173 and the various program structures that will be understood in one form to include the machine learning models discussed herein. One example of such configurable parameters is that associated with how a human-machine interface (HMI) may set up on the wearable electronic device 100, system 1 or remote computing device 900 to allow interaction with a user as the caregiver C. More particular examples of such configurable parameters include the way an ADL, IADL or HAR activity may be presented to such user, including configuring the HMI to provide customizable displays, audio alerts, thresholds or the like. In one form, the output of an HAR, ADL or IADL study may be as a daily activity report where understanding of behavior patterns may be used for other diagnostic or treatment approaches such as for pharmacologic research to study the efficacy of medications such as anti-depressants or anti-psychotics on the individual being monitored with the wearable electronic device 100.

ADLs, examples of which may include eating, cooking, bathing and toileting, communication, dressing, grooming, hygiene and ambulatory functions, are good indicators of the cognitive and physical capabilities of a person P being monitored. In one form, assessment of ADL may be performed by one of various models, such as those based on the approach pioneered by Sidney Katz, MD and entitled *Index of Independence of Activities for Daily Living*, where the sensed, measured and related collected LEAP data can be used in conjunction with machine learning that may be present within system 1. In one form, this multiclass raw LEAP data may be correlated to ADL in a manner that allows inference-drawing that mimics the conventional observational approach taken by Katz. The present use of LEAP data and machine learning is advantageous in that it avoids the need for expert systems and their control programs that make extensive use of a priori rules (often numbering into the thousands) to produce meaningful conclusions in a real-time setting. This is not to say that expert systems may not have any utility; in fact, placing such resources into a configuration used by cloud 500 could take advantage of its parallel processing configuration to provide analytics and related clinical decision insight. For example, RBML such as learning classifier systems, association rule learning and artificial immune systems may act as a hybrid between purely rules-based approaches and purely machine learning-based approaches. More particularly, patient intervention strategies enabled by the collection and analysis of the data discussed herein by the wearable electronic device 100 and system 1 may help to identify problematic changes in health when such changes are imminent or emerging, rather than after the onset of an illness or other adverse health condition. In one form as will be discussed in conjunction with FIG. 15, the LEAP data may help to identify acute or crisis stages early in their development to allow proactive rather than reactive intervention.

As will be understood within the present disclosure, both inter-patient and intra-patient historical (that is to say, previously-acquired) information may be used to establish baseline data 1700 that may in turn be used for comparison to real-time (that is to say, presently-acquired) data such as the LEAP data acquired from the wearable electronic device 100. In this way, such comparisons may form the basis for determining that an individual's present activity, location or condition has changed relative to an accepted norm by an amount sufficient to warrant further caregiver C inquiry or intervention. Moreover, LEAP data, both historical and present (i.e. real-time) may be used for some or all forms of data analysis, including to build and test a machine learning model, while real-time or presently-acquired LEAP data may be operated upon by the model in order to perform one or more of CDS, diagnosis or the like. Thus, in one form, the LEAP data may serve as an exclusive basis for both baseline data 1700 and real-time data, while in another form, the LEAP data is used for just one or the other. As such, all forms of acquiring and using the LEAP data from the wearable electronic device 100 in order to evaluate a health condition of an individual in the manner discussed herein will be deemed to be within the scope of the present disclosure.

Algorithmically, various forms of sensed data from the wearable electronic device 100 may be stored in memory 173B, processed and analyzed by one or both of the system 1 and the wearable electronic device 100. As discussed previously, such data includes LEAP data. Examples of location data (which may have spatio-temporal components) include (1) time spent in the bedroom, bathroom, neighbor's room, dining area, entertainment/activity area, courtyard, garden, outside, inside or the like, (2) time spent out of a particular room (such as the bedroom), (3) number of bathroom visits or any other room per day, (4) number of times outside or any within other room, (5) number of times outside within a particular location, such as to smoke in a known or designated smoking area, (6) cumulative number of rooms visited, (7) a certain amount of time in the bathroom or any other room, (8) cumulative amount of time and duration spent within certain rooms, and (9) specific time spent within any other particular place of interest (such as a room where exercise equipment may be present or where physical therapy may routinely be administered). In one form, some or all of this data may be stored as part of an activity index to provide a measure of the locomotor or related physical activity of a person P; such an index may exist as a data structure in various formats, such as a lookup table or the like. From an understanding of this data, various intervention plans may be implemented. For example, a smoking cessation program may be developed based on analysis of the LEAP data that shows that the person P being monitored is making frequent visits to indoor or outdoor locations that are known to include designating smoking zones. In addition to using the LEAP data for analyzing the behavior of the person P wearing the wearable electronic device 100, by tracking the response of caregivers C in a hospital, assisted living facility or other place where multiple persons are being cared for, such as to a request initiated by the person P through the nurse call button 131, caregiver C activity and behavior may be more closely tracked.

Examples of activity data include (1) the number of activities attended, (2) the types of activities, (3) the amount of time spent in such activities, (4) the previously-mentioned activity index, (5) an amount of time inside of the patient's bedroom, as well as the number of rooms the patient may have visited, (6) how many times the nurse call button 131 was utilized, as well as the time of day nurse call button 131 was pressed and the amount of time it takes to clear the nurse call in addition to the identity of a staff member who cleared the nurse call, (7) the number of times the patient gets up in the middle of the night, (8) the number of times the patient gets up in the middle of the night and uses the bathroom, (9) the number of times the patient eats in the dining hall versus in their room throughout a week or other measurable unit of time. (10) the amount of time a patient is sitting, standing or moving, and (11) gait speed. In one form, the activity data may be made up exclusively of changes in location data over time, where the greater the change in location or a reduction in the amount of time to achieve such change could be indicative of a greater activity level. Conversely, a smaller amount of location change or a greater amount of time required to achieve such change could be indicative of a lower activity level. Similar use of environmental parameters (for example, temperature, humidity, air pressure, carbon monoxide, carbon dioxide, smoke or the like) and physiological parameters (for example, heart rate, breathing rate, temperature, respiration, pulse oximetry, blood sugar monitoring, respiratory rate, oxygen saturation, electrocardiogram, cardiac output index, systematic pressure, systematic systolic arterial pressure; systematic diastolic arterial pressure, systematic mean arterial pressure or the like may also be performed in order to gain a more complete understanding of an individual's activity within a given spatio-temporal context. Such information may also be stored in memory 173B for use in the analysis of an individual's health condition; for example, such information may be stored as numerical values of the respective category of the LEAP data that is being acquired. In one form, because one or both of the location and activity data have spatio-temporal components, it may be beneficial to treat individual frames of sensor 121 data as statistically independent, isolated portions of the input data such that through suitable extraction such data may be grouped into a feature vector format for subsequent use by a classifier or other machine learning algorithm or model.

In one form, the sensors 121 that are used as part of the wearable electronic device 100 and system 1 for combining and transmitting data related to ADL may be configured to acquire information associated with a specific activities (for example, to sense drawer opening, door opening, toilet flushing, weight load on a toilet seat, faucet use or the like), where the sensors 121 are capable of transmitting ADL State Related Data (ASRD). In a similar manner, the sensors 121 may be used to provide even relatively small changes in measured environmental parameters such as atmospheric pressure that can provide indicia of variations in height or elevation through activities such as climbing stairs, or changing between a sitting, standing and supine position traversing or the like. In addition, sensor 121 sampling rates (such as once per second or more) may be varied in order to acquire fine changes in the barometric pressure. In a similar manner, variations in temperature (such as going between indoors and outdoors) and humidity (such as being near the source of a faucet, bathtub, toilet or other source of running water) may be acquired. In this form, machine learning-based supervised classification may be used for successfully distinguishing these and other subtle changes in detailed ADL parameters. In one form, these and other parameters may be used to present a more thorough understanding of the patient's immediate environment. As previously mentioned, the sensed data may have a temporal component that in turn may be used to facilitate the machine learning process to conduct time series analysis or forecasting, such as through Bayesian or neural network approaches. Numerous examples of data that may have a temporal component include those associated with the LEAP data discussed herein, where more particularly, ambulatory activity may be acquired by one or more sensors 121 over a time sequence in order to divine speed, duration or changes in such activity. Temporal data associated with ADL may also include—in addition to time stamping-frequency of occurrence, duration of occurrence, elapsed time between occurrences, running averages of occurrences or the like. In one form, the measurement of the temporal data helps in establishing norms (such as those that may form part of an inter-patient or intra-patient baseline data 1700). This indexing of the data over the time dimension is valuable in helping to identify HAR traits, patterns or the like that in turn may be correlated to certain ADL and IADL markers that in turn can be used to assess the ambulatory and cognitive capability of a patient based on the data being collected by his or her wearable electronic device 100. As with other forms of acquired data, the temporal data may be subjected to a feature extraction process in order to allow comparison of potentially disparate pieces of information. For example, because various activities may be performed over periods of time that are compared to the sampling rate of the sensors 121, it may be beneficial to recognize such activities over one or more time-sampled sliding windows. Because the received data is unlikely to be identical (even for the same individual performing the same activity), it may be helpful to use statistical or structural filters in order to transform the raw data into a set of feature vectors for each given window. For example, statistical-based feature extraction may be used on raw activity data, while structural-based feature extraction may be used on the raw environmental data.

In such form, the system 1 may also include one or more BLE beacons 200 capable of broadcasting Beacon Related Data (BRD) in order to establish the location of the specific ADL. The wearable electronic device 100 is capable of receiving and storing BRD from a BLE beacon 200 and ASRD from the ADL sensor to establish the time at which the BRD and ASRD are received. In one form, the wearable electronic device 100 (1) combines the data related to the identity of the individual, time of reception, ASRD and BRD with the UUID in a manner suitable for RF transmission; (2) transmits the combined data to the gateway 300 or server 400; (3) optionally adds handshaking steps to verify data transmission using the UUID; (4) optionally adds steps that ensure that only data received within a specific time duration are combined; and (5) integrates signal activities from different types of beacons or tags that can trigger the wearable electronic device 100 to perform different functions, internal functioning or events the results of which may be pushed to the cloud 500 or internet through system 1. In addition, encryption or related security protocols may be included to ensure that the storage and transfer of Health Insurance Portability and Accountability Act (HIPAA)-compliant patient-identifying data stays protected.

EXAMPLE

The results of a trial implementation (i.e., study) of location pattern models is described next. The purpose of the study was to determine the feasibility of using location pattern models to monitor changes in movement patterns as an approach to reduce the fall rate of assisted living facility patients. The results of the study are based on data acquired with the wearable electronic device 100 to identify potential changes in health, as well as to reduce or prevent patient falls (such as previously discussed in conjunction with FIGS. 11A and 11B) at home or in an assisted living facility, LTC, skilled nursing facility, memory care unit or the like. Not only are falls and associated instability harmful in and of themselves, they also provide indicia of poor health, a chronic health condition, or decline in ambulatory status or cognitive function. Through the monitoring of movement patterns with the wearable electronic device 100 and other parts of the system 1, there is a potential to detect early changes in acute conditions such as UTI, pneumonia, agitation, medication side effects (including orthostatic hypotension, bradycardia or the like) as well as changes in gait, all of which are potential predictors of a fall. As previously mentioned, changes in gait could be tied to spatial navigation difficulties. In one form, a portion of the baseline data 1700 may be in the form of cognitive maps that can provide indicia of spatial navigation skills in order to provide early detection of a dementia-related health condition. In one form, fall detection may be achieved by (1) having movement be acquired by the sensors 121, (2) sending acquired data to the gateway 300 that in turn sends the data to the cloud 500 where it is analyzed by an API to distinguish normal movement from fall movement. In addition, the application server 420 may generate and send reports and alerts on the fall, as well as the location of the patient, to a family member or other interested caregiver C through the remote computing device 900. In another form, abnormal movement that is not indicative of a fall, such as coupling certain movement with unusual times of the day, may be used to provide indicia of certain rhythms (such as circadian activity) that could indicate sleeplessness, changes in mental status or the like. Moreover, certain movements (such as can be detected by activity sensors 121B) that are understood to describe fall precursors may be analyzed in order to correlate them to change in chronic obstructive pulmonary disease (COPD) status, changes in oxygen saturation or other signs of imminent adverse health conditions.

The study was also conducted to determine whether residents and staff of an assisted living or related health care facility would be accepting of the wearable electronic device 100, as well as of the practicality of using alerts related to changes in movement patterns in determining a change in health condition, potential fall risk or other information of interest to caregivers C. The design methodology included using several approaches. For example, a single cohort pre-post design was used to evaluate the use of the location pattern models in reducing falls. In addition, a descriptive design was used to address the acceptability and potential for implementation; this design was verified through the use of interviews and focus groups.

Ten assisted living facility residents at different facilities in the Chicago, Ill. area were identified as being at-risk for falls at one facility, and these residents formed the participant sample. These facilities have the capability to provide various services along the elderly care spectrum, including assisted living, long-term care (LTC) and memory unit capabilities. Location data was collected twenty four hours a day for two months, by residents having the wearable electronic device 100 affixed to their wrists. Patterns were monitored through automated detection and logging software. Alerts for a change in movement pattern were sent to facility management staff in situations where follow-up was deemed to be necessary. Facility management staff was also able to explore data further through detailed reports of resident patterns and behavior. During the study, movement pattern changes were based on: (1) the number of bathroom visits by the resident; (2) the number of times outside of the resident's normal room; (3) the amount of time the resident spent in the bedroom; (4) the number of times the resident gets up in the middle of the night; (5) the number of times the resident gets up in the middle of the night and uses the bathroom; (6) the amount of time the resident is moving and not moving; and (7) the amount of time spent in activity areas by the resident.

The results of the study and the data acquired for a single one of the residents showed patterns of behavior as follows. Initially, during the beginning of the week, the resident appears to stay in the facility, yet by Wednesday, the resident left the facility three times. This is significant as the data shows that this behavior is beyond the resident's usual (that is to say, baseline) pattern of walking around the facility parking lot. Additionally, the data showed that the resident was most active in the morning. As the day went on, the resident spent more time in the bedroom or—during the afternoon—the library. Lastly, the data showed that on Wednesday of the week of testing, the resident's other activity decreased dramatically. Additional outcomes to be measured in a subsequent study may provide indicia of (1) resident fall rate before and after the implementation of location pattern models or, as will be discussed in conjunction with FIG. 14C, the implementation of or changes in a medication regimen; (2) description of alerts (number, type, pattern) per study participant and per group; (3) description of characteristics of the participants associated with falls and with alerts; (4) using a geofence to follow an itinerant resident outside of the facility where he or she is residing and (5) the feasibility and usability of the wearable electronic device 100 from participant and staff perspectives. Based on this exemplary study, the potential exists to identify early changes in health status through tracking of activity or movement patterns by using system 1 with the wearable electronic device 100 as disclosed herein. In one particular form, the ability of one or both of the wearable electronic device 100 and system 1 to store and review data and real-time alerts in a post-event situation may be used to conduct a root cause analysis that in turn may serve as a predictor for future preventable events. With the root cause analysis using the LEAP data, causes for the failure of a previous treatment regimen may be uncovered. For example, correlations between a new or changed medication regimen and patient falls (the latter as evidenced by the LEAP data) may be uncovered. In one form of the example, a patient started taking a new medication at 8 AM every day, and that for the next three days, the patient had a falling episode, whereas that same patient's baseline data showed that prior to that, falls were happening no more than once a week. Other scenarios and examples of how analysis of these and other forms of LEAP data may be presented to a caregiver C, such as being displayed on a screen of the remote computing devices 900, as described next in conjunction with FIGS. 9 and 10A through 10F.

IV. Clinical Decision Support and Diagnosis of Health Conditions Identified with Device-Acquired Data The use of the wearable electronic device 100 to collect and transmit LEAP data may be better understood with recourse to two broad categories of health conditions, namely (A) infections and (B) neuropsychiatric conditions, as well as (C) other common ones.

Figure 10A:
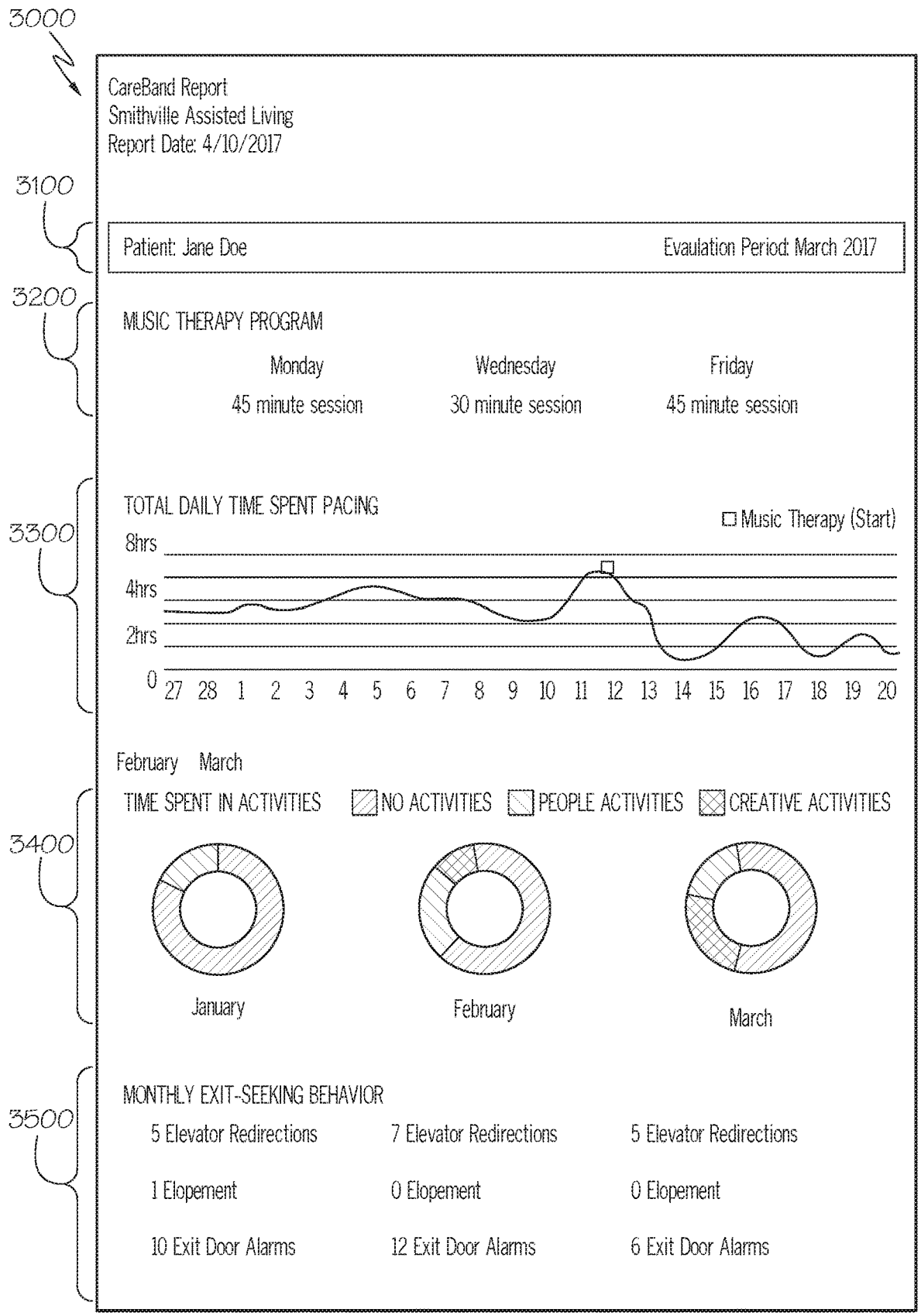
FIG. 10A depicts a notional dashboard that can be displayed to a caregiver on the remote computing device of FIG. 9 to identify a particular patient, along with the patient's planned and recent activities based on LEAP data that is generated by the wearable electronic device and system of FIG. 1 according to one or more embodiments shown or described herein.
Figure 10B:
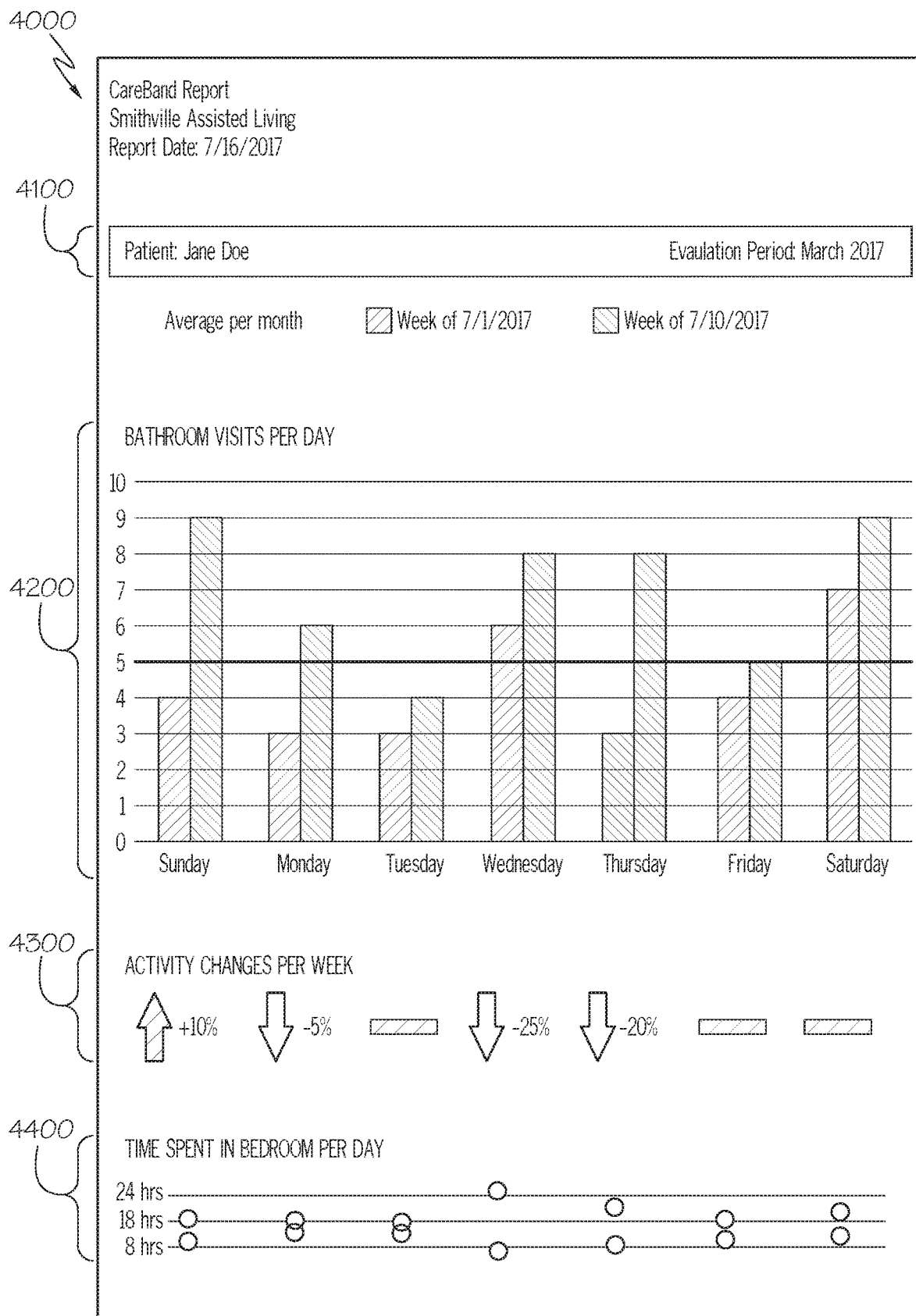
FIG. 10B depicts a notional dashboard that can be displayed to a caregiver on the remote computing device of FIG. 9 to identify a particular patient, along with a bar chart form of the patient's daily bathroom visits and a weekly comparison based on LEAP data that is generated by the wearable electronic device and system of FIG. 1 according to one or more embodiments shown or described herein.
Figures 10C, 10D:
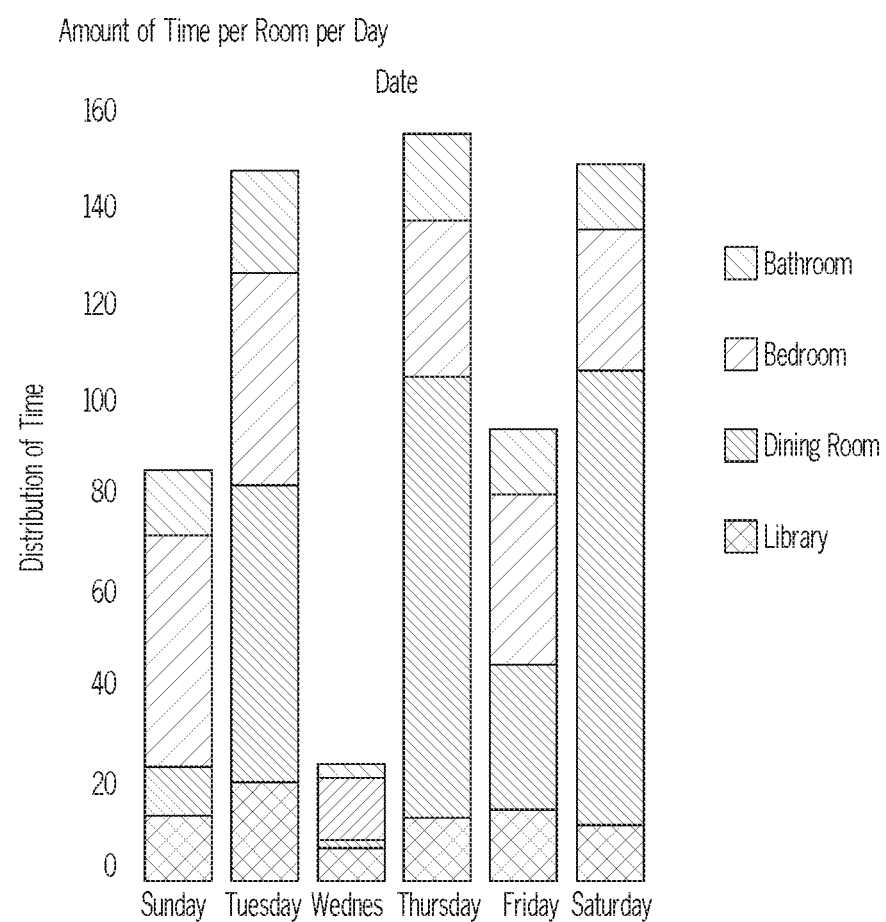
FIG. 10C depicts a notional dashboard that can be displayed to a caregiver on the remote computing device of FIG. 9 to identify the daily frequency of room visits by a particular patient over the course of a week and that is based on LEAP data that is generated by the wearable electronic device and system of FIG. 1 according to one or more embodiments shown or described herein.
FIG. 10D depicts in bar chart form a notional dashboard that can be displayed to a caregiver on the remote computing device of FIG. 9 to identify the amount of time that a particular patient spends in various rooms over the course of a week and that is based on LEAP data that is generated by the wearable electronic device and system of FIG. 1 according to one or more embodiments shown or described herein.
Figure 10E:
FIG. 10E depicts a notional dashboard in the form of a daily geolocation chart that can be displayed on the remote computing device of FIG. 9 to allow a caregiver to determine recent history of patient outdoor spatio-temporal movement patterns based on LEAP data generated by the wearable electronic device and system of FIG. 1 according to one or more embodiments shown or described herein.
Figure 10F:
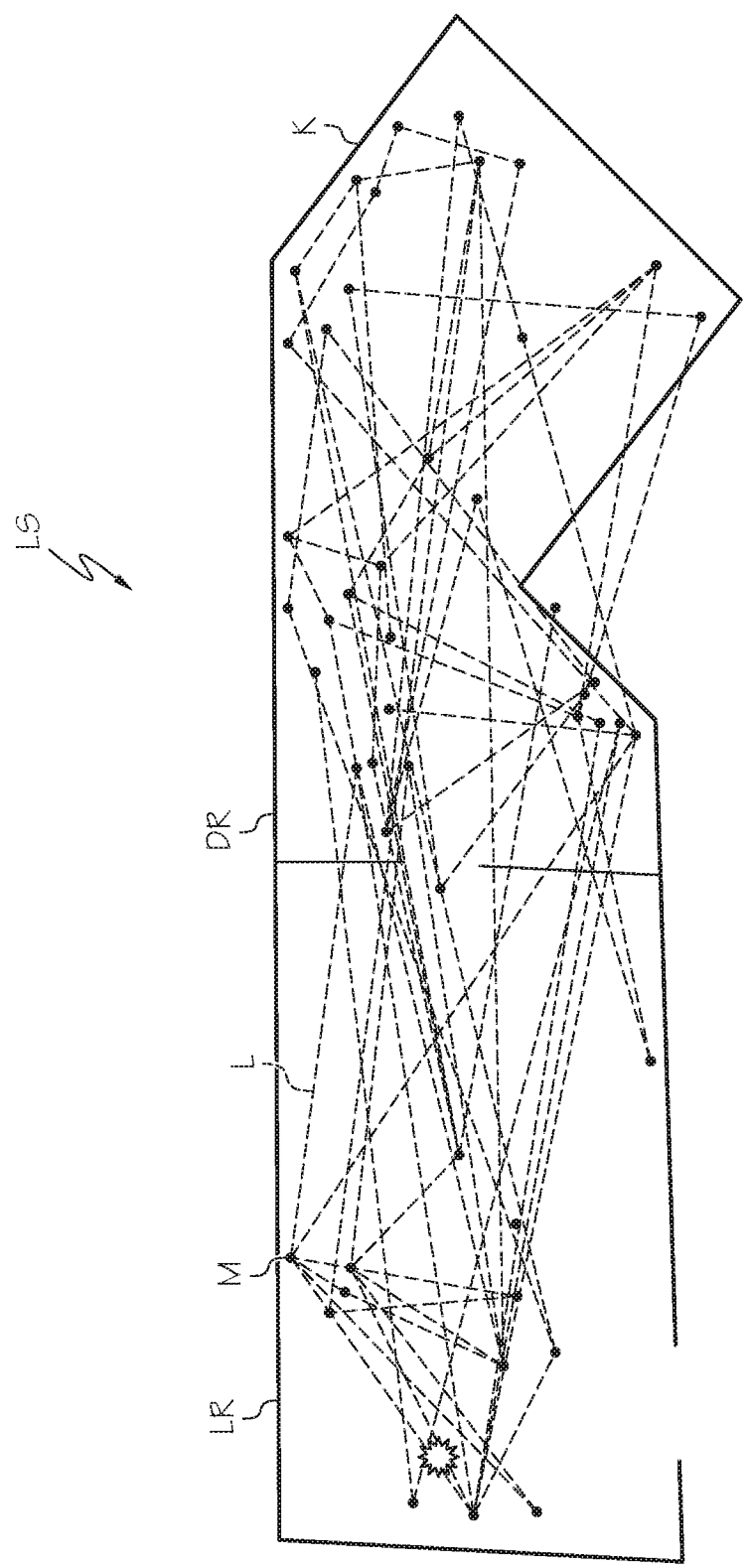
FIG. 10F depicts a series of time markers taken during a pilot program in order to demonstrate pacing or agitation raw data that is generated by the wearable electronic device and system of FIG. 1 according to one or more embodiments shown or described herein.

Referring next to FIG. 9 in conjunction with FIGS. 10A through 10F, a particular example of using the system 1 to collect data in order to identify changes in salient indicators of an at-risk patient (such as one with dementia, delirium or the like) is shown, such as for a UTI (FIG. 9), activity (FIGS. 10A through 10E) or agitation (FIG. 10F). More particularly, an example of the system 1 in operation is shown in FIG. 9, where a notional assisted living community, nursing home or related multi-patient facility is projected as an image on a display of or screen 910 of the remote computing device 900. In the non-limiting example shown, each patient room may be outfitted with a single BLE beacon 200. One or more BLE beacons 200 may be placed in a common area or perimeter. The display on the remote computing device 900 for caregivers C (including family members of those with health care or durable power of attorney) may be used to further demonstrate the influence of, or need for, care interventions. For example, incorporating this data into family care conferences may assist the operator of a facility in deciding what services the facility will be expected to provide for the patient in the future or as part of a changed care plan.

Referring with particularity to FIGS. 10A through 10F, various charts used to put the acquired LEAP data into user-friendly display format are shown to allow a caregiver C to determine whether a person P may be at risk of developing an adverse health condition such as an infection, pneumonia, sepsis, cognitive deficit, neuropsychiatric conditions (which may include agitation) or the like. All of the charts of FIGS. 10A through 10F are generated by the wearable electronic device 100 and system 1 of FIG. 1 and allow a caregiver C to determine person P spatio-temporal data as part of a time series analysis in order to correlate changes in the health condition of person P over a certain increment of time.

In one form, these charts may be displayed on one or more of the remote computing devices 900. For example, FIG. 10A shows a daily time and activities chart 3000 that identifies a particular patient 3100 as well as planned activities 3200 that in one form may be tailored to the particular needs of patient 3100. A time chart of patient 3100 engaged in pacing 3300 is shown to provide ready graphical indicia of periods of such pacing. Monthly activity circle charts 3400 and monthly exit-seeking activities 3500 are based on LEAP data that is generated by the wearable electronic device 100, where the latter may be a measure of wandering and elopement tendencies. FIG. 10B shows a daily bathroom visit chart 4000 in bar graph format; such information allows a caregiver C to readily determine whether a patient 4100 may be at risk of developing a UTI based on bar chart 4200 showing the number of bathroom visits per day. Up/down arrows give ready graphical indicia of activity changes per week 4300, while a comparable chart of the amount of time spent in the bedroom per day 4400. FIG. 10C shows a daily room frequency chart over the course of a notional week made up of the 15$^{th}$ through the 21$^{st}$ of a given month; from this, irregular patterns of visits to certain rooms may be readily identified. FIG. 10D shows a daily performance in bar chart form of the frequency of room visits over the period of a notional week to help track an individual from room to room, as well as show where the individual spends his or her time on a daily basis. As such, FIGS. 10C and 10D may be read together to provide not only the number of times a monitored patient goes into a particular room, but also the amount of time spent in such room, which can further help to identify unusual trends or patterns. FIG. 10E shows a geolocation chart where walks taken by a monitored individual outside a home H or related assisted care facility, nursing home, apartment or related dwelling of varying distances on three separate days may be used to infer peripatetic tendencies.

From tracked data, the wearable electronic device 100 will enable the following metrics to assist in measuring outcomes. First, the time spent in the bedroom per day 4400 may be used to show decreased nighttime bedroom use and nighttime wakefulness both of which may indicate escalation of behavioral symptoms. Likewise, increased daytime bedroom use may indicate depression and apathy symptoms, as well as the onset of infection or worsening of a known medical comorbid condition. Second, time spent in primary activity areas by daily quantity (for example, minutes versus hours) may be collected to show evidence of neuropsychiatric symptoms. Third, the previously-mentioned elopement and wandering episodes of the exit-seeking activities 3500 may be helpful in providing an indication to a caregiver C that additional patient oversight or wandering mitigation strategies may be needed. In addition, episodes of use of the nurse call button 131 by weekly quantity and time of day may provide indicia of anxiety. Moreover, time of day data may be helpful if associated with medication administration and side effects (examples: orthostasis associated with antihypertensive agent, bradycardia associated with antiarrhythmic, increased anxiety or discomfort prior to next medication dose timing affecting frequency of administration, increasing dyspnea or shortness of breath associate with worsening of co-morbid conditions) an example of which was discussed previously relating a new medication regimen and increases in the frequency of falling episodes. Likewise, special circumstances dictated by facility research intervention protocols as necessary may also be implemented.

The goals of effective management would include early detection of ongoing comorbid conditions, symptom relief and reduction of caregiver C distress. Management strategies can be influenced by active location data collection and evaluation. Algorithms include early detection change in a health condition associated with the onset of infections including UTI and pneumonia (frequently associated with episodes of aspiration), detecting escalating behavioral episodes of agitation and anxiety, monitoring for depression and apathy patterns of behavior, monitoring for signs of worsening comorbid conditions including congestive heart failure (CHF) and COPD with decreased activity patterns, and quantitating activity change after initiation of treatment programs tracking the influence of pharmacological and nonpharmacological interventions.

Machine learning models in general, Bayesian and neural networks in particular and even more particular types of time series-based feedforward neural networks (such as the previously-discussed LSTM networks that are part of a recurrent deep neural network, random forests and gradient boosting approaches) may help predict upcoming conditions based on previous-in-time (that is to say, temporal) data such as that associated with accelerometers and gyroscopes. Likewise, some of these approaches, such as random forests and gradient boosting, provide relatively high degrees of accuracy while also avoiding the tendency to overfit that can be common with other decision tree-based approaches. In one form, LSTMs and related time series models may be beneficial in analyzing at least location and activity data that could include historical aspects of the acquired data from the wearable electronic device 100. For example, an LSTM may be used to predict future elements of a given sequence based at least in part on such historical information. LSTMs may also be used in situations where information associated with multiple input variables is being acquired. In one form, LSTMs work best when there is a large amount of data being acquired. Likewise, in situations where location data plays a relatively significant role in analyzing a person P with the wearable electronic device 100, clustering-based approaches such as the previously-mentioned K-means clustering may be particularly beneficial, particularly when the amount of data being acquired is relatively small.

Referring with particularity to FIG. 10F, raw pacing data from a pilot program is shown. In the pilot program, physical therapists used a gym room with which to simulate a notional living space LS with individual living room LR, dining room DR and kitchen K in order to understand how a person P to be monitored moves within such an environment. Data was collected every few seconds over a period of one day, where the time markers M representing stationary behavior for more than three minutes. In one form, the time markers M may be used in conjunction with the linear distance L between sequential readouts of the time markers M to determine agitation-related parameters such as speed of movement, gait pattern, frequency of movement, time of day of movement or the like. This data, which in one form is acquired through the signals transmitted from the BLE beacons 200 to the first wireless communication sub-module 175A, may then be analyzed to determine if these movement-related activities can be correlated to pacing and patient agitation. Within the present disclosure, the term "pacing" is meant to distinguish normal levels of back-and-forth movement such as (a) within a room occupied by other people where the individual being monitored may be socializing, (b) changing the channels of a television, (c) preparing a meal in the kitchen K from those movements, particularly linear back-and-forth movements within a single room. In one form, the time markers M may be used to provide indicia of escalation or de-escalation of behavioral symptoms from a baseline value, as well as help a caregiver C evaluate the efficacy of interventions including both pharmacological and non-pharmacological interventions.

Figure 14A:
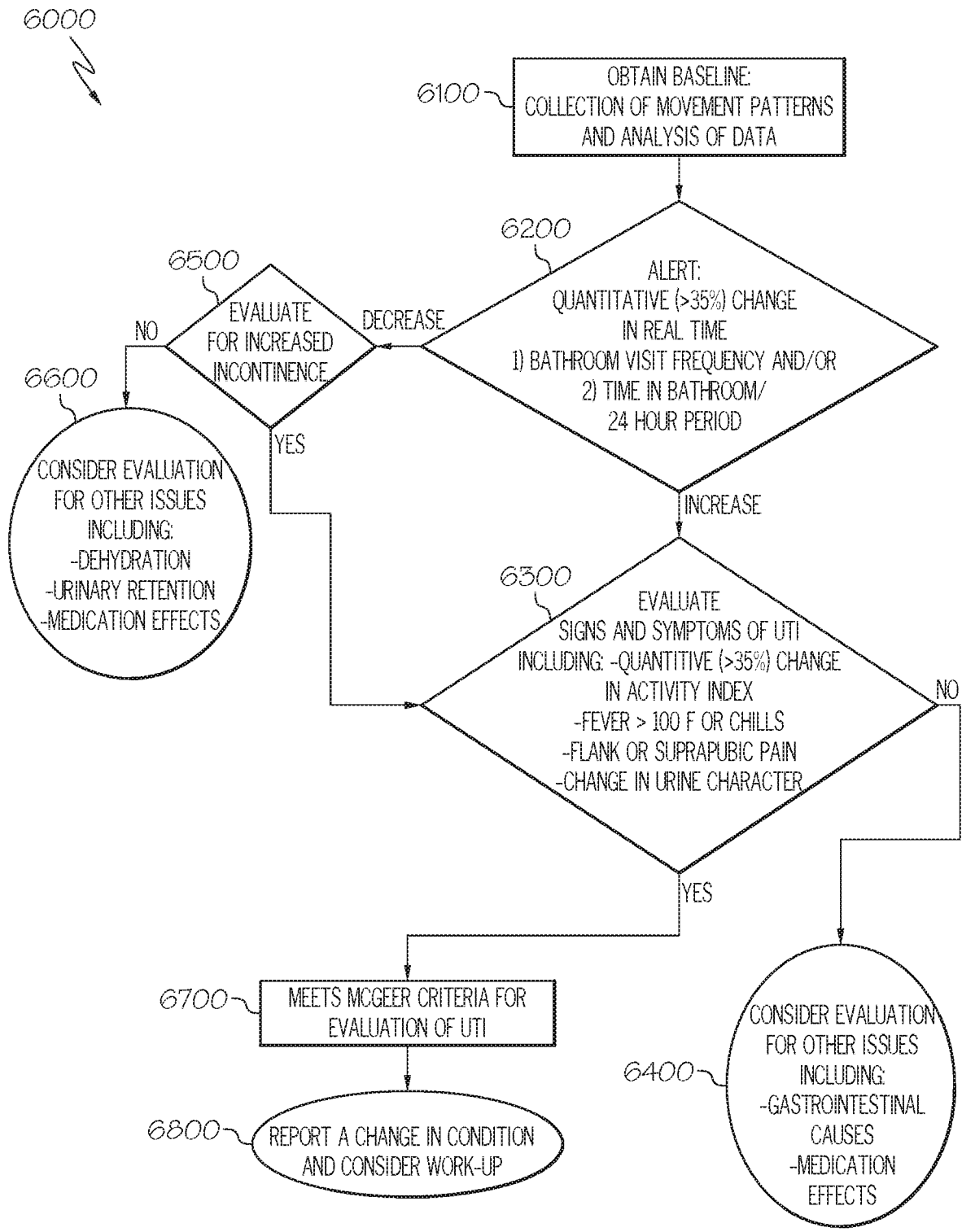
FIG. 14A depicts a program structure in the form of a flow diagram of how the wearable electronic device and system of FIG. 1 may be used to help a caregiver determine if a patient is at risk of developing a UTI.
Figure 14B:
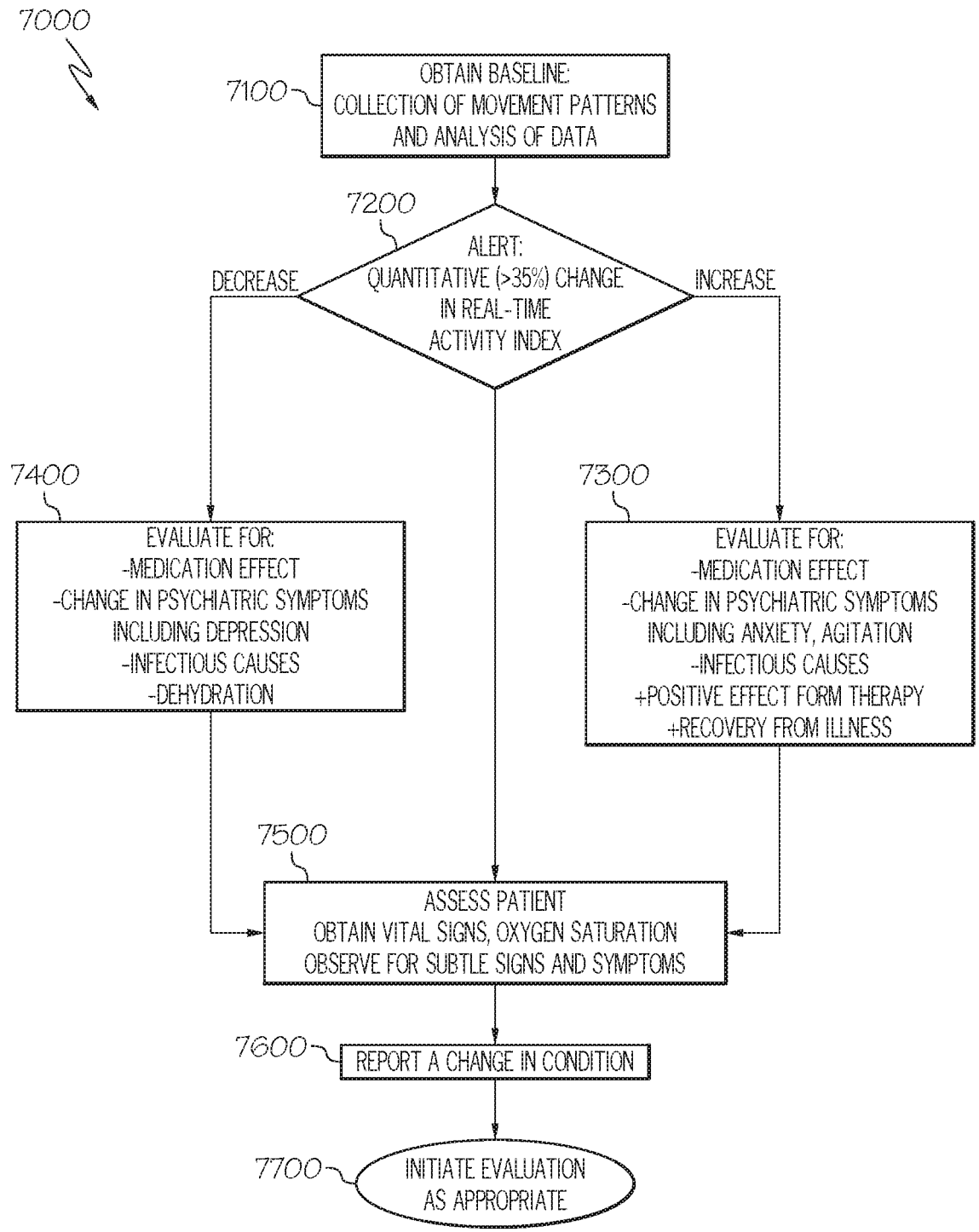
FIG. 14B depicts a program structure in the form of a flow diagram of how the wearable electronic device and system of FIG. 1 may be used to help a caregiver determine if a patient is at risk of developing neuropsychiatric complications.
Figure 14C:
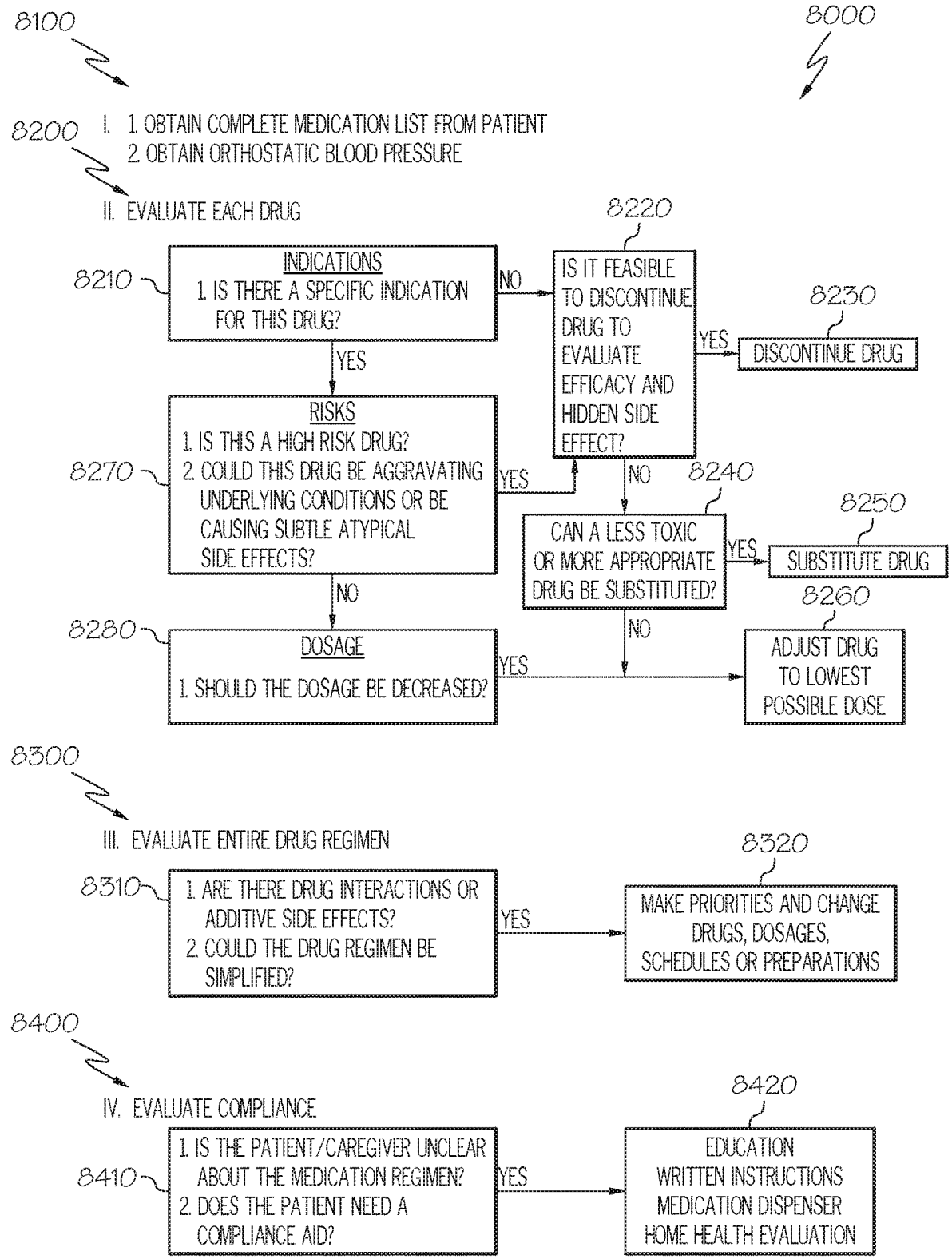
FIG. 14C depicts a program structure in the form of a flow diagram of how the wearable electronic device and system of FIG. 1 may be used to help a caregiver with a medication algorithm once a determination is made from a neuropsychiatric complication of FIG. 14B.

Referring next to FIGS. 14A through 14C in conjunction with FIGS. 9 through 10F, and in a manner roughly analogous to inferring HAR, ADL or IADL as discussed in conjunction with FIGS. 11A and 11B, the use of machine learning in the analysis of the various forms of data acquired by the wearable electronic device 100 may be employed to detect patterns in medical data that due to their complexity, volume or both would otherwise be difficult or impossible. By analyzing these patterns and presenting them to doctors, advanced practice clinicians, nurses and other caregivers C, a machine learning or other cognitive-simulating machine calculation can use such acquired data to identify changes in the salient indicators of the health of an at-risk person P. As mentioned above, the early detection of indicia of adverse health conditions such as a UTI, pneumonia or other infection, neuropsychiatric conditions, as well as other common conditions, in addition to early medication-based intervention or related treatment of any of these conditions, can help prevent avoidable hospitalizations or re-hospitalizations.

(A) Infections

Early identification of a change in condition (CIC), also referred to as an acute change of condition (ACOC), is a key factor in decreasing morbidity and rate of hospitalization or re-hospitalization, particularly for infection-prone, frail and elderly residents of assisted living facilities, nursing homes and related facilities. Significantly, patients with cognitive impairment and the onset of delirium (which is defined as confusion above a baseline and which in turn is related to the development or worsening of an illness, such as through sepsis and systemic inflammatory response syndrome (SIRS) that arises out of an individual's immune system response to such infection) may be unable to provide the information needed to help a caregiver C ascertain whether the person P meets one or more specific infection criteria. In such case, the wearable electronic device 100 data—as well as the analytics that can be generated by the system 1—can provide this necessary information on a real-time basis and alert the caregiver C of the early onset of ACOC. In addressing a change in functional status of a person P, the data being acquired by the wearable electronic device 100 and the accompanying analytics can provide an inference of such change through metrics such as the activity index that can provide a quantitative measurement of locomotor activity as a way to correlate such activity to impairments brought about by changes in health conditions such as an infection. In one form, the activity index may include or be used as part of a baseline with which to compare presently-acquired movement, position and related activity data in order to assess whether significant changes in locomotor capacity of person P is present.

Although shown in FIG. 9 as having a single BLE beacon 200 in bathroom BR, it will be appreciated that if more fine-grained detection is needed, there may be multiple such BLE beacons 200 arranged in various places within the bathroom BR in order to improve the spatio-temporal nature of the data being collected; this may be particularly beneficial in situations, where such data can provide to doctors, nurses and other caregivers C indicia of ADL (such as that gleaned from the data recording and analyzing activities associated with FIGS. 8, 11A and 11B) that in turn can provide advance warning of undesirable changes in the health of a patient, such as a UTI in the case of data being derived from the bathroom BR. In one form, when used in a machine learning mode of operation, the system 1 of the present disclosure is able to learn to extract features, as well as to be trained to identify patterns from the data that arises from ADL events in an experiential and ad hoc way (that is to say, without the need for the algorithms or models that are being used to analyze the data to be comprised entirely of a fixed set of program code). As previously mentioned, such learning may be supervised or unsupervised, depending on the needs of the particular health condition being analyzed.

As previously mentioned, one of the most significant contributors to avoidable hospitalizations or re-hospitalizations of patients pertains to infections in general and the high incidence of UTIs in particular, especially for the elderly and those suffering from dementia. In one form, the system 1 for UTI detection combines time-based data from bathroom visits and toilet flushes combined with other data acquired from the wearable electronic device 100. Additional information, such as that acquired from the facility schedule of events (such as that depicted in FIG. 10A) may be used, as well as other external data, such as that associated with the time of the year, weather or the like. Comparisons can be made from intra-patient or interpatient baseline data 1700 and subjected to machine learning analysis in an attempt to identify patterns or significant deviations from the norm. For example, a machine learning-based approach may be used in conjunction with the wearable electronic device 100 or the system 1 in order to acquire first and second (i.e., baseline and present) data about an individual so that two or more different states or related health conditions (as embodied in a data structure in memory 173B) may be compared based on the acquired first and second data. Various criteria may be used, an example of which is the Milliman Criteria that set forth targets in order to help individual patients attain certain outcome metrics following any type of intervention or procedure (such as surgery).

Referring with particularity to FIG. 14A, a program structure 6000 is shown in the form of a flow diagram of how one or both of the wearable electronic device 100 and system 1 of FIG. 1 may be used to help a caregiver C determine if the person P being monitored is at risk of developing a UTI. As previously mentioned, a baseline condition may first be ascertained, as shown in event 6100. In one form, this may include the collection of movement patterns and the subsequent analysis to determine HAR, ADL or IADL, as discussed previously in conjunction with FIGS. 11A and 11B. From this an alert in event 6200 may be generated (such as by logic device 173) if a significant deviation from the baseline-established a norm is detected. In the non-limiting example shown, a significant deviation may be a greater than 35% change in one or both of bathroom visit frequency and time spent in the bathroom over a daily period. Additional analysis—such as in the form of a decision tree—may be used depending on whether the quantitative change evidences and increase (event 6300) or decrease (event 6500) relative to the baseline. For example, if the change indicates an increase in these bathroom-related events, the subsequent event 6300 may include evaluating for UTI symptoms such as quantitative changes in the activity index, body temperature or the like, as well as qualitative changes in local pain, urine character or the like. Likewise, if the change indicates a decrease in these bathroom-related events, the subsequent event 6500 may include evaluating for increased incontinence. If the increase in bathroom-related events and subsequent evaluation event 6300 indicates negatively, then event 6400 may be used to consider evaluation for other issues such as gastrointestinal causes, medication effects or the like, whereas if the increase in bathroom-related events and subsequent evaluation event 6300 indicates in the affirmative, then a caregiver C may infer that the McGeer Criteria for a UTI has been met, after which a report event 6800 may be generated for consideration of one or more medical intervention activities. Likewise, if the change from event 6200 indicates a decrease in these bathroom-related events and the evaluation for increased incontinence event 6500 may indicate either positively or negatively, additional events may be undertaken, such as evaluating the person P for other conditions 6600 such as dehydration, urinary retention, medication effects or the like in situations where incontinence is no in evidence. Contrarily, in situations where increased incontinence may be present, the evaluation event 6300 may again be undertaken in a manner similar to situations where the alert from event 6200 does indicate an increase compared to the baseline 6100. Depending on this other conditions 6600 inquiry, the subsequent events 6400, 6700 and 6800 may further be undertaken.

One particularly useful set of diagnostic, treatment, and surveillance criteria for UTI analysis—particularly for nursing home patients—is the McGeer Criteria, while another is known as the Loeb Criteria that provides a consensus of localizing symptoms that in one form may be viewed as certain updates to the McGeer Criteria. Within the context of the present disclosure, it is recognized that both criteria differ in some respects, but also exhibit a lot of similarity. As such, it will be understood that the term "McGeer Criteria" is used herein as a shorthand for either approach for early identification of a UTI. In one form, the criteria may be patient-centered (that is to say, clinical), while in another, the criteria may be population-based (that is to say, surveillance). Relatively recent updates to the McGeer Criteria added a so-called Constitutional Criteria, particularly as it relates to residents of LTC facilities. In addition to revising some of the previous criteria, it also added leukocytosis as one of the criteria, as well as set forth additional ADL-related factors of what must be present for changes in functional status, such as acute change in mental status and acute functional decline. For example, an acute change in mental status diagnosis may be met by (1) an acute onset (that is to say, a new or worse condition from a baseline), (2) fluctuating behavior (that is to say, behavior that comes or goes or experiences changes in severity), (3) inattention (that is to say, a difficulty in focusing or inability to maintain attention) and (4) at least one of (4A) disorganized thinking (that is to say, thinking that is hard to follow or doesn't make sense) and (4B) altered level of consciousness (that is to say, sleepy, unarousable or lethargic).

Presumed UTIs are the most common reason that antimicrobials are prescribed for older adults. Thus, by implementing the McGeer Criteria using machine learning from data acquired through the wearable electronic device 100 and analyzed on system 1 as a way to identify whether a patient meets criteria for evaluation—and possible reduction in the likelihood—of developing a UTI prior to the patient developing symptoms may help to reduce the need for antimicrobial medications or other treatment. More particularly, the McGeer Criteria may differ slightly depending on whether or not the patient is using a catheter. The McGeer Criteria as presently implemented for UTIs of patients without an in-dwelling catheter includes two major criteria both of which must be present. The first major criteria (1) requires: at least one of (a) and (b), where (a) is acute dysuria or acute pain, swelling, or tenderness of the testes, epididymis, or prostate and (b) is fever or leukocytosis (as the so-called Constitutional Criteria), and further requires at least one of the following localizing urinary tract sub-criteria made up of (i) acute costovertebral angle pain or tenderness; (ii) suprapubic pain; (iii) gross hematuria; (iv) new or marked increase in incontinence; (v) new or marked increase in urgency; and (vi) new or marked increase in frequency. Likewise, in the absence of meeting the fever or leukocytosis of the first major criteria, a positive diagnosis of a UTI may also require the presence of two or more of (i) suprapubic pain, (ii) gross hematuria, (iii) new or marked increase in incontinence, (iv) new or marked increase in urgency and (v) new or marked increase in frequency. The second major criteria (2) requires a positive urine culture in the form of one of the following sub-criteria: (a) at least $10^5$ colony-forming units per milliliter (CFU/ml) of no more than two species of microorganisms in a voided urine sample, and (b) at least $10^2$ CFU/ml of any number of organisms in a specimen collected by in-and-out catheter.

In situations where the patient is using a catheter (often referred to as a catheter-associated symptomatic UTI scenario), two (slightly different) criteria must be satisfied. The first major criteria (1) requires one or more of the following with no alternate source: (a) fever; (b) rigors; (c) new onset of hypotension with no alternate site of infection; (d) new onset of confusion or functional decline along with leukocytosis; (e) new costovertebral angle pain or tenderness; (f) new or marked increase in suprapubic tenderness; (g) acute pain, swelling or tenderness of the testes, epididymis or prostate and (h) purulent discharge from around the catheter. The second major criteria (2) requires (if the urinary catheter removed within last two calendar days): (a) a voided urine culture with $\geq 10^5$ CFU/ml of no more than two species of microorganisms and (b) positive culture with $\geq 10^2$ CFU/ml of any microorganisms from straight in/out catheter specimen. Likewise, the second major criteria (2) requires (if the urinary catheter is in place) a positive culture with $\geq 10^5$ CFU/ml of any microorganisms from an indwelling catheter specimen.

The 2012 updates to the McGeer Criteria removed change in character of urine and worsening of mental or functional status. Nevertheless, a rough equivalent to the latter is now present in the form of ADL-related Constitutional Criteria where mental status change or acute functional status decline are determined, such as through the MDS 3.0. For example, the mental status change may be present if all of the following are detected: acute onset, fluctuating course, inattention and disorganized thinking or altered levels of consciousness. Likewise, acute functional status change may be present if there is a three-point decrease in ADL score based on seven ADL items including (1) bed mobility, (2) transfer, (3) locomotion within the LTC facility, (4) dressing, (5) toilet use, (6) personal hygiene and (7) eating.

In one form, analyzing whether an individual is at risk of developing a UTI includes applying machine learning logic, such as that associated with one or more of the machine learning models discussed herein, to the acquired LEAP data taken from the wearable electronic device 100. In one particular form, this may include using at least some of the machine codes that are stored on memory 173B of either the wearable electronic device 100 or the backhaul server 400 in conjunction with the respective processor 173A to execute at least a portion of the McGeer Criteria. For example the machine code may include that which executes an analysis to determine one of the criteria mentioned above particular examples of which may include the new or marked increase in urination urgency, the new or marked increase in urination frequency and the new or marked increase in incontinence. Significantly, these are among the criteria that can be measured either directly or indirectly (that is to say, inferred) through the sensors 121 and hybrid wireless communication module 175 and the resulting LEAP data. As such, directly-measured location properties, such as identification of a patient as being within the bathroom BR of FIG. 9 or other particular room, along with temporal data, such as how long or how frequently such patient is in the bathroom BR, as well as what time of the day the patient is in the bathroom, in conjunction with activity data, such as how rapidly or slowly the patient moves to and from the bathroom BR, and in addition to physiological data that may show heartrate, body temperature, excess shaking or the like, may be used to infer or predict a likelihood that the patient is suffering from—or is at risk of developing—a UTI. In one particular form, the measured values may be compared against accepted norms such as through contemporaneous or previously-acquired historical baseline data 1700, as discussed elsewhere in the present disclosure, as a way to increase the accuracy with which such inference or prediction is made.

Another common form of infection that plagues the elderly and those suffering from cognitive impairments is pneumonia a version of which is referred to as community-acquired pneumonia (CAP) that is a leading form of infectious disease that leads to patient hospitalization. Certain forms of the LEAP data may be particularly probative of an individual's likelihood of contracting pneumonia. For example, the location data may provide indicia that an individual has spent time in a location where the likelihood coming into contact with another who may have pneumonia is heightened. Similarly, activity, along with respiratory and other physiological data, may provide indicia of speed of movement, respiration rate, heat rate, shallowness of breathing or the like that can be correlated to the likelihood of pneumonia.

As with UTIs, pneumonia (which in one form is a subset of the larger group of maladies known as infections) may use similar criteria for CDS or diagnosis. For example, one form of output used for diagnosis or CDS of a pneumonia may require that all of the following conditions be satisfied: (1) a positive chest X-ray for either pneumonia or new infiltrate; (2) one or more of (a) new or increased cough or sputum, (b) reduced oxygen saturation (as well as a 3% decrease compared to a baseline), (c) abnormal lung exam new or changed (d) pleuritic chest pain or respiratory rate of greater than 25 breaths per minute; and (3) evidence of one or more constitutional criteria (that is to say, fever, leukocytosis, acute change in mental status from baseline and acute functional decline). Regarding pneumonia-specific conditions, there are well-established criteria for community-acquired pneumonia (CAP) and healthcare-associated pneumonia (HCAP). For example, CAP may further include minor criteria (such as high blood urea nitrogen levels, confusion or disorientation, hypotension, hypothermia, leukopenia, multilobar infiltrates, partial arterial oxygen pressure to fraction of inspired oxygen ratios, respiratory rates, thrombocytopenia) and major criteria (such as invasive mechanical ventilation or septic shock with need for vasopressors). Particular examples of diagnosis codes related to pneumonia may be found in the International Statistical Classification of Diseases and Related Health Problems (ICD) codes such as ICD10 examples of which include ICD10 001-139 (infectious diseases), ICD10 460-529 (respiratory system), as well as others.

There are various scoring systems to help determine if a patient has pneumonia, including the Pneumonia Severity Index (PSI) that consists of twenty clinical and laboratory parameters and is recommended by the American Thoracic Society (ATS)/Infectious Diseases Society of America (IDSA). Another scoring system is referred to as the CURB-65 score. The CURB-65 score is for a series of risk factors including (1) Confusion of new onset (defined as an abbreviated mental test score (AMTS), where a score of 7-8 or less suggests cognitive impairment), (2) blood Urea nitrogen greater than 7 millimoles per liter (or 19 mg/dL), (3) Respiratory rate of 30 breaths per minute or greater, (4) Blood pressure less than 90 mm Hg systolic or diastolic blood pressure 60 mm Hg or less and (5) Age 65 or older. CURB-65 simplifies the scoring system compared with PSI, but may reduce sensitivity for other pneumonia indicia, such as one referred to as a measure of death occurring within 30 days of a hospital admission known as 30-day mortality. Yet another score, known as the SMART-COP score (for Systolic blood pressure, Multilobar infiltrates, Albumin, Respiratory rate, Tachycardia, Confusion, Oxygen and pH) may be used. Still another approach, called (A-DROP) uses factors such as Age, Dehydration, Respiratory failure, Orientation disturbance and systolic blood Pressure, where the dehydration component is understood to be a common manifestation of an infection associated with decreased intake, as well as increased needs associated with a fever.

The authors of the present disclosure believe that certain physiological data as acquired by the wearable electronic device 100 may provide a better indication of a patient's true status, as well as provide a better prediction of such patient's outcome. For example, for the sensors 121 mentioned previously, certain physiological parameters, such as respiration rate, heart rate, unusual breathing patterns (such as wheezing or the like) and temperature, as well as the patient's location and activity (such as measured by one or both of the first and second wireless communication sub-modules 175A, 175B, as well as the sensors 121 configured as accelerometers, gyroscopes, magnetometers or the like) may be analyzed (such as by one or more of the machine learning models discussed herein) in order to provide a statistically-significant indication that the measured values of one or more of the various location, environment, activity and physiological parameters mean that an adverse health condition of the person P being monitored is imminent. In one form, the LEAP data acquired by the wearable electronic device 100 may be used as a supplement to one or more of the PSI, CURB-65, SMART-COP or A-DROP scores as a way to provide a higher degree of confidence or weighting that one or more of the parameters contributing to a pneumonia score is present.

As with the UTI as described above, in one form, analyzing whether an individual shows predictors of pneumonia onset versus risk for developing the illness may include applying machine learning logic to the acquired LEAP data. In particular, patterns arising from a particular combination of patient location, movement (or relative lack thereof) using the first and second wireless communication sub-modules 175A, 175B and physiological condition (using one or more of the sensors 121), possibly in conjunction with ambient environmental conditions (also using one or more of the sensors 121) allows for a data-driven predictive analytic approach to infer the likelihood of a pneumonia even absent direct clinical measurement of a patient's condition, such as through the conventional PSI, CURB-65, SMART-COP or A-DROP score approaches. In another form, the data may be used as a way to supplement such score-based symptom information.

Relatedly, the wearable electronic device 100 may be used to gain an understanding of the likelihood of an influenza outbreak. Influenza (or more commonly, the flu), which is defined as a highly contagious viral infection of the respiratory passages causing fever, severe aching, and excessive discharge or buildup of mucus in the nose or throat resulting with inflammation of the mucous membrane, is indicated by various symptoms that may be inferred from analysis of at least a portion of the acquired LEAP data in a manner analogous to UTIs and pneumonias. Some of the symptoms include fever, breathing difficulty, chills, headache, achy muscles, cough, nasal congestion, fatigue and sore throat. Sensors 121 configured to detect temperatures, excessive vibratory activity (such as that associated with severe coughing, rapid heartbeat, deep or labored breathing, among others) may be used to particularly ascertain unusual levels of physiological activity. As with the UTI and pneumonia, many of these symptoms may be ascertained from the previously-discussed sensors 121 that are configured with physiological data-acquiring capability.

Moreover, as with the UTI and pneumonia described above, analyzing whether an individual shows predictors of the onset of influenza may include applying machine learning logic to the acquired LEAP data to divine patterns arising from patient location, movement and physiological condition, possibly in conjunction with ambient environmental conditions, where the determination of whether the disease is either present or imminent may be made absent direct clinical measurement of the patient's condition through one or more of the symptoms that may in one form be specific to influenza. As with the other forms of infection, the data may be used in conjunction with score-based information such as that taken from a direct interaction between the patient and his or her physician.

(B) Neuropsychiatric Conditions

As with infections, criteria used to infer a neuropsychiatric condition of an individual associated with the wearable electronic device 100 may be based upon accepted disorder classifications, such as those found in the *Diagnostic and Statistical Manual of Mental Disorders, 5th* edition (DSM-5) that uses a disease coding system that corresponds with codes from ICD10. Such diagnostic classification may include anxiety disorders, bipolar and related disorders, depressive disorders, disruptive, impulse-control and conduct disorders, dissociative disorders, elimination disorders, feeding and eating disorders, gender dysphoria, neurocognitive disorders, neurodevelopmental disorders, obsessive-compulsive and related disorders, paraphilic disorders, personality disorders, schizophrenia spectrum and other psychotic disorders, sexual dysfunctions, sleep-wake disorders, somatic symptom and related disorders, substance-related and addictive disorders and trauma- and stressor-related disorders. If not diagnosed properly or in time, symptoms associated with one or more of these disorders can lead to serious persistent mental illness (SPMI), where failure to manage such may exacerbate other forms of disease progression that may in turn contribute to excess morbidity and mortality.

Figure 12:
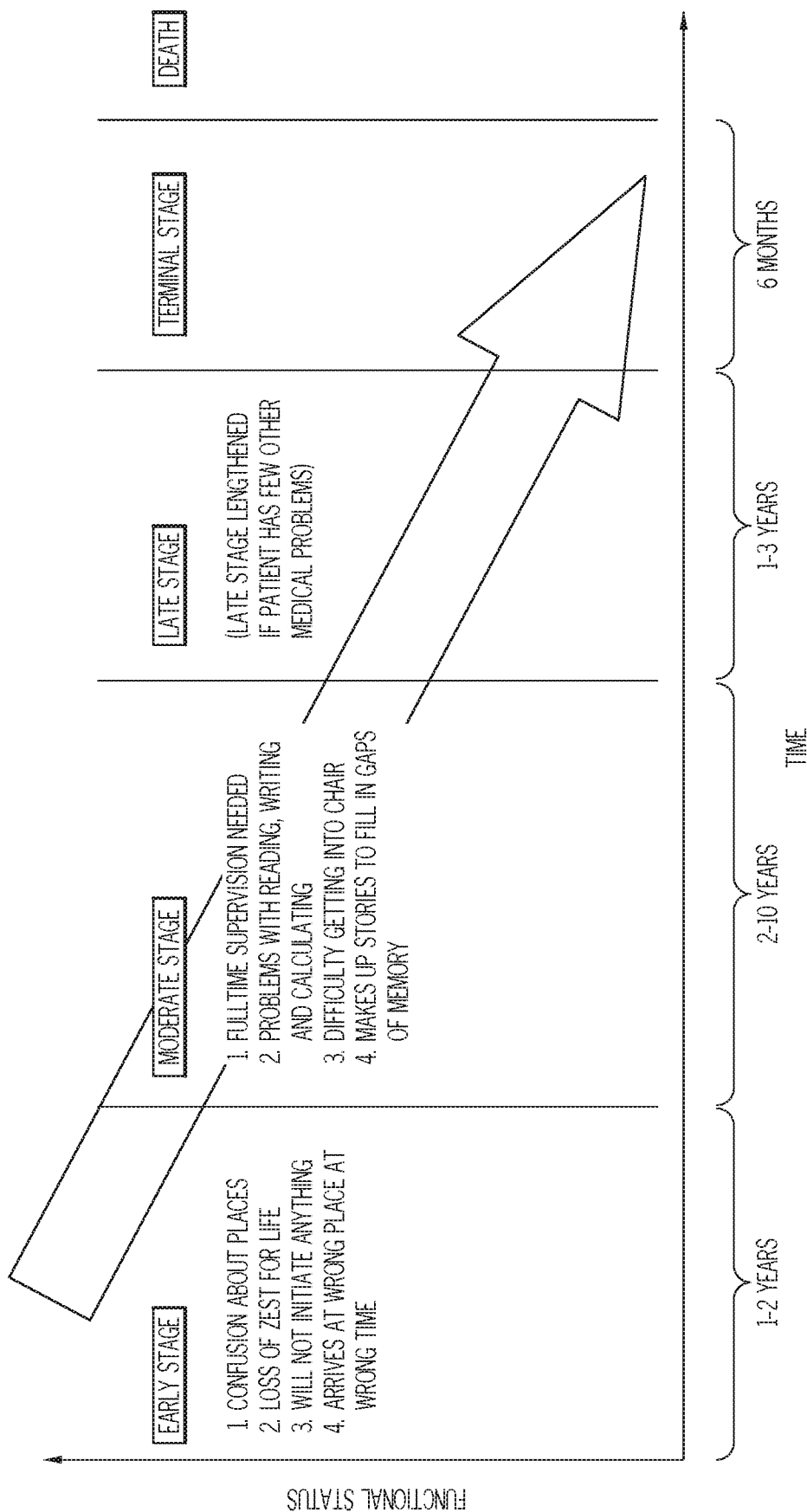
FIG. 12 depicts a data structure in the form of a dementia timeline chart to correlate the LEAP data gathered by the wearable electronic device and system of FIG. 1 to a change in functional status according to one or more embodiments shown or described herein.

Referring next to FIG. 12, a neurocognitive disorder of particular relevance to the present disclosure is dementia, which may be further classified as having major or mild variants. As such, while this and related cognitive impairments may be considered a psychiatric condition under DSM-5, within the present disclosure, such impairment may be categorized as a subset of a neuropsychiatric condition, or as a separate health condition, where either variant is deemed to be within the scope of the present disclosure, regardless of its semantic classification. Moreover within the present disclosure, while the terms "psychiatric" and "neuropsychiatric" imply different subsets of overlapping medical disciplines (specifically, psychiatry and neurology), they are treated interchangeably within the present disclosure for the purpose of correlating the various forms of LEAP data as acquired by the wearable electronic device 100 to certain corresponding adverse health conditions. Furthermore, the various forms of the LEAP data can be used as indicia of behavior or patterns (for example, increased patient agitation) that in turn can be attributed to or at least correlated with such conditions through changes in accepted patient norms irrespective of how one or more conditions—particularly those dealing with changes in mental status—are categorized under commonly-accepted medical diagnosis codes. For example, if an analysis based on the acquired LEAP data from the wearable electronic device 100 indicates that a patient is experiencing increased agitation, such increase may be either (a) an early warning sign of an imminent change in health condition (such as infections, dementia or other neuropsychiatric conditions) or (b) an indication of other adverse changes in health (including infections) where a diagnosis or suspicion of dementia or other neuropsychiatric conditions is already in place. Thus, regardless of whether a particular health condition is a malady in and of itself or merely the byproduct of another, the LEAP data acquired from the wearable electronic device 100 can be used, along with suitable analysis such as from the machine learning approaches discussed herein, to help caregivers C mitigate the effects of such condition. For example, a caregiver may be able to more readily identify when the person P being monitored is in an agitated or upset state even absent outward manifestations of such agitation.

In one form, agitation may be correlated to one or more neuropsychiatric conditions, including schizophrenia with increased negative symptoms (such as isolation, de-socialization or the like), dementia with psychosis and bipolar disorder or other conditions where antipsychotic medication is frequently prescribed. Within the present disclosure, the term "agitation" refers to a range of behavioral disturbances including aggression, combativeness, disinhibition, hyperactivity, shouting, pacing and exit-seeking. Moreover, even though agitation is semantically mentioned as being associated with or a subset of a psychiatric or neuropsychiatric condition, including dementia and associated cognitive impairments or declines, agitation may also be construed as a stand-alone condition in that the source of such agitation may be from an as-yet undiagnosed underlying adverse health condition (such as UTIs, delirium and other conditions). It will be appreciated that at all variants, irrespective of how they are grouped, are within the scope of the present disclosure.

A diagnosis of dementia (such as that which can identify whether a patient is in an early, moderate, late or terminal stage) requires that at least two core mental functions be impaired enough to interfere with daily living. These mental functions include ability to focus and pay attention, ability to reason and problem-solve, language skills, memory and visual perception. Dementia symptoms—some of which are shown in conjunction with FIG. 12—may include cognitive changes such as confusion and disorientation, difficulty communicating or finding words, difficulty handling complex tasks, difficulty reasoning or problem-solving, difficulty with planning and organizing and difficulty with coordination and motor functions memory loss. Dementia symptoms may also include psychological changes such as the previously-discussed agitation, as well as anxiety, depression, hallucinations, inappropriate behavior, paranoia and personality changes. Moreover, dementia may come in many forms, including Alzheimer's disease, frontotemporal dementia, Lewy body dementia, mild cognitive impairment (MCI), mixed dementia and vascular dementia, while additional diseases with dementia-like symptoms may include Huntington's disease, traumatic brain injury, Creutzfeldt-Jakob disease and Parkinson's disease. In addition to idiopathic etiologies, causes of dementia may include anoxia, brain tumors, high blood pressure, infections and immune disorders, lack of physical and social activity, metabolic problems and endocrine abnormalities, normal-pressure hydrocephalus, nutritional deficiencies, poisoning, reactions to medications, smoking, subdural hematomas, unhealthy dietary habits and vitamin D deficiencies.

The decrease in the functional status of person P as dementia progresses along the timeline may be grouped into various stages using a dementia trajectory chart where the functional status extends along the Y-axis and the timeline extends along the X-axis. In one form, dementia may be broken down into an early stage, a moderate stage, a late stage, a terminal stage and ultimately death. In the early stage (typically between one and two years after a diagnosis), relatively small anomalies can be noticed, including lack of initiation of activities, confusion about places and times (including arrival at an improper location at an improper time) and loss of love of life. Personal items tend to get lost, and the person P acts more withdrawn. Certain ADL or IADL-related events, such as a decline in skill sets, inability to manage money or inability to provide personal care for one's self are often observed. Irritability and suspicion of others is often a sign of the later parts of the early stage. In the moderate stage (typically between two and ten years after a diagnosis), the functional status declines more to the point where heightened levels of care may become necessary, including full time supervision and assistance with mobility, heightened problems with reading, writing and performing calculations, as well as making up stories in order to fill in the increasingly frequent gaps in memory. Telltale signs within this stage may include loss of impulse control, emotional lability, restlessness, sloppiness, outbursts of anger, frequent sleeping, nighttime wandering, incontinence of urine, childlike behavior, paranoia, diminished social activity, increased fall frequency of falls as well as falls in attempting to transfer from one place or position to another. At this stage, assisted living may be required for personal care, which may subsequently progress into nursing home placement. In the late stage (which may occur between one and three years after the moderate stage), telltale signs may include the patient becoming almost completely non-ambulatory, having poor safety awareness, increased rate of mental decline (particularly after an acute hospitalization event), forgetting when his or her last meal was eaten, little capacity for self-care, requires help with all bathing, dressing and eating activities, loss of bowel control, be prone to making verbal utterances not related to pain, increased amount of sleeping, difficulty in communicating with words, difficulty with liquids, coughing after taking a drink, lack of appetite and weight loss even with a good diet. In the terminal stage (which typically lasts no more than about six months), the patient experiences recurrent aspirations even with thick liquids, pressure ulcers even with frequent turnings and related good quality of care, as well as unawareness of external stimuli. Death often occurs as a result of sepsis, pneumonia, UTI or other infection. Delays in the diagnosis of these conditions may contribute to increased morbidity and mortality.

Referring next to FIG. 13, the neuropsychiatric symptoms of dementia affect individuals across all stages and etiologies. Furthermore, there tends to be a strong correlation between dementia and agitation. In fact, in the middle and later stages of the illness, as many as 50% of patients with dementia will exhibit agitation, while 70% will experience episodes of psychosis within the first six or seven years of the illness. In addition to agitation, symptoms may include aggression, depression, anxiety, delusions, hallucinations, apathy and disinhibition. Of these, agitation particularly appears to demonstrate a high degree of correlation with activity, where one approach known as the Cohen-Mansfield Agitation Inventory (CMAI) the short form of which is shown, possibly in conjunction with the Mini Mental State Exam (MMSE), may be used to not only correlate agitation and activity, but also assess how cognitive function may be correlated to activity. In another exemplary form, mean motor activity (MMA, such as measurable with an actigraph) can be used to correlate CMAI scores. For example, individuals identified as having a high agitation status may be inferred through the use of MMA and a related strong correlation with CMAI total scores in general and more detailed verbal agitation and non-aggressive physical agitation scores in particular from the CMAI. Another scale, referred to as the Pittsburgh Agitation Scale (PAS), is often broken down into four behavior groups for psychogeriatric analysis; these four groups include aberrant vocalizations, motor agitation, aggressiveness and resisting care. Significantly, many components of these four behavior groups may be based on parameters that may be directly sensed by the wearable electronic device 100 such that the results can populate a CMAI table or related data structure. For example, data collected from an audio variant of the sensors 121, as well as the location or movement variant of the sensors 121, all as disclosed herein, may be used to draw inferences about levels of patient agitation. In one form, the data acquired from the wearable electronic device 100 is used as part of a predictive model to determine impending agitation such that an alerted caregiver C has the opportunity to intervene through a primary outcome or secondary outcome action plan, care plan or the like before the use of psychotropic drugs (such as antidepressants, antiepileptics, anxiolytics, antipsychotics, and anticonvulsants) or hospitalization becomes necessary. In one form, various types of data may be collected in order to establish a correlation between movement-based activity and agitation. This data includes (1) intra-room and room-level movement data, (2) heart rate data, (3) PAS data and (4) qualitative observation data. Likewise, data that corresponds to sleeping patterns may also be used in order discern agitation or other changes in mental status. As mentioned elsewhere, the raw data can be cleansed and transformed into usable measurement data for further analysis.

In one form, the collection of various forms of LEAP data with the wearable electronic device 100 may be deemed to be a form of digital phenotyping when used in conjunction with a machine learning model in order to diagnose a psychiatric or neuropsychiatric condition without recourse to canonical classification approaches such as those associated with DSM-5. For example, one or more features may be extracted from the acquired LEAP data using linear (for example, short-time Fourier transform) or non-linear (such as fractal dimension) functions for subsequent use by a suitably-trained classification, regression or reinforcement model. In such form, the wearable electronic device 100 and machine learning model cooperate with one another as a device to conduct computational psychiatry, where the acquired LEAP data may be used to mathematically describe a patient's cognition in sufficient detail in order to correlate a representation of one or more psychiatric or neuropsychiatric conditions to the symptoms being observed through the data.

Through patterns in the LEAP data acquired by the wearable electronic device 100, the caregiver C may gain additional insight into whether a person P is at risk of developing an avoidable neuropsychiatric condition. For example, repetitive or obsessive movements by the person P being monitored, particularly when used in the context of a particular location or time of day and baseline data 1700, may be analyzed by the machine learning models discussed herein to provide indicia of the presence of such condition. Other patterns, examples of which include changes in sleep patterns, faster or slower mobility, pacing, fidgeting or the like may also be identified through analysis of the LEAP data. This in turn may allow a physician to better ascertain the efficacy of any medication being administered, as well as whether to adjust a particular dosage of such medication, in addition to whether a medication regimen should be commenced or terminated. As will be discussed in conjunction with FIG. 14C, the LEAP data may be used to help a physician perform a geriatric medication evaluation (also referred to as a geriatric medication algorithm) where activity-related information pertaining to a patient's gait, falling tendency, wandering tendency, level of agitation, restlessness or the like can help provide answers to an algorithmic series of questions used to determine the appropriateness of a particular medication regimen. Early detection of escalations in behavioral symptoms would be expected to improve efficacy of interventions and decrease adverse consequences. The LEAP data discussed herein contributes to the understanding of the need for a medication regimen, as well as the efficacy of specific dosage adjustments. This last decision support is particularly beneficial in light of statistics gathered over the last few decades that has shown a significant increase in the percentage of the adult population that is taking at least one prescription drug, as well as the number of adults taking three or more prescription drugs. A 2016 paper presented to the American Hospital Association noted that the total net spending on prescription drugs is almost $310 billion annually, making prescription drugs the fastest growing segment of the U.S. healthcare economy, and more importantly that a significant fraction of this money is going to waste as up to half of the 3.2 billion prescriptions written in the U.S. each year are not taken as directed, if even taken at all. This in turn leads to over $250 billion dollars of unnecessary costs, or roughly 13 percent of the country's total annual healthcare expenditures.

As with the various forms of infections described above, analyzing whether an individual is at risk of an adverse neuropsychiatric condition may include applying machine learning logic to the acquired LEAP data to determine whether any patterns can be gleaned arising from patient location, movement and physiological condition, possibly in conjunction with ambient environmental conditions. As with the infections, such a determination may be made without recourse to direct clinical measurement of the patient's condition. Also as with the various forms of infection discussed herein, the data may be used in comparison against baseline data 1700 such as that taken from a direct interaction between the patient and his or her physician, as well as from known norms of the patient or a similarly-situated group of patients with similar demographic or health condition attributes. For example, the baseline data 1700 may be in the form of a score-based criteria such as that of the previously-mentioned CMAI, PAS or the like in a manner analogous to the McGeer Criteria, PSI score, CURB-65 score, SMART-COP score, A-DROP score used for UTIs, pneumonia and other infections.

Autism is another form of neuropsychiatric condition that can at least be partially identified by LEAP data acquired with the wearable electronic device 100. In one form, the length of time that a student is willing to remain relatively motionless while in a classroom setting may be determined by one or more forms of the LEAP data, including the location data acquired by the first and second wireless communication sub-modules 175A, 175B, as well as activity data acquired from the group of activity sensors 121B. Such information may include a temporal component, so that such lengths of time may be compared against baseline data 1700. For example, if a norm is 45 minutes, and the individual is manifesting signs of movement at 30 minutes, then an indication of inattention may be inferred.

Referring with particularity to FIG. 14B, a program structure 7000 is shown in the form of a flow diagram of how one or both of the wearable electronic device 100 and system 1 of FIG. 1 may be used to help a caregiver C determine if the person P being monitored is at risk of developing a worsening psychiatric condition. As with the UTI analysis of the program structure 6000 that was previously mentioned in conjunction with FIG. 14A, a baseline condition may first be ascertained, as shown in event 7100. From this an alert in event 7200 may be generated (again, such as by logic device 173) if a significant deviation from the baseline-established a norm is detected. In the non-limiting example shown, a significant deviation may be a greater than 35% change in a real-time activity index relative to a baseline. Additional decision tree-like analysis may be used depending on whether the quantitative change evidences and increase (event 7300) or decrease (event 7400) relative to the baseline. For example, if the change indicates an increase in the real-time activity index, a subsequent evaluation may be for things such as the effect of a medication regimen, changes in psychiatric symptoms (including anxiety, agitation or the like), infectious causes, positive effects from prior therapy or recovery from a previous illness. Likewise, if the change indicates a decrease in the real-time activity index, a subsequent evaluation in event 7400 may be for things such as the effect of a medication regimen, changes in psychiatric conditions such as depression, infectious causes or dehydration. Regardless of whether the inquiry in event 7200 is indicative of an increase or decrease in real-time activity, event 7500 may be used to assess the person P in order to obtain vital signs. $O_2$ saturation, as well as to observe for subtle signs and symptoms, after which event 7600 may be used to report a change in the health condition of the person P being monitored, as well as event 7700 for an evaluation of the person P or consideration of one or more medical intervention activities. As previously mentioned, certain activities may be indicative of agitation or other anomalous behavior, and the early identification of agitation to allow the caregiver C to take corrective actions may be used to fend off a worsening condition.

Referring with particularity to FIG. 14C, a program structure 8000 is shown in the form of a flow diagram of how one or both of the wearable electronic device 100 and system 1 of FIG. 1 may be used to help a caregiver C determine the efficacy of a medication regimen for a person P who has been determined by the program structure 7000 of FIG. 14B to have a neuropsychiatric condition. In one form, activity-related data acquired by the wearable electronic device 100 can provide input that a caregiver C can use as part of an evaluation algorithm. In one form, such an algorithm may be used to reduce the extent of the medication regimen (called polypharmacy in situations where the regimen involves prescribing numerous different types of medications), as well as mitigation strategies where the medication regimen is deemed to be inappropriate and in need of change, such as the use of psychotropic medications in nursing home, assisted living or LTC facilities. In a manner analogous to using the LEAP data to establish a correlation between a new or changed medication regimen and an increased incidence of person P falling as discussed previously, the LEAP data may be used to correlate an inappropriate patient-specific medication regimen and an increased incidence of neuropsychiatric conditions. For example, evidence of outbursts, excessive wandering, pacing or movement-related agitation that can be gleaned from the LEAP data may be used to inform a caregiver C of the need for an intervention strategy such as a changed medication regimen or the like.

As with the UTI analysis of the program structure 6000 that was previously mentioned in conjunction with FIG. 14A, a baseline condition may first be ascertained, as shown in event 8100, particularly as it relates to things such as a current list of medications, current blood pressure or the like. From this an evaluation 8200 of each of the medications from the baseline may be conducted through a battery of decision tree-like questions, including whether there is a specific indication 8210 for the drug in question, the feasibility of discontinuing the drug 8220 (in the event that there is no indication from the previous inquiry), and if so to discontinue it 8230, or if not to ascertain whether a less toxic alternative 8240 might be appropriate, at which time either a substitute drug 8250 or a reduced dosage of the present drug 8260 might be appropriate. Contrarily, if the initial evaluation inquiry pertaining to a specific indication 8210 for the drug in question returns a yes answer, then a battery of risk 8270 questions may be asked to find out either the feasibility of discontinuing the drug 8220 or decrease in dosage 8280, at which time the decision to seek a reduced dosage of the present drug 8260 might be undertaken. After the evaluation 8200 of each of the medications is completed, an evaluation 8300 of the entire drug regimen may be conducted where-depending on whether there is a concern over drug interactions, side effects or there is a possibility of simplifying the regimen, a recommendation 8320 to prioritize drug dosages, schedules or preparations may be generated. In addition, an inquiry into whether the person P is willing or able to comply 8400 with medication-taking protocols can be pursued. In particular, once a battery of questions 8410 pertaining to the ability or willingness of a person P to comply are answered, the caregiver C may be in a better position to provide education 8420 in the form of written instructions, ordering a home health evaluation or the like.

As with the prior program structure 6000 of the UTI analysis, the use of the logic device 173 and its ancillary circuitry and components may be implemented in order to automate the process or take advantage of either rule-based algorithms or machine-learning based models with which to help with either CDS or a diagnosis in and of itself. From there, and also as with the prior program structure 6000 of the UTI analysis, the LEAP data being acquired from the wearable electronic device 100 may be used to provide actual environmental, activity or physiological conditions or events associated with the person P being medicated, as well as providing context in order to determine if such conditions or events are within acceptable limits or outside the norm. With regard to the context, other subtle signs of activity data, such as changes in gait, speed of movement, agitation, pacing or the like may also be used to help provide a more holistic picture of the health condition of person P, as can data associated with the ambient environment or location and data that provides physiological context such as body temperature, heart rate or the like.

(C) Other Conditions

Figure 15:
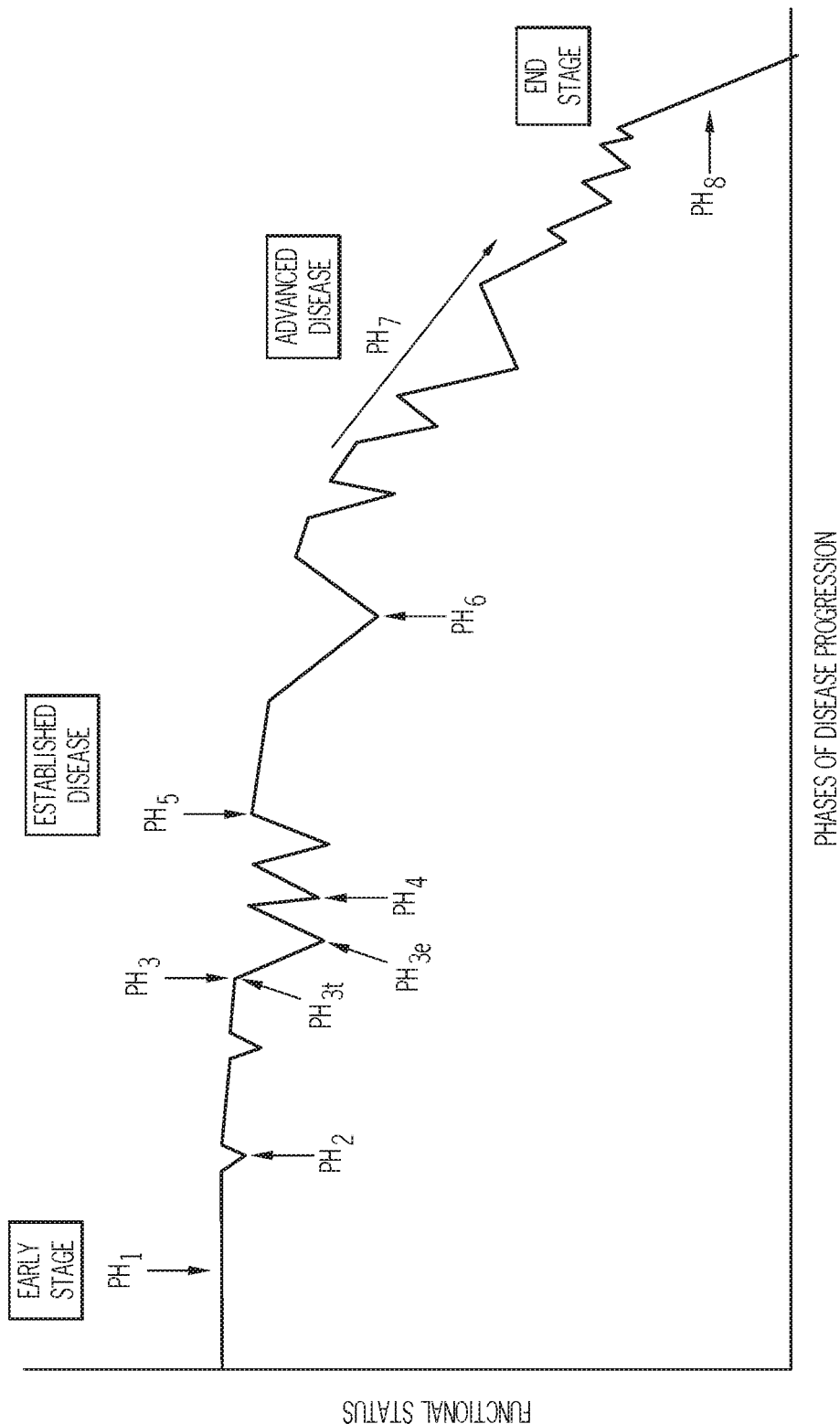
FIG. 15 depicts a data structure in the form of a chronic disease trajectory timeline chart to correlate the LEAP data gathered by the wearable electronic device and system of FIG. 1 to a change in functional status according to one or more embodiments shown or described herein.

Referring next to FIG. 15, a generalized model of chronic disease is depicted, where functional status decline over time shows a relatively common downward trajectory to that of the dementia timeline chart of FIG. 12. Within the present context, the trajectory model of chronic disease may be applied to the analysis of various health conditions such as congestive heart failure (CHF), chronic obstructive pulmonary disease (COPD), smoking cessation, as well as the previously-discussed neuropsychiatric condition, among others. Regardless of the chronic disease being analyzed, some generally identifiable phases PH along the trajectory may correspond to changes in the functional status, including an initial (or pre-trajectory) phase PH, where no signs or symptoms are present, a trajectory onset phase $PH_2$ where an initial onset of no signs or symptoms may be detected and where a diagnostic period may commence, a crisis phase $PH_3$ where a potentially life-threatening situation arises, an acute phase $PH_4$ that follows the crisis phase $PH_3$ and where signs or symptoms may be controlled by a prescribed regimen, a stable phase $PH_5$ that begins once signs or symptoms are controlled by the regimen, an unstable phase $PH_6$ where signs or symptoms are not controlled by the previously-adopted regimen, a downward phase $PH_7$ where progressive deterioration in mental and physical health is present and a dying phase $PH_8$ that correspond to the weeks, days or hours preceding death. It will be appreciated that the representation of the phases $PH_1$ through $P_H$ as shown are generalized, and that greater or lesser numbers of such identifiable phases PH may be present depending on the chronic disease being analyzed.

In one form, the use of the LEAP data from the wearable electronic device 100 may be particularly beneficial in CHF acute exacerbation scenarios to help overcome the traditional lack of general consensus on the best way to screen for asymptomatic ventricular dysfunction. For example, a CHF analysis might progress through various stages that include an early stage, an established disease stage, an advanced stage and an end stage that correspond generally to three of the identifiable phases PH along the trajectory. For example, at an early stage (which may generally correspond to trajectory onset phase $PH_2$), a person P may exhibit shortness of breath, swelling in lower extremities, weight gain or experience trouble sleeping. In this stage, symptoms tend to flare up such that the disease worsens with each episode. Once the person P reaches the established disease stage (which may generally correspond to phases $PH_3$ through $PH_5$), other symptoms may include ongoing cough or wheezing, lack of appetite or nausea, as well as rapid or irregular heartbeat. Next, when an advanced disease stage (which may generally correspond to phases $PH_6$ through $PH_7$) is reached, increased or racing heartrate, confusion, impaired thinking or the like may be noticed, as well as chest pain, increased anxiety, weight gain or loss, anasarca or edema leading to diuretic adjustments, decreases in albumin level or increases in brain natriuretic peptide (BNP) levels. The end stage (which may generally correspond to phase $PH_8$) may include constant chest pain, tiredness and weakness, breathlessness, difficulty walking, decreases in sodium level, anemia, evidence of kidney shutdown, refractory fluid overload or ascites. In ICD situations at this stage, there may be discussions with the patient or family member regarding turning off devices that are artificially prolonging life, palliative care or hospice options. In one form, a program structure in the form of a flow diagram similar to the ones of FIGS. 14A through 14C may be used to show how one or both of the wearable electronic device 100 and system 1 of FIG. 1 may be used to help a caregiver C determine if the person P being monitored is at risk of developing CHF, where corresponding questions, decision points and recommended responses specific to CHF are substituted for the ones pertaining to an infection or neuropsychiatric issue.

In a manner analogous to CHF, COPD stages may include an early stage, an established disease stage, an advanced stage and an end stage that correspond generally to three of the identifiable phases PH along the trajectory. For example, at an early stage (which may generally correspond to trajectory onset phase $PH_2$), a person P may exhibit repeated bronchitis, increased mucus production or occasional shortness of breath. As with CHF, in this stage the symptoms tend to flare up such that the disease worsens with each flare up. Once the person P reaches the established disease stage (which may generally correspond to phases $PH_3$ through $PH_5$), tightness in the chest, chronic coughing, frequent bronchitis, shortness of breath when walking, so-called "barrel" chest and pursed-lip breathing are often in evidence. Next, when an advanced disease stage (which may generally correspond to phases $PH_4$ through $PH_7$) is reached, manifestations may include constipation, sleeplessness and fatigue, poor appetite, increased pain and anxiety levels, shortness of breath with simple tasks, weight loss, orthopnea, sudden waking events accompanied by shortness of breath, increases in so-called "air hunger", limitations in activity, confusion and steroid dependence leading to complications. The end stage (which may generally correspond to phase $PH_8$) may include severe limits on activity, shortness of breath while talking, lack of appetite, depression and other events that may prompt a family member or caregiver C to initiate conversations about palliative care or hospice options. In one form, a program structure in the form of a flow diagram similar to the ones of FIGS. 14A through 14C may be used to show how one or both of the wearable electronic device 100 and system 1 of FIG. 1 may be used to help a caregiver C determine if the person P being monitored is at risk of developing COPD, where corresponding questions, decision points and recommended responses specific to COPD are substituted for the ones pertaining to an infection or neuropsychiatric issue.

It will be understood from the present disclosure that as with CHF and COPD, mental health diseases such as the neuropsychiatric conditions mentioned previously may extend along a trajectory that may include an early stage, an established disease stage, an advanced stage or late stage that correspond generally to three of the identifiable phases PH along the trajectory. For example, at an early stage (which may generally correspond to trajectory onset phase $PH_2$), a person P may exhibit a flat affect, lack of pleasure in everyday life, cognitive or memory problems, thought disorders, inability to function due to their behavioral issues (i.e., mania), sleep disturbances, aggression or agitation. As with CHF and COPD, in this stage the symptoms tend to flare up such that the disease worsens with each flare up. Once the person P reaches the established disease stage (which may generally correspond to phases $PH_3$ through $PH_5$), hallucinations, delusions, decreases in speech, substance abuse, as well as ongoing sleep disturbances, aggression and agitation are often in evidence. Next, when an advanced disease stage (which may generally correspond to phases $PH_6$ through $PH_7$) is reached, manifestations may include incontinence, dependency upon others for ADL (often accompanied with an inability to care for one's self), weight loss, ongoing sleep disturbances, aggression and agitation, as well as the need for repeated hospitalizations. Life expectancy with these diseases may involve a ten to twenty five year reduction due to one or more of the lifestyle attributes of the person P with a mental health condition. For example, a person P with one or more mental health problems may have a higher risk of physical illness due to: an increased tendency to be obese and smoke; the ongoing use of antipsychotic medications; increased risk of stroke, myocardial infarction and life threatening arrhythmias, among others. These phases While the general trajectory for all of these conditions is a downward worsening in functional status that ultimately ends in death, it is the presence of various acute, crisis or unstable stages along the trajectory that are of most interest to the present disclosure and the LEAP data being acquired by the wearable electronic device 100 for analysis on it or the system 1. Thus, in one form, dips D associated with certain acute events may signal transitions between subsequent ones of the identifiable phases PH along the downward trajectory. Using an acute event occurring at the crisis phase $PH_3$ (or established disease stage) from the CHF as an example, at least some of the acquired LEAP data may be analyzed (such as by one or more of the machine learning models discussed herein) in order to identify condition changes proactively at the threshold $PH_{3t}$ of these dips D (rather than retroactively at the end $PH_{3e}$) so that suitable medical intervention may be undertaken in enough time in order to avoid or mitigate the effect of these acute events. In one form, this may be part of a disease state management (DSM, also referred to as disease management) protocol to allow a holistic approach to healthcare monitoring, intervention and communication for a person P who exhibits one or more of these health conditions.

In one form, the previously-mentioned activity index provides a total score for an individual's activity level such that when compared against a baseline index (such as that which may form part of baseline data 1700), changes in status (including functional status such as that depicted in FIGS. 12 and 15) are readily identified through comparison of presently-acquired LEAP data and the activity index baseline. In one form, the acquired data that is being output from the wearable electronic device 100 through the third wireless communication sub-module 175C may include those previously mentioned, including the previously-discussed location data related to time spent in the bedroom, number of times going to the bathroom, or the like. In one form, the activity index may be preserved in memory 173B such that it describes a cumulative physical activity of the person P being monitored. In such form, the memory 173B may work in conjunction with the processor 173A to provide updates to the values stored in the activity index.

(D) Assessment of Data Acquired by the Wearable Electronic Device and Communication of a Diagnosed Health Condition Regardless of the health condition being analyzed, there is a need for the caregiver C or other user to draw an inference based on the acquired data. For example, increased incidents of drinking and toileting may be indicative of increases in bladder function, which in turn may be linked to a UTI. Likewise, significant increases in pacing or other itinerant behavior may portend an increased likelihood to wander, as well as provide indicia of bipolar disease, dementia with psychoses or other agitation-related conditions. Similarly, evidence of CHF or COPD may be gleaned from some of the acquired physiological data, possibly in conjunction with the location, activity or environmental data. In one form, diagnostics about these and other conditions may be more closely correlated with identifying variations from the norm rather than the patient's activity viewed in the abstract. In one form, this can be done by comparing present patient activity with an established baseline from existing data, including that from representative sample or demographic groups. In such cases, the use of a representative data set, in some cases along with the balanced, low-bias data set previously-discussed, may be employed. In another form, individualized baselines may also be used, as deviations from expected values may vary drastically from person to person. In this situation, acquiring data for each patient through the location-based functionality of the hybrid wireless communication module 175 and one or more of the sensors 121 of the wearable electronic device 100 facilitates the rapid formation of individualized baselines. Therefore, when such baseline data 1700 is compared to a particular, real-time (that is to say, present) set of data (also acquired through the wearable electronic device 100), a physician or other caregiver C can quickly ascertain if significant changes in a monitored individual's activity or other behavior warrant additional caregiver C intervention. For example, if a model (such as the one or more machine learning models discussed herein) makes a determination from the data acquired through the wearable electronic device 100 that the likelihood of a development of or worsening of these or other health conditions is imminent, an alert may be sent to the one or more remote computing devices 900 that are accessible by the caregivers C.

As such, the wearable electronic device 100 in one form acts as the cornerstone of not just CDS or diagnosis of a person P with imminent changes in health condition based on the acquired LEAP data, but also as a way for one caregiver C (for example, nurses, home health clinicians, assisted living facility personnel or the like) to convey the results of his or her patient evaluation to other caregivers C (for example, the physician) in a cross-disciplinary manner in order to help the latter assess whether significant deviations from the patient's health condition norms are worthy of changes in a treatment regimen for the patient. In one form, the LEAP data may form some or all of the data available to the caregiver C that in turn may be used as part of a Situation, Background, Assessment, Recommendation (SBAR) or other best practice-based clinical guideline such as those published by the Joint Commission, the Center for Disease Control (CDC), National Institute of Health (NIH), or other professional health-related societies. Within the present disclosure, it is the use of the SBAR's assessment component that is of most interest as the various pieces of patient information acquired by the LEAP data of the wearable electronic device 100, including vital signs such as temperature, pulse, respiration rate, blood pressure, $O_2$ saturation or the like, dyspnea, cough, fatigue, restlessness, anxiousness, confusion, anxiety or the like, may be used to complement the situation and background information as a way to more effectively convey such information to a physician or other caregiver C that is qualified to make a recommendation for the treatment of the patient, such as forming a patient action plan for the person P associated with the wearable electronic device 100.

The Food and Drug Administration (FDA) classifies software as a medical device (SaMD) into categories based on risk and intended purpose. The 21*st Century Cures Act* states that certain medical software is no longer considered to be regulated as a medical device, including that which provides limited CDS. On the other hand, software that allows image viewing for the purpose of making a diagnosis, software that offers treatment planning and software that is connected to a hardware medical device but is not needed by that hardware medical device to achieve its intended medical purpose that is not an accessory to the hardware medical device may be deemed to be SaMD.

In use, one or more signals associated with the LEAP data are detected by one or more of the sensors 121 and the first and second wireless communication sub-modules 175A, 175B. These and additional data—as well as the inferring of one or more criteria associated with a particular health condition—may be used to provide CDS that in turn may correlate to an action plan or related therapy recommendation. As such, the output from a machine learning model as discussed herein may be in the form of content variable, control variables or both. In such event, the output is not out of necessity mutually exclusive as some output may be used for CDS and actual diagnoses and attendant action plans, as well as for one or the other.

Thus, and in addition to helping with retrospective-oriented clinical analytics (that is to say, looking backwards to see what change in health condition event has already happened), the use of one or more of the machine learning models as discussed herein and that are acting upon the LEAP data acquired from the wearable electronic device 100 may also help with predictive analytics in order to understand what change in health condition event is likely to happen, as well as prescriptive analytics in order to form an action plan to mitigate or prevent any adverse changes in patient health. In one form, the use of neural networks, K-means clustering or other machine learning models as discussed herein may be used to perform diagnostics as a service (DaaS) such that it has SaMD functionality. The capability of such a predictive service may be used not only to diagnose (or help diagnose) certain adverse health conditions such as UTIs or cognitive or neuropsychiatric condition, but also to determine other health-related metrics as discussed previously, such as the chance of readmission to a hospital, length of hospital stays or the like. In another form (such as where diagnostics that leads to prescriptive analytics in order to form an action plan is avoided), SaMD functionality may be avoided.

CONCLUSION

The use of one or both of the wearable electronic device 100 and the accompanying system 1 to infer indicators of changing health of the wearer of the device through the monitoring of one or more forms of LEAP data is described herein. Besides using the wearable electronic device 100 for analyzing the change in an individual's health condition, other applications, such as for firefighters, schools (particularly those that deal with autistic children), military personnel and prison inmates, are also within the scope of the present disclosure. References in the present disclosure to the various forms, as well as to the previously-mentioned aspects, are meant to indicate that such forms or aspects may include one or more particular features, structures or related characteristics, but that each such form or aspect need not necessarily include all such particular features, structures or characteristics, and that any claimed combination of such features, structures or characteristics in part or in their entirety as described herein is has a basis in—and is therefore deemed to be within the scope of—the present disclosure.

Within the present disclosure, the acquisition of one or more portions of the LEAP data the wearable electronic device 100, as well as the possible subsequent use of such LEAP data (such as by the machine learning algorithms and models discussed herein) will be understood to include all or a portion of such data, either in the aggregate (that is to say, of all of the location, environmental, activity and physiological components), individually (that is to say, of any one of the location, environmental, activity and physiological components) or in combination (that is to say, of two or more of the location, environmental, activity and physiological components) unless the context specifically dictates otherwise. Likewise, such acquisition and possible subsequent use of such LEAP data will be understood to include all or a portion of the data collected within any one of the location, environmental, activity and physiological components, also only unless the context specifically dictates otherwise.

Within the present disclosure, data-driven features of interest (such as those used to infer one or more of the health conditions, behavior patterns or the like as described herein) may in one form be derived, processed, computed or otherwise established through the unique cooperation of the various structures described herein, including the data structures and program structures that may be embodied in corresponding machine code 173E that in turn may be operated upon by the computer-based logic device 173. In one form, the various operations performed by such machine code 173E and logic device 173 may be conceptually grouped into various modules for convenience of categorization purposes with the understanding that such grouping does not change the structural cooperation between such code and such device or devices. As such, certain operations—such as those associated with various portions of the five-step machine learning workflow 1000 as described herein—may conceptually be described or otherwise grouped into modular format without departing from the scope or intent of the present disclosure.

Within the present disclosure, it will be understood that sections, headings and sub-headings that are used herein are included for reference and to assist the reader with locating various sections. As such, these headings are not intended to limit the scope of the concepts described with respect thereto, and that such concepts may have applicability throughout some or all of the present disclosure.

Within the present disclosure, the term "patient" is meant to include a person (such as person P of FIGS. 4 and 5) who is either under short-term or long-term in-patient or out-patient care of a doctor, nurse or other professional caregiver C within a hospital or doctor's office, as well as a person P who either resides at home under a home health-care model, or is a resident either at home or within an assisted living model or related long-term or short-term care model. In addition, the term may be applied to a person P who is in need of health or location monitoring through the wearable electronic device 100, regardless of whether such person P is or is not under the present care of a doctor, nurse or other professional caregiver C. Accordingly, the various terms used herein to identify the wearer of the wearable electronic device 100 as a "person", "user", "individual" or "patient" are deemed to be equivalents within the present disclosure, and that any greater degree of specificity of such terms will be apparent from the context.

Within the present disclosure, it will be understood that the operations, functions, logical blocks, modules, circuits, and algorithm or model steps or events described may be implemented in hardware, software, firmware or any combination thereof. Moreover, if implemented in software, such operations may be stored on or transmitted over as one or more instructions or code on a computer-readable medium. The steps or events of a method, algorithm or ensuing model disclosed herein may be embodied in a processor-executable software module, which may reside on a tangible, non-transitory version of such computer-readable storage medium such that the medium be in any available form that permits access to the events or steps by a processor or related part of a computer. By way of example, and not limitation, such non-transitory computer-readable medium may comprise RAM, ROM, EEPROM, CD-ROM or other optical disk storage, magnetic disk storage or other magnetic storage devices, flash memory or any other form that may be used to store desired program code in the form of instructions or data structures and that may be accessed by a processor or related part of a computer. Combinations of the above should also be included within the scope of non-transitory computer-readable media. Additionally, the operations of a method, algorithm or model may reside as one or any combination or set of codes or instructions on a tangible, non-transitory machine readable medium or computer-readable medium, which may be incorporated into a computer program product.

Within the present disclosure, one or more of the following claims may utilize the term "wherein" as a transitional phrase. For the purposes of defining features discussed in the present disclosure, this term is introduced in the claims as an open-ended transitional phrase that is used to introduce a recitation of a series of characteristics of the structure and should be interpreted in like manner as the more commonly used open-ended preamble term "comprising."

Within the present disclosure, terms such as "preferably", "generally" and "typically" are not utilized to limit the scope of the claims or to imply that certain features are critical, essential, or even important to the disclosed structures or functions. Rather, these terms are merely intended to highlight alternative or additional features that may or may not be utilized in a particular embodiment of the disclosed subject matter. Likewise, it is noted that the terms "substantially" and "approximately" and their variants are utilized to represent the inherent degree of uncertainty that may be attributed to any quantitative comparison, value, measurement or other representation. As such, use of these terms represents the degree by which a quantitative representation may vary from a stated reference without resulting in a change in the basic function of the subject matter at issue.

Within the present disclosure, the use of the prepositional phrase "at least one of" is deemed to be an open-ended expression that has both conjunctive and disjunctive attributes. For example, a claim that states "at least one of A, B and C" (where A, B and C are definite or indefinite articles that are the referents of the prepositional phrase) means A alone, B alone, C alone, A and B together, A and C together, B and C together, or A, B and C together. By way of example within the present context, if a claim recites that data is being acquired from at least one of a first wireless communication sub-module and a second wireless communication sub-module, and if such data is being acquired from the first wireless communication sub-module alone, the second wireless communication sub-module alone or both of the first and second wireless communication sub-modules, then such data acquisition satisfies the claim.

Within the present disclosure, the following claims are not written in means-plus-function format and are not intended to be interpreted based on 35 USC 112(f) unless and until such claim limitations expressly use the phrase "means for" followed by a statement of function void of further structure.

Having described the subject matter of the present disclosure in detail and by reference to specific embodiments, it is noted that the various details disclosed in the present disclosure should not be taken to imply that these details relate to elements that are essential components of the various described embodiments, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure may be identified as preferred or particularly advantageous, it is contemplated that the present disclosure is not necessarily limited to these aspects.

It will be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the appended claims and their equivalents.

What is claimed is:
1. A wearable electronic device comprising:
 a wearable platform configured to be secured to an individual, the wearable platform including a processor and a non-transitory computer readable medium that are electrically coupled to one another;

a source of electric current;

a plurality of sensors at least one of which during operation thereof detects physiological data and at least one of environmental data and activity data;

a hybrid wireless communication module supported by the platform and receiving electric power from the source of electric current, the hybrid wireless communication module comprising:
  a first wireless communication sub-module that during operation thereof receives location data in the form of a beacon signal;
  a second wireless communication sub-module that during operation thereof receives location data in the form of a global navigation satellite system signal; and
  a third wireless communication sub-module that during operation thereof transmits a low-power wide area network signal that is configured to use a plurality of different adaptive network credentials that are configured to be received by a network;

a set of machine codes stored in the non-transitory computer-readable medium and operated upon by the processor, the set of machine codes comprising:
  a machine code to receive location data from at least one of the first and second wireless communication sub-modules;
  a machine code to receive at least one of the environmental data, activity data and physiological data from at least one of the plurality of sensors;
  a machine code to perform a machine learning model based on at least one of the received location data, environmental data, activity data and physiological data such that the machine learning model produces an output based on such data; and
  a machine code to transmit at least one of the received location data, environmental data, activity data, physiological data and output of the machine learning model through the third wireless communication sub-module using at least one of the plurality of different adaptive network credentials for the low-power wide area network signal.

2. The wearable electronic device of claim 1, wherein the hybrid wireless communication module does not comprise a cellular wireless communication sub-module.

3. The wearable electronic device of claim 1, wherein the wearable platform is selected from the group consisting of a wrist-worn band, an ankle-worn band, an article of clothing, a bandage, a pair of eyeglasses, a necklace, a pendant, a clothing-affixable pin, a clothing-affixable patch and a subcutaneous implant.

4. The wearable electronic device of claim 1, wherein the first wireless communication sub-module receives the location data in the form of a BLE signal.

5. The wearable electronic device of claim 1, wherein the third wireless communication sub-module transmits the low-power wide area network signal in the form of a LoRaWAN signal.

6. The wearable electronic device of claim 1, wherein the first wireless communication sub-module receives the location data in the form of a BLE signal and the third wireless communication sub-module transmits the low-power wide area network signal in the form of a LoRaWAN signal.

7. The wearable electronic device of claim 1, wherein the machine learning model comprises a classification model.

8. The wearable electronic device of claim 7, wherein the classification model comprises a neural network that is trained using at least a portion of the at least one of the received location data, environmental data, activity data and physiological data that is being transmitted by the third wireless communication sub-module.

9. The wearable electronic device of claim 8, whereupon operation of the trained neural network, a predictive analytics output is generated thereby that corresponds to a health condition of the individual.

10. The wearable electronic device of claim 1, wherein the machine learning model comprises a regression model.

11. The wearable electronic device of claim 1, wherein the machine learning model conducts at least one of a clinical decision support analysis and an activities of daily living analysis.

12. The wearable electronic device of claim 1, wherein the output produced by the machine learning model comprises at least a portion of a predictive analytics assessment of the individual corresponding to an adverse health condition comprising at least one of an infection and a neuropsychiatric symptom.

13. The wearable electronic device of claim 12, wherein the infection comprises a urinary tract infection.

14. The wearable electronic device of claim 12, wherein the neuropsychiatric symptom comprises at least one of wandering, agitation, apathy and depression.

15. The wearable electronic device of claim 1, wherein the machine learning model comprises an ensemble model.

16. The wearable electronic device of claim 15, wherein the ensemble model comprises at least one of boosting, bagging and stacking.

17. The wearable electronic device of claim 16, wherein the boosting comprises gradient boosting.

18. The wearable electronic device of claim 17, wherein at least one weak learner used in the gradient boosting is selected from the group consisting of decision-trees, support vector machines and k nearest neighbors.

19. The wearable electronic device of claim 1, wherein the machine learning model comprises a workflow configured to perform at least data acquisition, preprocessing and extraction such that the output is in the form of a feature vector of at least one of the received location data, environmental data, activity data and physiological data.

20. The wearable electronic device of claim 1, wherein the plurality of different adaptive network credentials comprise credentials that enable the low-power wide area network signal that is being transmitted to be able to switch between at least one of (a) a public network and a private network, (b) a public network and a different public network and (c) a private network and a different private network.

* * * * *